United States Patent
Smith et al.

(10) Patent No.: US 10,316,080 B2
(45) Date of Patent: Jun. 11, 2019

(54) PROTEIN-POLYMER-DRUG CONJUGATES

(71) Applicant: Asana Biosciences, LLC, Bridgewater, NJ (US)

(72) Inventors: Roger A. Smith, Chester Springs, PA (US); Nitin K. Damle, Berwyn, PA (US); Aleksandr V. Yurkovetskiy, Littleton, MA (US); Mao Yin, Needham, MA (US); Timothy B. Lowinger, Carlisle, MA (US); Joshua D. Thomas, Natick, MA (US); Cheri A. Stevenson, Haverhill, MA (US); Venu R. Gurijala, Lancaster, MA (US)

(73) Assignee: Asana BioSciences, LLC, Lawrenceville, NJ (US)

( * ) Notice: Subject to any disclaimer, the term of this patent is extended or adjusted under 35 U.S.C. 154(b) by 389 days.

(21) Appl. No.: 14/512,275

(22) Filed: Oct. 10, 2014

(65) Prior Publication Data

US 2015/0125474 A1 May 7, 2015

Related U.S. Application Data

(60) Provisional application No. 61/975,290, filed on Apr. 4, 2014, provisional application No. 61/890,065, filed on Oct. 11, 2013.

(51) Int. Cl.
| | |
|---|---|
| *A61K 47/68* | (2017.01) |
| *A61K 47/60* | (2017.01) |
| *C07K 16/18* | (2006.01) |
| *A61K 47/59* | (2017.01) |

(52) U.S. Cl.
CPC ............ *C07K 16/18* (2013.01); *A61K 47/59* (2017.08); *A61K 47/6843* (2017.08); *A61K 47/6883* (2017.08)

(58) Field of Classification Search
None
See application file for complete search history.

(56) References Cited

U.S. PATENT DOCUMENTS

| | | |
|---|---|---|
| 4,046,722 A | 9/1977 | Rowland |
| 4,256,746 A | 3/1981 | Miyashita et al. |
| 4,294,757 A | 10/1981 | Asai |
| 4,307,016 A | 12/1981 | Asai et al. |
| 4,313,946 A | 2/1982 | Powell et al. |
| 4,315,929 A | 2/1982 | Freedman et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,254 A | 5/1984 | Isley et al. |
| 4,460,560 A | 7/1984 | Tokes et al. |
| 4,486,414 A | 12/1984 | Pettit |
| 4,816,444 A | 3/1989 | Pettit et al. |
| 4,879,278 A | 11/1989 | Pettit et al. |
| 4,978,744 A | 12/1990 | Pettit et al. |
| 4,986,988 A | 1/1991 | Pettit et al. |
| 5,076,973 A | 12/1991 | Pettit et al. |
| 5,101,038 A | 3/1992 | Nakano et al. |
| 5,138,036 A | 8/1992 | Pettit et al. |
| 5,187,186 A | 2/1993 | Kanda et al. |
| 5,208,020 A | 5/1993 | Chari et al. |
| 5,410,024 A | 4/1995 | Pettit et al. |
| 5,416,064 A | 5/1995 | Chari et al. |
| 5,475,092 A | 12/1995 | Chari et al. |
| 5,504,191 A | 4/1996 | Pettit et al. |
| 5,521,284 A | 5/1996 | Pettit et al. |
| 5,530,097 A | 6/1996 | Pettit et al. |
| 5,554,725 A | 9/1996 | Pettit |
| 5,582,172 A | 12/1996 | Papisov et al. |
| 5,585,499 A | 12/1996 | Chari et al. |
| 5,599,902 A | 2/1997 | Pettit et al. |
| 5,635,483 A | 6/1997 | Pettit et al. |
| 5,663,149 A | 9/1997 | Pettit et al. |
| 5,665,860 A | 9/1997 | Pettit et al. |
| 5,714,586 A | 2/1998 | Kunstmann et al. |
| 5,739,116 A | 4/1998 | Hamann et al. |

(Continued)

FOREIGN PATENT DOCUMENTS

| | | |
|---|---|---|
| EP | 0112720 A2 | 7/1984 |
| EP | 0354787 A1 | 2/1990 |

(Continued)

OTHER PUBLICATIONS

Burke et al., "Design, Synthesis, and Biological Evaluation of Antibody-Drug Conjugates Comprised of Potent Camptothecin Analogues," Bioconj. Chem. 20.6(2009):1242-1250.
Hamblett et al., "Effects of Drug Loading on the Antitumor Activity of a Monoclonal Antibody Drug Conjugate," Clin. Cancer Res. 10(2004):7063-7070.
International Search Report and Written Opinion for Application No. PCT/US2014/060170 dated Feb. 9, 2015.
International Search Report and Written Opinion for Application No. PCT/US2014/060181 dated Feb. 9, 2015.
Lambert et al., "Drug-Conjugated Monoclonal Antibodies for the Treatment of Cancer," Curr. Opin. Pharmacal. 5 (2005):543-549.
Lash, "Making the Case for Antibody-Drug Conjugates," In Vivo. 28.11 (2010):32-38. (Article #2010800200).

(Continued)

*Primary Examiner* — Mark Halvorson
*Assistant Examiner* — Kauser M Akhoon
(74) *Attorney, Agent, or Firm* — DLA Piper LLP (US)

(57) ABSTRACT

A polymeric scaffold useful for conjugating with a protein based recognition-molecule (PBRM) to form a PBRM-polymer-drug conjugate is described herein. The scaffold includes one or more terminal maleimido groups. Also disclosed is a PBRM-polymer-drug conjugate prepared from the scaffold. Compositions comprising the conjugates, methods of their preparation, and methods of treating various disorders with the conjugates or their compositions are also described.

4 Claims, 8 Drawing Sheets

Specification includes a Sequence Listing.

(56) References Cited

U.S. PATENT DOCUMENTS

| | | |
|---|---|---|
| 5,763,263 A | 6/1998 | Dehlinger |
| 5,767,237 A | 6/1998 | Sakakibara et al. |
| 5,767,293 A | 6/1998 | Oku et al. |
| 5,780,588 A | 7/1998 | Pettit et al. |
| 5,789,405 A | 8/1998 | Oku et al. |
| 5,811,510 A | 9/1998 | Papisov |
| 5,846,545 A | 12/1998 | Chari et al. |
| 5,863,990 A | 1/1999 | Papisov |
| 5,886,026 A | 3/1999 | Hunter et al. |
| 5,958,398 A | 9/1999 | Papisov |
| 5,969,145 A | 10/1999 | Schinzer et al. |
| 6,034,065 A | 3/2000 | Pettit et al. |
| 6,043,372 A | 3/2000 | Schinzer et al. |
| 6,080,751 A | 6/2000 | Stehlin et al. |
| 6,096,757 A | 8/2000 | Bishop et al. |
| 6,117,659 A | 9/2000 | Ashley et al. |
| 6,121,029 A | 9/2000 | Schupp et al. |
| 6,124,431 A | 9/2000 | Sakakibara et al. |
| 6,207,704 B1 | 3/2001 | Liu et al. |
| 6,239,104 B1 | 5/2001 | Pettit et al. |
| 6,323,315 B1 | 11/2001 | Pettit et al. |
| 6,333,410 B1 | 12/2001 | Chari et al. |
| 6,340,701 B1 | 1/2002 | Chari et al. |
| 6,372,738 B2 | 4/2002 | Chari et al. |
| 6,436,931 B1 | 8/2002 | Chari et al. |
| 6,441,163 B1 | 8/2002 | Chari et al. |
| 6,534,660 B1 | 3/2003 | Yongxin et al. |
| 6,548,530 B1 | 4/2003 | Boger |
| 6,566,541 B2 | 5/2003 | Liu et al. |
| 6,586,618 B1 | 7/2003 | Zhao et al. |
| 6,596,757 B1 | 7/2003 | Chari et al. |
| 6,602,498 B2 | 8/2003 | Shen |
| 6,603,812 B1 | 8/2003 | Oprescu |
| 6,630,579 B2 | 10/2003 | Chari et al. |
| 6,660,742 B2 | 12/2003 | Lee |
| 6,680,311 B1 | 1/2004 | Al-Awar et al. |
| 6,716,821 B2 | 4/2004 | Zhao et al. |
| 6,747,021 B2 | 6/2004 | Corbett et al. |
| 6,756,397 B2 | 6/2004 | Zhao et al. |
| 6,822,086 B1 | 11/2004 | Papisov |
| 6,884,869 B2 | 4/2005 | Senter et al. |
| 6,911,197 B2 | 6/2005 | Shen |
| 6,956,036 B1 | 10/2005 | May et al. |
| 6,989,450 B2 | 1/2006 | Avery |
| 7,049,316 B2 | 5/2006 | Zhao et al. |
| RE39,151 E | 6/2006 | Chari et al. |
| 7,160,924 B2 | 1/2007 | Kinstler et al. |
| 7,276,497 B2 | 10/2007 | Chari et al. |
| 7,303,749 B1 | 12/2007 | Chari |
| 7,329,721 B2 | 2/2008 | Kozlowski et al. |
| 7,432,330 B2 | 10/2008 | Kozlowski et al. |
| 7,432,331 B2 | 10/2008 | Kozlowski et al. |
| 7,498,298 B2 | 3/2009 | Doronina et al. |
| 7,514,546 B2 | 4/2009 | Kingsman et al. |
| 7,553,816 B2 | 6/2009 | Senter et al. |
| 7,595,292 B2 | 9/2009 | Brocchini et al. |
| 7,659,361 B2 | 2/2010 | Kozlowski et al. |
| 7,790,150 B2 | 9/2010 | Papisov et al. |
| 7,838,619 B2 | 11/2010 | Papisov |
| 7,872,082 B2 | 1/2011 | Kozlowski et al. |
| 7,910,661 B2 | 3/2011 | Kozlowski et al. |
| 7,977,465 B2 | 7/2011 | Ng et al. |
| 7,994,272 B2 | 8/2011 | Kozlowski et al. |
| 8,030,459 B2 | 10/2011 | Papisov et al. |
| 8,034,959 B2 | 10/2011 | Ng et al. |
| 8,044,178 B2 | 10/2011 | Boghaert et al. |
| 8,058,385 B2 | 11/2011 | Kozlowski et al. |
| 8,106,131 B2 | 1/2012 | Kozlowski et al. |
| 8,227,555 B2 | 7/2012 | Kozlowski et al. |
| 8,227,558 B2 | 7/2012 | Kozlowski et al. |
| 8,304,511 B2 | 11/2012 | Kozlowski et al. |
| 8,309,094 B2 | 11/2012 | Gerber et al. |
| 8,454,946 B2 | 6/2013 | Shen |
| 8,562,965 B2 | 10/2013 | McManus et al. |
| 8,685,383 B2 | 4/2014 | Yurkovetskiy et al. |
| 8,765,111 B2 | 7/2014 | Shen |
| 8,808,679 B2 | 8/2014 | Yurkovetskiy et al. |
| 8,815,226 B2 | 8/2014 | Yurkovetskiy et al. |
| 8,821,850 B2 | 9/2014 | Yurkovetskiy et al. |
| 8,835,556 B2 | 9/2014 | Kozlowski et al. |
| 9,144,615 B2 * | 9/2015 | Yurkovetskiy |
| 9,254,339 B2 * | 2/2016 | Yurkovetskiy ............. A61K 47/48192 |
| 2002/0082362 A1 | 6/2002 | Brocchini et al. |
| 2002/0103136 A1 | 8/2002 | Feng |
| 2003/0083263 A1 | 5/2003 | Doronina et al. |
| 2004/0105840 A1 | 6/2004 | Kinstler et al. |
| 2004/0166089 A1 | 8/2004 | Yu et al. |
| 2005/0049387 A1 | 3/2005 | Van et al. |
| 2005/0169933 A1 | 8/2005 | Steeves et al. |
| 2005/0186174 A1 | 8/2005 | Bossard |
| 2006/0014222 A1 | 1/2006 | Kingsman et al. |
| 2006/0058512 A1 | 3/2006 | Shitara et al. |
| 2007/0190018 A1 | 8/2007 | Papisov |
| 2008/0176958 A1 | 7/2008 | Davis et al. |
| 2009/0148396 A1 | 6/2009 | Akullian et al. |
| 2010/0129314 A1 | 5/2010 | Singh et al. |
| 2010/0173382 A1 | 7/2010 | Boghaert et al. |
| 2010/0203007 A1 | 8/2010 | Li et al. |
| 2010/0305149 A1 | 12/2010 | Yurkovetskiy et al. |
| 2011/0020343 A1 | 1/2011 | Senter et al. |
| 2011/0070248 A1 | 3/2011 | Ichikawa et al. |
| 2011/0243880 A1 | 10/2011 | Yurkovetskiy et al. |
| 2012/0321583 A1 | 12/2012 | Yurkovetskiy et al. |
| 2012/0321585 A1 | 12/2012 | Griffith et al. |
| 2013/0101546 A1 | 4/2013 | Yurkovetskiy et al. |
| 2014/0017265 A1 | 1/2014 | Yurkovetskiy et al. |
| 2014/0193437 A1 | 7/2014 | Lin et al. |
| 2014/0256957 A1 | 9/2014 | Shen |
| 2016/0304617 A1 * | 10/2016 | Damle ................ C07K 16/30 |

FOREIGN PATENT DOCUMENTS

| | | |
|---|---|---|
| EP | 1036091 A1 | 9/2000 |
| EP | 2368914 A1 | 9/2011 |
| WO | 9719086 A1 | 5/1997 |
| WO | 9808849 A1 | 3/1998 |
| WO | 9822461 A1 | 5/1998 |
| WO | 9825929 A1 | 6/1998 |
| WO | 9838192 A1 | 9/1998 |
| WO | 9901124 A1 | 1/1999 |
| WO | 9902514 A2 | 1/1999 |
| WO | 9903848 A1 | 1/1999 |
| WO | 9907692 A2 | 2/1999 |
| WO | 9927890 A2 | 6/1999 |
| WO | 9928324 A1 | 6/1999 |
| WO | 9961432 A1 | 12/1999 |
| WO | 2000064486 | 11/2000 |
| WO | 2001010468 | 2/2001 |
| WO | 0124763 A2 | 4/2001 |
| WO | 02088172 A2 | 11/2002 |
| WO | 2004009774 A2 | 1/2004 |
| WO | 2004010957 A2 | 1/2004 |
| WO | 2005081711 A2 | 9/2005 |
| WO | 2006044986 A1 | 4/2006 |
| WO | 2007008848 A2 | 1/2007 |
| WO | 2007103288 A2 | 9/2007 |
| WO | 2007109567 A1 | 9/2007 |
| WO | 2007140371 A2 | 12/2007 |
| WO | 2008052187 A2 | 5/2008 |
| WO | 2008076333 A2 | 6/2008 |
| WO | 2009052249 A1 | 4/2009 |
| WO | 2009117531 A1 | 9/2009 |
| WO | 2010100430 A1 | 9/2010 |
| WO | 2010114940 A1 | 10/2010 |
| WO | 2010126552 A1 | 11/2010 |
| WO | 2010138719 A1 | 12/2010 |
| WO | 2011120053 A1 | 9/2011 |
| WO | 2011130598 A1 | 10/2011 |
| WO | 2012066581 A1 | 5/2012 |
| WO | 2012131527 A1 | 10/2012 |
| WO | 2012171020 A1 | 12/2012 |

(56) References Cited

FOREIGN PATENT DOCUMENTS

| WO | 2013041687 A1 | 3/2013 |
|---|---|---|
| WO | 2013173337 A2 | 11/2013 |

OTHER PUBLICATIONS

Moorthy S S Palanki et al: "Development of novel linkers to conjugate pharmacophores to a carrier antibody", Bioorganic & Medicinal Chemistry Letters, Pergamon, Amsterdam, NL, vol. 22, No. 13, May 8, 2012 (May 8, 2012), pp. 4249-4253, XP028490988, ISSN: 0960-894X, DOI: 10.1016/J.BMCL.2012.05.040 [retrieved on May 17, 2012] abstract Scheme 2; figure 3.
Noguchi et al., "Preparation and Properties of the Immunoconjugate Composed of Anti-Human Colon Cancer Monoclonal Antibody and Mitomycin C-Dextran Conjugate," Bioconj. Chem. 3.2(1992): 132-137.
Senter, "Potent Antibody Drug Conjugates for Cancer Therapy," Curr. Opin. Chem. Biol. 13(2009): 235-244.
Smith et al., "ASN004, a Novel 5T4-Targeted Dolaflexin™ ADC for the Treatment of Various Cancers", ASANA BioSciences Poster, Oct. 27-29, 2014.
Tumey et al., "Mild Method for Succinimide Hydrolysis on ADCs: Impact on ADC Potency, Stability, Exposure, and Efficacy." Bioconjug Chem. 2014; 25(10):1871-80.
Ulbrich et al. "HPMA Copolymers With pH-Controlled Release of Doxorubicin," J. Control. Release. 87.1-3 (2003):33-47.
Yurkovetskiy et al., "Advantages of Polyacetal Polymer-Based Antibody Drug Conjugates Employing Cysteine Bioconjugation", Mersana Poster, AACR Apr. 6 to Apr. 10, 2013, Abstract #4331.
Yurkovetskiy et al., "Advantages of Polyacetal Polymer-based Antibody Drug Conjugates: Application to Low Expression Targets", Mersana Poster, AACR Apr. 5-9, 2014, Abstract #2645.
Yurkovetskiy et al., "Fully Degradable Hydrophilic Polyals for Protein Modification," Biomacromolecules, American Chemial Society,. vol. 6, No. 5, Jan. 1, 2005, pp. 2648-2658, XP008057395.
Yurkovetskiy et al., "Polyacetal polymer-based anti-HER2 antibody-drug conjugate employing cysteine bioconjugation through thioether linkage", Mersana Poster #C238, EORTC Molecular Targets and Cancer Therapy, Oct. 19-23, 2013.
Zhao et al., "Synthesis and Evaluation of Hydrophilic Linkers for Antibody-Maytansinoid Conjugates." J. Med. Chem. 2011, 54, 3606-3623.
Damelin, Marc, et al., "Delineation of a Cellular Hierarchy in Lung Cancer Reveals an Oncofetal Antigen Expressed on Tumor-Initiating Cells", *Cancer Research: Tumor and Cell Biology*, American Associated for Cancer Research, 71(12), Jun. 15, 2011.
Sapra, Puja et al., "Long-Term Tumor Regression Induced by an Antibody-Drug Conjugate That Targets 5T4, an Oncofetal Antigen Expressed on Tumor-Initiating Cells", *Molecular Cancer Therapeutics*, vol. 12, No. 1, Jan. 2013, pp. 38-47.
Office Action received in corresponding Japanese Application No. 2016-521965 dated Jun. 1, 2018, and its English translation.
First Office Action received in corresponding Chinese Application No. 201480067401.7 dated Apr. 8, 2018, and its English translation.
Office Action received in counterpart Australasian Application No. 2014331645 dated Feb. 6, 2019.

\* cited by examiner

SEQUENCE LISTING

```
<160> NUMBER OF SEQ ID NOS: 8

<210> SEQ ID NO 1
<211> LENGTH: 242
<212> TYPE: PRT
<213> ORGANISM: Mus sp.

<400> SEQUENCE: 1

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser Pro Gly Lys Gly Leu Glu Trp Ile
        35                  40                  45

Gly Arg Ile Asn Pro Asn Asn Gly Val Thr Leu Tyr Asn Gln Lys Phe
    50                  55                  60

Lys Asp Lys Ala Thr Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Ser Thr Met Ile Thr Asn Tyr Val Met Asp Tyr Trp Gly Gln
            100                 105                 110

Gly Thr Ser Val Thr Val Ser Ser Gly Gly Gly Gly Ser Gly Gly Gly
        115                 120                 125

Gly Ser Gly Gly Gly Gly Ser Ser Ile Val Met Thr Gln Thr Pro Thr
    130                 135                 140

Ser Leu Leu Val Ser Ala Gly Asp Arg Val Thr Ile Thr Cys Lys Ala
145                 150                 155                 160

Ser Gln Ser Val Ser Asn Asp Val Ala Trp Tyr Gln Gln Lys Pro Gly
                165                 170                 175

Gln Ser Pro Lys Leu Leu Ile Ser Tyr Thr Ser Ser Arg Tyr Ala Gly
            180                 185                 190

Val Pro Asp Arg Phe Thr Gly Ser Gly Ser Gly Thr Asp Phe Thr Leu
        195                 200                 205

Thr Ile Ser Ser Val Gln Ala Glu Asp Ala Ala Val Tyr Phe Cys Gln
```

```
                    210                 215                 220

Gln Asp Tyr Asn Ser Pro Pro Thr Phe Gly Gly Gly Thr Lys Leu Glu
225                 230                 235                 240

Ile Lys

<210> SEQ ID NO 2
<211> LENGTH: 257
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Lys Ala Ser Gly Tyr Ser Phe Thr Gly Tyr
                20                  25                  30

Tyr Met His Trp Val Arg Gln Ala Pro Gly Lys Gly Leu Glu Trp Val
            35                  40                  45

Ser Arg Ile Asn Pro Asn Asn Gly Val Thr Leu Tyr Asn Gln Lys Phe
50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Thr Met Ile Thr Asn Tyr Val Met Asp Tyr Trp Gly Gln
            100                 105                 110

Gly Thr Leu Val Thr Val Ser Gly Gly Gly Gly Ser Gly Gly Gly
            115                 120                 125

Gly Ser Gly Gly Gly Ser Gly Gly Gly Ser Gly Gly Gly
            130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Lys Ala Ser
                165                 170                 175

Gln Ser Val Ser Asn Asp Val Ala Trp Tyr Gln Gln Lys Pro Gly Lys
            180                 185                 190

Ala Pro Lys Leu Leu Ile Tyr Tyr Thr Ser Ser Arg Tyr Ala Gly Val
        195                 200                 205

Pro Ser Arg Phe Ser Gly Ser Gly Ser Gly Thr Asp Phe Thr Leu Thr
210                 215                 220

Ile Ser Ser Leu Gln Pro Glu Asp Phe Ala Thr Tyr Tyr Cys Gln Gln
225                 230                 235                 240

Asp Tyr Asn Ser Pro Pro Thr Phe Gly Gly Gly Thr Lys Leu Glu Ile
            245                 250                 255

Lys

<210> SEQ ID NO 3
<211> LENGTH: 232
<212> TYPE: PRT
<213> ORGANISM: Homo sapiens

<400> SEQUENCE: 3

Glu Pro Lys Ser Ser Asp Lys Thr His Thr Cys Pro Pro Cys Pro Ala
1               5                   10                  15
```

```
Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
            130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Ser Thr Cys
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 5

Ala Ser Thr Xaa
1

<210> SEQ ID NO 6
<211> LENGTH: 478
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 6

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser Pro Gly Lys Gly Leu Glu Trp Ile
        35                  40                  45

Gly Arg Ile Asn Pro Asn Asn Gly Val Thr Leu Tyr Asn Gln Lys Phe
    50                  55                  60

Lys Asp Lys Ala Thr Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Ser Thr Met Ile Thr Asn Tyr Val Met Asp Tyr Trp Gly Gln
            100                 105                 110

Gly Thr Ser Val Thr Val Ser Ser Gly Gly Gly Ser Gly Gly Gly
        115                 120                 125

Gly Ser Gly Gly Gly Ser Ser Ile Val Met Thr Gln Thr Pro Thr
    130                 135                 140

Ser Leu Leu Val Ser Ala Gly Asp Arg Val Thr Ile Thr Cys Lys Ala
145                 150                 155                 160

Ser Gln Ser Val Ser Asn Asp Val Ala Trp Tyr Gln Gln Lys Pro Gly
                165                 170                 175

Gln Ser Pro Lys Leu Leu Ile Ser Tyr Thr Ser Ser Arg Tyr Ala Gly
            180                 185                 190

Val Pro Asp Arg Phe Thr Gly Ser Gly Ser Gly Thr Asp Phe Thr Leu
        195                 200                 205

Thr Ile Ser Ser Val Gln Ala Glu Asp Ala Ala Val Tyr Phe Cys Gln
    210                 215                 220

Gln Asp Tyr Asn Ser Pro Pro Thr Phe Gly Gly Gly Thr Lys Leu Glu
225                 230                 235                 240

Ile Lys Ala Ser Thr Cys Glu Pro Lys Ser Ser Asp Lys Thr His Thr
                245                 250                 255

Cys Pro Pro Cys Pro Ala Pro Glu Leu Leu Gly Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
        355                 360                 365

Lys Ala Lys Gly Gln Pro Arg Glu Pro Gln Val Tyr Thr Leu Pro Pro
    370                 375                 380

Ser Arg Asp Glu Leu Thr Lys Asn Gln Val Ser Leu Thr Cys Leu Val
```

```
                385                 390                 395                 400
Lys Gly Phe Tyr Pro Ser Asp Ile Ala Val Glu Trp Glu Ser Asn Gly
                    405                 410                 415

Gln Pro Glu Asn Asn Tyr Lys Thr Thr Pro Val Leu Asp Ser Asp
                420                 425                 430

Gly Ser Phe Phe Leu Tyr Ser Lys Leu Thr Val Asp Lys Ser Arg Trp
                    435                 440                 445

Gln Gln Gly Asn Val Phe Ser Cys Ser Val Met His Glu Ala Leu His
450                 455                 460

Asn His Tyr Thr Gln Lys Ser Leu Ser Leu Ser Pro Gly Lys
465                 470                 475

<210> SEQ ID NO 7
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Lys Ala Ser Gly Tyr Ser Phe Thr Gly Tyr
                20                  25                  30

Tyr Met His Trp Val Arg Gln Ala Pro Gly Lys Gly Leu Glu Trp Val
            35                  40                  45

Ser Arg Ile Asn Pro Asn Asn Gly Val Thr Leu Tyr Asn Gln Lys Phe
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Thr Met Ile Thr Asn Tyr Val Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Lys Ala Ser
                165                 170                 175

Gln Ser Val Ser Asn Asp Val Ala Trp Tyr Gln Gln Lys Pro Gly Lys
            180                 185                 190

Ala Pro Lys Leu Leu Ile Tyr Tyr Thr Ser Ser Arg Tyr Ala Gly Val
        195                 200                 205

Pro Ser Arg Phe Ser Gly Ser Gly Ser Gly Thr Asp Phe Thr Leu Thr
    210                 215                 220

Ile Ser Ser Leu Gln Pro Glu Asp Phe Ala Thr Tyr Tyr Cys Gln Gln
225                 230                 235                 240

Asp Tyr Asn Ser Pro Pro Thr Phe Gly Gly Gly Thr Lys Leu Glu Ile
                245                 250                 255

Lys Ala Ser Thr Cys Glu Pro Lys Ser Ser Asp Lys Thr His Thr Cys
            260                 265                 270
```

Pro Pro Cys Pro Ala Pro Glu Leu Leu Gly Gly Pro Ser Val Phe Leu
            275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
    355                 360                 365

Val Ser Asn Lys Ala Leu Pro Ala Pro Ile Glu Lys Thr Ile Ser Lys
370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
    435                 440                 445

Ser Phe Phe Leu Tyr Ser Lys Leu Thr Val Asp Lys Ser Arg Trp Gln
450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490

<210> SEQ ID NO 8
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (261)..(261)
<223> OTHER INFORMATION: Any amino acid

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Lys Ala Ser Gly Tyr Ser Phe Thr Gly Tyr
            20                  25                  30

Tyr Met His Trp Val Arg Gln Ala Pro Gly Lys Gly Leu Glu Trp Val
        35                  40                  45

Ser Arg Ile Asn Pro Asn Asn Gly Val Thr Leu Tyr Asn Gln Lys Phe
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Thr Met Ile Thr Asn Tyr Val Met Asp Tyr Trp Gly Gln
            100                 105                 110

Gly Thr Leu Val Thr Val Ser Ser Gly Gly Gly Gly Ser Gly Gly Gly

|     |     |     |     |     |     |     |     |     |     |     |     |
| --- | --- | --- | --- | --- | --- | --- | --- | --- | --- | --- | --- |
|     |     | 115 |     |     | 120 |     |     | 125 |     |     |     |
| Gly | Ser | Gly | Gly | Gly | Ser | Gly | Gly | Gly | Ser | Gly | Gly |
|     |     | 130 |     |     | 135 |     |     | 140 |     |     |     |
| Ser | Gly | Gly | Gly | Ser | Asp | Ile | Gln | Met | Thr | Gln | Ser | Pro | Ser | Ser |
| 145 |     |     |     | 150 |     |     |     | 155 |     |     | 160 |
| Leu | Ser | Ala | Ser | Val | Gly | Asp | Arg | Val | Thr | Ile | Thr | Cys | Lys | Ala | Ser |
|     |     |     |     | 165 |     |     |     | 170 |     |     |     | 175 |
| Gln | Ser | Val | Ser | Asn | Asp | Val | Ala | Trp | Tyr | Gln | Gln | Lys | Pro | Gly | Lys |
|     |     |     | 180 |     |     |     | 185 |     |     |     | 190 |
| Ala | Pro | Lys | Leu | Leu | Ile | Tyr | Tyr | Thr | Ser | Arg | Tyr | Ala | Gly | Val |
|     |     | 195 |     |     |     | 200 |     |     |     | 205 |
| Pro | Ser | Arg | Phe | Ser | Gly | Ser | Gly | Ser | Gly | Thr | Asp | Phe | Thr | Leu | Thr |
|     | 210 |     |     |     | 215 |     |     |     | 220 |
| Ile | Ser | Ser | Leu | Gln | Pro | Glu | Asp | Phe | Ala | Thr | Tyr | Tyr | Cys | Gln | Gln |
| 225 |     |     |     | 230 |     |     |     | 235 |     |     |     | 240 |
| Asp | Tyr | Asn | Ser | Pro | Pro | Thr | Phe | Gly | Gly | Gly | Thr | Lys | Leu | Glu | Ile |
|     |     |     |     | 245 |     |     |     | 250 |     |     |     | 255 |
| Lys | Ala | Ser | Thr | Xaa | Glu | Pro | Lys | Ser | Ser | Asp | Lys | Thr | His | Thr | Cys |
|     |     |     | 260 |     |     |     | 265 |     |     |     | 270 |
| Pro | Pro | Cys | Pro | Ala | Pro | Glu | Leu | Leu | Gly | Gly | Pro | Ser | Val | Phe | Leu |
|     |     | 275 |     |     |     | 280 |     |     |     | 285 |
| Phe | Pro | Pro | Lys | Pro | Lys | Asp | Thr | Leu | Met | Ile | Ser | Arg | Thr | Pro | Glu |
|     | 290 |     |     |     | 295 |     |     |     | 300 |
| Val | Thr | Cys | Val | Val | Val | Asp | Val | Ser | His | Glu | Asp | Pro | Glu | Val | Lys |
| 305 |     |     |     | 310 |     |     |     | 315 |     |     |     | 320 |
| Phe | Asn | Trp | Tyr | Val | Asp | Gly | Val | Glu | Val | His | Asn | Ala | Lys | Thr | Lys |
|     |     |     |     | 325 |     |     |     | 330 |     |     |     | 335 |
| Pro | Arg | Glu | Glu | Gln | Tyr | Asn | Ser | Thr | Tyr | Arg | Val | Val | Ser | Val | Leu |
|     |     |     | 340 |     |     |     | 345 |     |     |     | 350 |
| Thr | Val | Leu | His | Gln | Asp | Trp | Leu | Asn | Gly | Lys | Glu | Tyr | Lys | Cys | Lys |
|     |     | 355 |     |     |     | 360 |     |     |     | 365 |
| Val | Ser | Asn | Lys | Ala | Leu | Pro | Ala | Pro | Ile | Glu | Lys | Thr | Ile | Ser | Lys |
|     | 370 |     |     |     | 375 |     |     |     | 380 |
| Ala | Lys | Gly | Gln | Pro | Arg | Glu | Pro | Gln | Val | Tyr | Thr | Leu | Pro | Pro | Ser |
| 385 |     |     |     | 390 |     |     |     | 395 |     |     |     | 400 |
| Arg | Asp | Glu | Leu | Thr | Lys | Asn | Gln | Val | Ser | Leu | Thr | Cys | Leu | Val | Lys |
|     |     |     |     | 405 |     |     |     | 410 |     |     |     | 415 |
| Gly | Phe | Tyr | Pro | Ser | Asp | Ile | Ala | Val | Glu | Trp | Glu | Ser | Asn | Gly | Gln |
|     |     |     | 420 |     |     |     | 425 |     |     |     | 430 |
| Pro | Glu | Asn | Asn | Tyr | Lys | Thr | Thr | Pro | Pro | Val | Leu | Asp | Ser | Asp | Gly |
|     |     |     | 435 |     |     |     | 440 |     |     |     | 445 |
| Ser | Phe | Phe | Leu | Tyr | Ser | Lys | Leu | Thr | Val | Asp | Lys | Ser | Arg | Trp | Gln |
|     |     |     | 450 |     |     |     | 455 |     |     |     | 460 |
| Gln | Gly | Asn | Val | Phe | Ser | Cys | Ser | Val | Met | His | Glu | Ala | Leu | His | Asn |
| 465 |     |     |     | 470 |     |     |     | 475 |     |     |     | 480 |
| His | Tyr | Thr | Gln | Lys | Ser | Leu | Ser | Leu | Ser | Pro | Gly | Lys |
|     |     |     |     | 485 |     |     |     | 490 |

PROTEIN-POLYMER-DRUG CONJUGATES

RELATED APPLICATIONS

The present application claims the benefit of the filing date of U.S. Provisional Application Nos. 61/890,065, filed Oct. 11, 2013, entitled Protein-Polymer-Drug Conjugates, and 61/975,290, filed Apr. 4, 2014, entitled Protein-Polymer-Drug Conjugates, the disclosures of which are hereby incorporated herein by reference.

SEQUENCE LISTING

The instant application contains a Sequence Listing which has been submitted electronically in ASCII format and is hereby incorporated by reference in its entirety. Said ASCII copy, created on Nov. 20, 2014, is named ASANA3.0A-010 (E)_SL.txt and is 20,383 bytes in size.

BACKGROUND OF THE INVENTION

Traditionally, pharmaceuticals have primarily consisted of small molecules that are dispensed orally (as solid pills and liquids) or as injectables. Over the past three decades, formulations (i.e., compositions that control the route and/or rate of drug delivery and allow delivery of the therapeutic agent at the site where it is needed) have become increasingly common and complex. Nevertheless, many questions and challenges regarding the development of new treatments as well as the mechanisms with which to administer them remain to be addressed. For example, many drugs exhibit limited or otherwise reduced potencies and therapeutic effects because they are either generally subject to partial degradation before they reach a desired target in the body, or accumulate in tissues other than the target, or both.

One objective in the field of drug delivery systems, therefore, is to deliver medications intact to specifically targeted areas of the body through a system that can stabilize the drug and control the in vivo transfer of the therapeutic agent utilizing either physiological or chemical mechanisms, or both.

Antibody-drug conjugates have been developed as target-specific therapeutic agents. Antibodies against various cancer cell-surface antigens have been conjugated with different cytotoxic agents that inhibit various essential cellular targets such as microtubules (maytansinoids, auristatins, taxanes: U.S. Pat. Nos. 5,208,020; 5,416,064; 6,333,410; 6,441,163; 6,340,701; 6,372,738; 6,436,931; 6,596,757; and 7,276,497); DNA (calicheamicin, doxorubicin, CC-1065 analogs; U.S. Pat. Nos. 5,475,092; 5,585,499; 5,846,545; 6,534,660; 6,756,397; and 6,630,579). Antibody conjugates with some of these cytotoxic drugs are actively being investigated in the clinic for cancer therapy (Ricart, A. D., and Tolcher, A. W., 2007, *Nature Clinical Practice*, 4, 245-255; Krop et al., 2010, *J. Clin. Oncol.*, 28, 2698-2704). However, existing antibody-drug conjugates have exhibited a few limitations. A major limitation is their inability to deliver a sufficient concentration of drug to the target site because of the limited number of targeted antigens and the relatively moderate cytotoxicity of cancer drugs like methotrexate, daunorubicin, maytansinoids, taxanes, and vincristine. One approach to achieving significant cytotoxicity is by linkage of a large number of drug molecules either directly or indirectly to the antibody. However such heavily modified antibodies often display impaired binding to the target antigen and fast in vivo clearance from the blood stream. Therefore, there is a need to improve the ability to deliver a sufficient concentration of a drug to the target such that maximum cytotoxicity for the drug is achieved.

SUMMARY OF THE INVENTION

The present invention relates to a protein-polymer-drug conjugate that is biodegradable, biocompatible and exhibits high drug load as well as strong binding to target antigen. The present invention also relates to a polymeric scaffold useful to conjugate with a protein based recognition-molecule (PBRM) so as to obtain the protein-polymer-drug conjugate.

In another aspect, the invention relates to a polymeric scaffold of Formula (Id) useful to conjugate with a protein based recognition-molecule (PBRM):

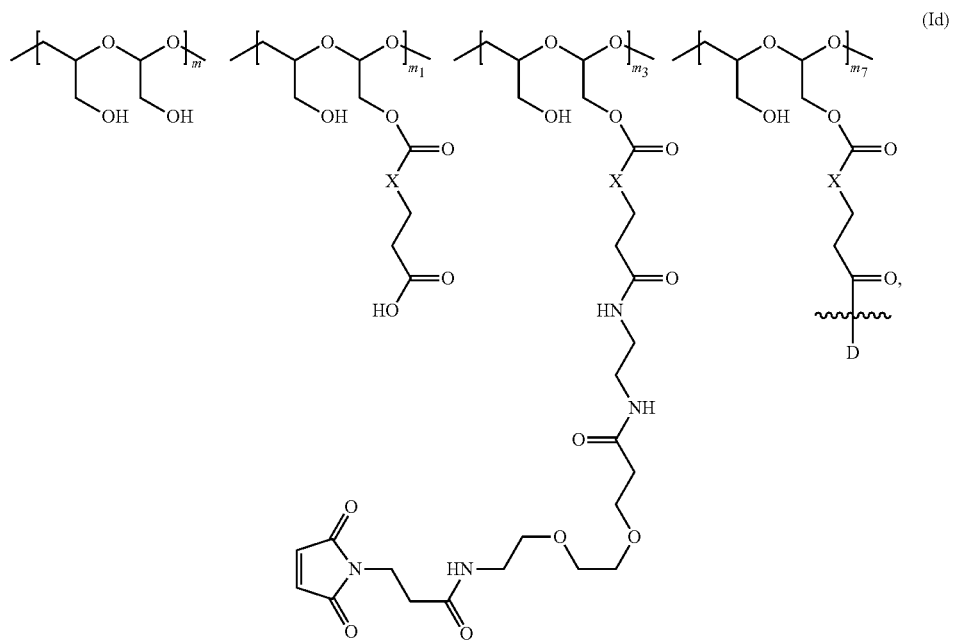

wherein:

the scaffold comprises poly(1-hydroxymethylethylene hydroxymethyl-formal) (PHF) having a molecular weight ranging from about 2 kDa to about 40 kDa;

each occurrence of D independently is a therapeutic agent having a molecular weight of ≤5 kDa, and the $-\xi-$ between D and the carbonyl group denotes direct or indirect attachment of D to the carbonyl group, X is $CH_2$, O, or NH;

m is an integer from 1 to about 300, $m_1$ is an integer from 1 to about 140, $m_7$ is an integer from 1 to about 40, $m_3$ is an integer from 1 to about 18, and the sum of m, $m_1$, $m_3$, and $m_7$ ranges from about 15 to about 300.

The scaffold of Formula (Id) can include one or more of the following features:

When the PHF in Formula (Id) has a molecular weight ranging from about 2 kDa to about 20 kDa, $m_7$ is an integer from 1 to about 20, $m_3$ is an integer from 1 to about 10, $m_1$ is an integer from 1 to about 70 and the sum of m, $m_1$, $m_3$ and $m_7$ ranges from about 15 to about 150.

When the PHF in Formula (Id) has a molecular weight ranging from about 3 kDa to about 15 kDa, $m_7$ is an integer from 2 to about 15, $m_3$ is an integer from 1 to about 8, $m_1$ is an integer from 2 to about 50 and the sum of m, $m_1$, $m_3$ and $m_7$ ranges from about 20 to about 110.

When the PHF in Formula (Id) has a molecular weight ranging from about 5 kDa to about 10 kDa, $m_7$ is an integer from about 3 to about 10, $m_3$ is an integer from 1 to about 5, $m_1$ is an integer from about 5 to about 35 and the sum of m, $m_1$, $m_3$ and $m_7$ ranges from about 40 to about 75.

Each occurrence of the maleimido moiety in the "$m_3$" unit of Formula (Id) is yet to form a covalent bond with a functional group of the PBRM.

In one embodiment, the sum of $m_1$ and $m_7$ is an integer from 2 to about 180.

The scaffold of Formula (Id) can further comprise a PBRM conjugated to the D-containing scaffold via one or more maleimido group of the D-containing scaffold forming a protein-polymer-drug conjugate. For example, the scaffold of Formula (Id) further comprises one PBRM conjugated to the D-containing scaffold via two or more maleimido groups (e.g., up to five) of the scaffold. For example, one PBRM is connected to one or more D-containing polymeric scaffold of Formula (Id).

In certain embodiments, the polymer drug conjugate (Id) when conjugated to a PBRM is of Formula (Ie):

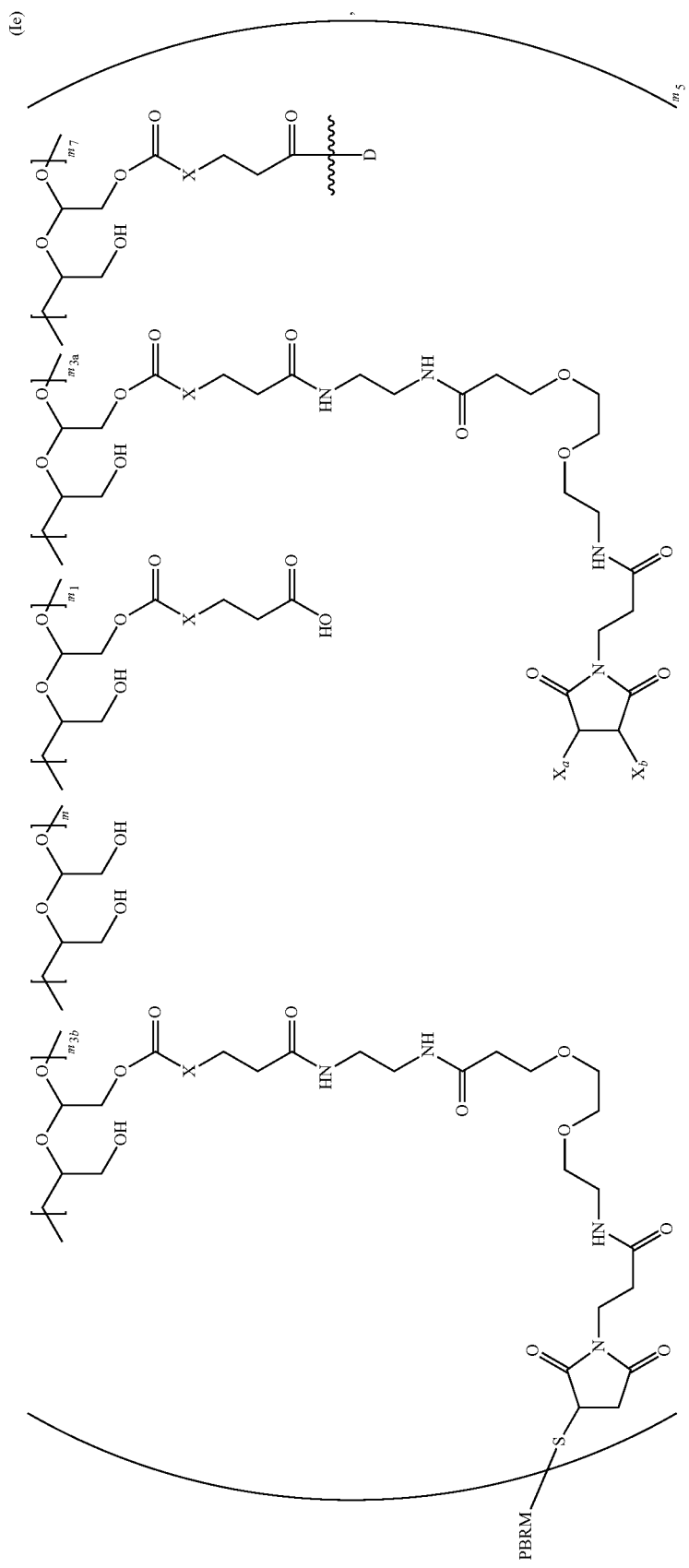

wherein:

one of $X_a$ and $X_b$ is H and the other is a maleimido blocking moiety, or $X_a$ and $X_b$, together with the carbon atoms to which they are attached form a carbon-carbon double bond;

$m_{3a}$ is an integer from 0 to about 17, $m_{3b}$ is an integer from 1 to about 8, wherein the sum of $m_{3a}$ and $m_{3b}$ is $m_3$, the sum of m, $m_1$, $m_7$, $m_{3a}$, and $m_{3b}$ ranges from about 15 to about 300, and $m_5$ is an integer from 1 to about 10.

In the protein-polymer-drug conjugate of Formula (Id), each D can be the same or different moiety and each PBRM can be the same or different moiety.

In certain embodiments the ratio between D and PBRM can be about 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In some embodiments, the ratio between D and PBRM can be about 20:1, 19:1, 18:1, 17:1, 16:1, 15:1, 14:1, 13:1, 12:1, 11:1 or 10:1.

In other embodiments, the ratio between D and PBRM can be about 18:1, 17:1, 16:1, 15:1, 14:1, 13:1 or 12:1.

In certain embodiments the ratio between PHF and PBRM can be about 10:1, 9:1, 8:1, 7:1, 6:1, 5:1, 4:1, 3:1, or 2:1.

In some embodiments, the ratio between PHF and PBRM can be about 6:1, 5:1, 4:1, 3:1, or 2:1.

In other embodiments, the ratio between PHF and PBRM can be about 4:1, 3:1, or 2:1.

In one embodiment, D is a) an auristatin compound; (b) a calicheamicin compound; (c) a duocarmycin compound; (d) a topoisomerase inhibitor, (e) a pyrrolobenzodiazepine compound; (f) a vinca compound; (g) a protein synthesis inhibitor; (h) a RNA polymerase inhibitor; (i) a tubulin binding compound; or an analog thereof.

In certain embodiment, D is a) an auristatin compound; (b) a calicheamicin compound; (c) a duocarmycin compound; (d) a camptothecin compound, (e) a pyrrolobenzodiazepine compound; (f) a vinca compound; or an analog thereof.

In one embodiment, the auristatin compound is auristatin, Dolastatin, monomethylauristatin E (MMAE), monomethylauristatin F (MMAF), auristatin F hydroxypropyl amide (AF HPA), or auristatin F phenylenediamine (AFP).

In one embodiment, the duocarmycin or analog thereof is duocarmycin A, duocarmycin B1, duocarmycin B2, duocarmycin C1, duocarmycin C2, duocarmycin D, duocarmycin SA, CC-1065, adozelesin, bizelesin, or carzelesin.

In one embodiment, the camptothecin compound is camptothecin, CPT-11 (irinotecan), SN-38, or topotecan.

In one embodiment, the pyrrolobenzodiazepine compound is a pyrrolobenzodiazepine monomer, a symmetrical pyrrolobenzodiazepine dimer or an unsymmetrical pyrrolobenzodiazepine dimer.

In one embodiment, D is AF HPA and the ratio between AF HPA and PBRM can be about 30:1, 29:1, 28:1, 27:1, 26:1, 25:1, 24:1, 23:1, 22:1, 21:1, 25:1, 20:1, 19:1, 18:1, 17:1, 16:1, 15:1, 14:1, 13:1, 12:1, 11:1, 10:1, 9:1, 8:1, 7:1 or 6:1.

In another embodiment, the ratio between AF HPA and PBRM can be about 20:1, 19:1, 18:1, 17:1, 16:1, 15:1, 14:1, 13:1, 12:1, 11:1 or 10:1.

In yet other embodiments, the ratio between AF HPA and PBRM can be about 18:1, 17:1, 16:1, 15:1, 14:1, 13:1 or 12:1.

In another aspect, the invention relates to a polymeric scaffold of Formula (Ia) useful to conjugate with a protein based recognition-molecule (PBRM):

(Ia)
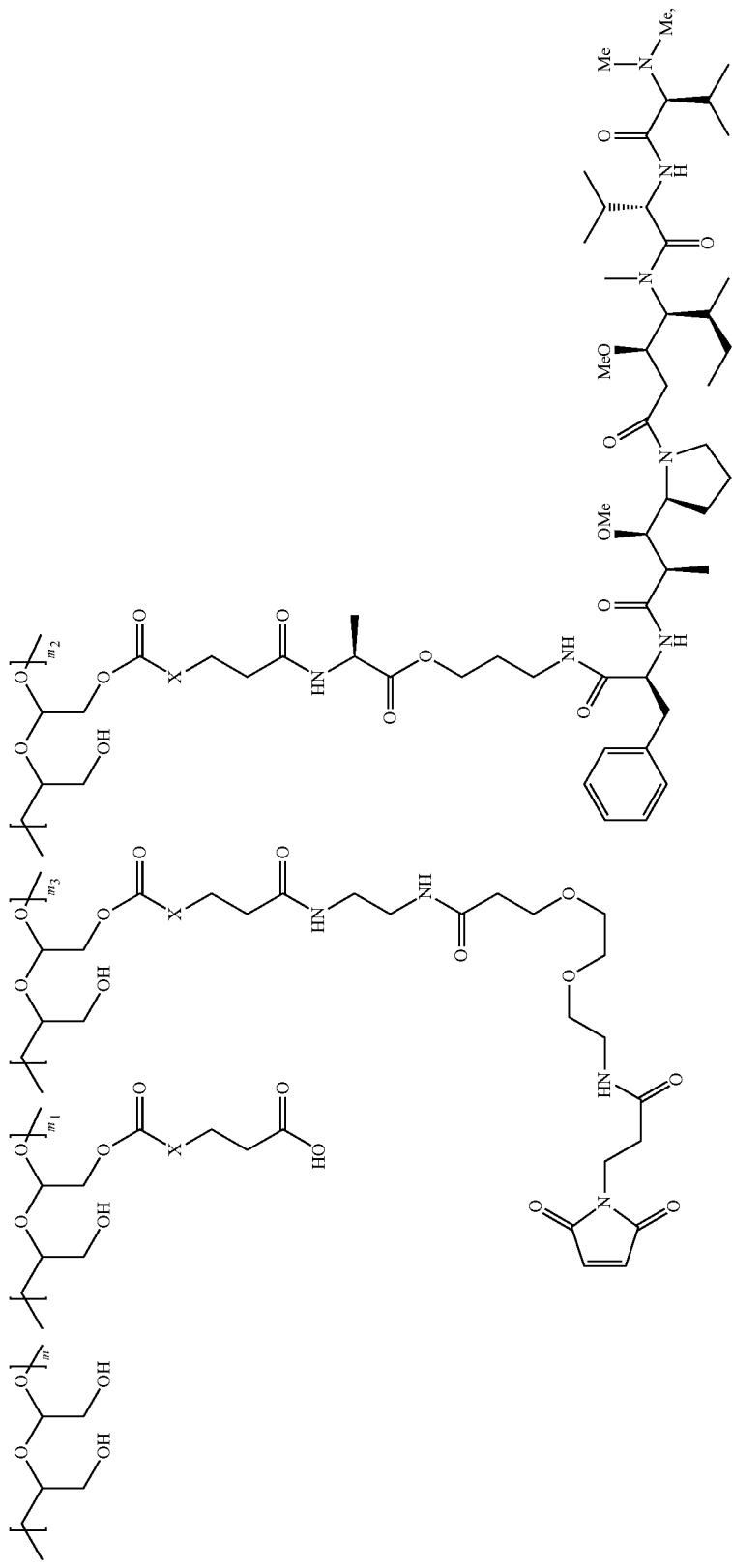

wherein:

the scaffold comprises poly(1-hydroxymethylethylene hydroxymethyl-formal) (PHF) having a molecular weight ranging from about 2 kDa to about 40 kDa;

X is $CH_2$, O, or NH;

m is an integer from 1 to about 300, $m_1$ is an integer from 1 to about 140, $m_2$ is an integer from 1 to about 40, $m_3$ is an integer from 1 to about 18, and the sum of m, $m_1$, $m_2$ and $m_3$ ranges from about 15 to about 300.

The scaffold of Formula (Ia) can include one or more of the following features:

When the PHF in Formula (Ia) has a molecular weight ranging from about 2 kDa to about 20 kDa, $m_2$ is an integer from 1 to about 20, $m_3$ is an integer from 1 to about 10, $m_1$ is an integer from 1 to about 70 and the sum of m, $m_1$, $m_2$ and $m_3$ ranges from about 15 to about 150.

When the PHF in Formula (Ia) has a molecular weight ranging from about 3 kDa to about 15 kDa, $m_2$ is an integer from 2 to about 15, $m_3$ is an integer from 1 to about 8, $m_1$ is an integer from 2 to about 50 and the sum of m, $m_1$, $m_2$ and $m_3$ ranges from about 20 to about 110.

When the PHF in Formula (Ia) has a molecular weight ranging from about 5 kDa to about 10 kDa, $m_2$ is an integer from about 3 to about 10, $m_3$ is an integer from 1 to about 5, $m_1$ is an integer from about 5 to about 35 and the sum of m, $m_1$, $m_2$ and $m_3$ ranges from about 40 to about 75.

Each occurrence of the maleimido moiety in the "$m_3$" unit of Formula (Ia) is yet to form a covalent bond with a functional group of the PBRM.

In one embodiment, the scaffold of Formula (Ia) is of Formula (A) or (A1):

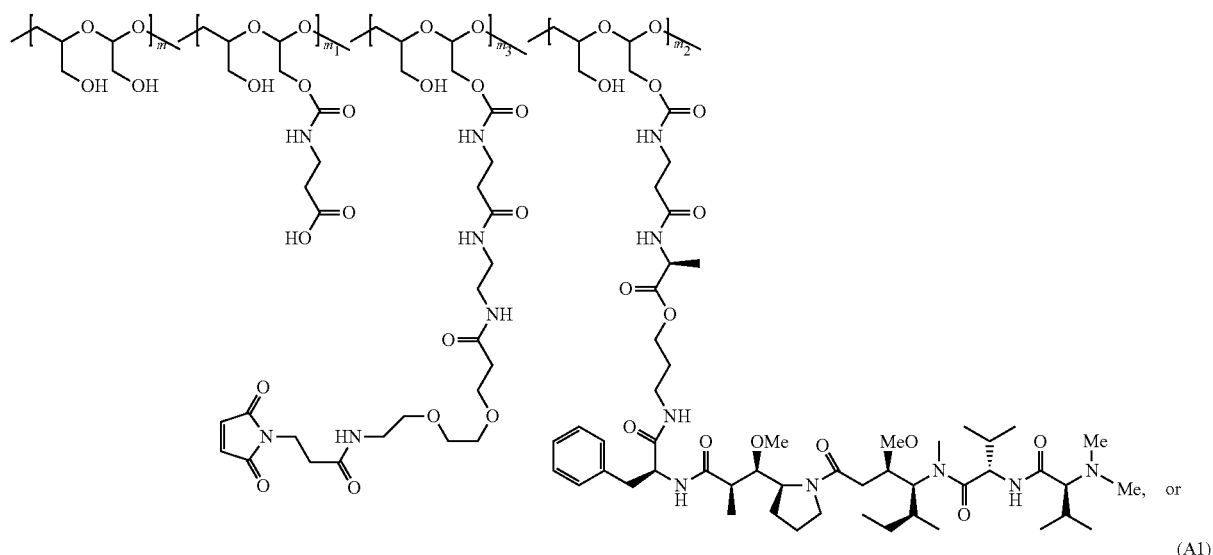

(A)

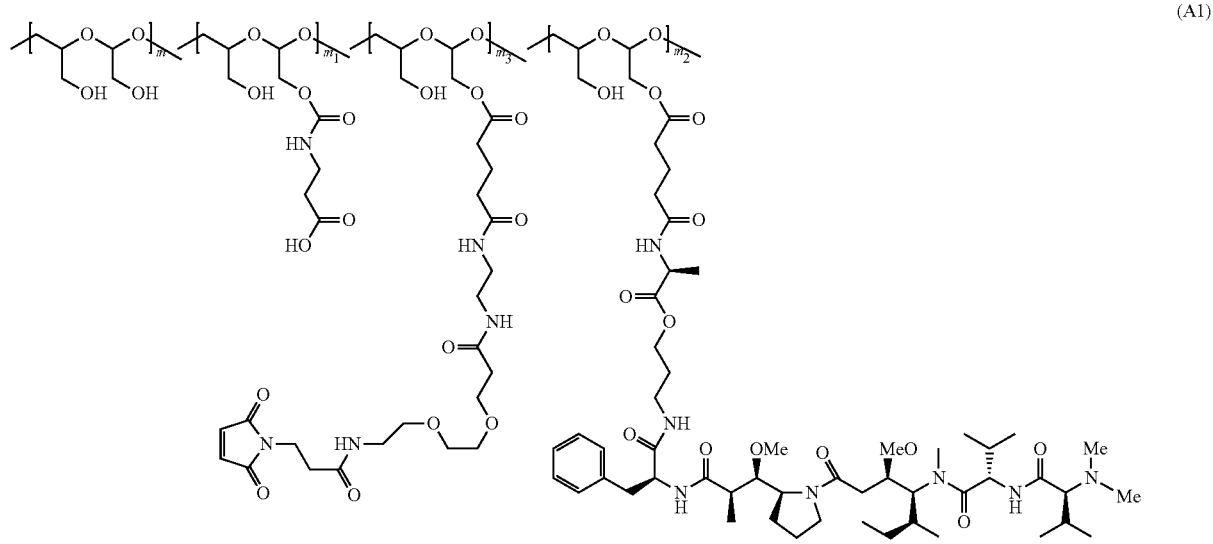

(A1)

wherein:

the PHF has a molecular weight ranging from about 5 kDa to about 10 kDa;

m is an integer from 1 to about 75, $m_1$ is an integer from about 5 to about 35, $m_2$ is an integer from about 3 to about 10, $m_3$ is an integer from 1 to about 5, and the sum of m, $m_1$, $m_2$ and $m_3$ ranges from 40 to about 75.

For example, each occurrence of the maleimido moiety in the "$m_3$" unit of Formula (A) or (A1) is yet to form a covalent bond with a functional group of the PBRM.

The scaffold of Formula (Ia) further comprises a PBRM conjugated to the scaffold via one or more maleimido groups of the polymer scaffold. For example, the scaffold of Formula (Ia) further comprises one PBRM conjugated to the scaffold via two or more maleimido groups (e.g., up to five) of the scaffold.

The PBRM has a molecular weight of about 40 kDa or greater (e.g., 60 kDa or greater; 80 kDa or greater; 100 kDa or greater; 120 kDa or greater; 140 kDa or greater; 160 kDa or greater; 180 kDa or greater; or 200 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, or 100-140 kDa).

The PBRM has a molecular weight of about 40 kDa or greater (e.g., 60 kDa or greater; 80 kDa or greater; 100 kDa or greater; 120 kDa or greater; 140 kDa or greater; 160 kDa or greater; 180 kDa or greater; or 200 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, or 100-140 kDa) and has a sulfhydryl (i.e., —SH or thiol) group.

The PBRM is conjugated to the drug-carrying polymeric conjugate via the sulfhydryl group of the PBRM connected to the maleimido group of the drug-carrying polymeric conjugate, see, e.g., the sulfur atom (—S—) in the "$m_{3b}$" unit inside the parentheses of any of Formulae disclosed herein, for example, Formula (Ib), (B), (B1) or (Ie). In embodiments, the sulfur atom is part of the PBRM and is derived from a sulfhydryl (thiol) group in the PBRM that was reacted with the maleimido group to form an attachment (sulfide bond) to the drug-carrying polymeric conjugate.

One PBRM is connected to one or more drug-carrying polymeric scaffold of Formula (Ia).

The scaffold comprising the PBRM is of Formula (Ib):

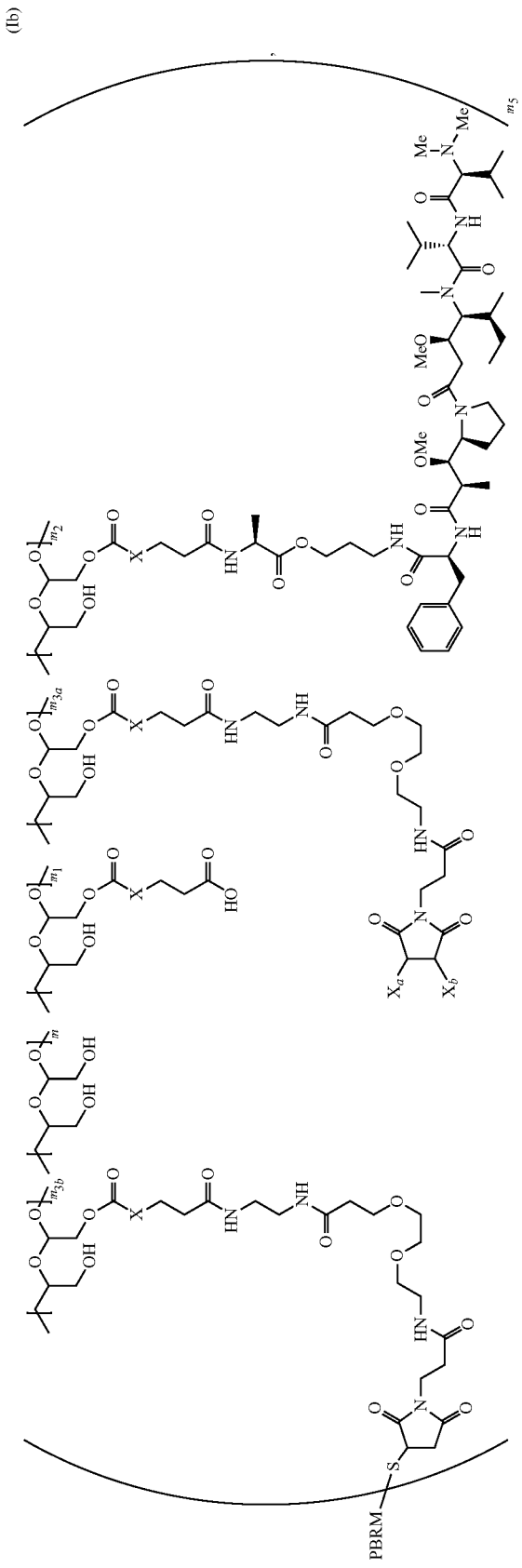

wherein:

one of $X_a$ and $X_b$ is H and the other is a maleimido blocking moiety, or $X_a$ and $X_b$, together with the carbon atoms to which they are attached form a carbon-carbon double bond;

$m_{3a}$ is an integer from 0 to about 17, $m_{3b}$ is an integer from 1 to about 8, wherein the sum of $m_{3a}$ and $m_{3b}$ is $m_3$ (e.g., an integer from 1 to about 18), the sum of m, $m_1$, $m_2$, $m_{3a}$, and $m_{3b}$ ranges from about 15 to about 300, and $m_5$ is an integer from 1 to about 10.

The scaffold of Formula (Ib) can include one or more of the following features:

The PBRM has a molecular weight of about 40 kDa or greater (e.g., 60 kDa or greater; 80 kDa or greater; 100 kDa or greater; 120 kDa or greater; 140 kDa or greater; 160 kDa or greater; 180 kDa or greater; or 200 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, or 100-140 kDa).

The PBRM has a sulfhydryl (i.e., —SH or thiol) group.

The total number of the covalent bonds (e.g., sulfide bond) formed between the PHF and the PBRM (or total number of attachment points) is 10 or less.

When the PHF in Formula (Ib) has a molecular weight ranging from about 2 kDa to about 20 kDa, the sum of m, $m_1$, $m_2$, $m_{3a}$ and $m_{3b}$ ranges from about 15 to about 150, $m_1$ is an integer from 1 to about 70, $m_2$ is an integer from 1 to about 20, $m_{3a}$ is an integer from 0 to about 9, $m_{3b}$ is an integer from 1 to about 8 and $m_5$ is an integer from 2 to about 8.

When the PHF in Formula (Ib) has a molecular weight ranging from about 3 kDa to about 15 kDa, the sum of m, $m_1$, $m_2$, $m_{3a}$ and $m_{3b}$ ranges from about 20 to about 110, $m_1$ is an integer from 2 to about 50, $m_2$ is an integer from 2 to about 15, $m_{3a}$ is an integer from 0 to about 7, $m_{3b}$ is an integer from 1 to about 8 and $m_5$ is an integer from 2 to about 4.

When the PHF in Formula (Ib) has a molecular weight ranging from about 5 kDa to about 10 kDa, the sum of m, $m_1$, $m_2$, $m_{3a}$ and $m_{3b}$ ranges from about 40 to about 75, $m_1$ is an integer from about 5 to about 35, $m_2$ is an integer from about 3 to about 10, $m_{3a}$ is an integer from 0 to about 4, $m_{3b}$ is an integer from 1 to about 5 and $m_5$ is an integer from 2 to about 4.

In certain embodiments, the ratio between auristatin F hydroxylpropyl amide ("AF HPA") and PBRM can be about 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In some embodiments, the ratio between AF HPA and PBRM can be about 20:1, 19:1, 18:1, 17:1, 16:1, 15:1, 14:1, 13:1, 12:1, 11:1 or 10:1.

In other embodiments, the ratio between AF HPA and PBRM can be about 18:1, 17:1, 16:1, 15:1, 14:1, 13:1 or 12:1.

In certain embodiments, the ratio between PHF and PBRM can be about 10:1, 9:1, 8:1, 7:1, 6:1, 5:1, 4:1, 3:1, or 2:1.

In some embodiments, the ratio between PHF and PBRM can be about 6:1, 5:1, 4:1, 3:1, or 2:1.

In other embodiments, the ratio between PHF and PBRM can be about 4:1, 3:1, or 2:1.

The maleimido blocking moieties (e.g., $X_a$ or $X_b$) are moieties that can be covalently attached to one of the two olefin carbon atoms upon reaction of the maleimido group with a thiol-containing compound of Formula (II):

$$R_{90}-(CH_2)_d-SH \quad (II)$$

wherein:

$R_{90}$ is $NHR_{91}$, OH, $COOR_{93}$, $CH(NHR_{91})COOR_{93}$ or a substituted phenyl group;

$R_{93}$ is hydrogen or $C_{1-4}$ alkyl;

$R_{91}$ is hydrogen, $CH_3$ or $CH_3CO$ and d is an integer from 1 to 3.

In one embodiment, the maleimido blocking compound of Formula (II) can be cysteine, N-acetyl cysteine, cysteine methyl ester, N-methyl cysteine, 2-mercaptoethanol, 3-mercaptopropanoic acid, 2-mercaptoacetic acid, mercaptomethanol (i.e., $HOCH_2SH$), benzyl thiol in which phenyl is substituted with one or more hydrophilic substituents, or 3-aminopropane-1-thiol. The one or more hydrophilic substituents on phenyl comprise OH, SH, methoxy, ethoxy, COOH, CHO, $COC_{1-4}$ alkyl, $NH_2$, F, cyano, $SO_3H$, $PO_3H$, and the like.

In another aspect, the maleimido blocking group is —S—$(CH_2)_d$—$R_{90}$, in which, $R_{90}$ is OH, COOH, or $CH(NHR_{91})COOR_{93}$;

$R_{93}$ is hydrogen or $CH_3$;

$R_{91}$ is hydrogen or $CH_3CO$; and d is 1 or 2.

In another embodiment, the maleimido blocking group is —S—$CH_2$—$CH(NH_2)COOH$.

In some embodiments, the maleimido blocking group is water soluble.

The scaffold of Formula (Ib) is of Formula (B) or (B1):

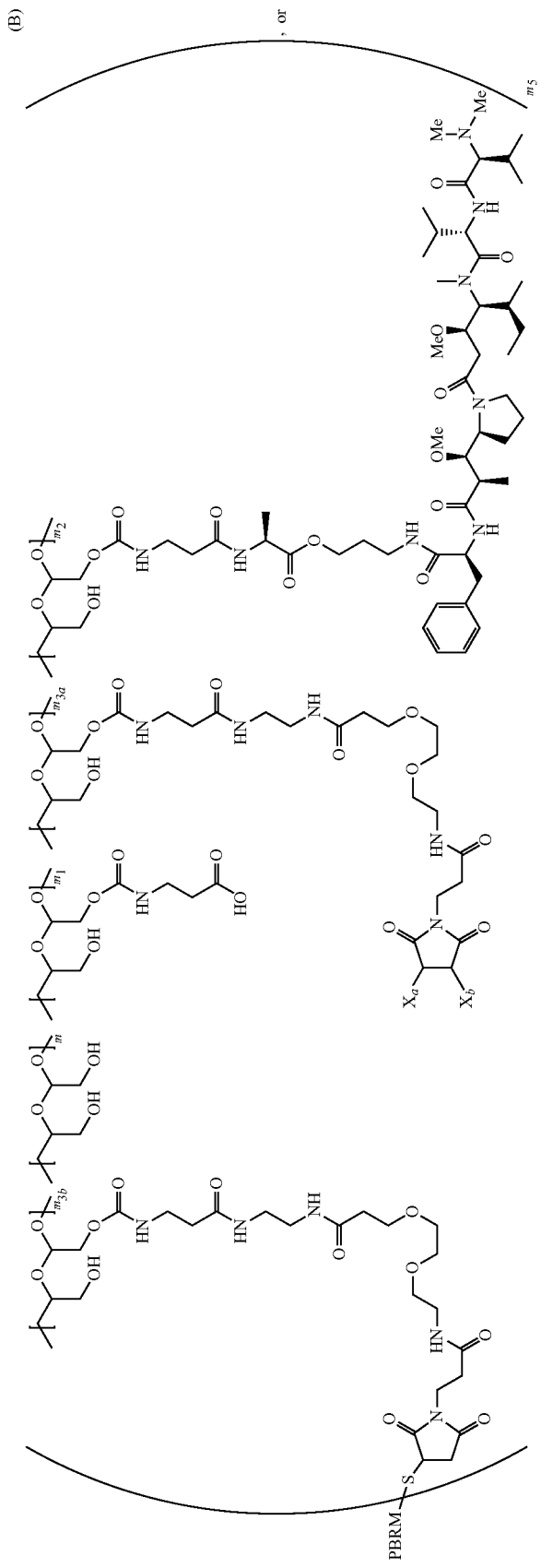

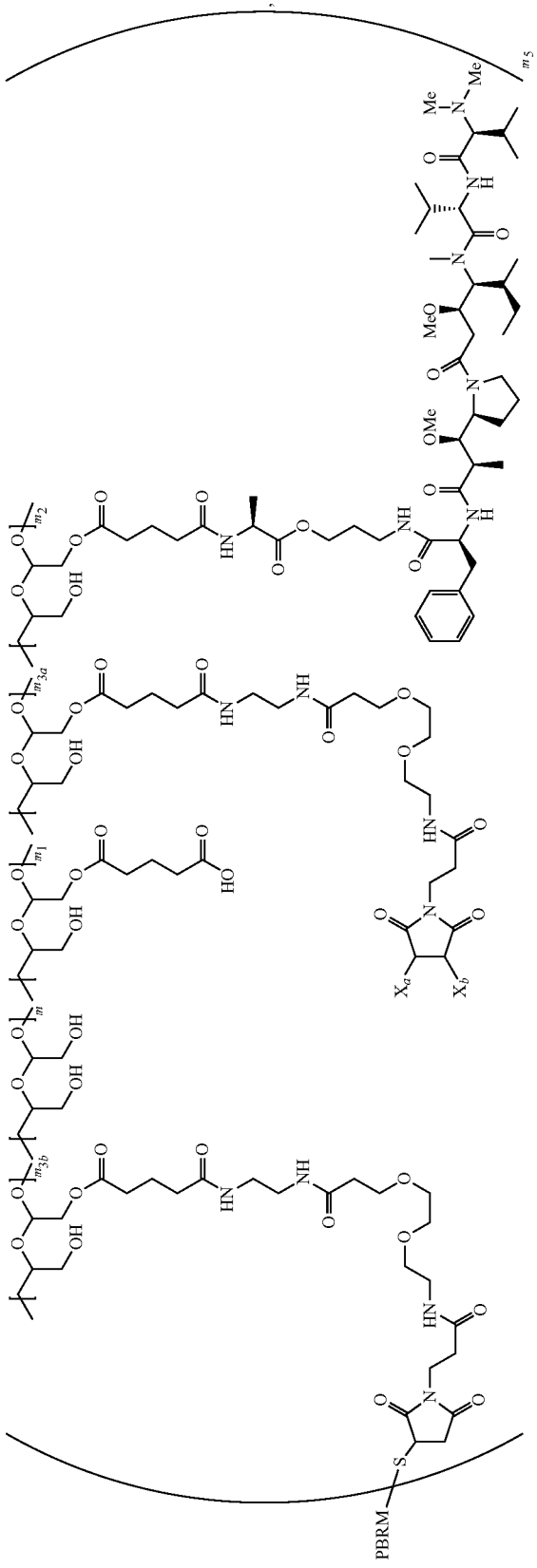

wherein:

the PHF has a molecular weight ranging from 5 kDa to 10 kDa;

m is an integer from 1 to 75, $m_1$ is an integer from about 5 to about 35, $m_2$ is an integer from about 3 to about 10, $m_{3a}$ is an integer from 0 to about 4, $m_{3b}$ is an integer from 1 to about 5, the sum of m, $m_1$, $m_2$, $m_{3a}$, and $m_{3b}$ ranges from about 40 to about 75, and $m_5$ is an integer from 2 to about 4.

In certain embodiments, in Formula (B) or (B1), the total number of attachment points is 10 or less.

The invention also provides for polymeric scaffolds of Formula (Ic):

the sum of m, $m_6$, and $m_3$ ranges from about 15 to about 300.

The scaffold of Formula (Ic) can include one or more of the following features:

When the PHF in Formula (Ic) has a molecular weight ranging from about 2 kDa to about 20 kDa, the sum of m, $m_6$ and $m_3$ ranges from about 15 to about 150, $m_6$ is an integer from 2 to about 90, and $m_3$ is an integer from 1 to about 10.

When the PHF in Formula (Ic) has a molecular weight ranging from about 3 kDa to about 15 kDa, the sum of m, $m_6$, and $m_3$ ranges from about 20 to about 110, $m_6$ is an integer from about 4 to about 65, and $m_3$ is an integer from 1 to about 8.

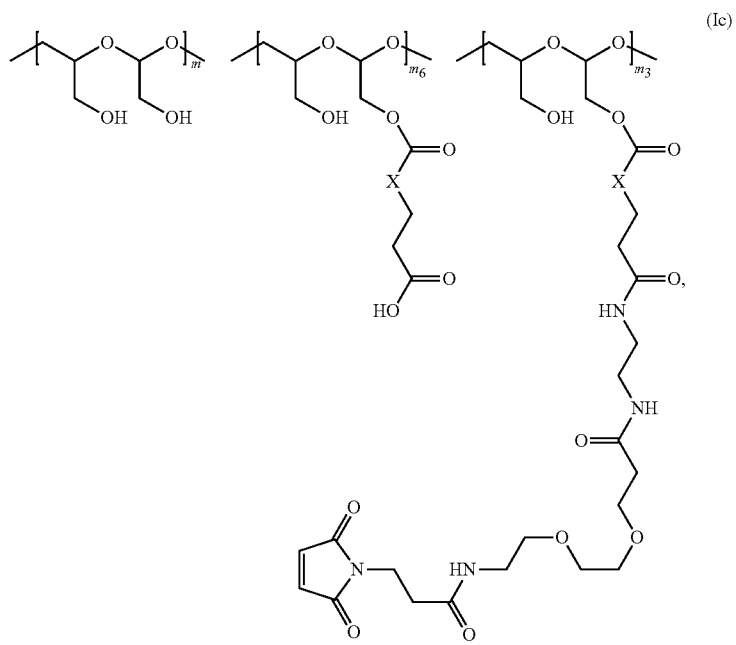

(Ic)

wherein:

the scaffold comprises PHF having a molecular weight ranging from about 2 kDa to about 40 kDa;

X is $CH_2$, O, or NH;

m is an integer from 1 to about 300, $m_6$ is an integer from 2 to about 180, $m_3$ is an integer from 1 to about 18, and When the PHF in Formula (Ic) has a molecular weight ranging from about 5 kDa to about 10 kDa, the sum of m, $m_6$ and $m_3$ ranges from about 40 to about 75, $m_6$ is an integer from about 8 to about 45, and $m_3$ is an integer from 1 to about 5.

Each occurrence of the maleimido moiety in the "$m_3$" unit of Formula (Ic) is yet to form a covalent bond with a functional group of the PBRM.

The scaffold of Formula (Ic) is of Formula (C) or (C1):

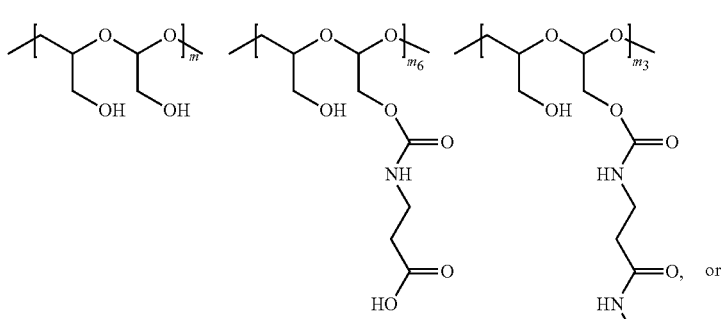

(C)

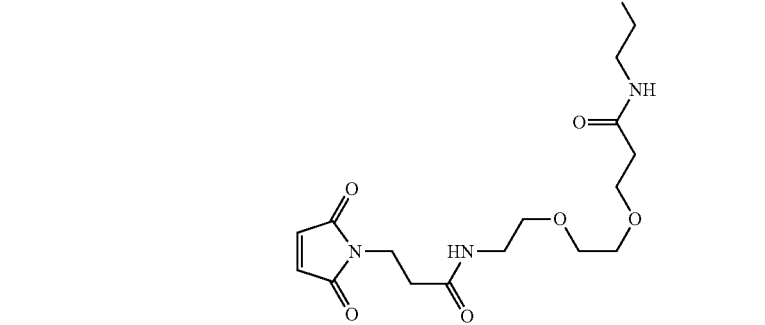

(C1)

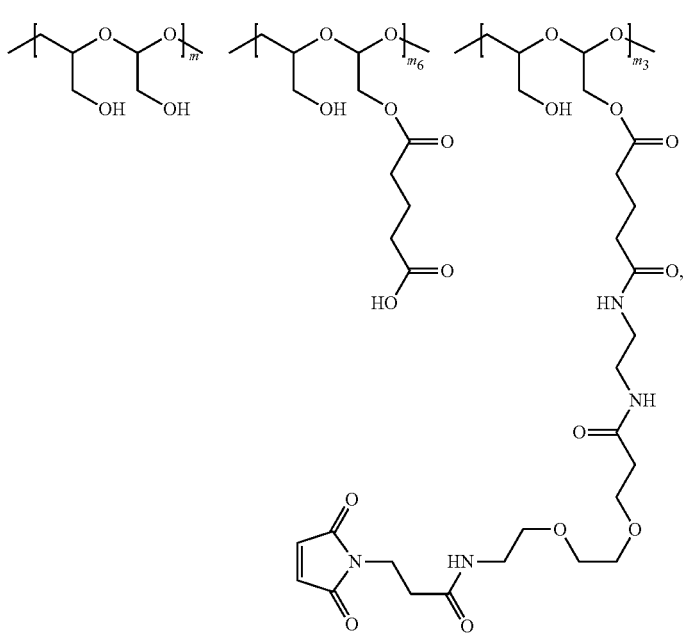

wherein:

the PHF has a molecular weight ranging from about 5 kDa to about 10 kDa;

m is an integer from 1 to about 75, $m_6$ is an integer from about 8 to about 45, $m_3$ is an integer from 1 to about 5, and the sum of m, $m_6$, and $m_3$ ranges from about 40 to about 75.

Each occurrence of the maleimido moiety in the "$m_3$" unit of Formula (C) or (C1) is yet to form a covalent bond with a functional group of the PBRM.

The scaffold of Formula (Ic) can further comprise one or more drug molecules ("D") connected to the PHF.

In one embodiment, the D-containing scaffold of Formula (Ic) is of Formula (Id).

In Formulae disclosed herein, such as Formula (Ia), (Ib,) (Ic), (Id), (Ie), (A), (A1), (B), (B1), (C), (C1) or (E), the disconnection or gap between the polyacetal units indicates that the units can be connected to each other in any order. Further, in certain Formulae (e.g., those in Table D) disclosed herein, the bracketed structures, i.e., polyacetal monomer units, are not accompanied with the number of repeating units (e.g., $m_1$, $m_2$, $m_3$, etc.) for the purpose of simplifying illustration and should not be construed as having only one repeating unit each.

Examples of PBRM include but are not limited to, full length antibodies such as IgG and IgM, antibody fragments such as Fabs, scFv, scFvFc, camelids, Fab2, and the like, small proteins, and peptides.

In one embodiment, the PBRM is a full length antibody or humanized anti-5T4 scFvFc antibody. For example, the PBRM is a ligand (LG) comprises an immunoglobulin or functional fragment thereof which targets human oncofetal protein 5T4.

In a further embodiment, a therapeutic drug and targeting conjugate useful in anti-neoplastic therapies is provided. The therapeutic drug and targeting conjugate comprises (a) a ligand (LG) which comprises an immunoglobulin or functional fragment thereof which targets human oncofetal protein 5T4, the ligand (e.g., which in some embodiments has a molecular weight of about 40 kDa or greater) having bound thereto $m_5$ of polymeric scaffolds of (b), wherein $m_5$ is one to about ten; and (b) a polymeric scaffold comprising poly(1-hydroxymethylethylene hydroxymethyl-formal) (PHF) which has a molecular weight ranging from about 2 kDa to about 40 kDa, wherein the polymeric scaffold comprises randomly arranged monomeric units m, $m_1$, $m_2$, $m_{3a}$, and $m_{3b}$, defined as follows:

(i) $m_{3a}$:

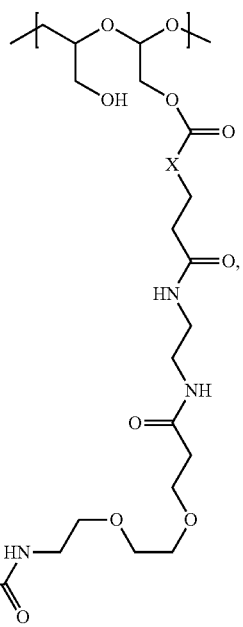

wherein $m_{3a}$ is absent or 1 to about 17 monomeric $m_{3a}$ units are present in the polymer scaffold, and in each unit, $X_a$ and $X_b$ are independently selected from (A) one is H and the other is a maleimido blocking moiety, or (B) $X_a$ and $X_b$, together with the carbon atoms to which they are attached form a carbon-carbon double bond;

(ii) $m_{3b}$:

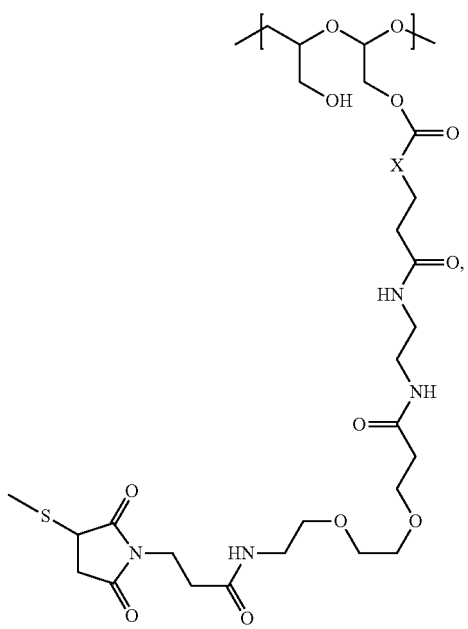

wherein the sulfide bond (—S—) forms the point of attachment to LG, and wherein 1 to about 8 monomer $m_{3b}$ units are present in the polymeric scaffold, wherein the sum of $m_{3a}$ and $m_{3b}$ is 1 to 18, and wherein the sulfur atom is part of the ligand (LG), (iii) m:

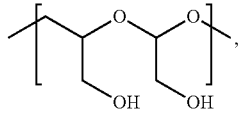

wherein 1 to about 300 monomer m units are present in the polymeric scaffold;

(iv) $m_1$:

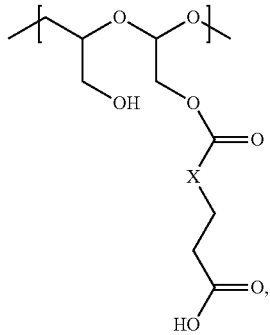

wherein 1 to about 140 monomeric m1 units are present in the polymer scaffold; and (v): $m_2$:

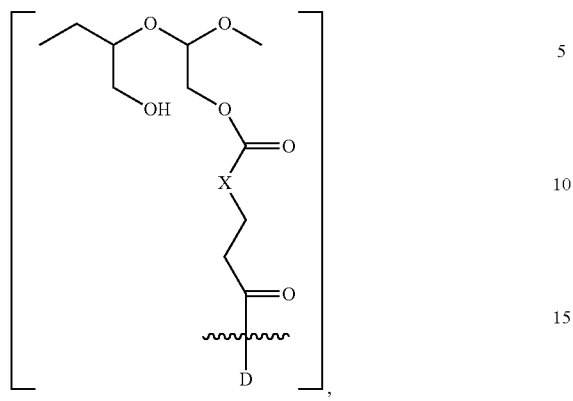

wherein 1 to about 40 monomeric $m_2$ units are present in the polymer scaffold; wherein in each of the monomeric units m, $m_1$, $m_2$, $m_{3a}$, and $m_{3b}$, X is $CH_2$, O or NH, and the sum of m, $m_1$, $m_2$, $m_{3a}$, and $m_{3b}$ ranges from about 15 to about 300, and wherein each occurrence of D independently is a therapeutic agent having a molecular weight of ≤5 kDa, and the ⸺ between D and the carbonyl group denotes direct or indirect attachment of D to the carbonyl group.

In one embodiment, the therapeutic drug and targeting conjugate has the following structure:

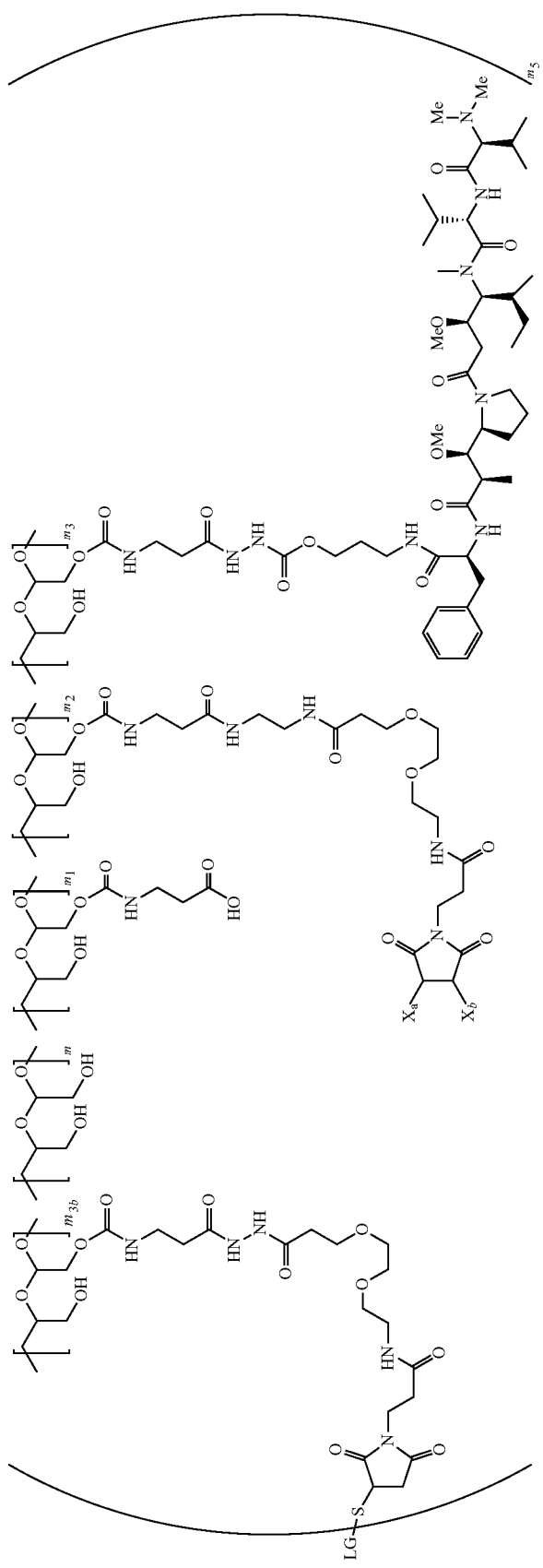

wherein:

the PHF has a molecular weight ranging from 5 kDa to 10 kDa; m is 1 to 75, $m_1$ is about 5 to about 35, $m_2$ is about 3 to about 10, $m_{3a}$ is 0 to about 4, $m_{3b}$ is 1 to about 5, the sum of m, $m_1$, $m_2$, $m_{3a}$, and $m_{3b}$ is about 40 to about 75, and $m_5$ is 2 to about 4.

In a further embodiment, a therapeutic anti-5T4 drug targeting conjugate useful in anti-neoplastic therapies is provided. The conjugate comprises a polymeric scaffold comprising a poly(1-hydroxymethylethylene hydroxymethyl-formal) (PHF) having a molecular weight from about 2 kDa to about 40 kDa, wherein the conjugate is of the following structure:

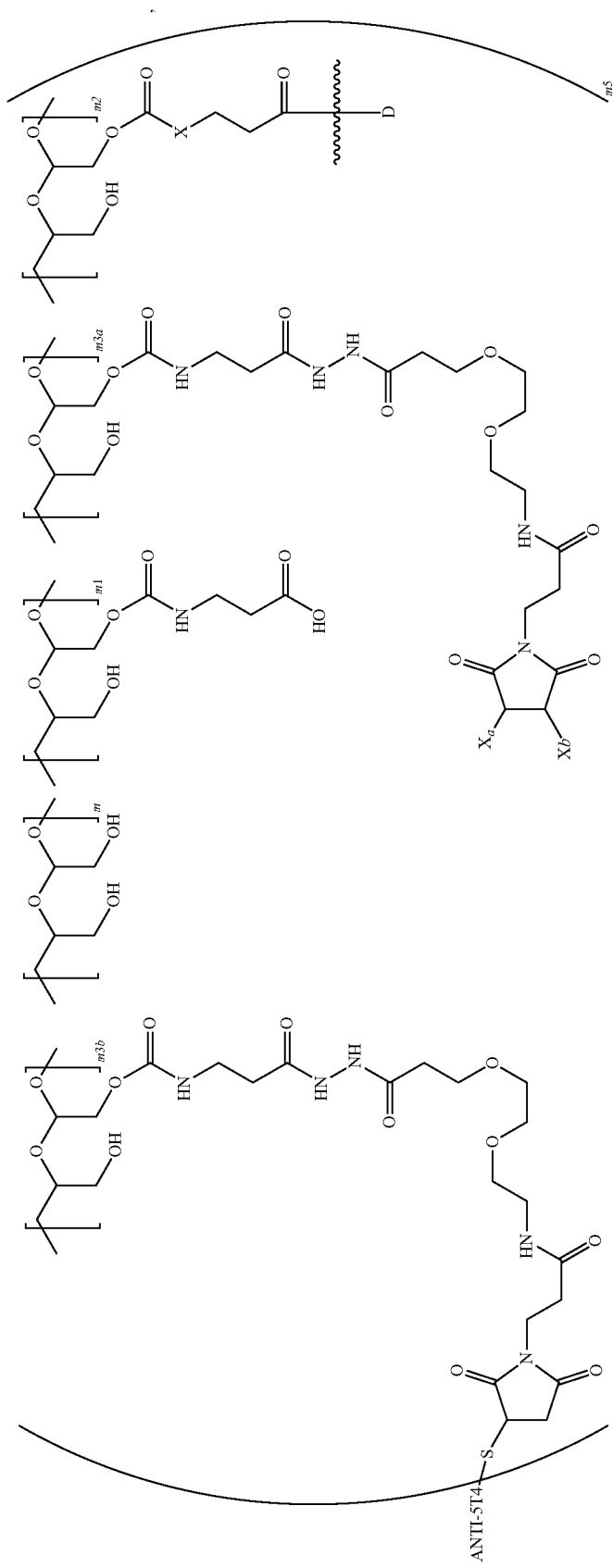

wherein $m_5$ is 1 to 10; m is an integer from 1 to about 300; $m_1$ is an integer from 1 to about 140; $m_2$ is an integer from 1 to about 40; $m_{3a}$ is an integer from 0 to about 17; $m_{3b}$ is an integer from 1 to about 8; wherein the sum of $m_{3a}$ and $m_{3b}$ is an integer from 1 to about 18; and the sum of m, $m_1$, $m_2$ and $m_3$ ranges from about 15 to about 300; X is NH; one of Xa or Xb is H and the other is a maleimido blocking moiety; and where each occurrence of D independently is a therapeutic agent having a molecular weight of ≤5 kDa, and the $-\xi-$ between D and the carbonyl group denotes direct or indirect attachment of D to the carbonyl group; wherein the ANTI-5T4 is an anti-5T4 ligand which comprises an immunoglobulin or a functional fragment thereof which is selective for human oncofetal antigen 5T4. For example, the molecular weight of the anti-5T4 is at least about 40 kDa.

In still a further embodiment, a therapeutic drug and targeting conjugate useful in anti-neoplastic therapies is provided which comprises anti-5T4 and a poly(1-hydroxymethylethylene hydroxymethyl-formal) (PHF) polymeric scaffold comprising the units shown below which may be randomly connected to each other:

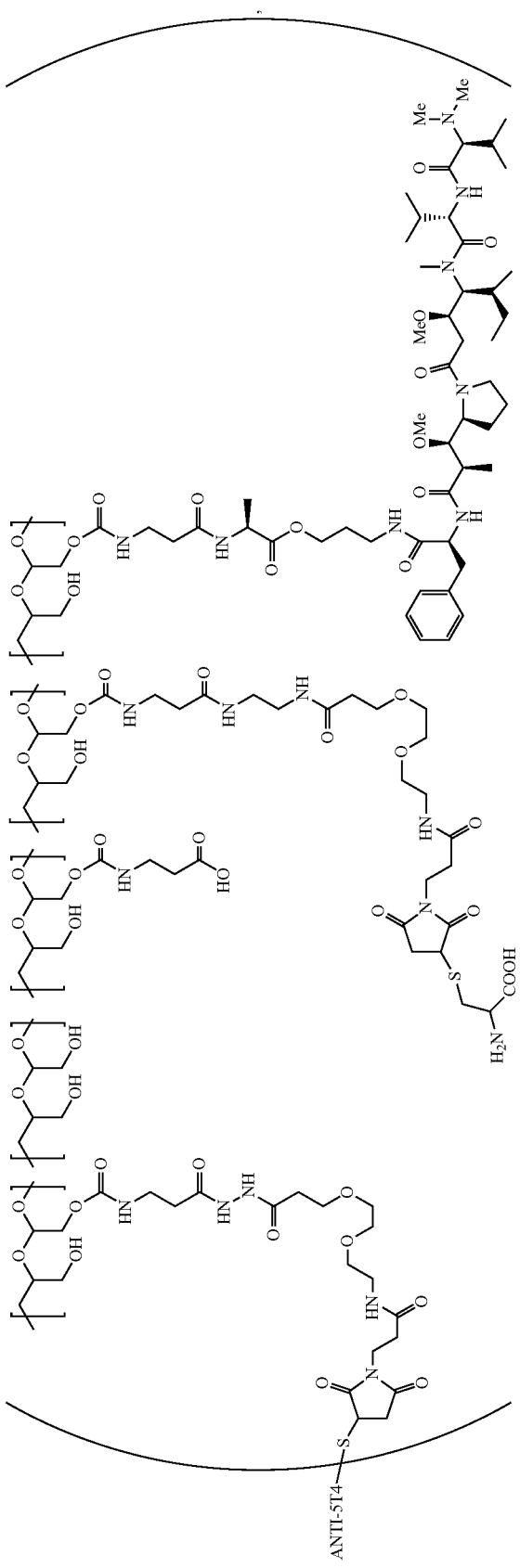

wherein:

ANTI-5T4 is a single chain antibody construct comprising the amino sequence designated as SEQ ID NO: 7; the PHF has a molecular weight ranging from about 2 kDa to about 40 kDa; the average polymeric scaffold to anti-5T4 antibody ratio is about 2:1 to about 3:1 or about 3:1 to about 4:1 and the AF HPA to anti-5T4 antibody ratio is about 12:1 to about 18:1.

In some embodiments, the polymeric scaffold of the invention contains randomly arranged monomeric units m, $m_1$, $m_2$, $m_{3a}$, and $m_{3b}$. In some embodiments, the polymeric scaffold of the invention contains randomly arranged monomeric units m, $m_1$, $m_2$, and $m_{3b}$.

In some embodiments, the polymeric scaffold of the invention contains randomly arranged monomeric units m, $m_1$, $m_7$, $m_{3a}$, and $m_{3b}$. In some embodiments, the polymeric scaffold of the invention contains randomly arranged monomeric units m, $m_1$, $m_7$, and $m_{3b}$.

In another aspect, the invention provides compositions comprising the conjugates, methods for their preparation, and methods of use thereof in the treatment of various disorders, including, but not limited to cancer. The target cancer can be anal, astrocytoma, leukemia, lymphoma, head and neck, liver, testicular, cervical, sarcoma, hemangioma, esophageal, eye, laryngeal, mouth, mesothelioma, skin, myeloma, oral, rectal, throat, bladder, breast, uterus, ovary, prostate, lung, colon, pancreas, renal, or gastric cancer.

The invention further relates to a pharmaceutical composition comprising a polymeric scaffold or conjugate described herein and a pharmaceutically acceptable carrier.

In yet another aspect, the invention relates to a method of diagnosing a disorder in a subject suspected of having the disorder. The method comprises administering an effective amount of the conjugate described herein to the subject suspected of having the disorder or performing an assay to detect a target antigen/receptor in a sample from the subject so as to determine whether the subject expresses target antigen or receptor.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

One of the advantages of the present invention is that the protein-polymer-drug conjugates or the polymeric scaffolds described herein greatly enhances the bioavailability of the drugs to be delivered and/or enhances the bioavailability of the protein attached to the polymeric carrier. Another advantage of the present invention is that the efficacy of the protein-polymer-drug conjugates described herein increases or at least remains substantially the same with increases in the drug load of the conjugates. Yet another advantage of the present invention is that the protein-polymer conjugates via thiol conjugation to the cysteine moiety of the protein exhibits substantially improved stability. Other features and advantages of the invention will be apparent from the following detailed description and claims.

DETAILED DESCRIPTION OF CERTAIN PREFERRED EMBODIMENTS OF THE INVENTION

Figure 1:
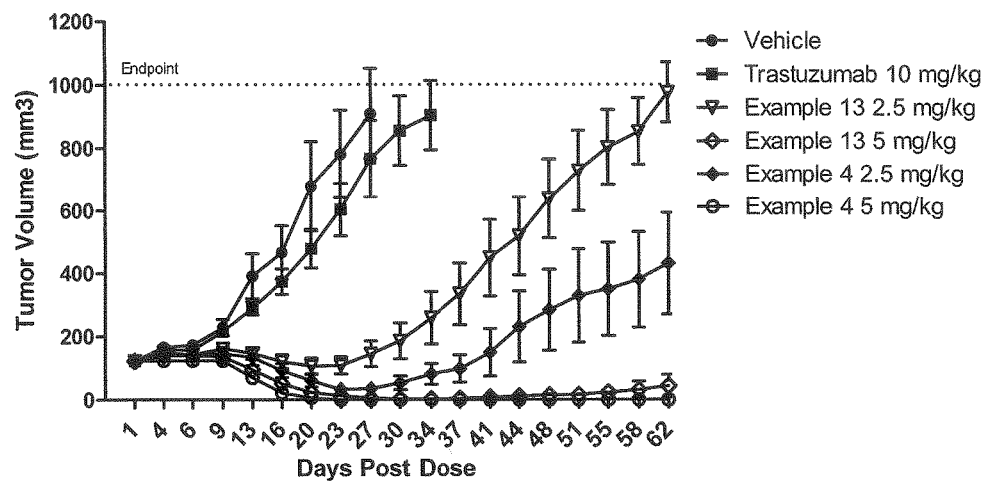
FIG. 1 shows the tumor response in mice inoculated subcutaneously with BT474 tumors (n=10 for each group) after IV administration as a single dose on day 1 of vehicle; PBRM (trastuzumab) at 10 mg/kg; PBRM-polymer-drug conjugates described in Example 4 or Example 13, at 2.5 mg/kg and 5 mg/kg.

The present invention provides novel protein-polymer-drug conjugates, polymeric scaffolds for making the conjugates, synthetic methods for making the conjugates or polymeric scaffolds, pharmaceutical compositions containing them and various uses of the conjugates.

The present invention also provides novel polymer-drug conjugates, synthetic methods for making the conjugates, pharmaceutical compositions containing them and various uses of the conjugates.

The present invention further provides novel drug derivatives, synthetic methods for making the derivatives, pharmaceutical compositions containing them and various uses of the drug derivatives.

Definitions/Terminology

Certain compounds of the present invention and definitions of specific functional groups are also described in more detail herein. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups.

The use of the articles "a", "an", and "the" in both the following description and claims are to be construed to cover both the singular and the plural, unless otherwise indicated herein or clearly contradicted by context. The terms "comprising", "having", "being of" as in "being of a chemical formula", "including", and "containing" are to be construed as open terms (i.e., meaning "including but not limited to") unless otherwise noted. For example, a polymeric scaffold of a certain formula includes all the monomer units shown in the formula and may also include additional monomer units not shown in the formula. Additionally, whenever "comprising" or another open-ended term is used in an embodiment, it is to be understood that the same embodiment can be more narrowly claimed using the intermediate term "consisting essentially of" or the closed term "consisting of:"

The term "about", "approximately", or "approximate", when used in connection with a numerical value, means that a collection or range of values is included. For example, "about X" includes a range of values that are ±20%, ±10%, ±5%, ±2%, ±1%, ±0.5%, ±0.2%, or ±0.1% of X, where X is a numerical value. In one embodiment, the term "about" refers to a range of values which are 5% more or less than the specified value. In another embodiment, the term "about" refers to a range of values which are 2% more or less than the specified value. In another embodiment, the term "about" refers to a range of values which are 1% more or less than the specified value.

Recitation of ranges of values are merely intended to serve as a shorthand method of referring individually to each separate value falling within the range, unless otherwise indicated herein, and each separate value is incorporated into the specification as if it were individually recited herein. A range used herein, unless otherwise specified, includes the two limits of the range. For example, the expressions "x being an integer between 1 and 6" and "x being an integer of 1 to 6" both mean "x being 1, 2, 3, 4, 5, or 6", i.e., the terms "between X and Y" and "range from X to Y, are inclusive of X and Y and the integers there between.

All methods described herein can be performed in any suitable order unless otherwise indicated herein or otherwise clearly contradicted by context. The use of any and all examples, or exemplary language (e.g., "such as") provided herein, is intended merely to better illustrate the invention and is not to be construed as a limitation on the scope of the claims unless explicitly otherwise claimed. No language in the specification is to be construed as indicating that any non-claimed element is essential to what is claimed.

"Antibody" refers to a full-length antibody or functional fragment of an antibody comprising an immunoglobulin. By a "functional fragment" it is meant a sufficient portion of the immunoglobulin or antibody is provided that the moiety effectively binds or complexes with the cell surface molecule for its target cell population, e.g., human oncofetal antigen.

As used herein, a human oncofetal antigen includes, e.g., tumor associated proteins such as alpha fetoprotein, carcinoembryonic antigen, prostate specific antigen, and oncofetal antigen protein (also known as immature laminin receptor protein, and which has been associated with, e.g., bowel and renal carcinomas).

An immunoglobulin may be purified, generated recombinantly, generated synthetically, or combinations thereof, using techniques known to those of skill in the art. While immunoglobulins within or derived from IgG antibodies are particularly well-suited for use in this invention, immunoglobulins from any of the classes or subclasses may be selected, e.g., IgG, IgA, IgM, IgD and IgE. Suitably, the immunoglobulin is_of the class IgG including but not limited to IgG subclasses (IgG1, 2, 3 and 4) or class IgM which is able to specifically bind to a specific epitope on an antigen. Antibodies can be intact immunoglobulins derived from natural sources or from recombinant sources and can be immunoreactive portions of intact immunoglobulins. Antibodies may exist in a variety of forms including, for example, polyclonal antibodies, monoclonal antibodies, camelized single domain antibodies, intracellular antibodies ("intrabodies"), recombinant antibodies, anti-idiotypic antibodies, domain antibodies, linear antibody, multispecific antibody, antibody fragments, such as, Fv, Fab, F(ab)$_2$, F(ab)$_3$, Fab', Fab'-SH, F(ab')$_2$, single chain variable fragment antibodies (scFv), tandem/bis-scFv, Fc, pFc', scFvFc (or scFv-Fc), disulfide Fv (dsfv), bispecific antibodies (bc-scFv) such as BiTE antibodies; camelid antibodies, resurfaced antibodies, humanized antibodies, fully human antibodies, single-domain antibody (sdAb, also known as NANOBODY®), chimeric antibodies, chimeric antibodies comprising at least one human constant region, dual-affinity antibodies such as, dual-affinity retargeting proteins (DART™), divalent (or bivalent) single-chain variable fragments (di-scFvs, bi-scFvs) including but not limited to minibodies, diabodies, triabodies or tribodies, tetrabodies, and the like, and multivalent antibodies. "Antibody fragment" refers to at least a portion of the variable region of the immunoglobulin molecule that binds to its target, i.e., the antigen-binding region. As used herein, the term "antibody" refers to both the full-length antibody and antibody fragments unless otherwise specified.

"Protein based recognition-molecule" or "PBRM" refers to a molecule that recognizes and binds to a cell surface marker or receptor such as, a transmembrane protein, surface immobilized protein, or protoglycan. Examples of PBRMs include but are not limited to, antibodies (e.g., Trastuzumab, Cetuximab, Rituximab, Bevacizumab, Epratuzumab, Veltuzumab, Labetuzumab, B7-H4, B7-H3, CA125, CD33, CXCR2, EGFR, FGFR1, FGFR2, FGFR3, FGFR4, HER2, NaPi2b, c-Met, NOTCH1, NOTCH2, NOTCH3, NOTCH4, PD-L1, c-Kit, MUC1 and anti-5T4) or peptides (LHRH receptor targeting peptides, EC-1 peptide), lipocalins, such as, for example, anticalins, proteins such as, for example, interferons, lymphokines, growth factors, colony stimulating factors, and the like, peptides or peptide mimics, and the like. The protein based recognition molecule, in addition to targeting the modified polymer conjugate to a specific cell, tissue or location, may also have certain therapeutic effect such as antiproliferative (cytostatic and/or cytotoxic) activity against a target cell or pathway. The protein based recognition molecule comprises or may be engineered to comprise at least one chemically reactive group such as, —COOH, primary amine, secondary amine —NHR, —SH, or a chemically reactive amino acid moiety or side chains such as, for example, tyrosine, histidine, cysteine, or lysine. In one embodiment, a PBRM may be a ligand (LG) or targeting moiety which specifically binds or complexes with a cell surface molecule, such as a cell surface receptor or antigen, for a given target cell population. Following specific binding or complexing of the ligand with its receptor, the cell is permissive for uptake of the ligand or ligand-drug-conjugate, which is then internalized into the cell. As used herein, a ligand that "specifically binds or complexes with" or "targets" a cell surface molecule preferentially associates with a cell surface molecule via intermolecular forces. For example, the ligand can preferentially associate with the cell surface molecule with a Kd of less than about 50 nM, less than about 5 nM, or less than 500 pM. Techniques for measuring binding affinity of a ligand to a cell surface molecule are well-known; for example, one suitable technique, is termed surface plasmon resonance (SPR). In one embodiment, the ligand is used for targeting and has no detectable therapeutic effect as separate from the drug which it delivers. In another embodiment, the ligand functions both as a targeting moiety and as a therapeutic or immunomodulatory agent (e.g., to enhance the activity of the active drug or prodrug).

"Biocompatible" as used herein is intended to describe compounds that exert minimal destructive or host response effects while in contact with body fluids or living cells or tissues. Thus a biocompatible group, as used herein, refers to an aliphatic, cycloalkyl, heteroaliphatic, heterocycloalkyl, aryl, or heteroaryl moiety, which falls within the definition of the term biocompatible, as defined above and herein. The term "Biocompatibility" as used herein, is also taken to mean that the compounds exhibit minimal interactions with recognition proteins, e.g., naturally occurring antibodies, cell proteins, cells and other components of biological systems, unless such interactions are specifically desirable. Thus, substances and functional groups specifically intended to cause the above minimal interactions, e.g., drugs and prodrugs, are considered to be biocompatible. Preferably (with exception of compounds intended to be cytotoxic, such as, e.g., antineoplastic agents), compounds are "biocompatible" if their addition to normal cells in vitro, at concentrations similar to the intended systemic in vivo concentrations, results in less than or equal to 1% cell death during the time equivalent to the half-life of the compound in vivo (e.g., the period of time required for 50% of the compound administered in vivo to be eliminated/cleared), and their administration in vivo induces minimal and medically acceptable inflammation, foreign body reaction, immunotoxicity, chemical toxicity and/or other such adverse effects. In the above sentence, the term "normal cells" refers to cells that are not intended to be destroyed or otherwise significantly affected by the compound being tested.

"Biodegradable": As used herein, "biodegradable" polymers are polymers that are susceptible to biological processing in vivo. As used herein, "biodegradable" compounds or moieties are those that, when taken up by cells, can be broken down by the lysosomal or other chemical machinery or by hydrolysis into components that the cells can either reuse or dispose of without significant toxic effect on the cells. The term "biocleavable" as used herein has the same meaning of "biodegradable". The degradation fragments preferably induce little or no organ or cell overload or pathological processes caused by such overload or other adverse effects in vivo. Examples of biodegradation processes include enzymatic and non-enzymatic hydrolysis, oxidation and reduction. Suitable conditions for non-enzymatic hydrolysis of the biodegradable protein-polymer-drug conjugates (or their components, e.g., the biodegradable polymeric carrier and the linkers between the carrier and the antibody or the drug molecule) described herein, for example, include exposure of the biodegradable conjugates to water at a temperature and a pH of lysosomal intracellular compartment. Biodegradation of some protein-polymer-drug conjugates (or their components, e.g., the biodegradable polymeric carrier and the linkers between the carrier and the antibody or the drug molecule), can also be enhanced extracellularly, e.g., in low pH regions of the animal body, e.g., an inflamed area, in the close vicinity of activated macrophages or other cells releasing degradation facilitating factors. In certain preferred embodiments, the effective size of the polymer carrier at pH~7.5 does not detectably change over 1 to 7 days, and remains within 50% of the original polymer size for at least several weeks. At pH~5, on the other hand, the polymer carrier preferably detectably degrades over 1 to 5 days, and is completely transformed into low molecular weight fragments within a two-week to several-month time frame. Polymer integrity in such tests can be measured, for example, by size exclusion HPLC. Although faster degradation may be in some cases preferable, in general it may be more desirable that the polymer degrades in cells with the rate that does not exceed the rate of metabolization or excretion of polymer fragments by the cells. In preferred embodiments, the polymers and polymer biodegradation byproducts are biocompatible.

"Bioavailability": The term "bioavailability" refers to the systemic availability (i.e., blood/plasma levels) of a given amount of drug or compound administered to a subject. Bioavailability is an absolute term that indicates measurement of both the time (rate) and total amount (extent) of drug or compound that reaches the general circulation from an administered dosage form.

"Maleimido blocking compound": as used herein refers to a compound that can react with maleimide to convert it to succinimide and "maleimido blocking moiety" refers to the chemical moiety attached to the succinimide upon conversion. In certain embodiments, the maleimido blocking compound is a compound having a terminal thiol group for reacting with the maleimide. In certain embodiments, the maleimido blocking compound is water soluble such that the reaction with maleimide can take place in an aqueous solution. For example, the resulting maleimido blocking moiety is water soluble or hydrophilic. In one embodiment, the maleimido blocking compound is cysteine, N-acetyl cysteine, cysteine methyl ester, N-methyl cysteine, 2-mercaptoethanol, 3-mercaptopropanoic acid, 2-mercaptoacetic acid, mercaptomethanol (i.e., $HOCH_2SH$), benzyl thiol in which phenyl is substituted with one or more hydrophilic substituents, or 3-aminopropane-1-thiol.

"Hydrophilic": The term "hydrophilic" as it relates to substituents, e.g., on the polymer monomeric units or on a maleimido blocking moiety to render them hydrophilic or water soluble, does not essentially differ from the common meaning of this term in the art, and denotes chemical moieties which contain ionizable, polar, or polarizable atoms, or which otherwise may be solvated by water molecules. Thus a hydrophilic group, as used herein, refers to an aliphatic, cycloalkyl, heteroaliphatic, heterocycloalkyl, aryl or heteroaryl moiety, which falls within the definition of the term hydrophilic, as defined above. Examples of particular hydrophilic organic moieties which are suitable include, without limitation, aliphatic or heteroaliphatic groups comprising a chain of atoms in a range of between about one and twelve atoms, hydroxyl, hydroxyalkyl, amine, carboxyl, amide, carboxylic ester, thioester, aldehyde, nitryl, isonitryl, nitroso, hydroxylamine, mercaptoalkyl, heterocycle, carbamates, carboxylic acids and their salts, sulfonic acids and their salts, sulfonic acid esters, phosphoric acids and their salts, phosphate esters, polyglycol ethers, polyamines, polycarboxylates, polyesters and polythioesters. In certain embodiments, hydrophilic substituents comprise a carboxyl group (COOH), an aldehyde group (CHO), a ketone group ($COC_{1-4}$ alkyl), a methylol ($CH_2OH$) or a glycol (for example, $CHOH—CH_2OH$ or $CH—(CH_2OH)_2$), $NH_2$, F, cyano, $SO_3H$, $PO_3H$, and the like.

The term "hydrophilic" as it relates to the polymers of the invention generally does not differ from usage of this term in the art, and denotes polymers comprising hydrophilic functional groups as defined above. In a preferred embodiment, hydrophilic polymer is a water-soluble polymer. Hydrophilicity of the polymer can be directly measured through determination of hydration energy, or determined through investigation between two liquid phases, or by chromatography on solid phases with known hydrophobicity, such as, for example, C4 or C18.

"Polymeric Carrier": The term polymeric carrier, as used herein, refers to a polymer or a modified polymer, which is suitable for covalently attaching to or can be covalently attached to one or more drug molecules with a designated linker and/or one or more PBRMs with a designated linker.

"Physiological conditions": The phrase "physiological conditions", as used herein, relates to the range of chemical (e.g., pH, ionic strength) and biochemical (e.g., enzyme concentrations) conditions likely to be encountered in the extracellular fluids of living tissues. For most normal tissues, the physiological pH ranges from about 7.0 to 7.4. Circulating blood plasma and normal interstitial liquid represent typical examples of normal physiological conditions.

"Polysaccharide", "carbohydrate" or "oligosaccharide": The terms "polysaccharide", "carbohydrate", or "oligosaccharide" are known in the art and refer, generally, to substances having chemical formula $(CH_2O)_n$, where generally n>2, and their derivatives. Carbohydrates are polyhydroxyaldehydes or polyhydroxyketones, or change to such substances on simple chemical transformations, such as hydrolysis, oxidation or reduction. Typically, carbohydrates are present in the form of cyclic acetals or ketals (such as, glucose or fructose). These cyclic units (monosaccharides) may be connected to each other to form molecules with few (oligosaccharides) or several (polysaccharides) monosaccharide units. Often, carbohydrates with well defined number, types and positioning of monosaccharide units are called oligosaccharides, whereas carbohydrates consisting of mixtures of molecules of variable numbers and/or positioning of monosaccharide units are called polysaccharides. The terms "polysaccharide", "carbohydrate", and "oligosaccharide", are used herein interchangeably. A polysaccharide may include natural sugars (e.g., glucose, fructose, galactose, mannose, arabinose, ribose, and xylose) and/or derivatives of naturally occurring sugars (e.g., 2'-fluororibose, 2'-deoxyribose, and hexose).

"Drug": As used herein, the term "drug" refers to a compound which is biologically active and provides a desired physiological effect following administration to a subject in need thereof (e.g., an active pharmaceutical ingredient).

"Prodrug": As used herein the term "prodrug" refers to a precursor of an active drug, that is, a compound that can be transformed to an active drug. Typically such a prodrug is subject to processing in vivo, which converts the drug to a physiologically active form. In some instances, a prodrug may itself have a desired physiologic effect. A desired physiologic effect may be, e.g., therapeutic, cytotoxic, immunomodulatory, or the like.

"Cytotoxic": As used herein the term "cytotoxic" means toxic to cells or a selected cell population (e.g., cancer cells). The toxic effect may result in cell death and/or lysis. In certain instances, the toxic effect may be a sublethal destructive effect on the cell, e.g., slowing or arresting cell growth. In order to achieve a cytotoxic effect, the drug or prodrug may be selected from a group consisting of a DNA damaging agent, a microtubule disrupting agent, or a cytotoxic protein or polypeptide, amongst others.

"Cytostatic": As used herein the term "cytostatic" refers to a drug or other compound which inhibits or stops cell growth and/or multiplication.

"Small molecule": As used herein, the term "small molecule" refers to molecules, whether naturally-occurring or artificially created (e.g., via chemical synthesis) that have a relatively low molecular weight. Preferred small molecules are biologically active in that they produce a local or systemic effect in animals, preferably mammals, more preferably humans. In certain preferred embodiments, the small molecule is a drug and the small molecule is referred to as "drug molecule" or "drug" or "therapeutic agent". In certain embodiments, the drug molecule has MW less than or equal to about 5 kDa. In other embodiments, the drug molecule has MW less than or equal to about 1.5 kDa. In embodiments, the drug molecule is selected from vinca alkaloids, auristatins, duocarmycins, kinase inhibitors, MEK inhibitors, KSP inhibitors, PI3 kinase inhibitors, calicheamicins, SN38, camptothecin, topoisomerase inhibitors, non-natural camptothecins, protein synthesis inhibitor, RNA polymerase inhibitor, pyrrolobenzodiazepines, maytansinoids, DNA-binding drugs, DNA intercalation drugs and analogs thereof. Preferably, though not necessarily, the drug is one that has already been deemed safe and effective for use by an appropriate governmental agency or body, e.g., the FDA. For example, drugs for human use listed by the FDA under 21 C.F.R. §§ 330.5, 331 through 361, and 440 through 460; drugs for veterinary use listed by the FDA under 21 C.F.R. §§ 500 through 589, incorporated herein by reference, are all considered suitable for use with the present hydrophilic polymers. Classes of drug molecules that can be used in the practice of the present invention include, but are not limited to, anti-cancer substances, radionuclides, vitamins, anti-AIDS substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, imaging agents. Many large molecules are also drugs and such large molecules may be used in the conjugates and other constructs described herein. Examples of suitable large molecules include, e.g., amino acid based molecules. Amino acid based molecules may encompass, e.g., peptides, polypeptides, enzymes, antibodies, immunoglobulins, or functional fragments thereof, among others.

A more complete, although not exhaustive, listing of classes and specific drugs suitable for use in the present invention may be found in "Pharmaceutical Substances: Syntheses, Patents, Applications" by Axel Kleemann and Jurgen Engel, Thieme Medical Publishing, 1999 and the "Merck Index: An Encyclopedia of Chemicals, Drugs, and Biologicals", Edited by Susan Budavari et al., CRC Press, 1996, both of which are incorporated herein by reference. In preferred embodiments, the drug used in this invention is a therapeutic agent that has antiproliferative (cytostatic and/or cytotoxic) activity against a target cell or pathway. The drug may have a chemically reactive group such as, for example, —COOH, primary amine, secondary amine —NHR, —OH, —SH, —C(O)H, —C(O)R, —C(O)NHR$^{2b}$, C(S)OH, —S(O)$_2$OR$^{2b}$, —P(O)$_2$OR$^{2b}$, —CN, —NC or —ONO, in which R is an aliphatic, heteroaliphatic, carbocyclic or heterocycloalkyl moiety and R$^{2b}$ is a hydrogen, an aliphatic, heteroaliphatic, carbocyclic, or heterocyclic moiety.

"Drug derivative" or "modified drug" or the like as used herein, refers to a compound that comprises the drug molecule intended to be delivered by the conjugate of the invention and a functional group capable of attaching the drug molecule to the polymeric carrier.

"Active form" as used herein refers to a form of a compound that exhibits intended pharmaceutical efficacy in vivo or in vitro. In particular, when a drug molecule intended to be delivered by the conjugate of the invention is released from the conjugate, the active form can be the drug itself or its derivatives, which exhibit the intended therapeutic properties. The release of the drug from the conjugate can be achieved by cleavage of a biodegradable bond of the linker which attaches the drug to the polymeric carrier. The active drug derivatives accordingly can comprise a portion of the linker.

"Diagnostic label": As used herein, the term diagnostic label refers to an atom, group of atoms, moiety or functional group, a nanocrystal, or other discrete element of a composition of matter, that can be detected in vivo or ex vivo using analytical methods known in the art. When associated with a conjugate of the present invention, such diagnostic labels permit the monitoring of the conjugate in vivo. Alternatively or additionally, constructs and compositions that include diagnostic labels can be used to monitor biological functions or structures. Examples of diagnostic labels include, without limitation, labels that can be used in medical diagnostic procedures, such as, radioactive isotopes (radionuclides) for gamma scintigraphy and Positron Emission Tomography (PET), contrast agents for Magnetic Resonance Imaging (MRI) (for example paramagnetic atoms and superparamagnetic nanocrystals), contrast agents for computed tomography and other X-ray-based imaging methods, agents for ultrasound-based diagnostic methods (sonography), agents for neutron activation (e.g., boron, gadolinium), fluorophores for various optical procedures, and, in general moieties which can emit, reflect, absorb, scatter or otherwise affect electromagnetic fields or waves (e.g., gamma-rays, X-rays, radiowaves, microwaves, light), particles (e.g., alpha particles, electrons, positrons, neutrons, protons) or other forms of radiation, e.g., ultrasound.

The following are more general terms used throughout the present application:

"Animal": The term animal, as used herein, refers to humans as well as non-human animals, at any stage of development, including, for example, mammals, birds, reptiles, amphibians, fish, worms and single cells. Cell cultures and live tissue samples are considered to be pluralities of animals. Preferably, the non-human animal is a mammal (e.g., a rodent, a mouse, a rat, a rabbit, a monkey, a dog, a cat, a primate, or a pig). An animal may be a transgenic animal or a human clone. The term "subject" encompasses animals.

"Efficient amount": In general, as it refers to an active agent or drug delivery device, the term "efficient amount" refers to the amount necessary to elicit the desired biological response. As will be appreciated by those of ordinary skill in this art, the efficient amount of an agent or device may vary depending on such factors as the desired biological endpoint, the agent to be delivered, the composition of the encapsulating matrix, the target tissue, etc. For example, the efficient amount of microparticles containing an antigen to be delivered to immunize an individual is the amount that results in an immune response sufficient to prevent infection with an organism having the administered antigen.

"Natural amino acid" as used herein refers to any one of the common, naturally occurring L-amino acids found in naturally occurring proteins: glycine (Gly), alanine (Ala), valine (Val), leucine (Leu), isoleucine (Ile), lysine (Lys), arginine (Arg), histidine (His), proline (Pro), serine (Ser), threonine (Thr), phenylalanine (Phe), tyrosine (Tyr), tryptophan (Trp), aspartic acid (Asp), glutamic acid (Glu), asparagine (Asn), glutamine (Gln), cysteine (Cys) and methionine (Met).

"Unnatural amino acid" as used herein refers to any amino acid which is not a natural amino acid. This includes, for example, amino acids that comprise -, -, -, D-, L-amino acyl residues. More generally, the unnatural amino acid comprises a residue of the general formula

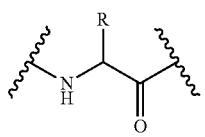

wherein the side chain R is other than the amino acid side chains occurring in nature. Exemplary unnatural amino acids, include, but are not limited to, sarcosine (N-methylglycine), citrulline (cit), homocitrulline, -ureidoalanine, thiocitrulline, hydroxyproline, allothreonine, pipecolic acid (homoproline), α-aminoisobutyric acid, tert-butylglycine, tert-butylalanine, allo-isoleucine, norleucine, α-methylleucine, cyclohexylglycine, -cyclohexylalanine, -cyclopentylalanine, α-methylproline, phenylglycine, α-methylphenylalanine and homophenylalanine.

"Amino acyl": More generally, the term amino acyl, as used herein, encompasses natural amino acid and unnatural amino acids.

"Polyamide": refers to homo- or hetero-polymers of natural amino acid and unnatural amino acids. Illustrative homopolymers include, but are not limited to, poly-lysine, poly-arginine, poly-glutaric acid, and the like. Illustrative heteropolymers include, but are not limited to, polymers comprising peptides fragments selected from peptidases, lysozymes, metalloproteinases, and the like.

"PHF" refers to poly(1-hydroxymethylethylene hydroxymethyl-formal).

As used herein, the terms "polymer unit", "monomeric unit", "monomer", "monomer unit", "unit" all refer to a repeatable structural unit in a polymer.

As used herein, "molecular weight" or "MW" of a polymer or polymeric carrier/scaffold or polymer conjugates refers to the weight average molecular weight unless otherwise specified.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The present invention is intended to include all isomers of the compound, which refers to and includes, optical isomers, and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in a mixture with one or more other isomers.

Polymeric Carriers

In certain exemplary embodiments, the conjugates of the invention find use in biomedical applications, such as drug delivery and tissue engineering, and the carrier is biocompatible and biodegradable. In certain embodiments, the carrier is a soluble polymer, nanoparticle, gel, liposome, micelle, suture, implant, etc. In certain embodiments, the term "soluble polymer" encompasses biodegradable biocompatible polymer such as a polyal (e.g., hydrophilic polyacetal or polyketal). In certain other embodiments, the carrier is a fully synthetic, semi-synthetic or naturally-occurring polymer. In certain other embodiments, the carrier is hydrophilic.

In certain exemplary embodiments, the carriers used in the present invention are biodegradable biocompatible polyals comprising at least one hydrolysable bond in each monomer unit positioned within the main chain. This ensures that the degradation process (via hydrolysis/cleavage of the monomer units) will result in fragmentation of the polymer conjugate to the monomeric components (i.e., degradation), and confers to the polymer conjugates of the invention their biodegradable properties. The properties (e.g., solubility, bioadhesivity and hydrophilicity) of biodegradable biocompatible polymer conjugates can be modified by subsequent substitution of additional hydrophilic or hydrophobic groups. Examples of biodegradable biocompatible polymers suitable for practicing the invention can be found inter alia in U.S. Pat. Nos. 5,811,510; 5,863,990; 5,958,398; 7,838,619 and 7,790,150; and U.S. Publication No. 2006/0058512; each of the above listed patent documents is incorporated herein by reference in its entirety. Guidance on the significance, preparation, and applications of this type of polymers may be found in the above-cited documents. In certain embodiments, it is anticipated that the present invention will be particularly useful in combination with the above-referenced patent documents, as well as U.S. Pat. Nos. 5,582,172 and 6,822,086, each of the above listed patent documents is incorporated herein by reference in its entirety.

The conjugates of this invention are hydrophilic, hydrolysable and comprise drug molecules (e.g., vinca alkaloids or derivatives, topoisomerase inhibitors, such as, for example, SN38, camptothecin, topotecan, exatecan, non-natural camptothecin compounds or derivatives; auristatins, dolastatins, nemorubicine and its derivatives, PNU-159682, anthracycline, duocarmycins, kinase inhibitors (e.g., PI3 kinase inhibitors or MEK inhibitors), KSP inhibitors, calicheamicins, pyrrolobenzodiazepines, maytansinoids, elinafide, DNA-binding drugs, DNA intercalation drugs, and stereoisomers, isosteres, analogs and derivatives thereof) and antibodies (e.g., Trastuzumab, Cetuximab, Rituximab, Bevacizumab, Epratuzumab, Veltuzumab, Labetuzumab, B7-H4, B7-H3, CA125, CD33, CXCR2, EGFR, FGFR1, FGFR2, FGFR3, FGFR4, HER2, NaPi2b, c-Met, NOTCH1, NOTCH2, NOTCH3, NOTCH4, PD-L1, NaPi2b, c-Kit, MUC1, and anti-5T4) or peptides (LHRH receptor targeting peptides, EC-1 peptide) covalently attached to the polymer carrier via linkages that contain one or more biodegradable bonds. Thus, in certain exemplary embodiments, carriers suitable for practicing the present invention are polyals having at least one acetal/ketal oxygen atom in each monomer unit positioned within the main chain. As discussed above, this ensures that the degradation process (via hydrolysis/cleavage of the polymer acetal/ketal groups) will result in fragmentation of the polyal conjugate to low molecular weight components (i.e., degradation). In certain embodiments, biodegradable biocompatible polymer carriers, used for preparation of polymer conjugates of the invention, are naturally occurring polysaccharides, glycopolysaccharides, and synthetic polymers of polyglycoside, polyacetal, polyamide, polyether, and polyester origin and products of their oxidation, fictionalization, modification, cross-linking, and conjugation.

In certain other embodiments, the carrier is a hydrophilic biodegradable polymer selected from the group consisting of carbohydrates, glycopolysaccharides, glycolipids, glyco-conjugates, polyacetals, polyketals, and derivatives thereof.

In certain exemplary embodiments, the carrier is a naturally occurring linear and/or branched biodegradable biocompatible homopolysaccharide selected from the group consisting of cellulose, amylose, dextran, levan, fucoidan, carraginan, inulin, pectin, amylopectin, glycogen and lixenan.

In certain other exemplary embodiments, the carrier is a naturally occurring linear and branched biodegradable biocompatible heteropolysaccharide selected from the group consisting of agarose, hyluronan, chondroitinsulfate, dermatansulfate, keratansulfate, alginic acid and heparin.

In yet other exemplary embodiments, the polymeric carrier comprises a copolymer of a polyacetal/polyketal and a hydrophilic polymer selected from the group consisting of polyacrylates, polyvinyl polymers, polyesters, polyorthoesters, polyamides, polypeptides, and derivatives thereof.

In yet another embodiment, the polymeric carrier is dextrin that is produced by the hydrolysis of a starch obtained from various natural products such as, for example, wheat, rice, maize and tapioca. Depending on the structure of the starch starting material each dextrin comprises a unique distribution of α-1,4 linkages and α-1,6 linkages. Since the rate of biodegradability of α-1,6 linkages is typically less than that for α-1,4 linkages, preferably the percentage of α-1,6 linkages is less than 10% and more preferably less than 5%. In one embodiment the molecular weight of the dextrin is in the range of about 2 kDa to about 40 kDa, more preferably from about 2 kDa to about 20 kDa, or from about 3 kDa to about 15 kDa or from about 5 kDa to about 10 kDa.

In certain embodiments, the carrier comprises polysaccharides activated by selective oxidation of cyclic vicinal diols of 1,2-, 1,4-, 1,6-, and 2,6-pyranosides, and 1,2-, 1,5-, 1,6-furanosides, or by oxidation of lateral 6-hydroxy and 5,6-diol containing polysaccharides prior to conjugation with drug molecules or PBRMs.

In still other embodiments, the polymeric carrier comprises a biodegradable biocompatible polyacetal wherein at least a subset of the polyacetal repeat structural units have the following chemical structure:

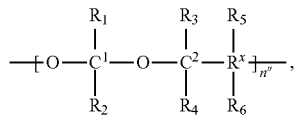

wherein for each occurrence of the n bracketed structure, one of $R_1$ and $R_2$ is hydrogen, and the other is a biocompatible group and includes a carbon atom covalently attached to $C^1$; $R^x$ is a carbon atom covalently attached to $C^2$; $n''$ is an integer; each occurrence of $R_3$, $R_4$, $R_5$ and $R_6$ is a biocompatible group and is independently hydrogen or an organic moiety; and for each occurrence of the bracketed structure n, at least one of $R_1$, $R_2$, $R_3$, $R_4$, $R_5$ and $R_6$ comprises a functional group suitable for coupling. In certain embodiments, the functional group is a hydroxyl moiety.

In one embodiment, the polymeric carrier comprises activated hydrophilic biodegradable biocompatible polymers comprising from 0.1% to 100% polyacetal moieties whose backbone is represented by the following chemical structure:

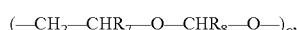

(—CH$_2$—CHR$_7$—O—CHR$_8$—O—)$_o$, wherein:

R$_7$ and R$_8$ are independently hydrogen, hydroxyl, hydroxy alkyl (e.g., —CH$_2$OH, —CH(OH)—CH(OH), —CHO, —CH(OH)—CHO or -carbonyl; and o is an integer from 20 to 2000.

In yet other embodiments, the polymeric carrier comprises a biodegradable biocompatible polyketal wherein at least a subset of the polyketal repeatable structural units have the following chemical structure:

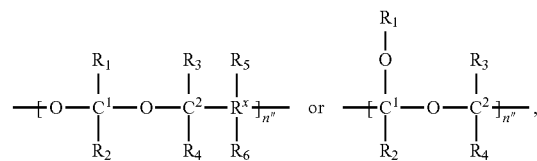

wherein each occurrence of $R_1$ and $R_2$ is a biocompatible group and $R^x$, $R_3$, $R_4$, $R_5$, $R_6$ and are as defined herein.

In certain embodiments, the ketal units are monomers of Formula (IIa) or (IIb):

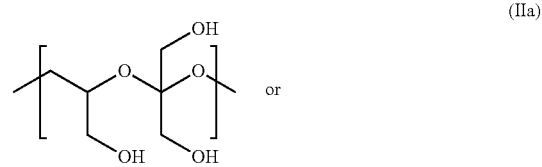

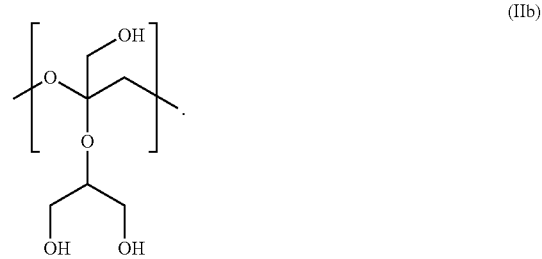

Biodegradable, biocompatible polyketal polymers and their methods of making have been described in U.S. Pat. Nos. 5,811,510, 7,790,150 and 7,838,619, which are hereby incorporated by reference in their entireties.

In one embodiment, the polymeric carrier can be obtained from partially oxidized dextran (1→6)-D-glucose) followed by reduction. In this embodiment, the polymer comprises a random mixture of the unmodified dextran (A), partially oxidized dextran acetal units (B) and exhaustively dextran acetal units (C) of the following structures:

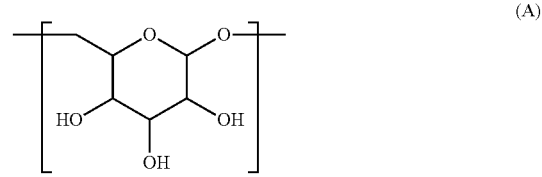

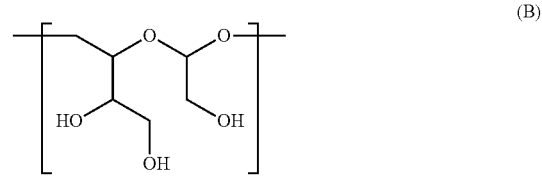

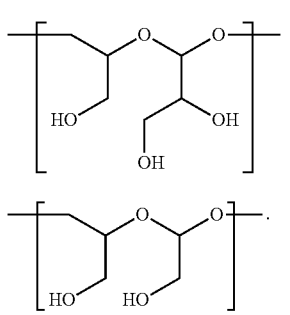

(B)

(C)

In another embodiment, the polymeric carrier comprises unmodified acetal units, i.e., polyacetal segments. In some embodiments, the polyacetals can be derived from exhaustively oxidized dextran followed by reduction. These polymers have been described in references, see, e.g., U.S. Pat. No. 5,811,510, which is hereby incorporated by reference for its description of polyacetals at column 2, line 65 to column 8, line 55 and their synthesis at column 10, line 45 to column 11, line 14. In one embodiment, the unmodified polyacetal polymer is a poly(hydroxymethylethylene hydroxymethyl formal) polymer (PHF).

In addition to poly(hydroxymethylethylene hydroxymethyl formal) polymers, the backbone of the polymeric carrier can also comprise co-polymers of poly(hydroxymethylethylene hydroxymethyl formal) blocks and other acetal or non-acetal monomers or polymers. For example, polyethylene glycol polymers are useful as a stealth agent in the polymer backbone because they can decrease interactions between polymer side chains of the appended functional groups. Such groups can also be useful in limiting interactions such as between serum factors and the modified polymer. Other stealth agent monomers for inclusion in the polymer backbone include, for example, ethyleneimine, methacrylic acid, acrylamide, glutamic acid, and combinations thereof.

The acetal or ketal units are present in the modified polymer in an amount effective to promote biocompatibility. The unmodified acetal or ketal unit can be described as a "stealth agent" that provides biocompatibility and solubility to the modified polymers. In addition, conjugation to a polyacetal or polyketal polymer can modify the susceptibility to metabolism and degradation of the moieties attached to it, and influence biodistribution, clearance and degradation.

The unmodified acetal units are monomers of Formula (III):

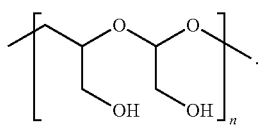

(III)

The molar fraction, n, of unmodified polyacetal units is the molar fraction available to promote biocompatibility, solubility and increase half-life, based on the total number of polymer units in the modified polymer. The molar fraction n may be the minimal fraction of unmodified monomer acetal units needed to provide biocompatibility, solubility, stability, or a particular half-life, or can be some larger fraction. The most desirable degree of cytotoxicity is substantially none, i.e., the modified polymer is substantially inert to the subject. However, as is understood by those of ordinary skill in the art, some degree of cytotoxicity can be tolerated depending on the severity of disease or symptom being treated, the efficacy of the treatment, the type and degree of immune response, and like considerations.

In one embodiment, the modified polymer backbone comprises units of Formula (IV):

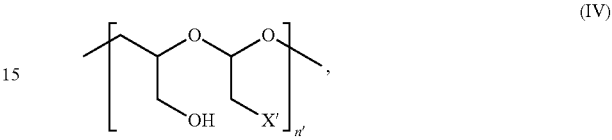

(IV)

wherein X' indicates the substituent for the hydroxyl group of the polymer backbone. As shown in Formula (IV) and the other formulae described herein, each polyacetal unit has a single hydroxyl group attached to the glycerol moiety of the unit and an X' group (or another substituent such as -$L^D$-D attached to the glycolaldehyde moiety of the unit. This is for convenience only and it should be construed that the polymer having units of Formula (IV) and other formulae described herein can contain a random distribution of units having a X' group (or another substituent such as a linker comprising a maleimide terminus) attached to the glycolaldehyde moiety of the units and those having a single X' group (or another substituent such as a linker comprising a maleimide terminus) attached to the glycerol moiety of the units as well as units having two X' groups (or other substituents such as a linker comprising a maleimide terminus) with one attached to the glycolaldehyde moiety and the other attached to the glycerol moiety of the units.

In one embodiment, biodegradable biocompatible polyals suitable for practicing the present invention have a molecular weight of between about 0.5 and about 300 kDa. For example, the biodegradable biocompatible polyals have a molecular weight of between about 1 and about 300 kDa (e.g., between about 1 and about 200 kDa, between about 2 and about 300 kDa, between about 2 and about 200 kDa, between about 5 and about 100 kDa, between about 10 and about 70 kDa, between about 20 and about 50 kDa, between about 20 and about 300 kDa, between about 40 and about 150 kDa, between about 50 and about 100 kDa, between about 2 and about 40 kDa, between about 6 and about 20 kDa, or between about 8 and about 15 kDa). For example, the biodegradable biocompatible polyal used for the polymer scaffold or conjugate of the invention is PHF having a molecular weight of between about 2 and about 40 kDa (e.g., about 2-20 kDa, 3-15 kDa, or 5-10 kDa.)

In one embodiment, the biodegradable biocompatible polyals suitable for practicing the present invention are modified before conjugating with a drug or a PBRM. For example, the polyals contains —C(=O)—X—(CH$_2$)$_v$—C(=O)— with X being CH$_2$, O, or NH, and v being an integer from 1 to 6. Table A below provides some examples of the modified polyals suitable for conjugating with a drug or PBRM or derivatives thereof. Unless otherwise specified, reference numbers in Tables A through D below correspond to the Example numbers described herein; the term "ND" means not determined; and X is CH$_2$, O, or NH.

TABLE A

| Ref # | Polymer Scaffold |
|---|---|
| X = NH Ex 2<br>X = CH$_2$ Ex 11 | |

Therapeutic Agents

In certain embodiments, the therapeutic agent is a small molecule having a molecular weight preferably ≤ about 5 kDa, more preferably ≤ about 4 kDa, more preferably ≤ about 3 kDa, most preferably ≤ about 1.5 kDa or ≤ about 1 kDa.

In certain embodiments, the therapeutic agent has an IC$_{50}$ of about less than 1 nM.

In another embodiment, the therapeutic agent has an IC$_{50}$ of about greater than 1 nM, for example, the therapeutic agent has an IC$_{50}$ of about 1 to 50 nM.

Some therapeutic agents having an IC$_{50}$ of greater than about 1 nM (e.g., "less potent drugs") are unsuitable for conjugation with a PBRM using art-recognized conjugation techniques. Without wishing to be bound by theory, such therapeutic agents have a potency that is insufficient for use in targeted PBRM-drug conjugates using conventional techniques as sufficient copies of the drug (i.e., more than 8) cannot be conjugated using art-recognized techniques without resulting in diminished pharmacokinetic and physiochemical properties of the conjugate. However sufficiently high loadings of these less potent drugs can be achieved using the conjugation strategies described herein thereby resulting in high loadings of the therapeutic agent while maintaining the desirable pharmacokinetic and physiochemical properties. Thus, the invention also relates to a PBRM-polymer-drug conjugate which includes a PBRM, PHF and at least eight therapeutic agent moieties, wherein the therapeutic agent has an IC$_{50}$ of greater than about 1 nM.

In certain embodiments, about 0.3 to about 15% monomers comprise a therapeutic agent, more preferably about 2 to about 12%, and even more preferably about 5 to about 10%.

The small molecule therapeutic agents used in this invention (e.g., antiproliferative (cytotoxic and cytostatic) agents capable of being linked to a polymer carrier) include cytotoxic compounds (e.g., broad spectrum), angiogenesis inhibitors, cell cycle progression inhibitors, PI3K/m-TOR/AKT pathway inhibitors, MAPK signaling pathway inhibitors, kinase inhibitors, protein chaperones inhibitors, HDAC inhibitors, PARP inhibitors, Wnt/Hedgehog signaling pathway inhibitors and RNA polymerase inhibitors.

Broad spectrum cytotoxins include, but are not limited to, DNA-binding, intercalating or alkylating drugs, microtubule stabilizing and destabilizing agents, platinum compounds, topoisomerase I inhibitors and protein synthesis inhibitors.

Exemplary DNA-binding, intercalation or alkylating drugs include, CC-1065 and its analogs, anthracyclines (doxorubicin, epirubicin, idarubicin, daunorubicin, nemorubicin and its derivatives, PNU-159682), bisnapththalimide compounds such as elinafide (LU79553). and its analogs, alkylating agents, such as calicheamicins, dactinomycines, mitromycines, pyrrolobenzodiazepines, and the like. Exemplary CC-1065 analogs include duocarmycin SA, duocarmycin A, duocarmycin C1, duocarmycin C2, duocarmycin B1, duocarmycin B2, duocarmycin D, DU-86, KW-2189, adozelesin, bizelesin, carzelesin, seco-adozelesin, and related analogs and prodrug forms, examples of which are described in U.S. Pat. Nos. 5,475,092; 5,595,499; 5,846,545; 6,534,660; 6,586,618; 6,756,397 and 7,049,316. Doxorubicin and its analogs include those described in U.S. Pat. No. 6,630,579. Calicheamicins include, e.g., enediynes, e.g., esperamicin, and those described in U.S. Pat. Nos. 5,714,586 and 5,739,116. Duocarmycins include those described in U.S. Pat. Nos. 5,070,092; 5,101,038; 5,187,186; 6,548,530; 6,660,742; and 7,553,816 B2; and Li et al., Tet Letts., 50:2932-2935 (2009).

Pyrrolobenzodiazepines (PBD) and analogs thereof include those described in Denny, Exp. Opin. Ther. Patents., 10(4):459-474 (2000) and Antonow and Thurston, Chem. Rev., 2815-2864 (2010).

Exemplary microtubule stabilizing and destabilizing agents include taxane compounds, such as paclitaxel, docetaxel, tesetaxel and carbazitaxel; maytansinoids, auristatins and analogs thereof, vinca alkaloid derivatives, epothilones and cryptophycins.

Exemplary maytansinoids or maytansinoid analogs include maytansinol and maytansinol analogs, maytansine or DM-1 and DM-4 are those described in U.S. Pat. Nos. 5,208,020; 5,416,064; 6,333.410; 6,441,163; 6,716,821; RE39,151 and 7,276,497. In certain embodiments, the cytotoxic agent is a maytansinoid, another group of anti-tubulin agents (ImmunoGen, Inc.; see also Chari et al., 1992, Cancer Res. 52:127-131), maytansinoids or maytansinoid analogs. Examples of suitable maytansinoids include maytansinol and maytansinol analogs. Suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 6,333,410; 5,475,092; 5,585,499; and 5,846,545.

Exemplary auristatins include auristatin E (also known as a derivative of dolastatin-10), auristatin EB (AEB), auristatin EFP (AEFP), monomethyl auristatin E (MMAE), monomethyl auristatin F (MMAF), auristatin F, auristatin F phenylenediamine (AFP), auristatin F HPA and dolastatin. Suitable auristatins are also described in U.S. Publication Nos. 2003/0083263, 2011/0020343, and 2011/0070248; PCT Application Publication Nos. WO 09/117,531, WO 2005/081711, WO 04/010957; WO 02/088172 and WO01/24763, and U.S. Pat. Nos. 7,498,298; 6,884,869; 6,323,315; 6,239,104; 6,124,431; 6,034,065; 5,780,588; 5,767,237; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, the disclosures of which are incorporated herein by reference in their entirety.

Exemplary vinca alkaloids include vincristine, vinblastine, vindesine, and navelbine (vinorelbine). Suitable Vinca alkaloids that can be used in the present invention are also disclosed in U.S. Publication Nos. 2002/0103136 and 2010/0305149, and in U.S. Pat. No. 7,303,749 B1, the disclosures of which are incorporated herein by reference in their entirety.

Exemplary epothilone compounds include epothilone A, B, C, D, E and F, and derivatives thereof. Suitable epothilone compounds and derivatives thereof are described, for example, in U.S. Pat. Nos. 6,956,036; 6,989,450; 6,121,029; 6,117,659; 6,096,757; 6,043,372; 5,969,145; and 5,886,026; and WO 97/19086; WO 98/08849; WO 98/22461; WO 98/25929; WO 98/38192; WO 99/01124; WO 99/02514; WO 99/03848; WO 99/07692; WO 99/27890; and WO 99/28324; the disclosures of which are incorporated herein by reference in their entirety.

Exemplary cryptophycin compounds are described in U.S. Pat. Nos. 6,680,311 and 6,747,021.

Exemplary platinum compounds include cisplatin (PLATINOL), carboplatin (PARAPLATIN), oxaliplatin (ELOXATINE), iproplatin, ormaplatin, and tetraplatin.

Still other classes of compounds or compounds with these or other cytotoxic modes of action may be selected, including, e.g., mitomycin C, mitomycin A, daunorubicin, doxorubicin, morpholino-doxorubicin, cyanomorpholino-doxorubicin, aminopterin, bleomycin, 1-(chloromethyl)-2,3-dihydro-1H-benzo[e]indol-5-ol, pyrrolobenzodiazepine (PBD) polyamide and dimers thereof. Other suitable cytotoxic agents include, for example, puromycins, topotecan, rhizoxin, echinomycin, combretastatin, netropsin, estramustine, cryptophysins, cemadotin, discodermolide, eleutherobin, and mitoxantrone.

Exemplary topoisomerase I inhibitors include camptothecin, camptothecin derivatives, camptothecin analogs and non-natural camptothecins, such as, for example, CPT-11 (irinotecan), SN-38, GI-147211C, topotecan, 9-aminocamptothecin, 7-hydroxymethyl camptothecin, 7-aminomethyl camptothecin, 10-hydroxycamptothecin, (20S)-camptothecin, rubitecan, gimatecan, karenitecin, silatecan, lurtotecan, exatecan, diflomotecan, belotecan, lurtotecan and 539625. Other camptothecin compounds that can be used in the present invention include those described in, for example, J. Med. Chem., 29:2358-2363 (1986); J. Med. Chem., 23:554 (1980); J. Med. Chem., 30:1774 (1987).

Angiogenesis inhibitors include, but are not limited, MetAP2 inhibitors, VEGF inhibitors, PlGF inhibitors, VGFR inhibitors, PDGFR inhibitors, MetAP2 inhibitors. Exemplary VGFR and PDGFR inhibitors include sorafenib (Nexavar), sunitinib (Sutent) and vatalanib. Exemplary MetAP2 inhibitors include fumagillol analogs, meaning any compound that includes the fumagillin core structure, including fumagillamine, that inhibits the ability of MetAP-2 to remove $NH_2$-terminal methionines from proteins as described in Rodeschini et al., J. Org. Chem., 69, 357-373, 2004 and Liu, et al., Science 282, 1324-1327, 1998. Non limiting examples of "fumagillol analogs" are disclosed in J. Org. Chem., 69, 357, 2004; J. Org. Chem., 70, 6870, 2005; European Patent Application 0 354 787; J. Med. Chem., 49, 5645, 2006; Bioorg. Med. Chem., 11, 5051, 2003; Bioorg. Med. Chem., 14, 91, 2004; Tet. Lett. 40, 4797, 1999; WO99/61432; U.S. Pat. Nos. 6,603,812; 5,789,405; 5,767,293; 6,566,541; and 6,207,704.

Exemplary cell cycle progression inhibitors include CDK inhibitors such as, for example, BMS-387032 and PD0332991; Rho-kinase inhibitors such as, for example GSK429286; checkpoint kinase inhibitors such as, for example, AZD7762; aurora kinase inhibitors such as, for example, AZD1152, MLN8054 and MLN8237; PLK inhibitors such as, for example, BI 2536, BI6727 (Volasertib), GSK461364, ON-01910 (Estybon); and KSP inhibitors such as, for example, SB 743921, SB 715992 (ispinesib), MK-0731, AZD8477, AZ3146 and ARRY-520.

Exemplary PI3K/m-TOR/AKT signaling pathway inhibitors include phosphoinositide 3-kinase (PI3K) inhibitors, GSK-3 inhibitors, ATM inhibitors, DNA-PK inhibitors and PDK-1 inhibitors.

Exemplary PI3 kinase inhibitors are disclosed in U.S. Pat. No. 6,608,053, and include BEZ235, BGT226, BKM120, CAL101, CAL263, demethoxyviridin, GDC-0941, GSK615, IC87114, LY294002, Palomid 529, perifosine, PI-103, PF-04691502, PX-866, SAR245408, SAR245409, SF1126, Wortmannin, XL147 and XL765.

Exemplary AKT inhibitors include, but are not limited to AT7867.

Exemplary MAPK signaling pathway inhibitors include MEK, Ras, JNK, B-Raf and p38 MAPK inhibitors.

Exemplary MEK inhibitors are disclosed in U.S. Pat. No. 7,517,994 and include GDC-0973, GSK1120212, MSC1936369B, AS703026, RO5126766 and RO4987655, PD0325901, AZD6244, AZD 8330 and GDC-0973.

Exemplary B-raf inhibitors include CDC-0879, PLX-4032, and SB590885.

Exemplary B p38 MAPK inhibitors include BIRB 796, LY2228820 and SB 202190.

Receptor tyrosine kinases (RTK) are cell surface receptors which are often associated with signaling pathways stimulating uncontrolled proliferation of cancer cells and neoangiogenesis. Many RTKs, which over express or have mutations leading to constitutive activation of the receptor, have been identified, including, but not limited to, VEGFR, EGFR, FGFR, PDGFR, EphR and RET receptor family receptors. Exemplary specific RTK targets include ErbB2, FLT-3, c-Kit, and c-Met.

Exemplary inhibitors of ErbB2 receptor (EGFR family) include but not limited to AEE788 (NVP-AEE 788), BIBW2992, (Afatinib), Lapatinib, Erlotinib (Tarceva), and Gefitinib (Iressa).

Exemplary RTK inhibitors targeting more then one signaling pathway (multitargeted kinase inhibitors) include AP24534 (Ponatinib) that targets FGFR, FLT-3, VEGFR-PDGFR and Bcr-Abl receptors; ABT-869 (Linifanib) that targets FLT-3 and VEGFR-PDGFR receptors; AZD2171 that targets VEGFR-PDGFR, Flt-1 and VEGF receptors; CHR-258 (Dovitinib) that targets VEGFR-PDGFR, FGFR, Flt-3, and c-Kit receptors; Sunitinib (Sutent) that targets VEGFR, PDGFR, KIT, FLT-3 and CSF-IR; Sorafenib (Nexavar) and Vatalanib that target VEGFR, PDGFR as well as intracellular serine/threonine kinases in the Raf/Mek/Erk pathway.

Exemplary protein chaperon inhibitors include HSP90 inhibitors. Exemplary HSP90 inhibitors include 17AAG derivatives, BIIB021, BIIB028, SNX-5422, NVP-AUY-922 and KW-2478.

Exemplary HDAC inhibitors include Belinostat (PXD101), CUDC-101, Droxinostat, ITF2357 (Givinostat, Gavinostat), JNJ-26481585, LAQ824 (NVP-LAQ824, Dacinostat), LBH-589 (Panobinostat), MC1568, MGCD0103 (Mocetinostat), MS-275 (Entinostat), PCI-24781, Pyroxamide (NSC 696085), SB939, Trichostatin A and Vorinostat (SAHA).

Exemplary PARP inhibitors include iniparib (BSI 201), olaparib (AZD-2281), ABT-888 (Veliparib), AG014699, CEP 9722, MK 4827, KU-0059436 (AZD2281), LT-673, 3-aminobenzamide, A-966492, and AZD2461.

Exemplary Wnt/Hedgehog signaling pathway inhibitors include vismodegib (RG3616/GDC-0449), cyclopamine (11-deoxojervine) (Hedgehog pathway inhibitors) and XAV-939 (Wnt pathway inhibitor)

Exemplary RNA polymerase inhibitors include amatoxins. Exemplary amatoxins include -amanitins, -amanitins, -amanitins, -amanitins, amanullin, amanullic acid, amaninamide, amanin, and proamanullin.

Examplary protein synthesis inhibitors include trichothecene compounds.

In one embodiment the drug of the invention is a topoisomerase inhibitor (such as, for example, a non-natural camptothecin compound), vinca alkaloid, kinase inhibitor (e.g., PI3 kinase inhibitor (GDC-0941 and PI-103)), MEK inhibitor, KSP inhibitor, RNA polymerase inhibitor, protein synthesis inhibitor, PARP inhibitor, docetaxel, paclitaxel, doxorubicin, duocarmycin, auristatin, dolastatin, calicheamicins, topotecan, SN38, camptothecin, exatecan, nemorubicin and its derivatives, PNU-159682, CC1065, elinafide, trichothecene, pyrrolobenzodiazepines, maytansinoids, DNA-binding drugs or a platinum compound, and analogs thereof. In specific embodiments, the drug is a derivative of SN-38, camptothecin, topotecan, exatecan, calicheamicin, exatecan, nemorubicin, PNU-159682, anthracycline, maytansinoid, taxane, trichothecene, CC1065, elinafide, vindesine, vinblastine, PI-103, AZD 8330, dolastatin, auristatin E, auristatin F, a duocarmycin compound, ispinesib, pyrrolobenzodiazepine, ARRY-520 and stereoisomers, isosteres and analogs thereof.

In another embodiment, the drug used in the invention is a combination of two or more drugs, such as, for example, PI3 kinase inhibitors and MEK inhibitors; broad spectrum cytotoxic compounds and platinum compounds; PARP inhibitors and platinum compounds; broad spectrum cytotoxic compounds and PARP inhibitors.

In yet another embodiment, the drug used in the invention is auristatin F-hydroxypropylamide-L-alanine.

In one embodiment, the Vinca alkaloid is a compound of Formula (V):

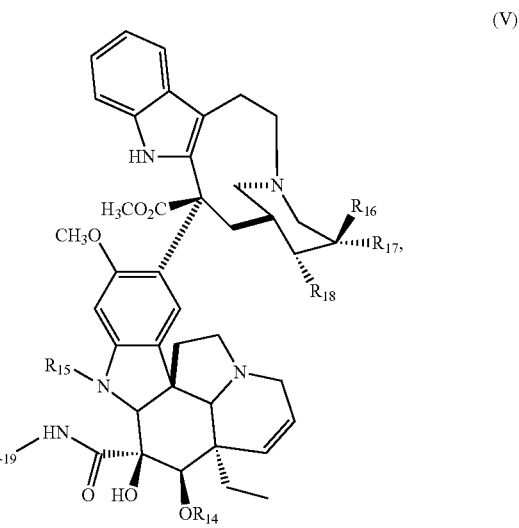

(V)

wherein:

$R_{14}$ is hydrogen, —C(O)—$C_{1-3}$ alkyl or —C(O)-chloro substituted $C_{1-3}$ alkyl;

$R_{15}$ is hydrogen, —CH$_3$ or —CHO;

when $R_{17}$ and $R_{18}$ are taken independently, $R_{18}$ is hydrogen, and either $R_{16}$ or $R_{17}$ is ethyl and the other is hydroxyl;

when $R_{17}$ and $R_{18}$ are taken together with the carbon to which they are attached to form an oxiran ring, $R_{16}$ is ethyl;

$R_{19}$ is hydrogen, OH, amino group, alkyl amino or —[C($R_{20}R_{21}$)]$_a$—$R_{22}$;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{22}$ is —OH, —NH$_2$, —COOH, —$R_{82}$—C(O)(CH$_2$)$_c$—C(H)($R_{23}$)—N(H)($R_{23}$), —$R_{82}$—C(O)(CH$_2$)$_d$—(OCH$_2$—CH$_2$)$_f$—N(H)($R_{23}$) or —$R_{82}$—(C(O)—CH($X^2$)—NH)$_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is hydrogen or $X^2$ and $NR_{77}$ form a nitrogen containing heterocyclic moiety;

$R_{82}$ is —NH or oxygen;

a is an integer from 1 to 6;

c is an integer from 0 to 3;

d is an integer from 1 to 3; and f is an integer from 1 to 12.

Further examples of Vinca alkaloids are described in U.S. Pat. No. 8,524,214B2 and US 2002/0103136.

In one embodiment the Vinca alkaloid of Formula (V) is a compound of Formula (VI):

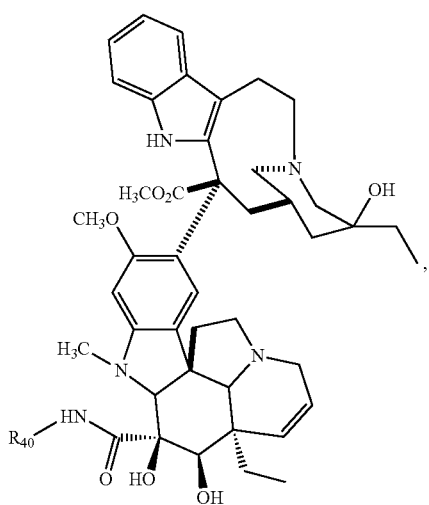
(VI)
wherein:
$R_{40}$ is hydrogen, —OH, —NH$_2$, or any of the following structures:
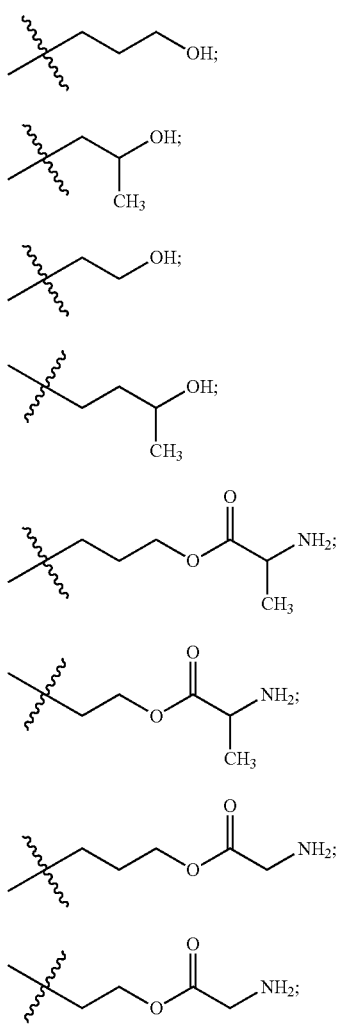
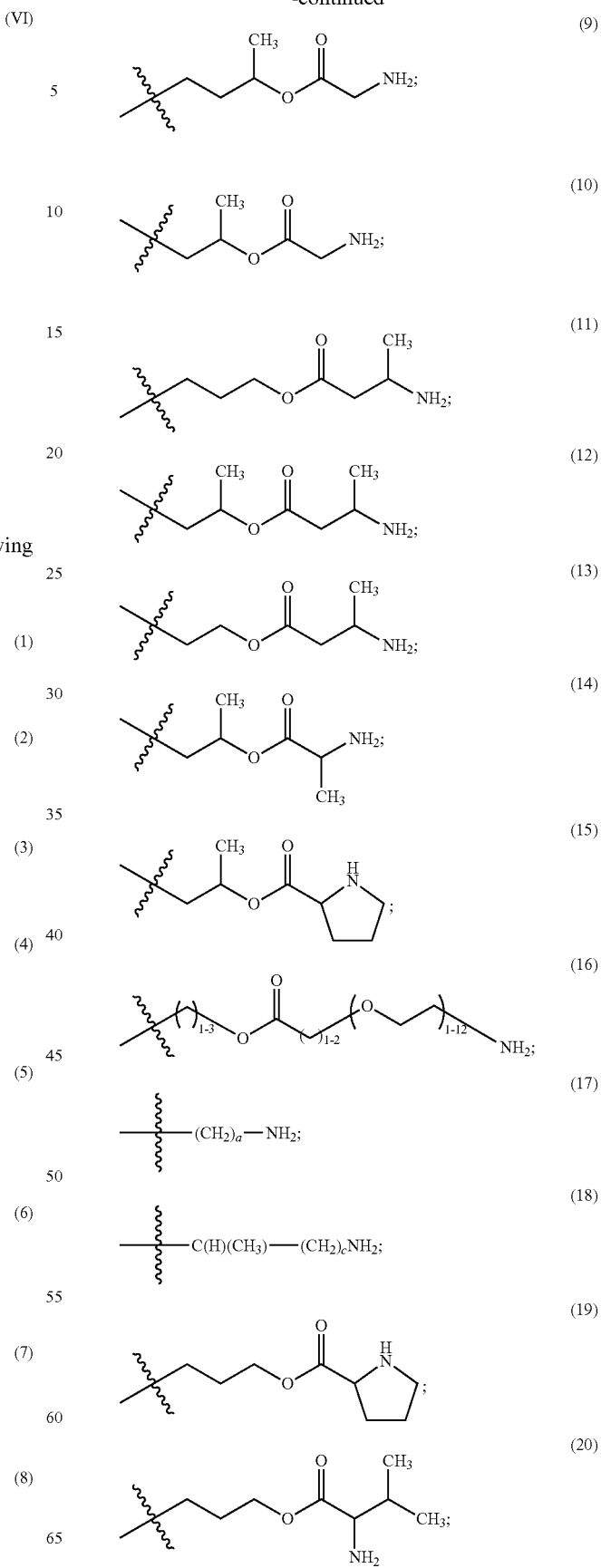

-continued
(21)
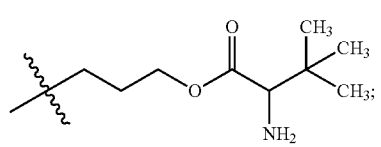
(22)
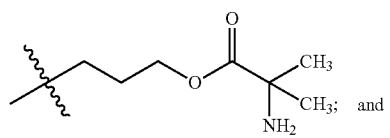
and
(23)
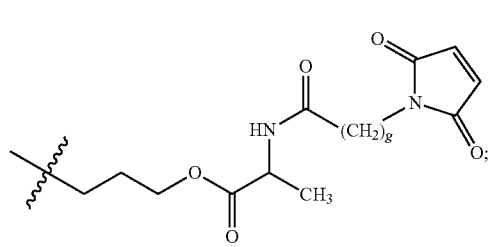
wherein:
  a is an integer from 1 to 6;
  g is an integer from 2 to 6; and
  c is an integer from 0 to 3.
In one embodiment, in Formula (VI), $R_{40}$ is
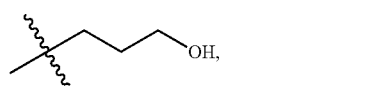 [SMILES: *CCCO]
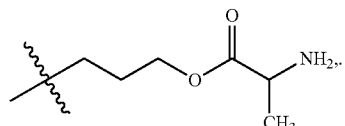
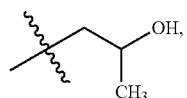
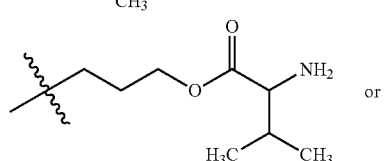
or
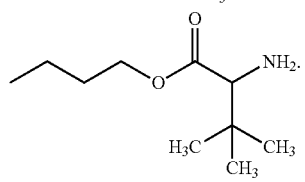
In another embodiment, $R_{40}$ is
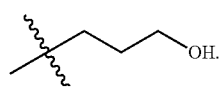
In another embodiment, the compound of Formula (VI) is a compound of Formula (VIa), (VIb), (VIc) or (VId):
(VIa)
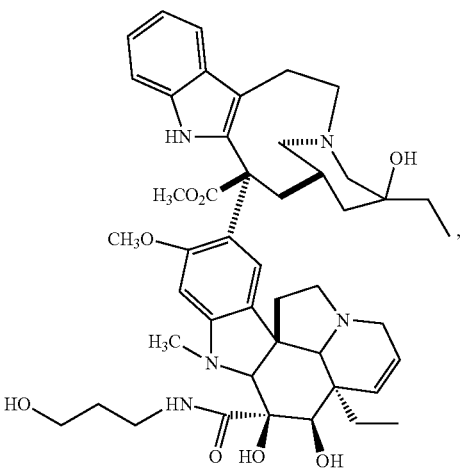
(VIb)
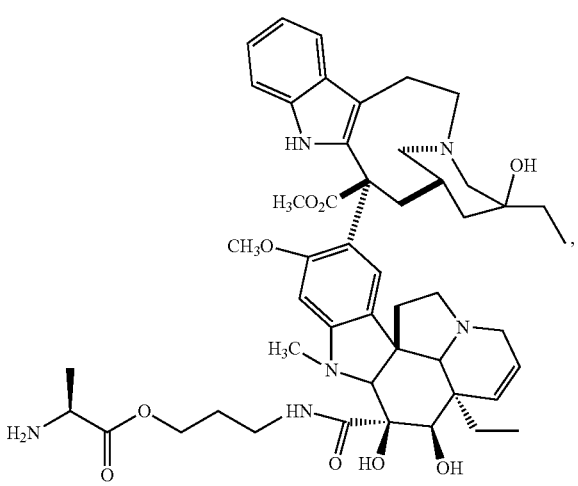
(VIc)
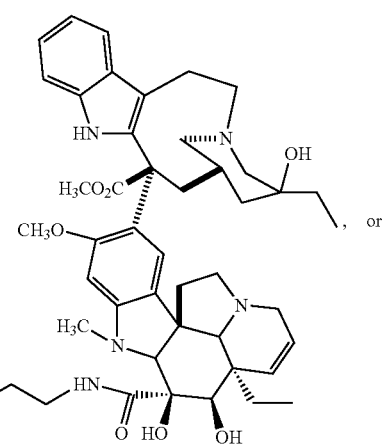
, or -continued (VId)

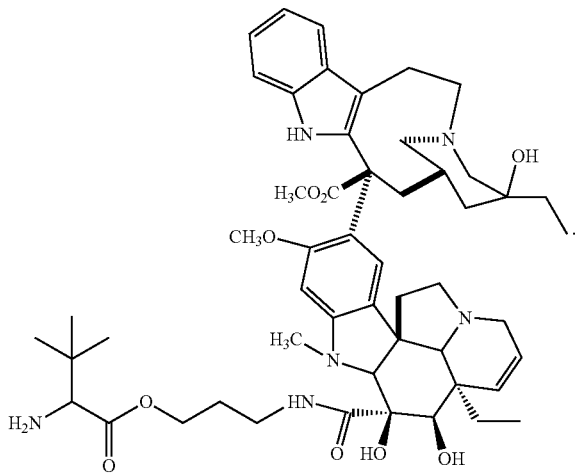

In another embodiment, the topoisomerase inhibitor is a camptothecin compound of Formula (VII):

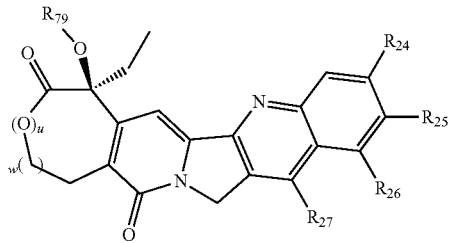

(VII)

wherein:

$R_{24}$ is —H, —Cl, —F, —OH or alkyl; or $R_{24}$ and $R_{25}$, may be taken together to form an optionally substituted five- or six-membered ring;

$R_{25}$ is —H, —F, —OH, —CH$_3$, —CH=N—O-t-Butyl, —CH$_2$CH$_2$Si(CH$_3$)$_3$, —Si((CH$_3$)$_2$)-t-butyl, —O—C(O)—$R_{29}$;

$R_{29}$ is —NH$_2$, —$R_{28}$—C$_{1-6}$ alkyl-$R_{22}$, 5 to 12-membered heterocycloalkyl, $R_{28}$—C$_{5-12}$ heterocycloalkyl-C$_{1-6}$ alkyl-$R_{22}$ or —$R_{28}$—C$_{1-6}$ alkyl-C$_{6-12}$ aryl-C$_{1-6}$ alkyl-$R_{22}$; or $R_{29}$ is $R_{47}$ as defined herein;

$R_{26}$ is —H, —CH$_2$—N(CH$_3$)$_2$, NH$_2$, or NO$_2$;

$R_{27}$ is —H, ethyl, N-methyl piperidine, cycloalkyl, —CH$_2$OH, —CH$_2$CH$_2$NHCH(CH$_3$)$_2$, or —N-4-methylcyclohexylamine;

$R_{79}$ is —H or —C(O)—$R_{28}$—[C($R_{20}R_{21}$)]$_a$—$R_{22}$;

each of $R_{20}$ and $R_{21}$ independently is hydrogen, C$_{1-6}$ alkyl, C$_{6-10}$ aryl, hydroxylated C$_{6-10}$ aryl, polyhydroxylated C$_{6-10}$ aryl, 5 to 12-membered heterocycle, C$_{3-8}$ cycloalkyl, hydroxylated C$_{3-8}$ cycloalkyl, polyhydroxylated C$_{3-8}$ cycloalkyl or a side chain of a natural or unnatural amino acid;

$R_{22}$ is —OH, —NH$_2$, —COOH, —$R_{82}$—C(O)(CH$_2$)$_c$—C(H)($R_{23}$)—N(H)($R_{23}$), —$R_{82}$—C(O)(CH$_2$)$_d$—(OCH$_2$—CH$_2$)$_f$—N(H)($R_{23}$), or —$R_{82}$—(C(O)—CH(X$^2$)—NH)$_d$—$R_{77}$;

each $R_{23}$ independently is hydrogen, C$_{1-6}$ alkyl, C$_{6-10}$ aryl, C$_{3-8}$ cycloalkyl, —COOH, or —COO—C$_{1-6}$ alkyl;

$X^2$ is a side chain of a natural or unnatural amino acid;

$R_{77}$ is a hydrogen or $X^2$ and NR$_{77}$ form a nitrogen containing cyclic compound;

$R_{82}$ is —NH or oxygen;

or $R_{26}$ and $R_{27}$ when taken together with the two carbon atoms to which they attach and the third carbon atom connecting the two carbon atoms form an optionally substituted six-membered ring;

$R_{28}$ is absent, NH or oxygen;

a is an integer from 1 to 6;

c is an integer from 0 to 3;

d is an integer from 1 to 3;

f is an integer from 1 to 12;

u is an integer 0 or 1;

w is an integer 0 or 1; and with the proviso that the compound of Formula (VII) must contain at least one of $R_{29}$ and $R_{79}$.

In one embodiment the camptothecin compound of Formula (VII) is a compound of Formula (VIII), (VIIIa), or (VIIIb), or Formula (XXV) or (XXVa):

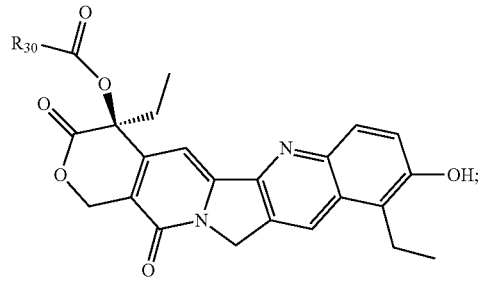

(VIII)

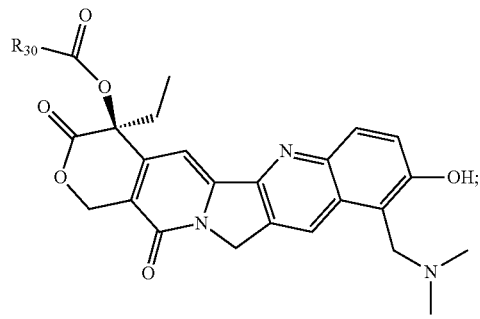

(VIIIa)

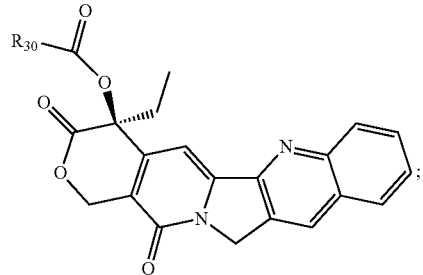

(VIIIb)

-continued (XXV)

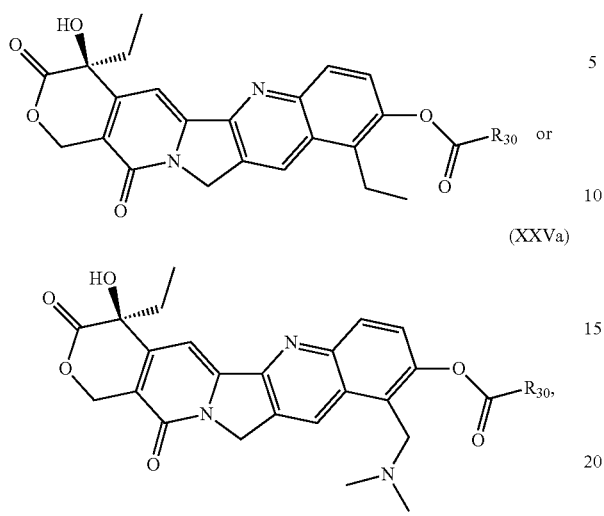

(XXVa)

wherein $R_{30}$ is —$NH_2$, —$R_{28}$—$[C(R_{20}R_{21})]_a$—$R_{22}$, —$R_{28}$—$C_{1-6}$ alkyl-$R_{22}$, 5 to 12-membered heterocycloalkyl, $R^{28}$—$C_{5-12}$ heterocycloalkyl-$C_{1-6}$ alkyl-$R_{22}$ or —$R_{28}$—$C_{1-6}$ alkyl-$C_{6-12}$ aryl-$C_{1-6}$ alkyl-$R_{22}$;

$R_{28}$ is absent, NH or oxygen;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{22}$ is —OH, —$NH_2$, —COOH, —$R_{82}$—$C(O)(CH_2)_c$—$C(H)(R_{23})$—$N(H)(R_{23})$, —$R_{82}$—$C(O)(CH_2)_d$—$(OCH_2$—$CH_2)_f$—$N(H)(R_{23})$ or —$R_{82}$—$(C(O)$—$CH(X^2)$—$NH)_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is —NH or oxygen;

a is an integer from 1 to 6;

c is an integer from 0 to 3;

d is an integer from 1 to 3; and f is an integer from 1 to 12.

In some embodiments $R_{30}$ is any one of the following structures:

(1)
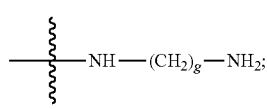

(2)
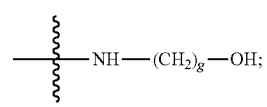

(3)
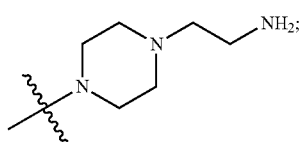

(4)
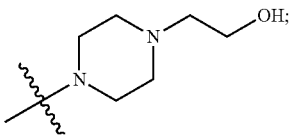

(5)
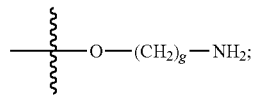

(6)
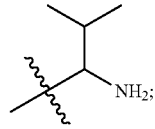

(7)
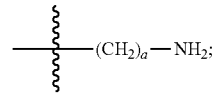

(8)
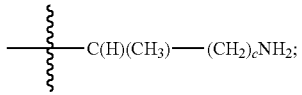

(9)
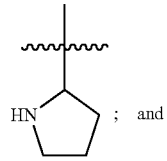

(10)
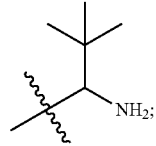

wherein:

a is an integer from 1 to 6;

c is an integer from 0 to 3; and g is an integer from 2 to 6.

In one embodiment, in Formula (VII), $R_{30}$ is:

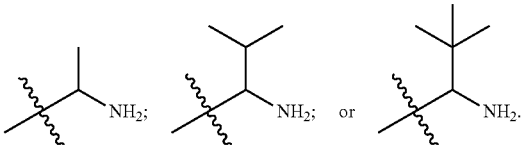

In another embodiment, the compound of Formula (VII) is a compound of Formula (VIIa), (VIIb), (VIIc), (VIId), (VIIe) or (VIIf):

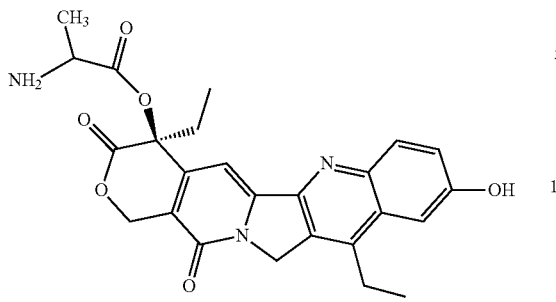

(VIIa)

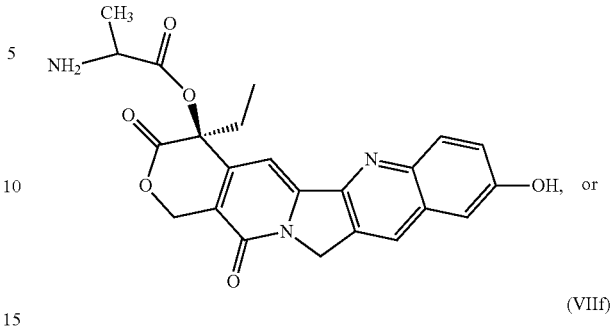

(VIIe)

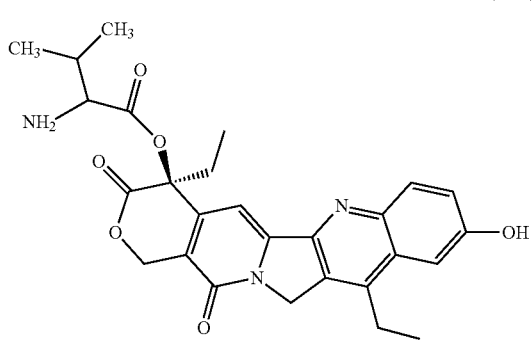

(VIIb)

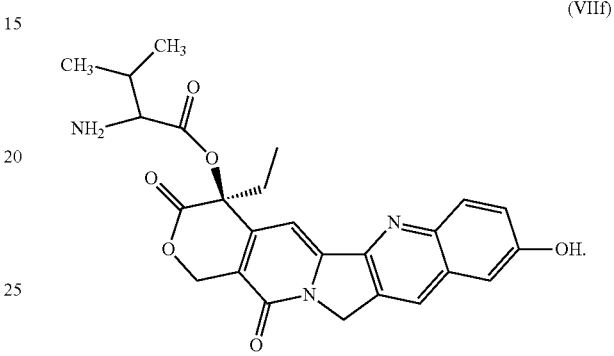

(VIIf)

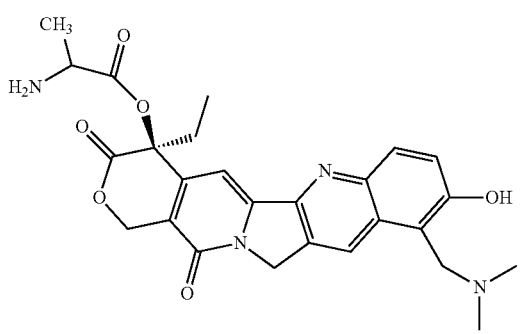

(VIIc)

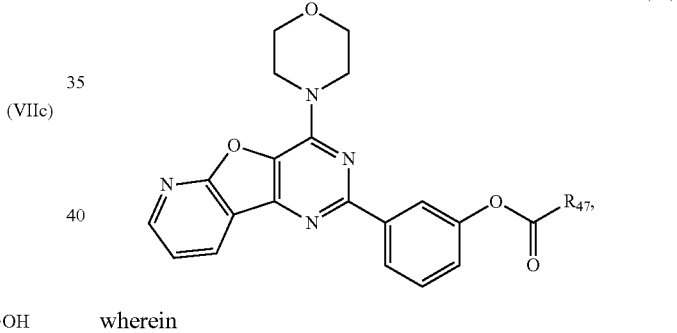

In another embodiment the PI3 kinase inhibitor is a compound of Formula (IX):

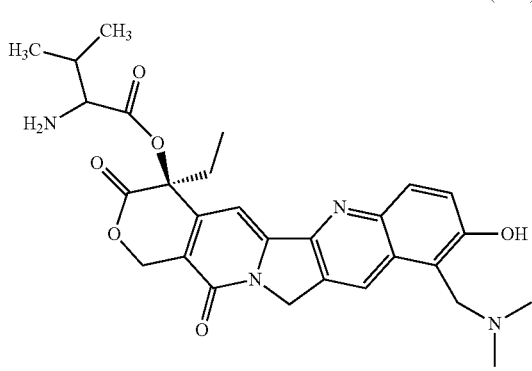

(VIId)

(IX)

wherein
$R_{47}$ is an amino group, $-R_9-[C(R_{20}R_{21})]_a-R_{10}$, $-R_9-C_{5-12}$ heterocycloalkyl-$C_{1-6}$ alkyl-$R_{10}$, 5 to 12-membered heterocycloalkyl, or $-R_9-C_{6-10}$ aryl;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{10}$ is $-OH$, $-NHR_{83}$, $-N-(R_{83})R_{11}$, $-COOH$, $-R_{82}-C(O)(CH_2)_c-C(H)(R_{23})-N(H)(R_{23})$, $-R_{82}-C(O)(CH_2)_d-(OCH_2-CH_2)_f-N(H)(R_{23})$, $-R_{82}-(C(O)-CH(X^2)-NH)_d-R_{77}$ or $-R_{82}-C(O)-[C(R_{20}R_{21})]_a-R_{82}-R_{83}$;

each $R_{23}$ independently is hydrogen, $C_{1-6}$ alkyl, $C_{6-10}$ aryl, $C_{3-8}$ cycloalkyl, $-COOH$, or $-COO-C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is $-NH$ or oxygen;

$R_9$ is absent, $N-(R_{83})$ or oxygen;

$R_{83}$ is hydrogen or $CH_3$;

$R_{11}$ is:

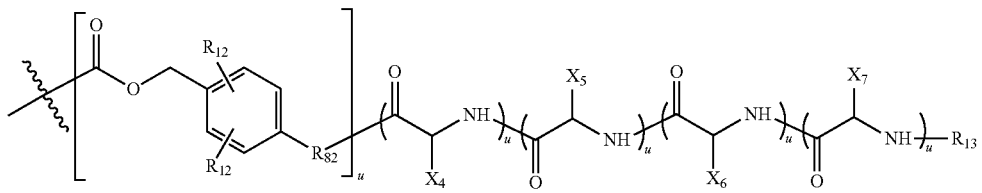

each $R_{12}$ independently is hydrogen, chloride, —$CH_3$ or —$OCH_3$;

$R_{13}$ is hydrogen or —C(O)—$(CH_2)_d$—$(OCH_2$—$CH_2)_f$—$NH_2$;

$R_{82}$ is —NH or oxygen $X_4$ is the side chain of lysine, arginine, citrulline, alanine or glycine;

$X_5$ is the side chain of phenylalanine, valine, leucine, isoleucine or tryptophan;

each of $X_6$ and $X_7$ is independently the side chain of glycine, alanine, serine, valine or proline;

a is an integer from 1 to 6;

c is an integer from 0 to 3;

d is an integer from 1 to 3;

f is an integer from 1 to 12; and each u independently is an integer 0 or 1;

or $R_{11}$ is —$Y_u$—$W_q$—$R_{88}$, wherein:

Y is any one of the following structures:

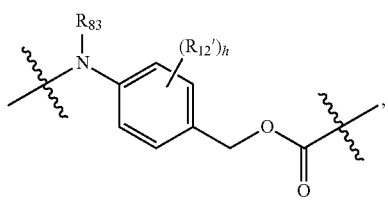

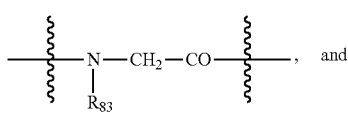, and

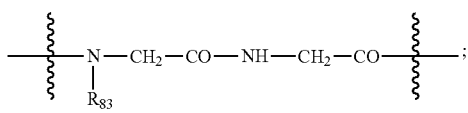

in each of which the terminal $NR_{83}$ group of Y is proximal to $R_{88}$;

$R_{83}$ is hydrogen or $CH_3$;

each W is an amino acid unit;

each $R_{12}'$ independently is halogen, —$C_{1-8}$ alkyl, —O—$C_{1-8}$ alkyl, nitro or cyano;

$R_{88}$ is hydrogen or —C(O)—$(CH_2)_{ff}$—$(NH$—$C(O))_{aa}$-$E_j$-$(CH_2)_{bb}$—$R_{85}$ $R_{85}$ is $NH_2$ or OH;

E is —$CH_2$— or —$CH_2CH_2O$—;

u is an integer 0 or 1;

q is an integer from 0 to 12;

aa is an integer 0 or 1;

bb is an integer 0 or 2;

ff is an integer from 0 to 10;

h is an integer from 0 to 4;

j is an integer from 0 to 12; and when E is —$CH_2$—, bb is 0 and j is an integer from 0 to 10; and when E is —$CH_2CH_2$—O—, bb is 2 and j is an integer from 1 to 12;

or $R_{11}$ is

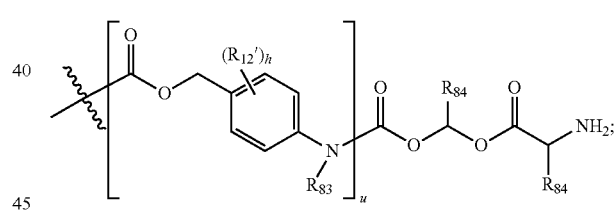

wherein:

$R_{83}$ is hydrogen or $CH_3$;

$R_{84}$ is $C_{1-6}$ alkyl or $C_{6-10}$ aryl;

each $R_{12}'$ independently is halogen, —$C_{1-8}$ alkyl, —O—$C_{1-8}$ alkyl, nitro or cyano;

h is an integer from 0 to 4; and u is an integer 0 or 1.

In some embodiments, $R_{11}$ is:

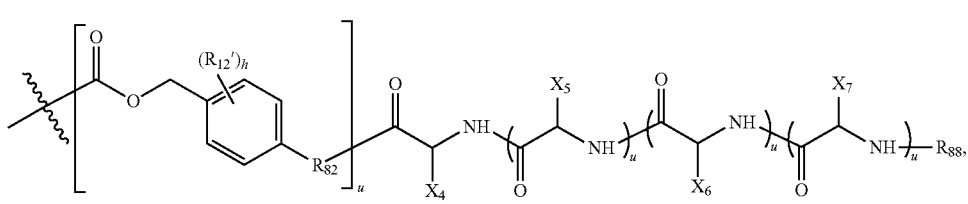

wherein:

each $R_{12}'$ independently is chloride, —$CH_3$ or —$OCH_3$;

$R_{88}$ is hydrogen or —C(O)—$(CH_2)_{ff}$$(CH_2$—$CH_2O)_j$—$CH_2$—$CH_2$—$NH_2$;

$R_{82}$ is —NH or oxygen $X_4$ is the side chain of lysine, arginine, citrulline, alanine or glycine;

$X_5$ is the side chain of phenylalanine, valine, leucine, isoleucine or tryptophan;

each of $X_6$ and $X_7$ is independently the side chain of glycine, alanine, serine, valine or proline;

ff is an integer from 1 to 3;

j is an integer from 1 to 12 h is an integer from 0 to 4; and each u independently is an integer 0 or 1.

In some embodiments,

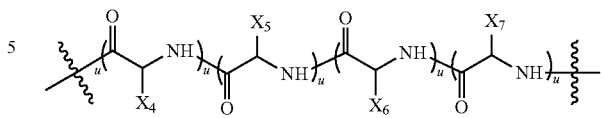

is citrulline-valine; lysine-phenylalanine; citrulline-phenylalanine; citrulline-leucine; citrulline-valine-glycine-glycine; glycine-phenylalanine-glycine-glycine; valine; proline; leucine or isoleucine.

In another embodiment, $R_{11}$ is any one of the following structures:

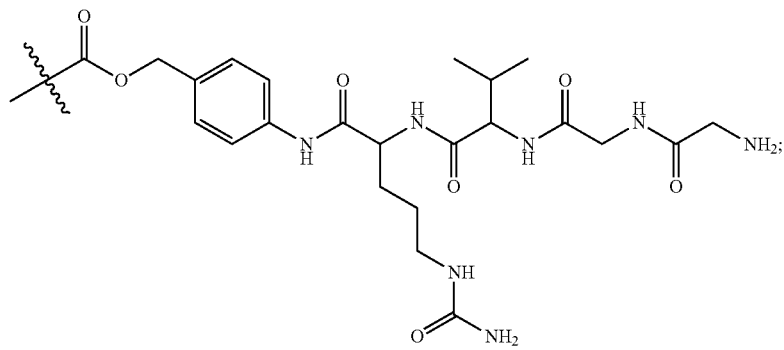

(1)

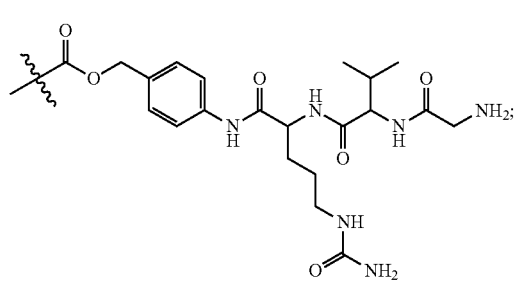

(2)

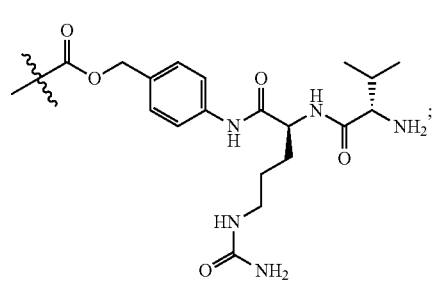

(3)

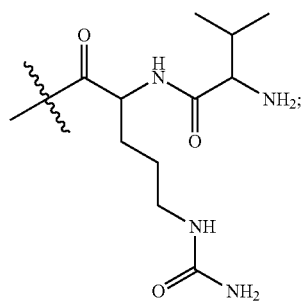

(4)

(5)
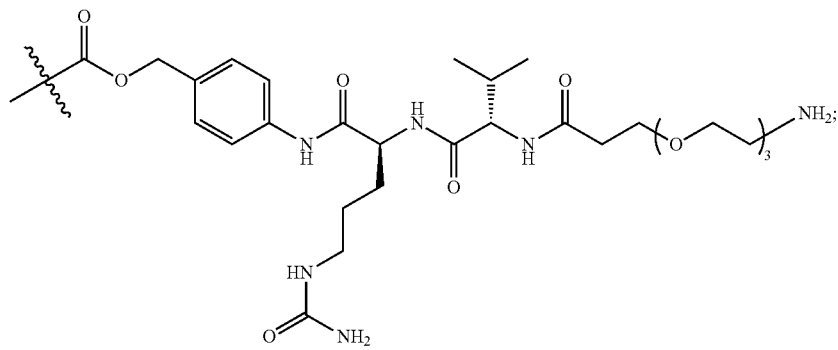
(6)
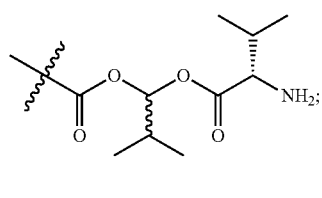
(7)
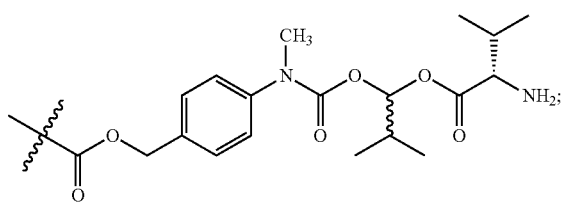
(8)
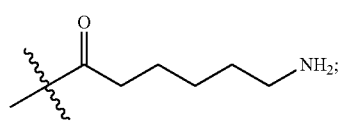
(9)
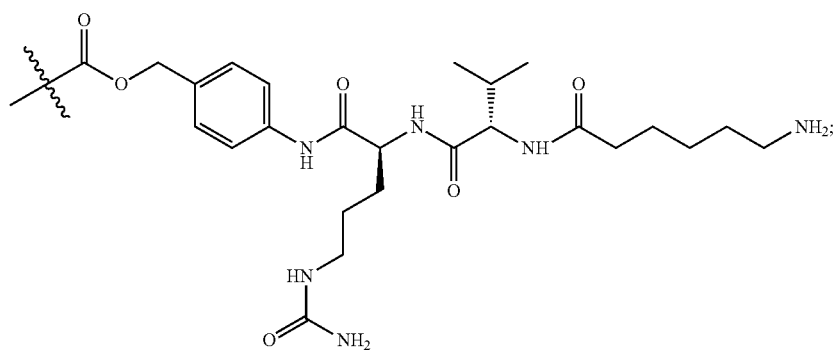
(10)
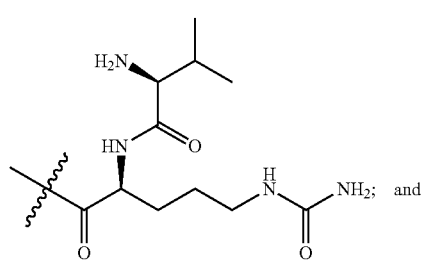
and

(11)
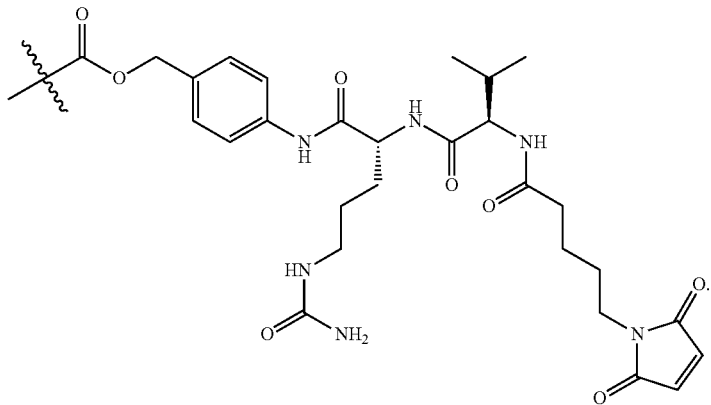
In some embodiments $R_{47}$ is any one of the following structures:
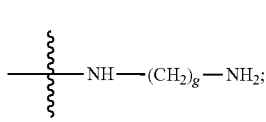  (1)
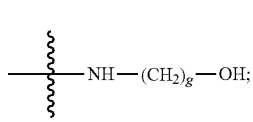  (2)
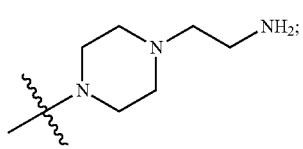  (3)
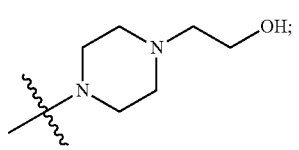  (4)
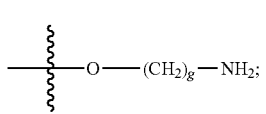  (5)
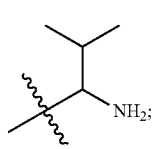  (6)
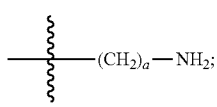  (7)
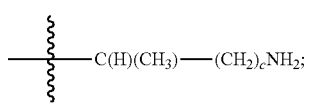  (8)
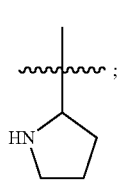  (9)
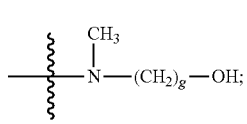  (10)
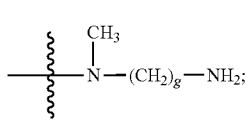  (11)
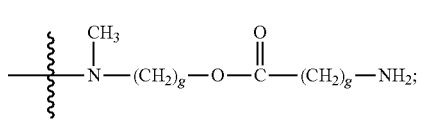  (12)
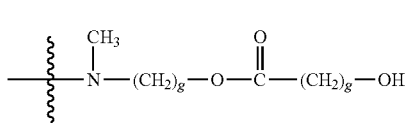  (13)
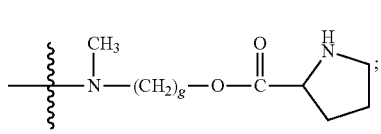  (14)

-continued
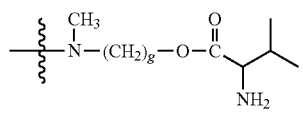
(15)
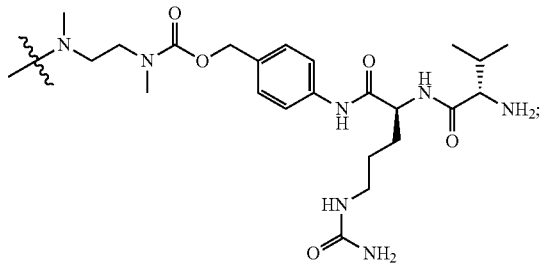
(16)
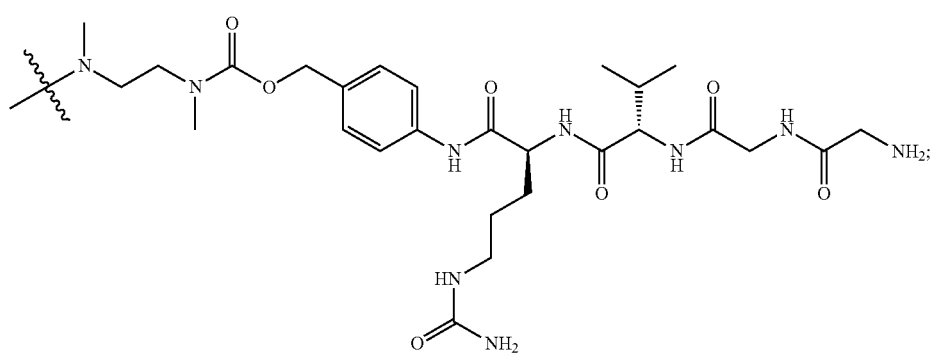
(17)
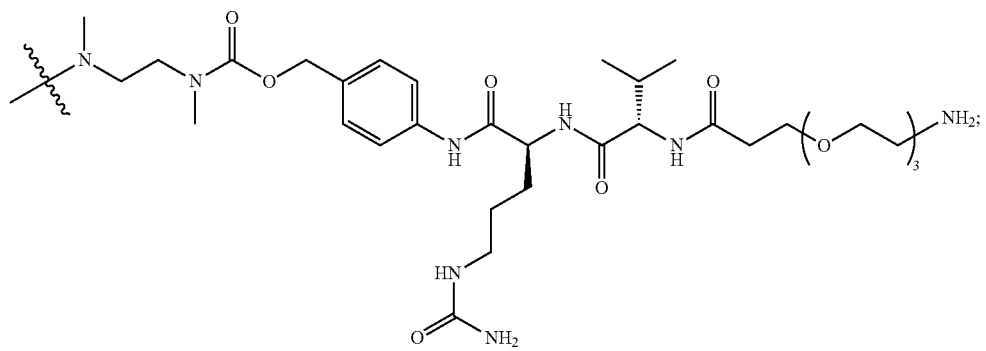
(18)
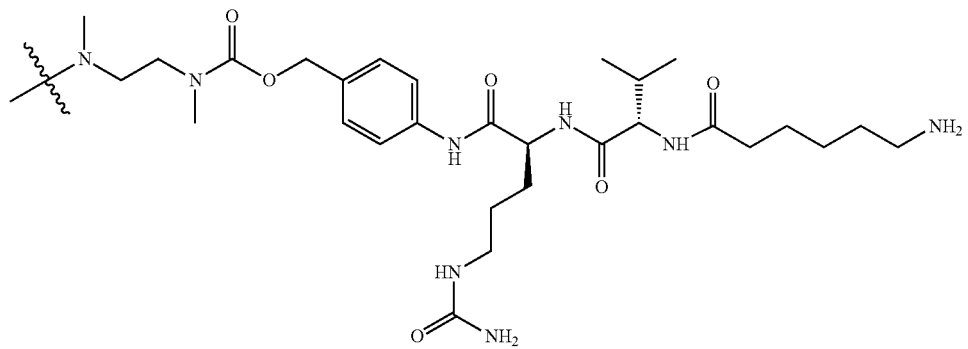
(19)
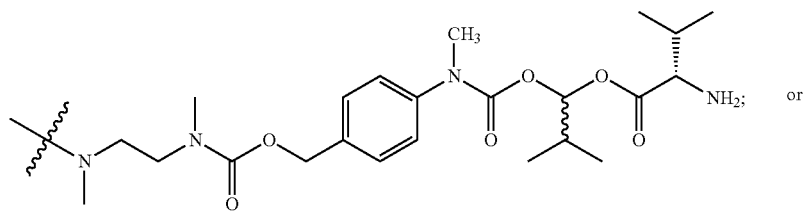
(20)
or (21)

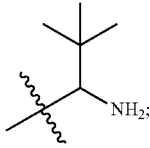

wherein:
a is an integer from 1 to 6;
c is an integer from 0 to 3; and
g is an integer from 2 to 6.

In another embodiment the auristatin is a compound of Formula (X):

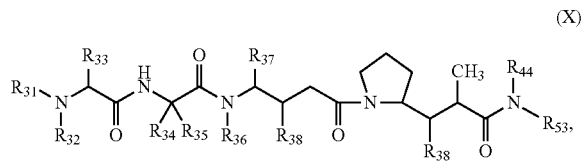

wherein:
each of $R_{31}$ and $R_{32}$ independently is hydrogen or $C_{1-8}$ alkyl and at most one of $R_{31}$ and $R_{32}$ is hydrogen;

$R_{33}$ is hydrogen, $C_{1-8}$ alkyl, $C_{3-8}$ carbocycle, $C_{6-10}$ aryl, $C_{1-8}$ alkyl-$C_{6-10}$ aryl, $X^1$—($C_{3-8}$ carbocycle), $C_{3-8}$ heterocycle or $X^1$—($C_{3-8}$ heterocycle);

$R_{34}$ is hydrogen, $C_{1-8}$ alkyl, $C_{3-8}$ carbocycle, $C_{6-10}$ aryl, $X^1$—$C_{6-10}$ aryl, $X^1$—($C_{3-8}$ carbocycle), $C_{3-8}$ heterocycle or $X^1$—($C_{3-8}$ heterocycle);

$R_{35}$ is hydrogen or methyl;

or $R_{34}$ and $R_{35}$, together with the carbon atom to which they attach form a carbocyclic ring having the formula —$(CR_{55}R_{41})_b$— wherein each of $R_{55}$ and $R_{41}$ independently is hydrogen or $C_{1-8}$ alkyl and b is an integer from 3 to 7;

$R_{36}$ is hydrogen or $C_{1-8}$ alkyl;

$R_{37}$ is hydrogen, $C_{1-8}$ alkyl, $C_{3-8}$ carbocycle, $C_{6-10}$ aryl, —$X^1$—$C_{6-10}$ aryl, —$X^1$—($C_{3-8}$ carbocycle), $C_{3-8}$ heterocycle or —$X^1$—($C_{3-8}$ heterocycle);

each $R_{38}$ independently is hydrogen, OH, $C_{1-8}$ alkyl, $C_{3-8}$ carbocycle or O—($C_{1-8}$ alkyl);

$R_{53}$ is:

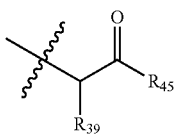

or $R_{54}$ $R_{39}$ is H, $C_{1-8}$ alkyl, $C_{6-10}$ aryl, —$X^1$—$C_{6-10}$ aryl, $C_{3-8}$ carbocycle, $C_{3-8}$ heterocycle, —$X^1$—$C_{3-8}$ heterocycle, —$C_{1-8}$ alkylene-$NH_2$, or $(CH_2)_2SCH_3$ each $X^1$ independently is $C_{1-10}$ alkylene or $C_{3-10}$ cycloalkylene;

$R_{44}$ is hydrogen or $C_{1-8}$ alkyl;

$R_{45}$ is $X^3$—$R_{42}$ or NH—$R_{19}$;

$X^3$ is O or S;

$R_{19}$ is hydrogen, OH, amino group, alkyl amino or —[C$(R_{20}R_{21})]_a$—$R_{22}$;

$R_{42}$ is an amino group, $C_{1-6}$ alkyl amino or —[C$(R_{20}R_{21})]_a$—$R_{22}$;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{22}$ is —OH, —NHR$_{23}$, —COOH, —$R_{82}$—C(O)(CH$_2$)$_c$—C(H)(R$_{23}$)—N(H)(R$_{23}$), —$R_{82}$—C(O)(CH$_2$)$_d$—(OCH$_2$—CH$_2$)$_f$—N(H)(R$_{23}$) or —$R_{82}$—(C(O)—CH(X$^2$)—NH)$_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is a hydrogen or $X^2$ and NR$_{77}$ form a nitrogen containing cyclic compound;

$R_{82}$ is —NH or oxygen;

$R_{54}$ is —C(R$_{56}$)$_2$—C(R$_{56}$)$_2$—$C_{6-10}$ aryl, —C(R$_{56}$)$_2$—C(R$_{56}$)$_2$—$C_{3-8}$ heterocycle or —C(R$_{56}$)$_2$—C(R$_{56}$)$_2$—$C_{3-8}$ carbocycle;

$R_{56}$ is independently selected from H, OH, $C_{1-8}$ alkyl, $C_{3-8}$ carbocycle, —O—$C_{1-8}$ alkyl, —O—C(O)—$R_{29}$ and —O—$R_{23}$—O—$C_{1-6}$ alkyl-$NH_2$;

$R_{29}$ is an amino group, 5 to 12-membered heterocycloalkyl, —$R_{28}$—$C_{1-6}$ alkyl-$R_{22}$, $R_{28}$—$C_{5-12}$ heterocycloalkyl-$C_{1-6}$ alkyl-$R_{22}$, —[C$(R_{20}R_{21})]_a$—$R_{22}$, or —$R_{28}$—$C_{1-6}$ alkyl-$C_{6-12}$ aryl-$C_{1-6}$ alkyl-$R_{22}$; or $R_{29}$ is $R_{47}$ as defined herein;

$R_{28}$ is absent, NH or oxygen;

a is an integer from 1 to 6;

c is an integer from 0 to 3;

d is an integer from 1 to 3; and f is an integer from 1 to 12.

In some embodiments, in the auristatin compound of Formula (X):

$R_{39}$ is benzyl or

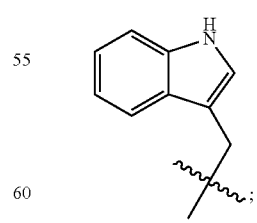

and $R_{44}$ is hydrogen.

In another embodiment the auristatin is a compound of Formula (Xa):

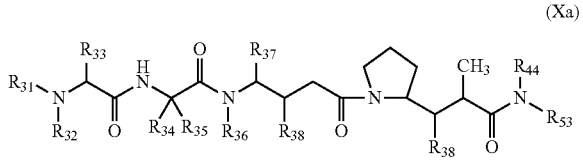

(Xa)

wherein:

R$_{33}$ through R$_{38}$, and R$_{44}$ are as defined herein, one of R$_{31}$ and R$_{32}$ is hydrogen or C$_{1-8}$ alkyl and the other is:

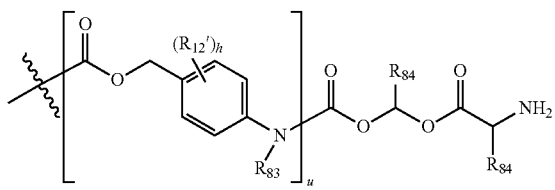

wherein:

R$_{83}$ is hydrogen or CH$_3$;

R$_{84}$ is C$_{1-6}$ alkyl or C$_{6-10}$ aryl;

each R$_{12}$' independently is halogen, —C$_{1-8}$ alkyl, —O—C$_{1-8}$ alkyl, nitro or cyano;

h is an integer from 0 to 4; and u is an integer 0 or 1;

R$_{53}$ is:

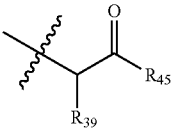

or R$_{54}$

R$_{39}$ is H, C$_{1-8}$ alkyl, C$_{6-10}$ aryl, —X$^1$—C$_{6-10}$ aryl, C$_{3-8}$ carbocycle, C$_{3-8}$ heterocycle, —X$^1$—C$_{3-8}$ heterocycle, —C$_{1-8}$ alkylene-NH$_2$, or (CH$_2$)$_2$SCH$_3$, each X$^1$ independently is C$_{1-10}$ alkylene or C$_{3-10}$ cycloalkylene;

R$_{45}$ is X$^3$—R$_{42}$ or NH—R$_{19}$;

X$^3$ is O or S;

R$_{19}$ is hydrogen, OH, amino group, alkyl amino or —[C(R$_{20}$R$_{21}$)]$_a$—R$_{22}$;

R$_{42}$ is H, an amino group, C$_{1-6}$ alkyl amino or —[C(R$_{20}$R$_{21}$)]$_a$—R$_{22}$;

each of R$_{20}$ and R$_{21}$ independently is hydrogen, C$_{1-6}$ alkyl, C$_{6-10}$ aryl, hydroxylated C$_{6-10}$ aryl, polyhydroxylated C$_{6-10}$ aryl, 5 to 12-membered heterocycle, C$_{3-8}$ cycloalkyl, hydroxylated C$_{3-8}$ cycloalkyl, polyhydroxylated C$_{3-8}$ cycloalkyl or a side chain of a natural or unnatural amino acid;

R$_{22}$ is —OH, —NHR$_{23}$, —COOH, —R$_{82}$—C(O)(CH$_2$)$_c$—C(H)(R$_{23}$)—N(H)(R$_{23}$), —R$_{82}$—C(O)(CH$_2$)$_d$—(OCH$_2$—CH$_2$)$_f$—N(H)(R$_{23}$) or —R$_{82}$—(C(O)—CH(X$^2$)—NH)$_d$—R$_{77}$;

each R$_{23}$ independently is hydrogen, C$_{1-6}$ alkyl, C$_{6-10}$ aryl, C$_{3-8}$ cycloalkyl, —COOH, or —COO—C$_{1-6}$ alkyl;

X$^2$ is a side chain of a natural or unnatural amino acid;

R$_{77}$ is a hydrogen or X$^2$ and NR$_{77}$ form a nitrogen containing cyclic compound;

R$_{82}$ is —NH or oxygen;

R$_{54}$ is —C(R$_{56}$)$_2$—C(R$_{56}$)$_2$—C$_{6-10}$ aryl, —C(R$_{56}$)$_2$—C(R$_{56}$)$_2$—C$_{3-8}$ heterocycle or —C(R$_{56}$)$_2$—C(R$_{56}$)$_2$—C$_{3-8}$ carbocycle;

R$_{56}$ is independently selected from H, OH, C$_{1-8}$ alkyl, C$_{3-8}$ carbocycle, —O—C$_{1-8}$ alkyl, —O—C(O)—R$_{29}$ and —O—R$_{23}$—O—C$_{1-6}$ alkyl-NH$_2$;

R$_{29}$ is an amino group, 5 to 12-membered heterocycloalkyl, —R$_{28}$—C$_{1-6}$ alkyl-R$_{22}$, R$_{28}$—C$_{5-12}$ heterocycloalkyl-C$_{1-6}$ alkyl-R$_{22}$, —[C(R$_{20}$R$_{21}$)]$_a$—R$_{22}$, or —R$_{28}$—C$_{1-6}$ alkyl-C$_{6-12}$ aryl-C$_{1-6}$ alkyl-R$_{22}$; or R$_{29}$ is R$_{47}$ as defined herein;

R$_{28}$ is absent, NH or oxygen;

a is an integer from 1 to 6;

c is an integer from 0 to 3;

d is an integer from 1 to 3; and f is an integer from 1 to 12.

In one embodiment, the auristatin compound of Formula (Xa) is a compound of Formula (XIa) or Formula (XIb):

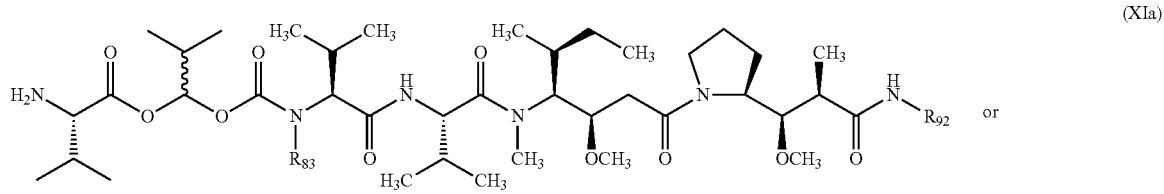

(XIa)

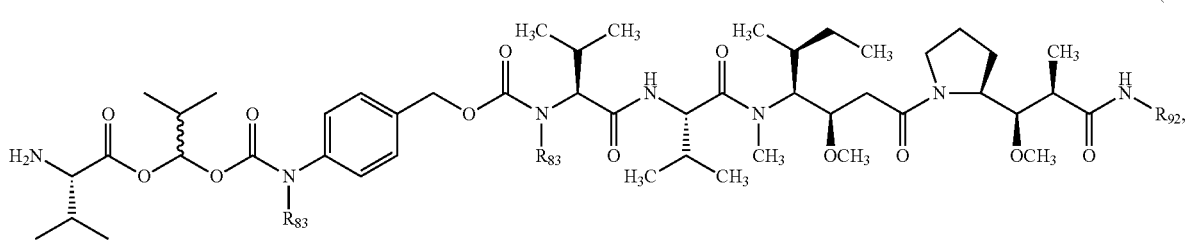

(XIb)

wherein:
R$_{92}$ is:
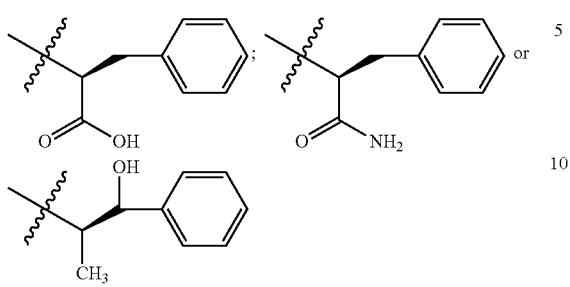
and
R$_{83}$ is hydrogen or CH$_3$.
In one embodiment the auristatin of Formula (X) is a compound of Formula (XI), Formula (XII) or Formula (XIII):
wherein the compound of Formula (XI) is:
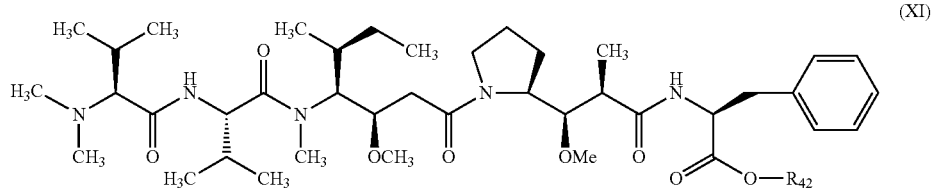
(XI)
wherein R$_{42}$ is —CH$_3$ or any one of the following structures:
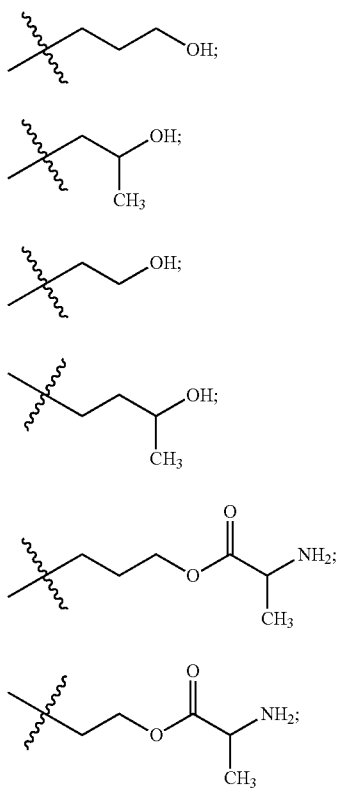
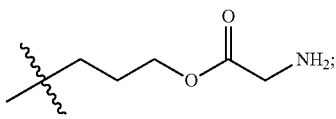
(7)
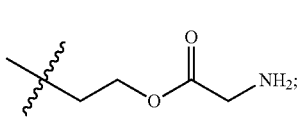
(8)
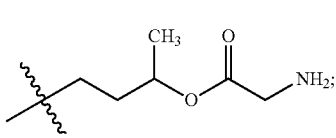
(9)
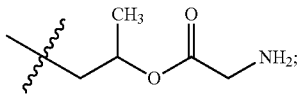
(10)
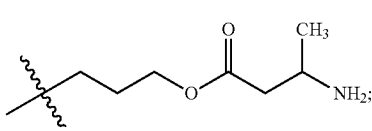
(11)
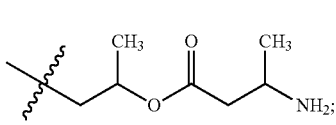
(12)
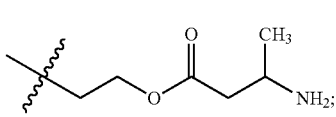
(13)
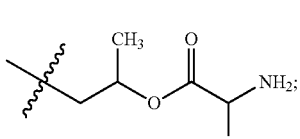
(14)
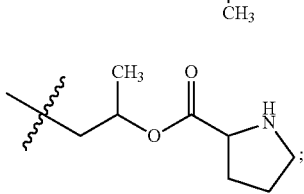
(15)

-continued
(16) 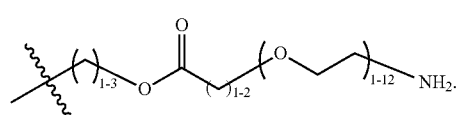
(17) —(CH₂)ₐ—NH₂;
(18) —C(H)(CH₃)—(CH₂)꜀NH₂;
(19) 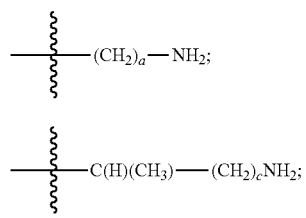
(20) 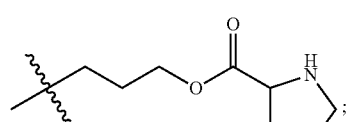
(21) 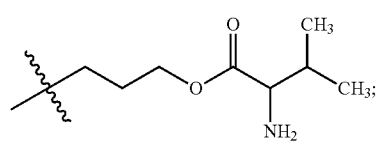
(22) 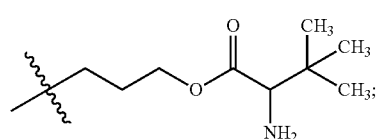 and
(23) 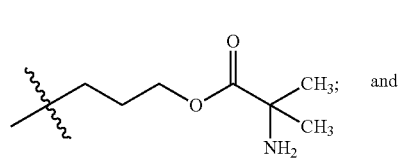
wherein:
a is an integer from 1 to 6;
c is an integer from 0 to 3; and
g is an integer from 2 to 6;
wherein the compound of Formula (XII) is:
wherein $R_{40}$ is hydrogen, —OH, —NH₂, or any of the following structures:
(1) 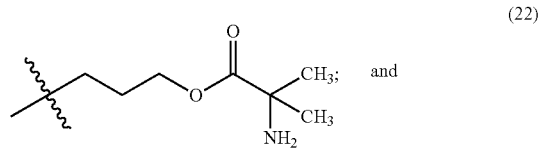
(2)
(3)
(4)
(5)
(6)
(7)
(8)
(9)
(10)
(XII) 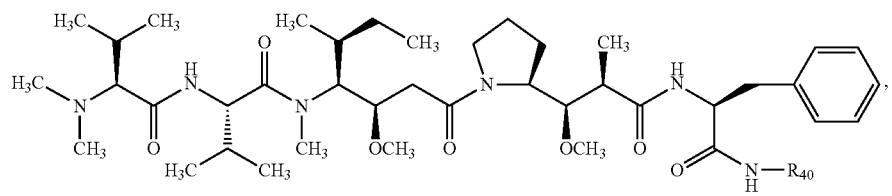

-continued
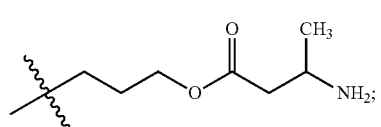 (11)
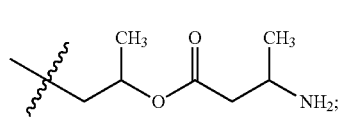 (12)
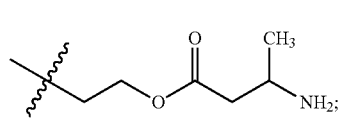 (13)
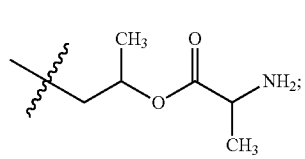 (14)
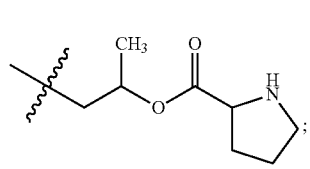 (15)
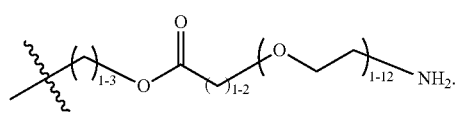 (16)
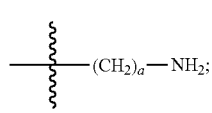 (17)
—(CH$_2$)$_a$—NH$_2$;
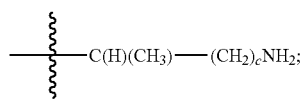 (18)
—C(H)(CH$_3$)—(CH$_2$)$_c$NH$_2$;
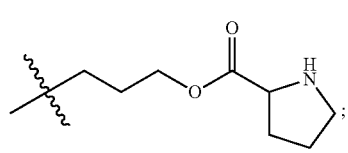 (19)
-continued
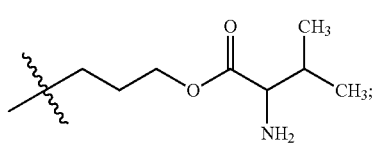 (20)
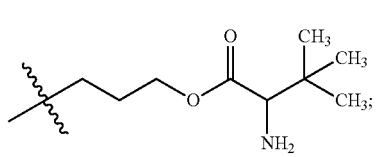 (21)
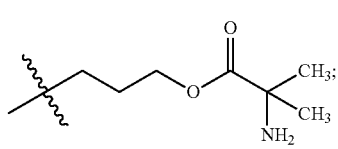 (22)
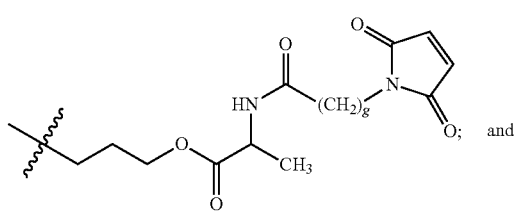 (23)
and
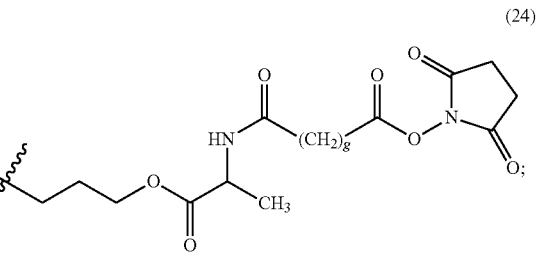 (24)
wherein:
a is an integer from 1 to 6;
g is an integer from 2 to 6; and
c is an integer from 0 to 3;
wherein the compound of Formula (XIII) is:
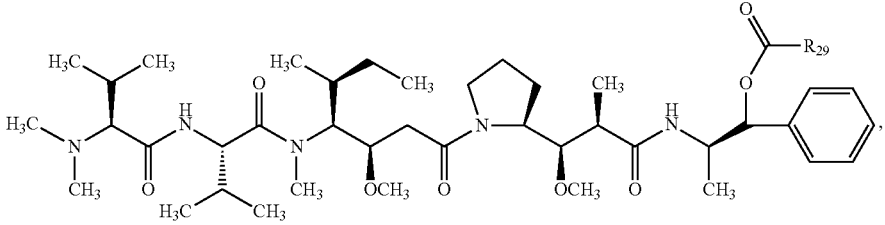 (XIII)

wherein $R_{29}$ is an amino group, 5 to 12-membered heterocycloalkyl, —$R_{28}$—$C_{1-6}$ alkyl-$R_{22}$, $R_{28}$—$C_{5-12}$ heterocycloalkyl-$C_{1-6}$ alkyl-$R_{22}$, —$R_{28}$—[$C(R_{20}R_{21})]_a$—$R_{22}$, or —$R_{28}$—$C_{1-6}$ alkyl-$C_{6-12}$ aryl-$C_{1-6}$ alkyl-$R_{22}$; or $R_{29}$ is $R_{47}$ as defined herein;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{22}$ is —OH, —$NHR_{23}$, —COOH, —$R_{82}$—C(O)(CH$_2$)$_c$—C(H)(R$_{23}$)—N(H)(R$_{23}$), —$R_{82}$—C(O)(CH$_2$)$_d$—(OCH$_2$—CH$_2$)$_f$—N(H)(R$_{23}$) or —$R_{82}$—(C(O)—CH(X$^2$)—NH)$_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is —NH or oxygen;

$R_{28}$ is absent, NH or oxygen;

a is an integer from 1 to 6;

c is an integer from 0 to 3;

d is an integer from 1 to 3; and f is an integer from 1 to 12.

In one embodiment, in Formula (XII), $R_{40}$ is

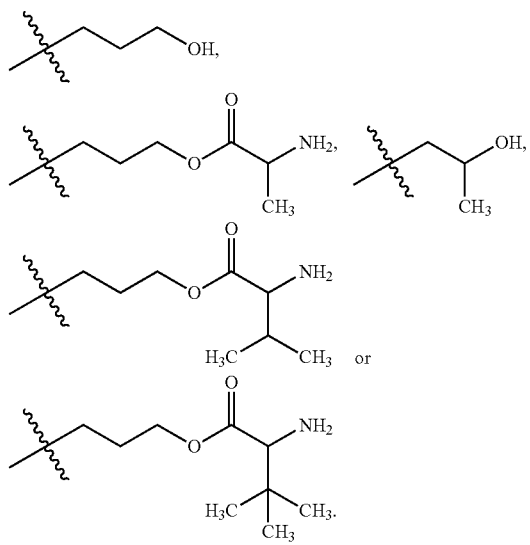

In another embodiment, the compound of Formula (XII) is a compound of Formula (XIIb) or (XIIc):

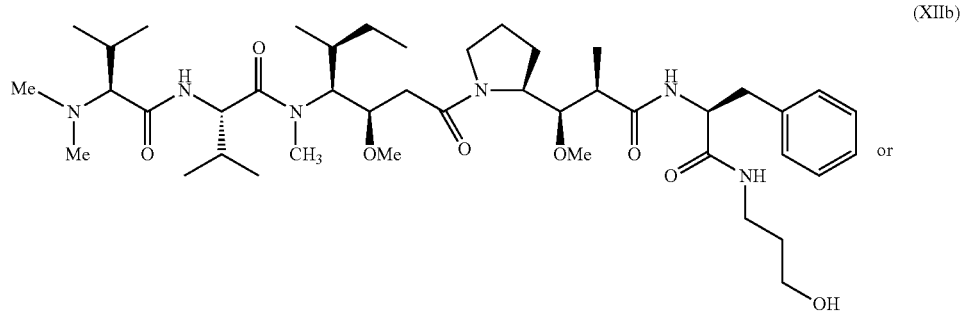

(XIIb)

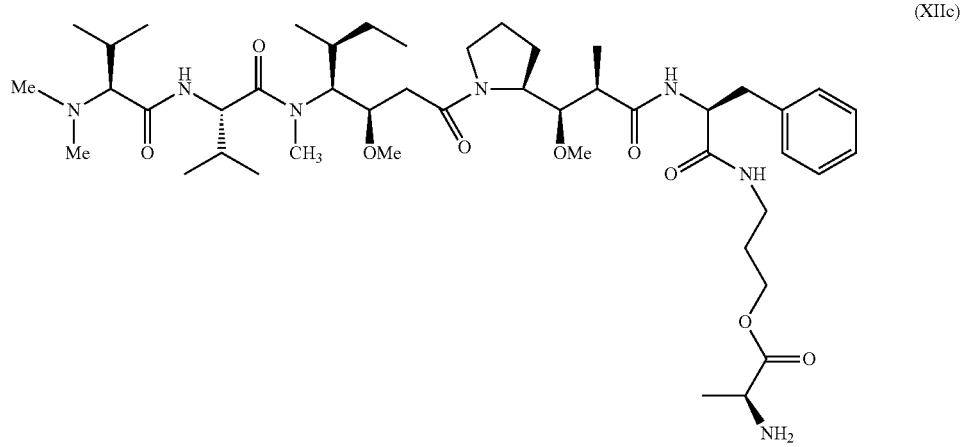

(XIIc)

In one embodiment in the compound of Formula (XIII), $R_{29}$ is —$NH_2$, 5 membered heterocycloalkyl, —$R_{28}$—$C_{1-6}$ alkyl-$R_{22}$, $R_{28}$—$C_{5-12}$ heterocycloalkyl-$C_{1-6}$ alkyl-$R_{22}$ or —$R_{28}$—$C_{1-6}$ alkyl-$C_{6-12}$ aryl-$C_{1-6}$ alkyl-$R_{22}$; or $R_{29}$ is $R_{47}$ as defined herein;

$R_{28}$ is absent, NH or oxygen;

$R_{22}$ is —OH, —$NHR_{23}$, —COOH, —$R_{82}$—C(O)($CH_2$)$_c$—C(H)($R_{23}$)—N(H)($R_{23}$), —$R_{82}$—C(O)($CH_2$)$_d$—(O$CH_2$—$CH_2$)$_f$—N(H)($R_{23}$) or —$R_{82}$—(C(O)—CH($X^2$)—NH)$_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is —NH or oxygen;

c is an integer from 0 to 3;

d is an integer from 1 to 3; and f is an integer from 1 to 12.

In yet another embodiment, $R_{29}$ is any one of the following structures:

(1)
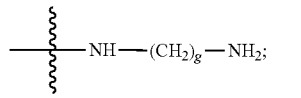

(2)
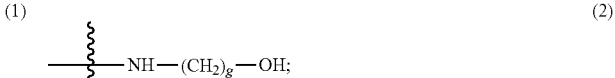

(3)
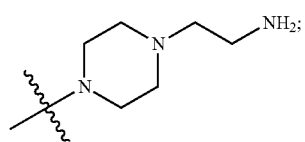

(4)
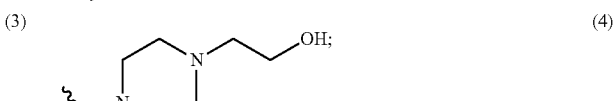

(5)
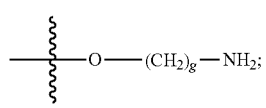

(6)

(7)
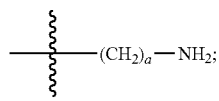

(8)
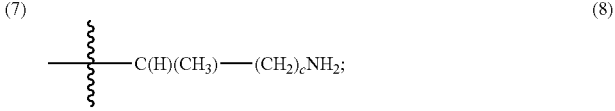

(9)
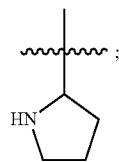

(10)
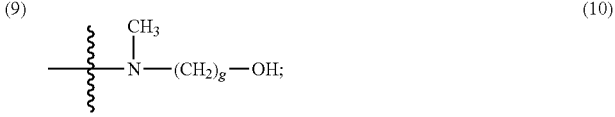

(11)
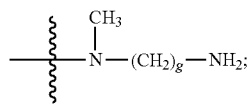

(12)
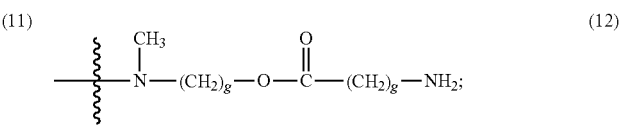

(13)
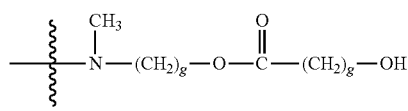

(14)
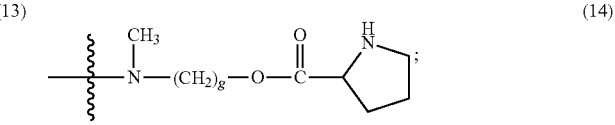

(15)
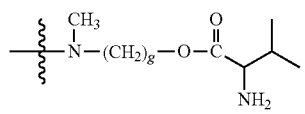

(16)
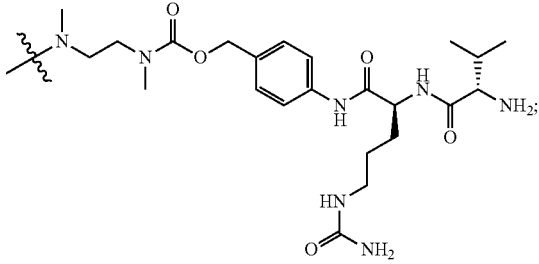

(17)
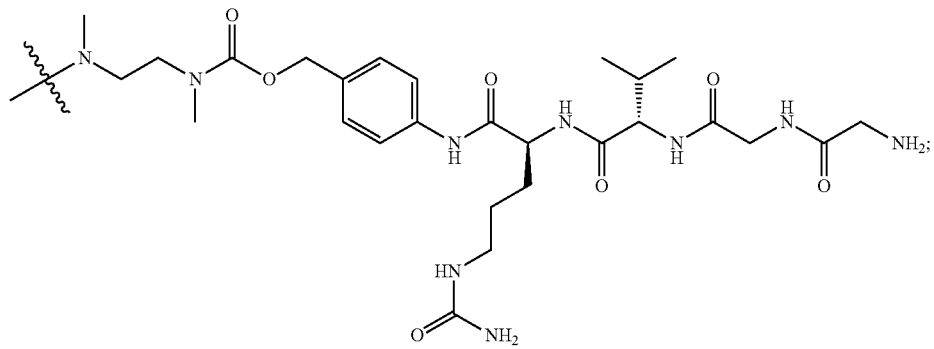
(18)
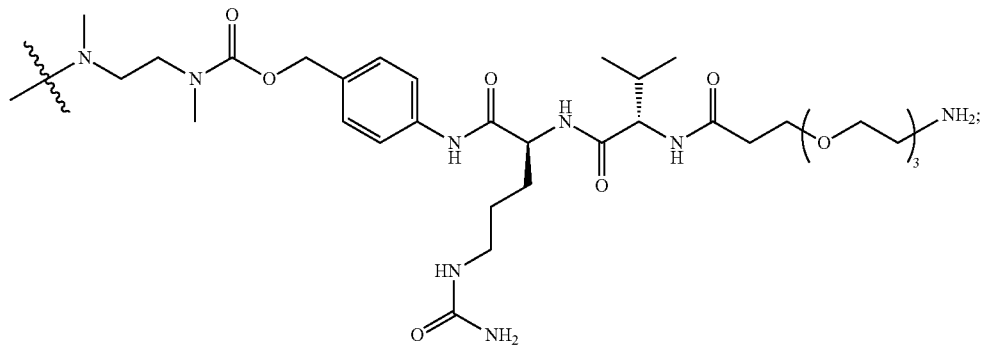
(19)
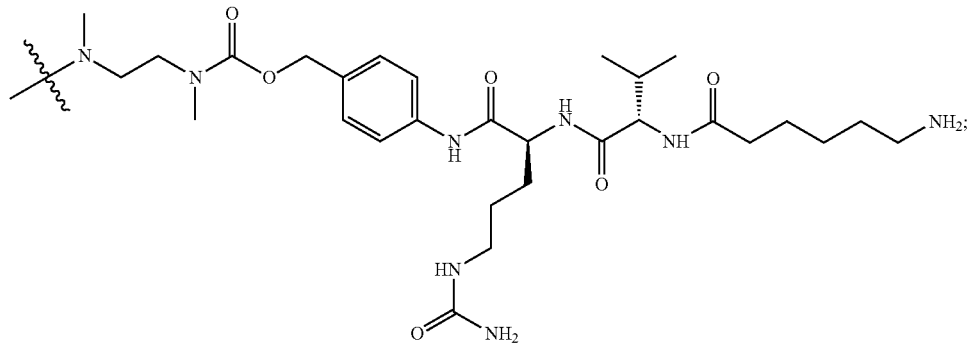
(20)
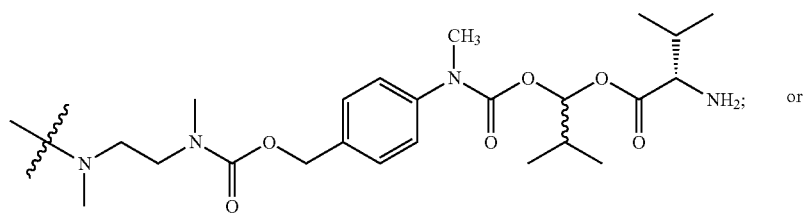 or
(21)
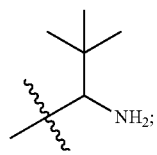

wherein:
a is an integer from 1 to 6;
c is an integer from 0 to 3; and
g is an integer from 2 to 6.

In one embodiment, the MEK inhibitor is a compound of Formula (XIV):

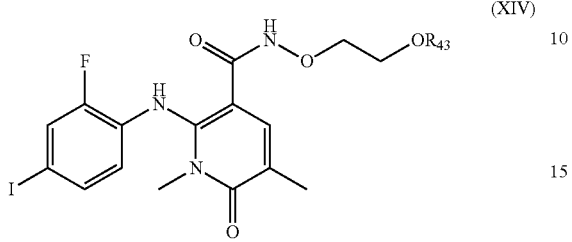
(XIV)

wherein $R_{43}$ is H or —$R_{46}$—$R_{47}$;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{22}$ is —OH, —$NH_2$, —COOH, —$R_{82}$—C(O)($CH_2$)$_c$—C(H)($R_{23}$)—N(H)($R_{23}$), —$R_{82}$—(C(O)($CH_2$)$_d$—O$CH_2$—$CH_2$)$_f$—N(H)($R_{23}$) or —$R_{82}$—(C(O)—CH($X^2$)—NH)$_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is —NH or oxygen;

$R_{46}$ is —C(O)—; —C(O)—O—, —C(O)—NH—, or absent;

$R_{47}$ is as defined herein;

a is an integer from 1 to 6;
c is an integer from 0 to 3;
d is an integer from 1 to 3; and
f is an integer from 1 to 12.

Further examples of the MEK inhibitor are disclosed in U.S. Pat. No. 7,517,994 B2.

In some embodiments $R_{43}$ is —C(O)—($CH_2$)$_a$—$NH_2$, or —C(O)—C(H)($CH_3$)—($CH_2$)$_c$—$NH_2$; in which a is an integer from 1 to 6; and c is an integer from 0 to 3.

In another embodiment, the duocarmycin compound is a compound of Formula (XV):

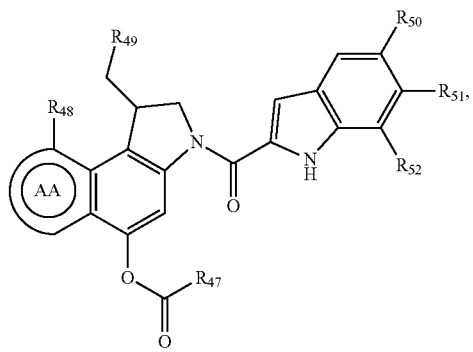
(XV)

wherein:
$R_{47}$ is as defined herein;
$R_{48}$ is hydrogen, —COO$C_{1-6}$ alkyl, —COOH, —$NH_2$ or —$CH_3$;
$R_{49}$ is Cl, Br or —OH;
$R_{50}$ is hydrogen, —$OCH_3$,

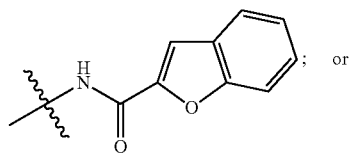; or

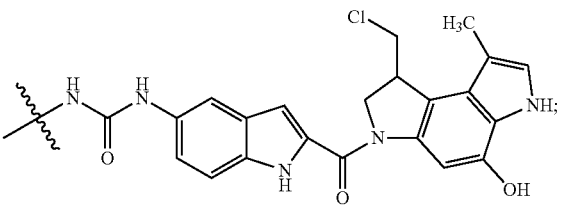

each of $R_{51}$ and $R_{52}$ independently is hydrogen or —$OCH_3$; and ring AA is either a phenyl or pyrrolyl ring.

Further examples of duocarmycin compounds are disclosed in U.S. Pat. No. 7,553,816.

In one embodiment the duocarmycin compound of Formula (XV) is a compound of Formula (XVI), (XVII), (XVIII) or (XIX):

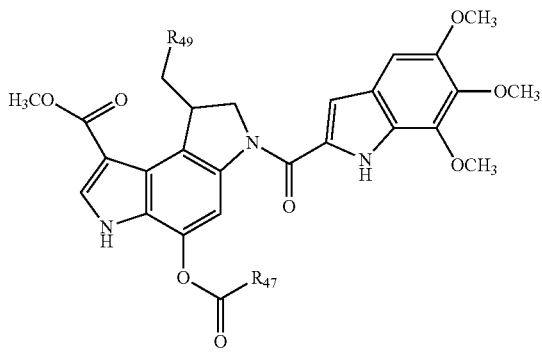
(XVI)

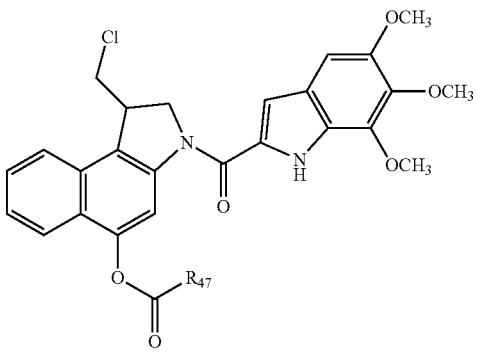
(XVII)

(XVIII)
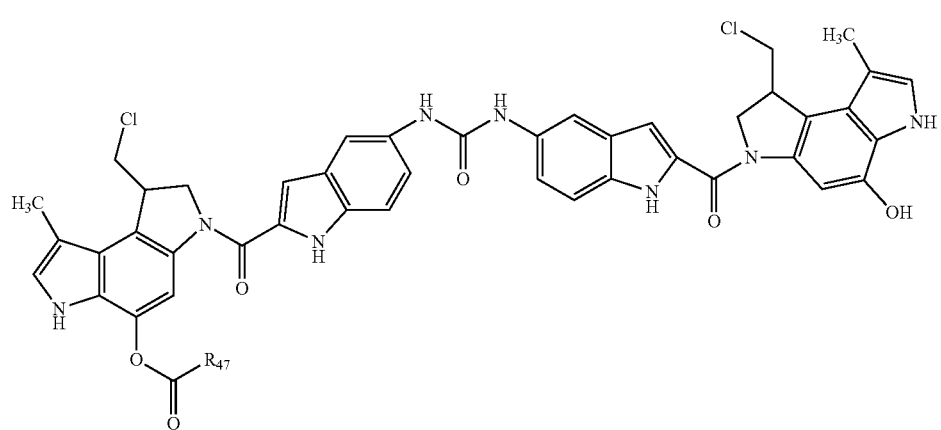
(XIX)
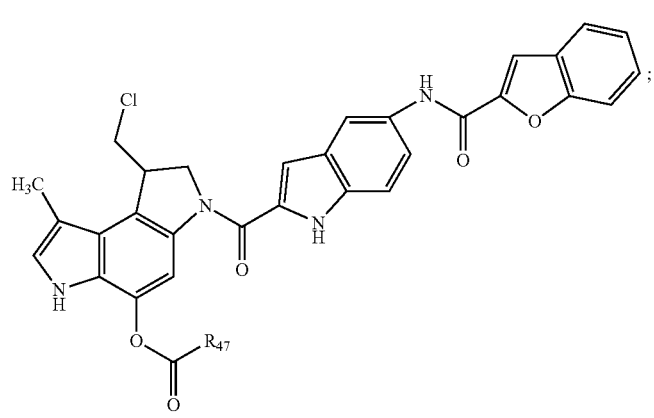

wherein:

R$_{49}$ is Cl, Br or —OH; and

R$_{47}$ is as defined herein.

In another embodiment, the duocarmycin compound is a duocarmycin SA compound of Formula (XX): U.S. Pat. No. 5,101,038; or (XXI):

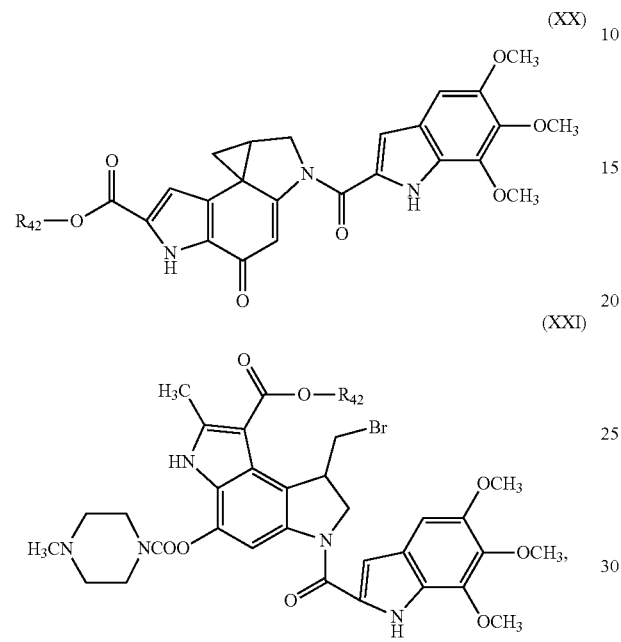

wherein:

R$_{42}$ is C$_{1-6}$ alkyl amino or —[C(R$_{20}$R$_{21}$)]$_a$—R$_{22}$;

each of R$_{20}$ and R$_{21}$ independently is hydrogen, C$_{1-6}$ alkyl, C$_{6-10}$ aryl, hydroxylated C$_{6-10}$ aryl, polyhydroxylated C$_{6-10}$ aryl, 5 to 12-membered heterocycle, C$_{3-8}$ cycloalkyl, hydroxylated C$_{3-8}$ cycloalkyl, polyhydroxylated C$_{3-8}$ cycloalkyl or a side chain of a natural or unnatural amino acid;

R$_{22}$ is —OH, —NH$_2$, —COOH, —R$_{82}$—C(O)(CH$_2$)$_c$—C(H)(R$_{23}$)—N(H)(R$_{23}$), —R$_{82}$—C(O)(CH$_2$)$_d$—(OCH$_2$—CH$_2$)$_f$—N(H)(R$_{23}$), or —R$_{82}$—(C(O)—CH(X$^2$)—NH)$_d$—R$_{77}$;

each R$_{23}$ independently is hydrogen, C$_{1-6}$ alkyl, C$_{6-10}$ aryl, C$_{3-8}$ cycloalkyl, —COOH, or —COO—C$_{1-6}$ alkyl;

X$^2$ is a side chain of a natural or unnatural amino acid;

R$_{77}$ is a hydrogen or X$^2$ and NR$_{77}$ form a nitrogen containing cyclic compound;

R$_{82}$ is —NH or oxygen;

a is an integer from 1 to 6;

c is an integer from 0 to 3;

d is an integer from 1 to 3; and f is an integer from 1 to 12.

In some embodiments, R$_{42}$ is any one of the following structures:

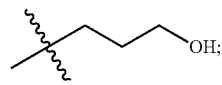 (1)

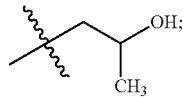 (2)

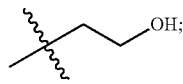 (3)

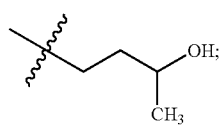 (4)

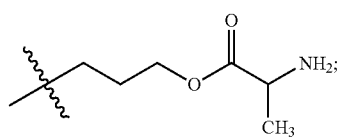 (5)

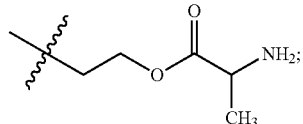 (6)

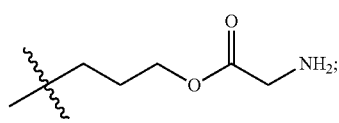 (7)

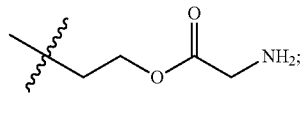 (8)

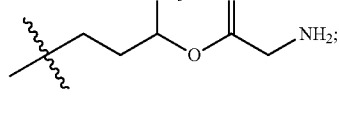 (9)

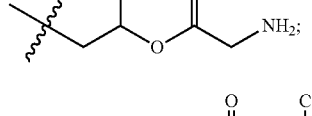 (10)

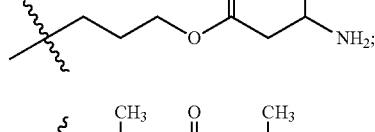 (11)

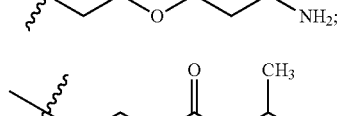 (12)

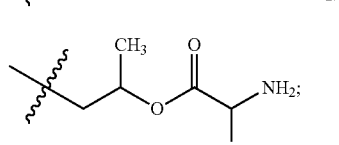 (13)

(14)

(15)
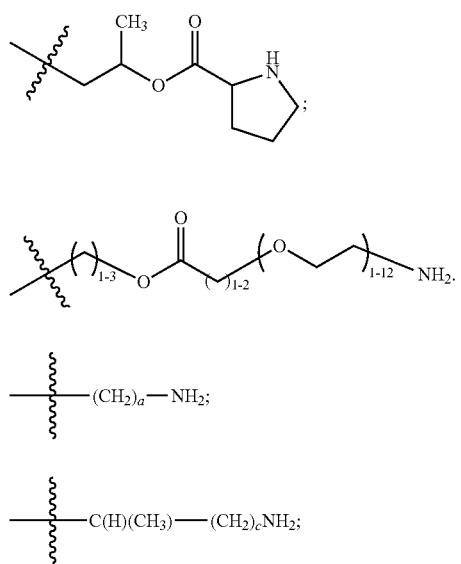
wherein:
  a is an integer from 1 to 6;
  g is an integer from 2 to 6; and
  c is an integer from 0 to 3.
In another embodiment, the KSP inhibitor compound is a compound of Formula (XXVI):
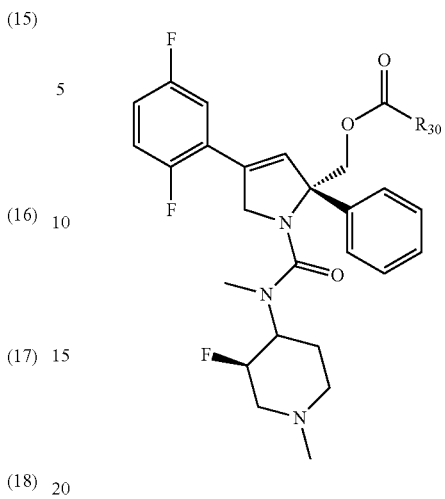
wherein $R_{30}$ is as defined herein.
In some embodiments $R_{30}$ is:
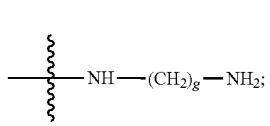 (1)
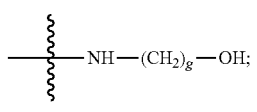 (2)
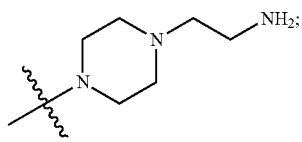 (3)
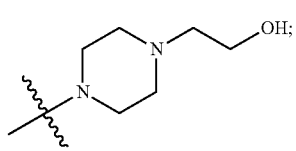 (4)
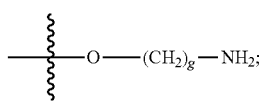 (5)
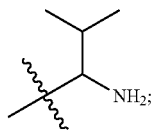 (6)
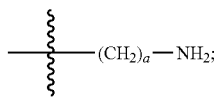 (7)
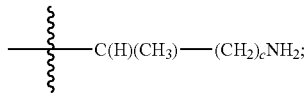 (8)

(9)

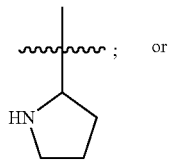 or (XXVIII)

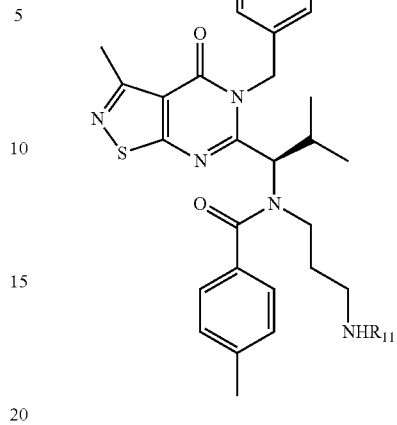

(10)

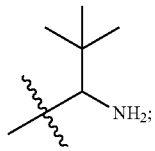

wherein:

a is an integer from 1 to 6;

c is an integer from 0 to 3; and g is an integer from 2 to 6.

In another embodiment, the duocarmycin compound is Duocarmycin A, Duocarmycin B1, Duocarmycin B2, Duocarmycin C1, Duocarmycin C2, Duocarmycin D, CC-1065, Adozelesin, Bizelesin or Carzelesin In another embodiment the KSP inhibitor compound is a compound of Formula (XXVII), (XXVIII) or (XXIX):

(XXVII)

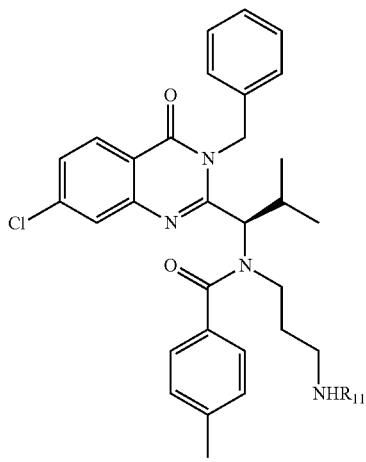

(XXIX)

wherein:

$R_{11}$ is as defined herein.

One skilled in the art of therapeutic agents will readily understand that each of the therapeutic agents described herein can be modified in such a manner that the resulting compound still retains the specificity and/or activity of the original compound. The skilled artisan will also understand that many of these compounds can be used in place of the therapeutic agents described herein. Thus, the therapeutic agents of the present invention include analogs and derivatives of the compounds described herein.

Table B below provides more examples of the therapeutic agents and derivatives thereof suitable for conjugation to form the polymer-drug-protein conjugates or polymer-drug scaffolds of the invention. Spectral data of certain compounds are also provided (ND in the table means "not determined"). These examples may also be the active form of the drug when it is released from the conjugates in vitro or in vivo.

TABLE B
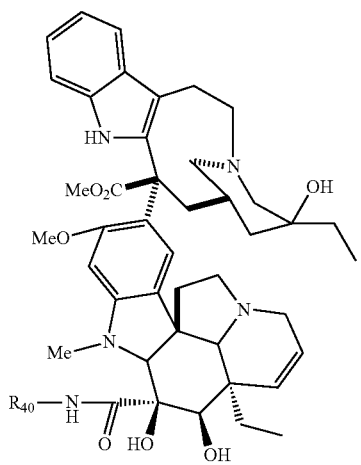
(VI)
R₄₀
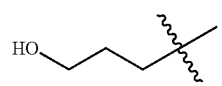 [SMILES: *CCCO]
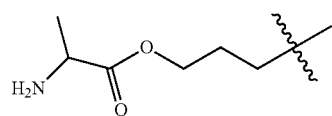 [SMILES: *CCCOC(=O)C(C)N]
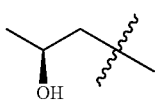 [SMILES: *C[C@H](C)O]
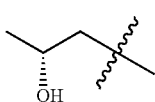
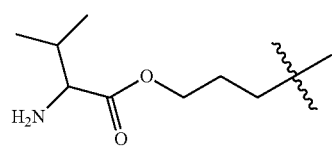 [SMILES: *CCCOC(=O)C(N)C(C)C]
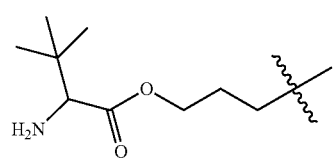 [SMILES: *CCCOC(=O)C(N)C(C)(C)C]

TABLE B-continued
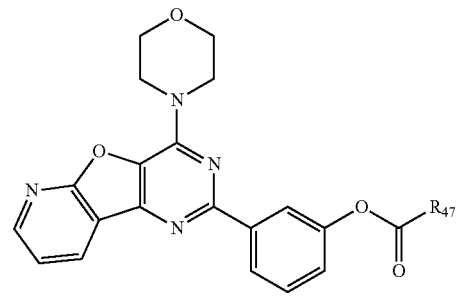
(IX)
| $R_{47}$ | m/z |
|---|---|
| 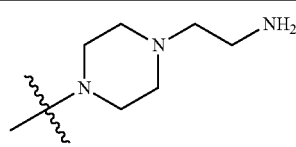 | ND |
| 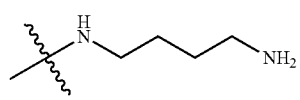 | ND |
| 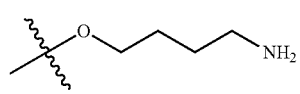 [SMILES: *OCCCCN] | ND |
| 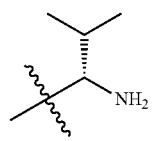 [SMILES: *[C@@H](N)C(C)C] | ND |
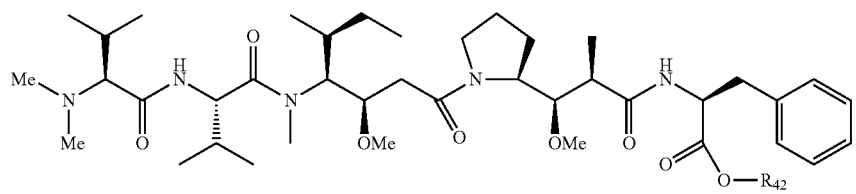
(XI)
| $R_{42}$ | m/z |
|---|---|
| H | |
| —CH$_3$ | 760 |
| 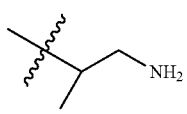 [SMILES: *C(C)CN] | 802.6 |
| 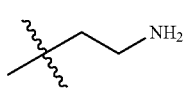 | 790 |
| 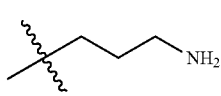 [SMILES: *CCCN] | 804 |

TABLE B-continued (XII)

| $R_{40}$ | m/z |
|---|---|
| —H | |
| (4-hydroxybutyl) | 803.5 |
| (3-hydroxypropyl) | 789.1 |
| (Boc-Ala ester of butanol linker) | 974.2 |
| (Ala ester of butanol linker) | 874.5 |
| (Val ester of butanol linker) | 902.2 |
| (aminoethyl) | ND |
| (aminopropyl) | ND |
| —OH | 788 |
| (2-hydroxypropyl, R) | 803.4 |
| (2-hydroxypropyl, S) | 803.4 |
| (isobutyrate ester) | 874.4 |

TABLE B-continued

| Structure | Value |
|---|---|
| (structure) | 874.4 |
| (structure) | 874.4 |
| (structure) | 874.4 |
| (structure) | 900.2 |
| (structure) | 900.2 |
| (structure) | 900.5 |
| (structure) | 900.5 |
| (structure) | 1016.6 |

TABLE B-continued
(XIII)
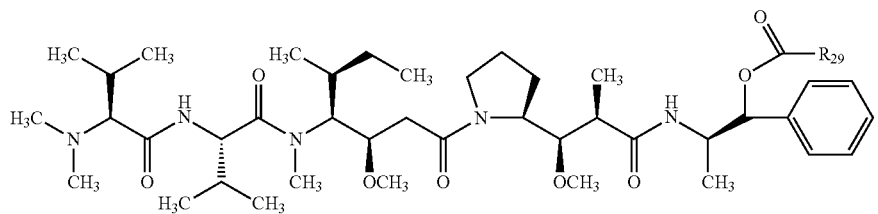
| —C(O)—R$_{29}$ | m/z |
|---|---|
| 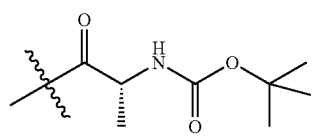 [SMILES: *C(=O)[C@@H](C)NC(=O)OC(C)(C)C] | 903.2 |
| 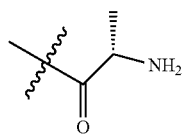 | 803.1 |
| 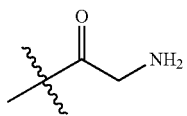 [SMILES: *C(=O)CN] | 790 |
| 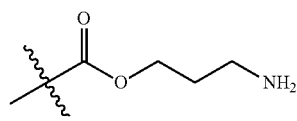 [SMILES: *C(=O)OCCCN] | 832.6 |
| 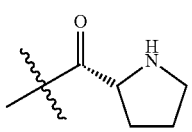 | 829.1 |
| 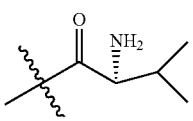 [SMILES: *C(=O)[C@@H](N)C(C)C] | 802 |

TABLE B-continued
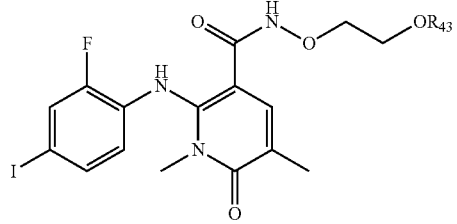
(XIV)
| R43 | m/z |
|---|---|
| 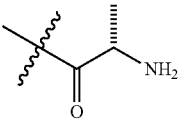 [SMILES: *C(=O)[C@H](C)N] | ND |
| 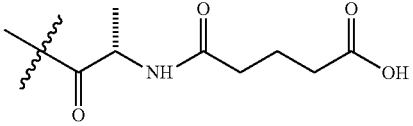 [SMILES: *C(=O)[C@H](C)NC(=O)CCCC(=O)O] | 644.9 |
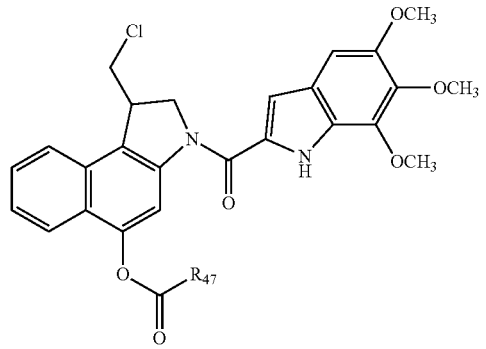
(XVII)
| R47 | m/z |
|---|---|
| 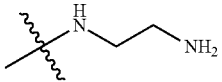 [SMILES: *NCCN] | 553.1 |
| 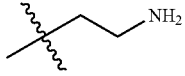 | 538.1 |
| 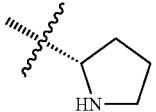 | 564.1 |
| 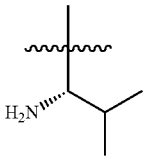 | 566.1 |

TABLE B-continued
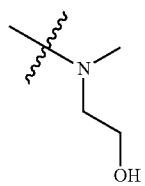 [SMILES: *N(C)CCO] 568.1
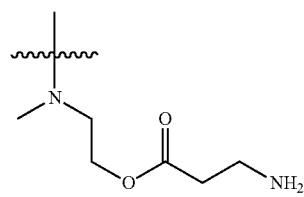 [SMILES: *N(C)CCOC(=O)CCN] ND
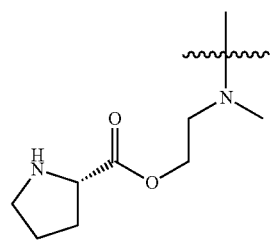 [SMILES: *N(C)CCOC(=O)[C@@H]1CCCN1] ND
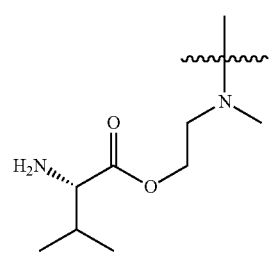 [SMILES: *N(C)CCOC(=O)[C@@H](N)C(C)C] 667.2
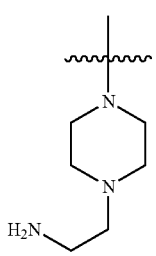 622.2
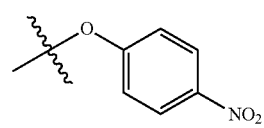 [SMILES: *Oc1ccc([N+](=O)[O-])cc1] 632.02

TABLE B-continued

| | 986.2 |
| | ND |
| | ND |

TABLE B-continued
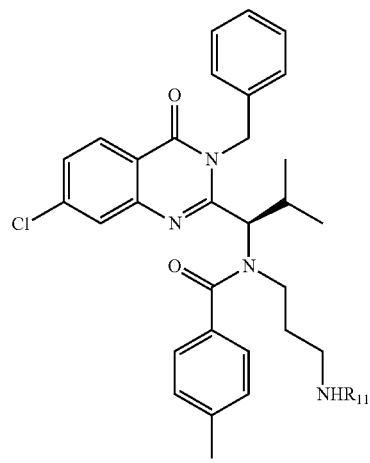
(XXVII)
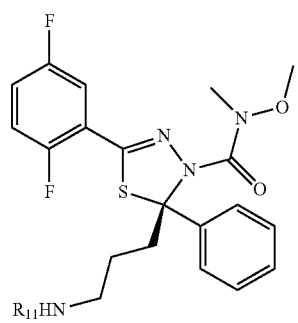
(XXVIII)
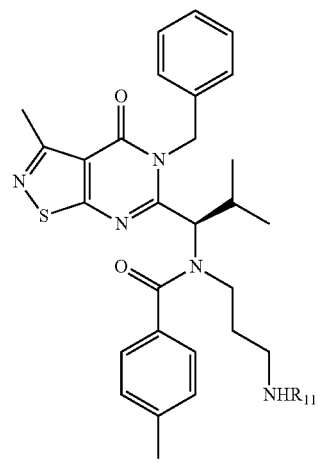
(XXIX)
| R₁₁ | m/z (XXVII) |
|---|---|

TABLE B-continued
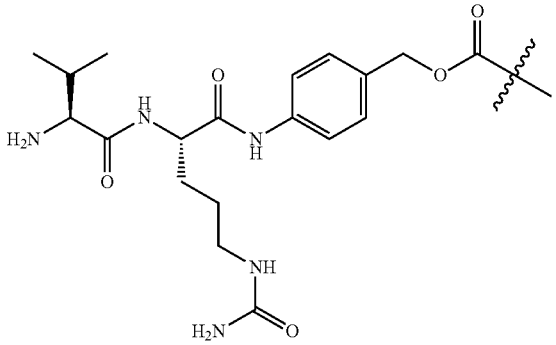 [SMILES: *C(=O)OCc1ccc(NC(=O)[C@H](CCCNC(N)=O)NC(=O)[C@@H](N)C(C)C)cc1]
922.3
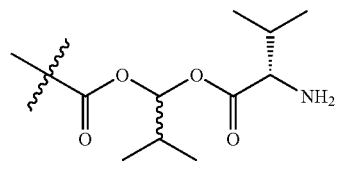 [SMILES: *C(=O)OC(OC(=O)[C@@H](N)C(C)C)C(C)C]
732.2
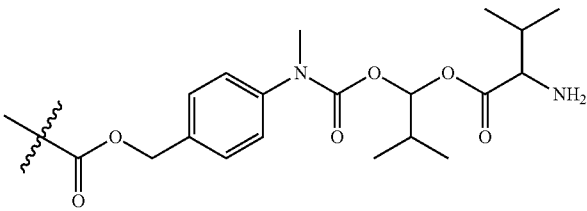 [SMILES: *C(=O)OCc1ccc(N(C)C(=O)OC(OC(=O)C(N)C(C)C)C(C)C)cc1]
ND
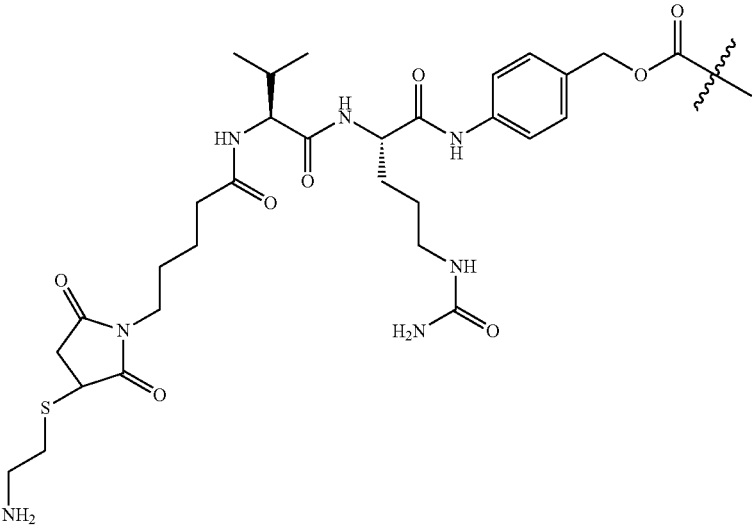 [SMILES: *C(=O)OCc1ccc(NC(=O)[C@H](CCCNC(N)=O)NC(=O)[C@@H](NC(=O)CCCCN2C(=O)CC(SCCN)C2=O)C(C)C)cc1]
ND
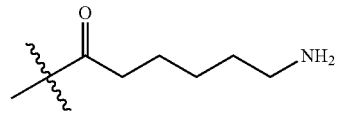 [SMILES: *C(=O)CCCCCN]
ND TABLE B-continued

[Chemical structure with annotation ND]

Protein-Based Recognition Molecules (PBRMs)

The protein-based recognition molecule directs the drug-polymer carrier conjugates to specific tissues, cells, or locations in a cell. The protein-based recognition molecule can direct the modified polymer in culture or in a whole organism, or both. In each case, the protein-based recognition molecule has a ligand that is present on the cell surface of the targeted cell(s) to which it binds with an effective specificity, affinity and avidity. In some embodiments, the protein-based recognition molecule targets the modified polymer to tissues other than the liver. In other embodiments the protein-based recognition molecule targets the modified polymer to a specific tissue such as the liver, kidney, lung or pancreas. The protein-based recognition molecule can target the modified polymer to a target cell such as a cancer cell, such as a receptor expressed on a cell such as a cancer cell, a matrix tissue, or a protein associated with cancer such as tumor antigen. Alternatively, cells comprising the tumor vasculature may be targeted. Protein-based recognition molecules can direct the polymer to specific types of cells such as specific targeting to hepatocytes in the liver as opposed to Kupffer cells. In other cases, protein-based recognition molecules can direct the polymer to cells of the reticular endothelial or lymphatic system, or to professional phagocytic cells such as macrophages or eosinophils. (In such cases the polymer itself might also be an effective delivery system, without the need for specific targeting).

In still other embodiments, the protein based recognition molecule can target the modified polymer to a location within the cell, such as the nucleus, the cytoplasm, or the endosome, for example. In specific embodiments, the protein based recognition molecule can enhance cellular binding to receptors, or cytoplasmic transport to the nucleus and nuclear entry or release from endosomes or other intracellular vesicles.

In specific embodiments the protein based recognition molecules include antibodies, proteins and peptides or peptide mimics In a preferred embodiment, the protein based recognition molecule comprises a sulfhydryl group and the protein based recognition molecule is conjugated to the polymer-drug conjugate by forming a covalent bond via the sulfhydryl group and a functional group of the polymer.

Exemplary antibodies or antibodies derived from Fab, Fab2, scFv or camel antibody heavy-chain fragments specific to the cell surface markers, include, but are not limited to, 5T4, AOC3, ALK, AXL, C242, CA-125, CCL11, CCR 5, CD2, CD3, CD4, CD5, CD15, CA15-3, CD18, CD19, CA19-9, CD20, CD22, CD23, CD25, CD28, CD30, CD31, CD33, CD37, CD38, CD40, CD41, CD44, CD44 v6, CD51, CD52, CD54, CD56, CD62E, CD62P, CD62L, CD70, CD74, CD79-B, CD80, CD125, CD138, CD141, CD147, CD152, CD 154, CD326, CEA, clumping factor, CTLA-4, CXCR2, EGFR (HER1), ErbB2, ErbB3, EpCAM, EPHA2, EPHB2, EPHB4, FGFR (i.e. FGFR1, FGFR2, FGFR3, FGFR4), FLT3, folate receptor, FAP, GD2, GD3, GPNMB, HGF, HER2, HER3, HMI.24, ICAM, ICOS-L, IGF-1 receptor, VEGFR1, EphA2, TRPV1, CFTR, gpNMB, CA9, Cripto, c-KIT, c-MET, ACE, APP, adrenergic receptor-beta2, Claudine 3, Mesothelin, MUC1, NaPi2b, NOTCH1, NOTCH2, NOTCH3, NOTCH4, RON, ROR1, PD-L1, PD-L2, B7-H3, B7-B4, IL-2 receptor, IL-4 receptor, IL-13 receptor, integrins (including $\alpha_4$, $\alpha_{v\ 3}$, $\alpha_{v\ 5}$, $\alpha_{v\ 6}$, $\alpha_{1\ 4}$, $\alpha_{4\ 1}$, $\alpha_{4\ 7}$, $\alpha_{5\ 1}$, $\alpha_{6\ 4}$, $\alpha_{IIb\ 3}$ intergins), IFN-α, IFN-γ, IgE, IgE, IGF-1 receptor, IL-1, IL-12, IL-23, IL-13, IL-22, IL-4, IL-5, IL-6, interferon receptor, ITGB2 (CD18), LFA-1 (CD11a), L-selectin (CD62L), mucin, MUC1, myostatin, NCA-90, NGF, PDGFRα, phosphatidylserine, prostatic carcinoma cell, *Pseudomonas aeruginosa*, rabies, RANKL, respiratory syncytial virus, Rhesus factor, SLAMF7, sphingosine-1-phosphate, TAG-72, T-cell receptor, tenascin C, TGF-1, TGF-2, TGF-β, TNF-α, TRAIL-R1, TRAIL-R2, tumor antigen CTAA16.88, VEGF-A, VEGFR2, vimentin, and the like.

In one embodiment the antibodies or antibody derived from Fab, Fab2, scFv or camel antibody heavy-chain fragments specific to the cell surface markers include CA-125, C242, CD3, CD19, CD22, CD25, CD30, CD31, CD33, CD37, CD40, CD44, CD51, CD54, CD56, CD62E, CD62P, CD62L, CD70, CD138, CD141, CD326, CEA, CTLA-4, EGFR (HER1), ErbB2, ErbB3, FAP, folate receptor, IGF-1 receptor, GD3, GPNMB, HGF, HER2, VEGF-A, VEGFR2, VEGFR1, EphA2, EpCAM, 5T4, TAG-72, tenascin C, TRPV1, CFTR, gpNMB, CA9, Cripto, ACE, APP, PDGFR α, phosphatidylserine, prostatic carcinoma cells, adrenergic receptor-beta2, Claudine 3, mucin, MUCL Mesothelin, IL-2 receptor, IL-4 receptor, IL-13 receptor and integrins (including $_{v\ 3}$, $_{v\ 5}$, $_{v\ 6}$, $_{1\ 4}$, $_{4\ 1}$, $_{5\ 1}$, $_{6\ 4}$ intergins), tenascin C, TRAIL-R2 and vimentin.

Exemplary antibodies include 3F8, abagovomab, abciximab (REOPRO), adalimumab (HUMIRA), adecatumumab, afelimomab, afutuzumab, alacizumab, ALD518, alemtuzumab (CAMPATH), altumomab, amatuximab, anatumomab, anrukinzumab, apolizumab, arcitumomab (CEA-SCAN), aselizumab, atlizumab (tocilizumab, Actemra, RoActemra), atorolimumab, bapineuzumab, basiliximab (Simulect), bavituximab, bectumomab (LYMPHOSCAN), belimumab (BENLYSTA), benralizumab, bertilimumab, besilesomab (SCINITIMUN), bevacizumab (AVASTIN), biciromab (FIBRISCINT), bivatuzumab, blinatumomab, brentuximab, briakinumab, canakinumab (ILARIS), cantuzumab, capromab, catumaxomab (REMOVAB), CC49, cedelizumab, certolizumab, cetuximab (ERBITUX), citatuzumab, cixutumumab, clenoliximab, clivatuzumab, conatumumab, CR6261, dacetuzumab, daclizumab (ZENAPAX), daratumumab, denosumab (PROLIA), detumomab, dorlimomab, dorlixizumab, ecromeximab, eculizumab (SOLIRIS), edobacomab, edrecolomab (PANOREX), efalizumab (RAPTIVA), efungumab (MYCOGRAB), elotuzumab, elsilimomab, enlimomab, epitumomab, epratuzumab, erlizumab, ertumaxomab (REXOMUN), etaracizumab (ABEGRIN), exbivirumab, fanolesomab (NEUTROSPEC), faralimomab, farletuzumab, felvizumab, fezakinumab, figitumumab, fontolizumab (HuZAF), foravirumab, fresolimumab, galiximab, gantenerumab, gavilimomab, gemtuzumab, girentuximab, glembatumumab, golimumab (SIMPONI), gomiliximab, ibalizumab, ibritumomab, igovomab (INDIMACIS-125), imciromab (MYOSCINT), infliximab (REMICADE), intetumumab, inolimomab, inotuzumab, ipilimumab, iratumumab, keliximab, labetuzumab (CEA-CIDE), lebrikizumab, lemalesomab, lerdelimumab, lexatumumab, libivirumab, lintuzumab, lucatumumab, lumiliximab, mapatumumab, maslimomab, matuzumab, mepolizumab (BOSATRIA), metelimumab, milatuzumab, minretumomab, mitumomab, morolimumab, motavizumab (NUMAX), muromonab-CD3 (ORTHOCLONE OKT3), nacolomab, naptumomab, natalizumab (TYSABRI), nebacumab, necitumumab, nerelimomab, nimotuzumab (THERACIM), nofetumomab, ocrelizumab, odulimomab, ofatumumab (ARZERRA), olaratumab, omalizumab (XOLAIR), ontecizumab, oportuzumab, oregovomab (OVAREX), otelixizumab, pagibaximab, palivizumab (SYNAGIS), panitumumab (VECTIBIX), panobacumab, pascolizumab, pemtumomab (THERAGYN), pertuzumab (OMNITARG), pexelizumab, pintumomab, priliximab, pritumumab, PRO140, rafivirumab, ramucirumab, ranibizumab (LUCENTIS), raxibacumab, regavirumab, reslizumab, rilotumumab, rituximab (RITUXAN), robatumumab, rontalizumab, rovelizumab (LEUKARREST), ruplizumab (ANTOVA), satumomab pendetide, sevirumab, sibrotuzumab, sifalimumab, siltuximab, siplizumab, solanezumab, sonepcizumab, sontuzumab, stamulumab, sulesomab (LEUKOSCAN), tacatuzumab (AFP-CIDE), tetraxetan, tadocizumab, talizumab, tanezumab, taplitumomab paptox, tefibazumab (AUREXIS), telimomab, tenatumomab, teneliximab, teplizumab, TGN1412, ticilimumab (tremelimumab), tigatuzumab, TNX-650, tocilizumab (atlizumab, ACTEMRA), toralizumab, tositumomab (BEXXAR), trastuzumab (HERCEPTIN), tremelimumab, tucotuzumab, tuvirumab, urtoxazumab, ustekinumab (STELERA), vapaliximab, vedolizumab, veltuzumab, vepalimomab, visilizumab (NUVION), volociximab (HUMASPECT), votumumab, zalutumumab (HuMEX-EGFr), zanolimumab (HuMAX-CD4), ziralimumab and zolimomab.

In some embodiments the antibodies are directed to cell surface markers for 5T4, CA-125, CEA, CD3, CD19, CD20, CD22, CD30, CD33, CD40, CD44, CD51, CTLA-4, EpCAM, HER2, EGFR (HER1), FAP, folate receptor, HGF, integrin $\alpha_v\beta_3$, integrin $\alpha_5\beta_1$, IGF-1 receptor, GD3, GPNMB, mucin, MUC1, phosphatidylserine, prostatic carcinoma cells, PDGFR $\alpha$, TAG-72, tenascin C, TRAIL-R2, VEGF-A and VEGFR2. In this embodiment the antibodies are abagovomab, adecatumumab, alacizumab, altumomab, anatumomab, arcitumomab, bavituximab, bevacizumab (AVASTIN), bivatuzumab, blinatumomab, brentuximab, cantuzumab, catumaxomab, capromab, cetuximab, citatuzumab, clivatuzumab, conatumumab, dacetuzumab, edrecolomab, epratuzumab, ertumaxomab, etaracizumab, farletuzumab, figitumumab, gemtuzumab, glembatumumab, ibritumomab, igovomab, intetumumab, inotuzumab, labetuzumab, lexatumumab, lintuzumab, lucatumumab, matuzumab, mitumomab, naptumomab estafenatox, necitumumab, oportuzumab, oregovomab, panitumumab, pemtumomab, pertuzumab, pritumumab, rituximab (RITUXAN), rilotumumab, robatumumab, satumomab, sibrotuzumab, taplitumomab, tenatumomab, tenatumomab, ticilimumab (tremelimumab), tigatuzumab, trastuzumab (HERCEPTIN), tositumomab, tremelimumab, tucotuzumab celmoleukin, volociximab and zalutumumab.

In specific embodiments the antibodies directed to cell surface markers for HER2 are pertuzumab or trastuzumab and for EGFR (HER1) the antibody is cetuximab or panitumumab; and for CD20 the antibody is rituximab and for VEGF-A is bevacizumab and for CD-22 the antibody is epratuzumab or veltuzumab and for CEA the antibody is labetuzumab.

Exemplary peptides or peptide mimics include integrin targeting peptides (RGD peptides), LHRH receptor targeting peptides, ErbB2 (HER2) receptor targeting peptides, prostate specific membrane bound antigen (PSMA) targeting peptides, lipoprotein receptor LRP1 targeting, ApoE protein derived peptides, ApoA protein peptides, somatostatin receptor targeting peptides, chlorotoxin derived peptides, and bombesin.

In specific embodiments the peptides or peptide mimics are LHRH receptor targeting peptides and ErbB2 (HER2) receptor targeting peptides Exemplary proteins comprise insulin, transferrin, fibrinogen-gamma fragment, thrombospondin, claudin, apolipoprotein E, Affibody molecules such as, for example, ABY-025, Ankyrin repeat proteins, ankyrin-like repeats proteins and synthetic peptides.

In some embodiments of the invention the protein-polymer-drug conjugates comprise broad spectrum cytotoxins in combination with cell surface markers for HER2 such as pertuzumab or trastuzumab; for EGFR such as cetuximab and panitumumab; for CEA such as labetuzumab; for CD20 such as rituximab; for VEGF-A such as bevacizumab; or for CD-22 such as epratuzumab or veltuzumab.

In other embodiments of the invention the protein-drug-polymer conjugates or protein-polymer conjugates used in the invention comprise combinations of two or more protein based recognition molecules, such as, for example, combination of bispecific antibodies directed to the EGF receptor (EGFR) on tumor cells and to CD3 and CD28 on T cells; combination of antibodies or antibody derived from Fab, Fab2, scFv or camel antibody heavy-chain fragments and peptides or peptide mimetics; combination of antibodies or antibody derived from Fab, Fab2, scFv or camel antibody heavy-chain fragments and proteins; combination of two bispecific antibodies such as CD3×CD19 plus CD28×CD22 bispecific antibodies.

In other embodiments of the invention the protein-drug-polymer conjugates or protein-polymer conjugates used in the invention comprise protein based recognition molecules are antibodies against antigens, such as, for example, Trastuzumab, Cetuximab, Rituximab, Bevacizumab, Epratuzumab, Veltuzumab, Labetuzumab, B7-H4, B7-H3, CA125, CD33, CXCR2, EGFR, FGFR1, FGFR2, FGFR3, FGFR4, HER2, NaPi2b, c-Met, NOTCH1, NOTCH2, NOTCH3, NOTCH4, PD-L1, c-Kit, MUC1 and 5T4.

In a specific embodiment of the invention, the protein-drug-polymer conjugates or protein-polymer conjugates of the invention comprise protein based recognition molecules which are antibodies against 5T4, such as, for example a humanized anti-5T4 scFvFc antibody.

Examples of suitable 5T4 targeting ligands or immunoglobulins include those which are commercially available, or have been described in the patent or non-patent literature, e.g., U.S. Pat. No. 8,044,178, U.S. Pat. No. 8,309,094, U.S. Pat. No. 7,514,546, EP1036091 (commercially available as TroVax™, Oxford Biomedica), EP2368914A1, WO 2013041687 A1 (Amgen), US 2010/0173382, and P. Sapra, et al., Mol. Cancer. Ther. 2013, 12:38-47. An anti-5T4 antibody is disclosed in U.S. Provisional Application No. 61/877,439, filed Sep. 13, 2013 and U.S. Provisional Application No. 61/835,858, filed Jun. 17, 2013. The contents of each of the patent documents and scientific publications are herein incorporated by reference in their entireties.

As used herein, the term "5T4 antigen-binding portion" refers to a polypeptide sequence capable of selectively binding to a 5T4 antigen. In exemplary conjugates, the 5T4 antigen-binding portion generally comprises a single chain scFv-Fc form engineered from an anti-5T4 antibody. A single-chain variable fragment (scFv-Fc) is a fusion protein of the variableregions of the heavy (VH) and light chains (VL) of an immunoglobulin, connected with a linker peptide, and further connected to an Fc region comprising a hinge region and CH2 and CH3 regions of an antibody (any such combinations of antibody portions with each other or with other peptide sequences is sometimes referred to herein as an "immunofusion" molecule). Within such a scFvFc molecule, the scFv section may be C-terminally linked to the N-terminus of the Fc section by a linker peptide.

At least a portion of the 5T4 antigen-binding portion of the immunofusion molecules may originate from a murine source. For example, one may obtain an immunofusion molecule by expressing a polynucleotide engineered to encode at least a murine anti-5T4 scFv region having the polypeptide sequence according to SEQ ID NO: 1 (see, e.g., U.S. Provisional Application No. 61/835,858, filed Jun. 17, 2013). Additionally, at least a portion of the 5T4-antigen binding portion may be generated to be chimeric or humanized according to well-known methods. See, Borras et al., J. Biol. Chem. 2010 Mar. 19; 285 (12):9054-66. Thus, one may obtain an immunofusion molecule having a 5T4-antigen binding portion with a humanized scFv portion by expressing a polynucleotide engineered to encode at least the polypeptide sequence according to SEQ ID NO: 2 (see, e.g., U.S. Provisional Application No. 61/835,858, filed Jun. 17, 2013).

In some examples, the Fv portion of the 5T4 antigen-binding portion may be engineered by well-known molecular biology techniques to comprise one or more amino acid substitutions in the VH region. The Fc portion of the 5T4 antigen binding portion preferably comprises a polypeptide sequence engineered from the human hinge, CH2 and CH3 regions of an anti-5T4 antibody. For example, it is possible to engineer a polynucleotide to encode at least an Fc portion having the polypeptide sequence according to SEQ ID NO: 3 (see, e.g., U.S. Provisional Application No. 61/835,858, filed Jun. 17, 2013).

A polynucleotide encoding a peptide wherein the single chain Fv and Fc regions are linked together may encode at least a chimeric 5T4 antigen-binding portion of conjugate having the polypeptide sequence according to SEQ ID NO: 6 or may encode a humanized 5T4 antigen-binding portion having the polypeptide sequence according to SEQ ID NOs: 7 or 8.

A polypeptide linker, such as one having the polypeptide sequence ASTC (SEQ ID NO: 4) or ASTX (SEQ ID NO: 5) (where "X" refers to any amino acid or a direct peptide bond between the adjacent amino acids), may fuse the C-terminus of ScFv portion to the N-terminus of the Fc portion of the 5T4 antigen-binding portion. Thus, it is possible to engineer a polynucleotide to encode at least a linker having the polypeptide sequence according to SEQ ID NOs: 4 or 5. While either SEQ ID NOs: 4 or 5 may be used as a linker, an immunofusion molecule having a peptide linker according to SEQ ID NO: 4 benefits from site-specific conjugation due to the presence of the cysteine residue.

Preferably, any amino acid substitution, insertion, or deletion or use of a peptidomimetic does not substantially reduce the affinity or specificity of the 5T4 antigen-binding portion. An immunofusion molecule having an amino acid substitution, insertion, or deletion or a peptidomimetic in the 5T4 antigen-binding portion preferably retains greater than 75%, preferably greater than 80%, preferably greater than 85%, preferably greater than 90%, or preferably greater than 95% of affinity or specificity for binding the 5T4 antigen compared to a conjugate with an unmodified 5T4-antigen binding portion.

Anti-5T4 single chain antibody-Fc fusion protein ("anti-5T4 scFv-Fc") was prepared in CHO DG44 cells, as disclosed in U.S. Provisional Application No. 61/835,858, filed Jun. 17, 2013.

```
SEQ ID NO: A: 5T4-specific murine scFv:
EVQLQQSGPDLVKPGASVKISCKASGYSFTGYYMHWVKQSPGKGLEWIGRINPNNGVTL

YNQKFKDKATLTVDKSSTTAYMELRSLTSEDSAVYYCARSTMITNYVMDYWGQGTSVT

VSSGGGGSGGGGSGGGGSSIVMTQTPTSLLVSAGDRVTITCKASQSVSNDVAWYQQKPG

QSPKLLISYTSSRYAGVPDRFTGSGSGTDFTLTISSVQAEDAAVYFCQQDYNSPPTFGGGT

KLEIK

SEQ ID NO: B: 5T4-specific humanized scFv:
EVQLVESGGGLVQPGGSLRLSCKASGYSFTGYYMHWVRQAPGKGLEWVSRINPNNGVT

LYNQKFKDRFTISRDNSKNTLYLQMNSLRAEDTAVYYCARSTMITNYVMDYWGQGTLV

TVSSGGGGSGGGGSGGGGSGGGGSGGGGSGGGGSDIQMTQSPSSLSASVGDRVTITCKA

SQSVSNDVAWYQQKPGKAPKLLIYYTSSRYAGVPSRFSGSGSGTDFTLTISSLQPEDFAT

YYCQQDYNSPPTFGGGTKLEIK
```

-continued

SEQ ID NO: C: Human Hinge-CH2-CH3 (Fcgamma1):
EPKSSDKTHTCPPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPGK

SEQ ID NO: Y: Site-specific conjugation-I:
ASTC

SEQ ID NO: Z: No site-specific conjugation-I:
ASTX

SEQ ID NO: D: Chimeric anti-5T4 scFv-Fc:
EVQLQQSGPDLVKPGASVKISCKASGYSFTGYYMHWVKQSPGKGLEWIGRINPNNGVTL

YNQKFKDKATLTVDKSSTTAYMELRSLTSEDSAVYYCARSTMITNYVMDYWGQGTSVT

VSSGGGGSGGGGSGGGGSSIVMTQTPTSLLVSAGDRVTITCKASQSVSNDVAWYQQKPG

QSPKLLISYTSSRYAGVPDRFTGSGSGTDFTLTISSVQAEDAAVYFCQQDYNSPPTFGGGT

KLEIKASTCEPKSSDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKEYKCKVSN

KALPAPIEKTISKAKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHNHYTQKSLSLSPGK

SEQ ID NO: E: Humanized anti-5T4 scFv-Fc (ASTC):
EVQLVESGGGLVQPGGSLRLSCKASGYSFTGYYMHWVRQAPGKGLEWVSRINPNNGVT

LYNQKFKDRFTISRDNSKNTLYLQMNSLRAEDTAVYYCARSTMITNYVMDYWGQGTLV

TVSSGGGGSGGGGSGGGGSGGGGSGGGGSGGGGSDIQMTQSPSSLSASVGDRVTITCKA

SQSVSNDVAWYQQKPGKAPKLLIYYTSSRYAGVPSRFSGSGSGTDFTLTISSLQPEDFAT

YYCQQDYNSPPTFGGGTKLEIKASTCEPKSSDKTHTCPPCPAPELLGGPSVFLFPPKPKDT

LMISRTPEVTCVVVDVSHEDPEVKFNWYVDGVEVHNAKTKPREEQYNSTYRVVSVLTV

LHQDWLNGKEYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQGNVFSCSV

MHEALHNHYTQKSLSLSPGK

SEQ ID NO: F: Humanized anti-5T4 scFv-Fc (ASTX):
EVQLVESGGGLVQPGGSLRLSCKASGYSFTGYYMHWVRQAPGKGLEWVSRINPNNGVT

LYNQKFKDRFTISRDNSKNTLYLQMNSLRAEDTAVYYCARSTMITNYVMDYWGQGTLV

TVSSGGGGSGGGGSGGGGSGGGGSGGGGSGGGGSDIQMTQSPSSLSASVGDRVTITCKA

SQSVSNDVAWYQQKPGKAPKLLIYYTSSRYAGVPSRFSGSGSGTDFTLTISSLQPEDFAT

YYCQQDYNSPPTFGGGTKLEIKASTXEPKSSDKTHTCPPCPAPELLGGPSVFLFPPKPKDT

LMISRTPEVTCVVVDVSHEDPEVKFNWYVDGVEVHNAKTKPREEQYNSTYRVVSVLTV

LHQDWLNGKEYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQGNVFSCSV

MHEALHNHYTQKSLSLSPGK

These antibodies may be produced recombinantly, synthetically, or by other suitable method known in the art. Such methods and constructs utilize the nucleic acid sequences encoding the polypeptides and peptide sequences identified herein. Alternatively, such methods and constructs for antibody production utilize sequences which are naturally or artificially modified, e.g., natural variants or codon optimized variants of the SEQ ID NOs provided herein (e.g., 1).

A variety of codon optimization schema are known in the art. See, e.g., UpGene™ and Optimizer™, which are web-based optimization methods. Additionally, a number of commercial institutions perform codon optimization using proprietary schema, e.g., SignGen Laboratories, DNA2.0, OpenX, amongst others.

These targeting ligands, the linkers and the drug or prodrug fragments described herein can be assembled into the therapeutic drug and targeting conjugate of the invention, for example according to the disclosed techniques and methods. Therapeutic and targeting conjugates of the invention, and methods for producing them, are described below by way of non-limiting example.

Conjugates or Polymeric Scaffolds

Conjugates of the invention comprise one or more occurrences of D, where D is a therapeutic agent, e.g., a drug, wherein the one or more occurrences of D may be the same or different.

In certain other embodiments, one or more occurrences of PBRM is attached to the polymeric carrier, wherein the one or more occurrences of PBRM may be the same or different. In certain other embodiments, one or more polymer carriers that contains one or more occurrences of D are connected to a PBRM (e.g., an antibody).

As discussed more generally above, in certain embodiments, each polymeric carrier independently, has about 0.1% to about 25% monomers comprising a D, more preferably about 0.5% to about 20%, more preferably about 1% to about 15%, and even more preferably about 2% to about 10%. For example, the polymeric carrier is PHF having a molecular weight of about 2 kDa to about 40 kDa and has about 0.3% to about 15% monomers comprising auristatin F, more preferably about 2%-12%, more preferably about 5%-10%.

In certain embodiments, when D is drug that has an $IC_{50}<10$ pM for antiproliferative activity in a broad range of cell lines, the polymeric carrier is PHF having a molecular weight of about 2 kDa to about 40 kDa and has about 0.1% to about 25% monomers comprising D, more preferably about 2%-10%, more preferably about 2%-5%.

In certain embodiments, the conjugate of this invention is of Formula (Id):

wherein:
each occurrence of D independently is a therapeutic agent having a molecular weight of ≤5 kDa, and the $-\xi-$ between D and the carbonyl group denotes direct or indirect attachment of D to the carbonyl group,
$m_1$ is an integer from 1 to about 140, and
$m_7$ is an integer from 1 to about 40, wherein the sum of $m_1$ and $m_7$ is $m_6$ (i.e., 2 to about 180).

In one embodiment, D is a) an auristatin compound; (b) a calicheamicin compound; (c) a duocarmycin compound; (d) a topoisomerase inhibitor, (e) a pyrrolobenzodiazepine compound; (f) a vinca compound; (g) a protein synthesis inhibitor; (h) a RNA polymerase inhibitor; (i) a tubulin binding compound; or an analog thereof.

In certain embodiment, D is (a) an auristatin compound; (b) a calicheamicin compound; (c) a duocarmycin compound; (d) a camptothecin compound, (e) a pyrrolobenzodiazepine compound; (f) a vinca compound; or an analog thereof.

For example, the auristatin compound is auristatin, dolastatin, monomethylauristatin E (MMAE), monomethylauristatin F (MMAF), auristatin F, AF HPA, phenylenediamine (AFP).

For example, the duocarmycin or an analog thereof is duocarmycin A, duocarmycin B1, duocarmycin B2, duocarmycin C1, duocarmycin C2, duocarmycin D, duocarmycin SA, CC-1065, adozelesin, bizelesin, or carzelesin.

For example, the camptothecin compound is camptothecin, CPT-11 (irinotecan), SN-38, or topotecan.

For example, the pyrrolobenzodiazepine compound is a pyrrolobenzodiazepine monomer, a symmetrical pyrrolobenzodiazepine dimer or an unsymmetrical pyrrolobenzodiazepine dimer.

The polymer-drug conjugate of Formula (Id) is useful for conjugation with a PBRM that has a molecular weight of about 40 kDa or greater (e.g., 60 kDa or greater; 80 kDa or greater; 100 kDa or greater; 120 kDa or greater; 140 kDa or

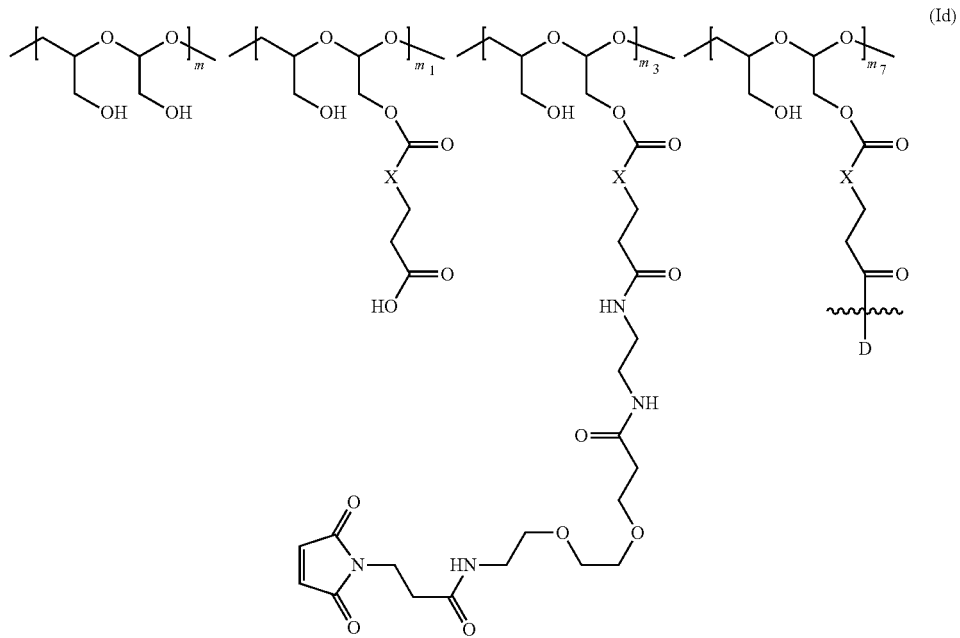

greater; 160 kDa or greater; 180 kDa or greater; or 200 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, or 100-140 kDa).

For example, for conjugating a PBRM having a molecular weight of 40 kDa or greater (e.g., 60 kDa or greater, 80 kDa or greater, 100 kDa or greater, 120 kDa or greater, 140 kDa or greater, 160 kDa or greater or 180 kDa or greater), the polymeric carrier of the scaffold of the invention is a polyacetal, e.g., a PHF having a molecular weight (i.e., MW of the unmodified PHF) ranging from about 2 kDa to about 40 kDa (e.g., about 2-20 kDa or about 3-15 kDa or about 5-10 kDa).

For example, for conjugating a PBRM having a molecular weight of 40 kDa to 200 kDa, the polymeric carrier of the scaffold of the invention is a polyacetal, e.g., a PHF having a molecular weight (i.e., MW of the unmodified PHF) ranging from about 2 kDa to about 40 kDa (e.g., about 2-20 kDa or about 3-15 kDa or about 5-10 kDa).

For example, for conjugating a PBRM having a molecular weight of 40 kDa to 80 kDa, the polymeric carrier of the scaffold of the invention is a polyacetal, e.g., a PHF having a molecular weight (i.e., MW of the unmodified PHF) ranging from about 2 kDa to about 40 kDa (e.g., about 2-20 kDa or about 3-15 kDa or about 5-10 kDa). For example the PHF has a molecular weight of about 5 kDa, 10 kDa or 15 kDa.

PBRMs in this molecular weight range include, but are not limited to, for example, antibody fragments, such as, for example, Fabs.

For example, for conjugating a PBRM having a molecular weight of 60 kDa to 120 kDa, the polymeric carrier of the scaffold of the invention is a polyacetal, e.g., a PHF having a molecular weight (i.e., MW of the unmodified PHF) ranging from about 2 kDa to about 40 kDa (e.g., about 2-20 kDa or about 3-15 kDa or about 5-10 kDa). For example the PHF has a molecular weight of about 5 kDa, 10 kDa or 15 kDa.

PBRMs in this molecular weight range include, but are not limited to, for example, camelids, Fab2, scFvFc, and the like.

For example, for conjugating a PBRM having a molecular weight of 140 kDa to 180 kDa, the polymeric carrier of the scaffold of the invention is a polyacetal, e.g., a PHF having a molecular weight (i.e., MW of the unmodified PHF) ranging from about 2 kDa to about 40 kDa (e.g., about 2-20 kDa or about 3-15 kDa or about 5-10 kDa). For example the PHF has a molecular weight of about 5 kDa, 10 kDa or 15 kDa.

PBRMs in this molecular weight range include, but are not limited to, for example, full length antibodies, such as, IgG, IgM.

In certain embodiments, the polymer drug conjugate (Id) when conjugated to a PBRM is of Formula (Ie):

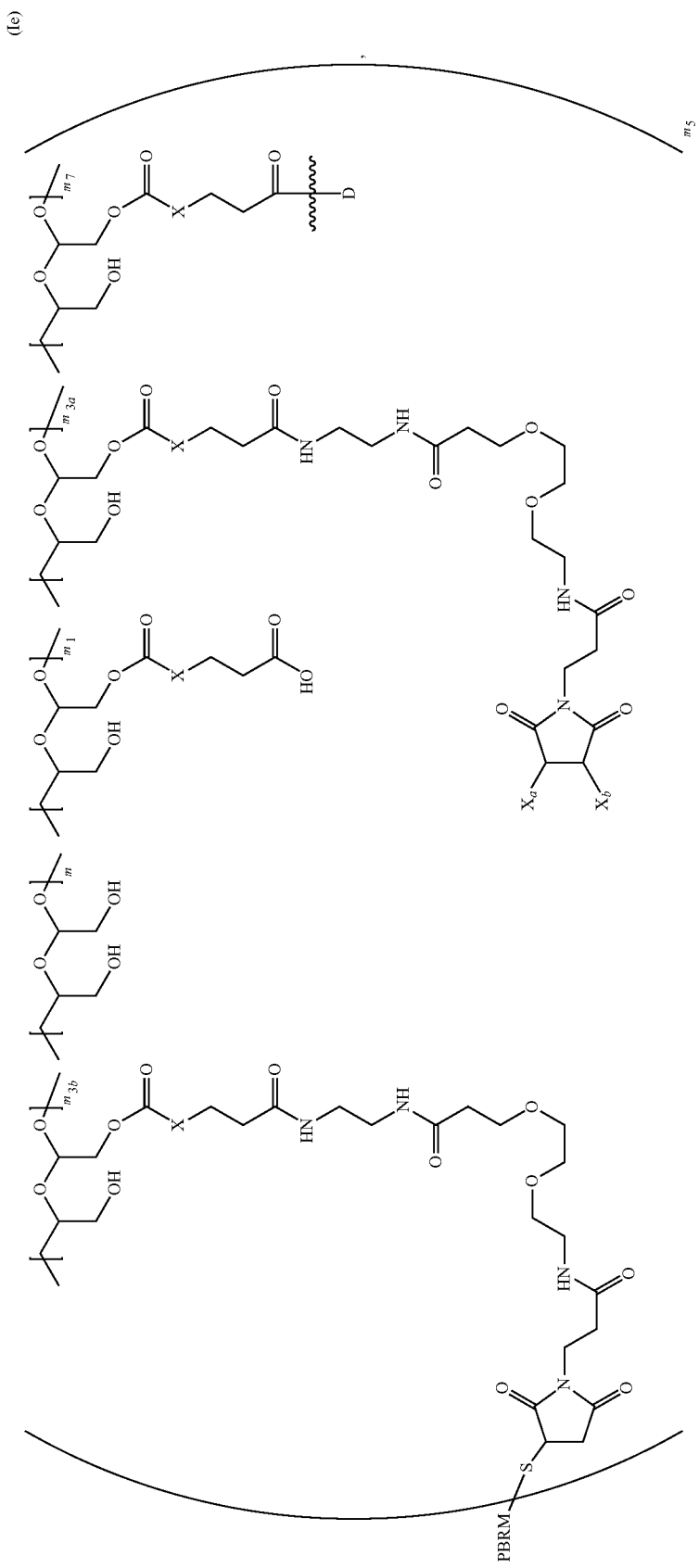

wherein:

one of $X_a$ and $X_b$ is H and the other is a maleimido blocking moiety, or $X_a$ and $X_b$, together with the carbon atoms to which they are attached form a carbon-carbon double bond;

$m_{3a}$ is an integer from 0 to about 17, $m_{3b}$ is an integer from 1 to about 8, wherein the sum of $m_{3a}$ and $m_{3b}$ is $m_3$, the sum of m, $m_1$, $m_7$, $m_{3a}$, and $m_{3b}$ ranges from about 15 to about 300, and $m_5$ is an integer from 1 to about 10.

The PBRM has a molecular weight of about 40 kDa or greater (e.g., 60 kDa or greater; 80 kDa or greater; 100 kDa or greater; 120 kDa or greater; 140 kDa or greater; 160 kDa or greater; 180 kDa or greater; or 200 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, or 100-140 kDa).

For example, the PBRM has a molecular weight of about 40 kDa or greater (e.g., 60 kDa or greater; 80 kDa or greater; 100 kDa or greater; 120 kDa or greater; 140 kDa or greater; 160 kDa or greater; 180 kDa or greater; or 200 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, or 100-140 kDa) and has a sulfhydryl (i.e., —SH or thiol) group.

For example, the total number of sulfide bonds formed between the PHF and the PBRM (or total number of attachment points) is 10 or less.

For example, the ratio between $m_7$ and $m_{3b}$ is greater than 1:1 and less than or equal to 10:1.

For example, the ratio between $m_7$ and $m_{3b}$ is about 9:1, 8:1, 7:1, 6:1, 5:1, 4:1, 3:1, or 2:1.

For example, the ratio between $m_7$ and $m_{3b}$ is between 2:1 and 8:1.

For example, the ratio between $m_7$ and $m_{3b}$ is about 8:1, 7:1, 6:1, 5:1, 4:1, 3:1, or 2:1.

For example, the ratio between $m_7$ and $m_{3b}$ is between 2:1 and 4:1.

For example, the ratio between $m_7$ and $m_{3b}$ is about 4:1, 3:1, or 2:1.

For example, when the PHF in Formula (Ie) has a molecular weight ranging from about 2 kDa to about 20 kDa, the sum of m, $m_1$, $m_7$, $m_{3a}$ and $m_{3b}$ ranges from about 15 to about 150, $m_1$ is an integer from 1 to about 70, $m_7$ is an integer from 1 to about 20, $m_{3a}$ is an integer from 0 to about 9, $m_{3b}$ is an integer from 1 to about 8 and $m_5$ is an integer from 2 to about 8.

For example, when the PHF in Formula (Ie) has a molecular weight ranging from about 3 kDa to about 15 kDa, the sum of m, $m_1$, $m_7$, $m_{3a}$ and $m_{3b}$ ranges from about 20 to about 110, $m_1$ is an integer from 2 to about 50, $m_7$ is an integer from 2 to about 15, $m_{3a}$ is an integer from 0 to about 7, $m_{3b}$ is an integer from 1 to about 8 and $m_5$ is an integer from 2 to about 4.

For example, when the PHF in Formula (Ie) has a molecular weight ranging from about 5 kDa to about 10 kDa, the sum of m, $m_1$, $m_7$, $m_{3a}$ and $m_{3b}$ ranges from about 40 to about 75, $m_1$ is an integer from about 5 to about 35, $m_7$ is an integer from about 3 to about 10, $m_{3a}$ is an integer from 0 to about 4, $m_{3b}$ is an integer from 1 to about 5 and $m_5$ is an integer from 2 to about 4.

In certain embodiments, the protein-polymer drug conjugate of this invention is of Formula (Ib) as described herein:

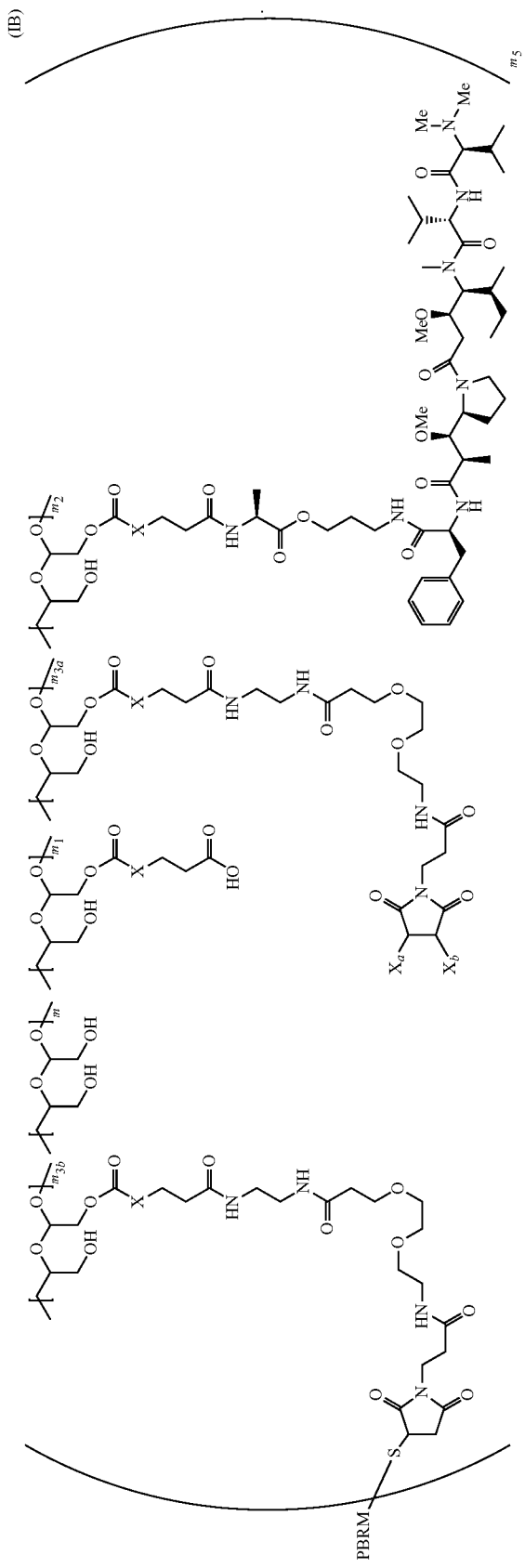

wherein:
one of $X_a$ and $X_b$ is H and the other is a maleimido blocking moiety, or $X_a$ and $X_b$, together with the carbon atoms to which they are attached form a carbon-carbon double bond;

$m_{3a}$ is an integer from 0 to about 17, $m_{3b}$ is an integer from 1 to about 8, wherein the sum of $m_{3a}$ and $m_{3b}$ is $m_3$, the sum of m, $m_1$, $m_2$, $m_{3a}$, and $m_{3b}$ ranges from about 15 to about 300, and $m_5$ is an integer from 1 to about 10.

For example, the PBRM has a molecular weight of about 40 kDa or greater (e.g., 60 kDa or greater; 80 kDa or greater; 100 kDa or greater; 120 kDa or greater; 140 kDa or greater; 160 kDa or greater; 180 kDa or greater; or 200 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, or 100-140 kDa).

For example, the total number of sulfide bonds formed between the PHF and the PBRM (or total number of attachment points) is 10 or less.

For example, the ratio between $m_2$ and $m_{3b}$ is greater than 1:1 and less than or equal to 10:1.

For example, the ratio between $m_2$ and $m_{3b}$ is about 9:1, 8:1, 7:1, 6:1, 5:1, 4:1, 3:1, or 2:1.

For example, the ratio between $m_2$ and $m_{3b}$ is between 2:1 and 8:1.

For example, the ratio between $m_2$ and $m_{3b}$ is about 8:1, 7:1, 6:1, 5:1, 4:1, 3:1, or 2:1.

For example, the ratio between $m_2$ and $m_{3b}$ is between 2:1 and 4:1.

For example, the ratio between $m_2$ and $m_{3b}$ is about 4:1, 3:1, or 2:1.

For example, when the PHF in Formula (Ib) has a molecular weight ranging from about 2 kDa to about 20 kDa, the sum of m, $m_1$, $m_2$, $m_{3a}$ and $m_{3b}$ ranges from about 15 to about 150, $m_1$ is an integer from 1 to about 70, $m_2$ is an integer from 1 to about 20, $m_{3a}$ is an integer from 0 to about 9, $m_{3b}$ is an integer from 1 to about 8 and $m_5$ is an integer from 2 to about 8.

For example, when the PHF in Formula (Ib) has a molecular weight ranging from about 3 kDa to about 15 kDa, the sum of m, $m_1$, $m_2$, $m_{3a}$ and $m_{3b}$ ranges from about 20 to about 110, $m_1$ is an integer from 2 to about 50, $m_2$ is an integer from 2 to about 15, $m_{3a}$ is an integer from 0 to about 7, $m_{3b}$ is an integer from 1 to about 8 and $m_5$ is an integer from 2 to about 4.

For example, when the PHF in Formula (Ib) has a molecular weight ranging from about 5 kDa to about 10 kDa, the sum of m, $m_1$, $m_2$, $m_{3a}$ and $m_{3b}$ ranges from about 40 to about 75, $m_1$ is an integer from about 5 to about 35, $m_2$ is an integer from about 3 to about 10, $m_{3a}$ is an integer from 0 to about 4, $m_{3b}$ is an integer from 1 to about 5 and $m_5$ is an integer from 2 to about 4.

For example, the maleimido blocking moieties are moieties that can be covalently attached to one of the two olefin carbon atoms upon reaction of the maleimido group with a thiol-containing compound of Formula (II):

$$R_{90}\text{---}(CH_2)_d\text{---}SH \qquad (II)$$

wherein:
$R_{90}$ is $NHR_{91}$, OH, $COOR_{93}$, $CH(NHR_{91})COOR_{93}$ or a substituted phenyl group;

$R_{93}$ is hydrogen or $C_{1-4}$ alkyl;

$R_{91}$ is hydrogen, $CH_3$ or $CH_3CO$ and d is an integer from 1 to 3.

For example, the maleimido blocking compound of Formula (II) can be cysteine, N-acetyl cysteine, cysteine methyl ester, N-methyl cysteine, 2-mercaptoethanol, 3-mercaptopropanoic acid, 2-mercaptoacetic acid, mercaptomethanol (i.e., $HOCH_2SH$), benzyl thiol in which phenyl is substituted with one or more hydrophilic substituents, or 3-aminopropane-1-thiol. The one or more hydrophilic substituents on phenyl comprise OH, SH, methoxy, ethoxy, COOH, CHO, $COC_{1-4}$ alkyl, $NH_2$, F, cyano, $SO_3H$, $PO_3H$, and the like.

For example, the maleimido blocking group is $\text{---}S\text{---}(CH_2)_d\text{---}R_{90}$, in which, $R_{90}$ is OH, COOH, or $CH(NHR_{91})COOR_{93}$;

$R_{93}$ is hydrogen or $CH_3$;

$R_{91}$ is hydrogen or $CH_3CO$; and d is 1 or 2.

For example, the maleimido blocking group is $\text{---}S\text{---}CH_2\text{---}CH(NH_2)COOH$.

For example, when the PHF has a molecular weight ranging from 2 kDa to 40 kDa, (e.g., about 2-20 kDa or about 3-15 kDa or about 5-10 kDa), the number of drugs per PHF (e.g., $m_2$) is an integer from 1 to about 40, (e.g., about 1-20 or about 2-15 or about 3-10). This scaffold can be used, for example, for conjugating a PBRM having a molecular weight of 40 kDa or greater (e.g., 60 kDa or greater; 80 kDa or greater; or 100 kDa or greater; 120 kDa or greater; 140 kDa or greater; 160 kDa or greater or 180 kDa or greater). In this embodiment the ratio of PBRM per PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:6, between about 1:2 and about 1:5, between about 1:2 and about 1:4 or between about 1:2 and about 1:3.

For example, when the PHF has a molecular weight ranging from 2 kDa to 40 kDa, (e.g., about 2-20 kDa or about 3-15 kDa or about 5-10 kDa), the number of drugs per PHF (e.g., $m_2$) is an integer from 1 to about 40, (e.g., about 1:20 or about 2-15 or about 3:10). This scaffold can be used, for example, for conjugating a PBRM having a molecular weight of 140 kDa to 180 kDa. In this embodiment the ratio of PBRM per PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:6, between about 1:2 and about 1:5, between about 1:2 and about 1:4 or between about 1:2 and about 1:3.

PBRMs in this molecular weight range include, but are not limited to, for example, full length antibodies, such as, IgG, IgM.

For example, when the PHF has a molecular weight ranging from 2 kDa to 40 kDa, (e.g., about 2-20 kDa or about 3-15 kDa or about 5-10 kDa), the number of drugs per PHF (e.g., $m_2$) is an integer from 1 to about 40, (e.g., about 1:20 or about 2:15 or about 3:10). This scaffold can be used, for example, for conjugating a PBRM having a molecular weight of 60 kDa to 120 kDa. In this embodiment the ratio of PBRM per PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:6, between about 1:2 and about 1:5, between about 1:2 and about 1:4 or between about 1:2 and about 1:3.

PBRMs in this molecular weight range include, but are not limited to, for example, antibody fragments such as, for example Fab2, scFcFv and camelids.

For example, when the PHF has a molecular weight ranging from 2 kDa to 40 kDa, (e.g., about 2-20 kDa or about 3-15 kDa or about 5-10 kDa), the number of drugs per PHF (e.g., $m_2$) is an integer from 1 to about 40, (e.g., about 1:20 or about 2-15 or about 3:10). This scaffold can be used, for example, for conjugating a PBRM having a molecular weight of 40 kDa to 80 kDa. In this embodiment the ratio of PBRM per PHF is between about 1:1 and about 1:10, between about 1:1 and about 1:9, between about 1:1 and about 1:8, between about 1:1 and about1:7, between about 1:1 and about 1:6, between about 1:1 and about 1:5, between about 1:1 and about 1:4, between about 1:1 and about 1:3, between about 1:1 and about 1:2, between about 1:2 and about 1:6, between about 1:2 and about 1:5, between about 1:2 and about 1:4 or between about 1:2 and about 1:3.

PBRMs in this molecular weight range include, but are not limited to, for example, antibody fragments, such as, Fabs.

In another aspect, the invention features a polymeric scaffold useful to conjugate with both a protein based recognition-molecule (PBRM) and a therapeutic agent (D). The D-free scaffold comprises a polymeric carrier, one or more linkers connected to the polymeric carrier which is suitable for connecting a PBRM to the polymeric carrier, and one or more linkers suitable for connecting a drug (D) to the polymeric carrier.

In certain embodiments, the conjugates are formed in several steps. These steps include (1) modifying a polymer so that it contains a functional group that can react with a functional group of the drug or its derivative; (2) reacting the modified polymer with the drug or its derivative so that the drug is linked to the polymer; (3) modifying the polymer-drug conjugate so that the polymer contains a functional group that can react with a functional group of the PBRM or its derivative; and (4) reacting the modified polymer-drug conjugate with the PBRM or its derivative to form the conjugate of this invention. Step (3) may be omitted if the modified polymer produced by step (1) contains a functional group that can react with a functional group of the PBRM or its derivative.

In another embodiment the conjugates are formed in several steps: (1) modifying a polymer so that it contains a functional group that can react with a functional group of a first drug or its derivative; (2) reacting the modified polymer with the first drug or its derivative so that the first drug is linked to the polymer; (3) modifying the polymer-drug conjugate so that it contains a different functional group that can react with a functional group of a second drug or its derivative (4) reacting the modified polymer-drug conjugate with the second drug or its derivative so that the second drug is linked to the polymer-drug conjugate; (5) modifying the polymer-drug conjugate containing 2 different drugs so that the polymer contains a functional group that can react with a functional group of the PBRM or its derivative; and (6) reacting the modified polymer-drug conjugate of step (5) with the PBRM or its derivative to form the conjugate of this invention. Steps (5) and (6) may be repeated if 2 different PBRM or its derivatives are to be conjugated to form a polymer-drug conjugate comprising two different drugs and two different PBRMs.

In yet another embodiment, the conjugates are formed in several steps. These steps include (1) modifying a polymer so that it contains a functional group that can react with a functional group of the drug or its derivative; (2) further modifying the polymer so that it also contains a functional group that can react with a functional group of the PBRM or its derivative; (3) reacting the modified polymer with the drug or its derivative so that the drug is linked to the polymer; and (4) reacting the modified polymer-drug conjugate with the PBRM or its derivative to form the conjugate of this invention. The sequence of steps (1) and (2) or that of steps (3) and (4) can be reversed. Further either step (1) or (2) may be omitted if the modified polymer contains a functional group that can react with both a functional group of the drug or its derivatives and a functional group of the PBRM or its derivative.

In another embodiment the conjugates are formed in several steps: (1) modifying a polymer so that it contains a functional group that can react with a functional group of a first drug or its derivative; (2) further modifying a polymer so that it contains a functional group that can react with a functional group of the PBRM or its derivative; (3) reacting the modified polymer with the first drug or its derivative so that the first drug is linked to the polymer; (4) modifying the polymer-drug conjugate so that it contains a different functional group that can react with a functional group of a second drug or its derivative (5) reacting the modified polymer-drug conjugate with the second drug or its derivative so that the second drug is linked to the polymer-drug conjugate; (6) reacting the modified polymer-drug conjugate containing 2 different drugs so that the polymer with the PBRM or its derivative to form the conjugate of this invention. Step (6) may be repeated if 2 different PBRM or its derivatives are to be conjugated to form a polymer-drug conjugate comprising two different drugs and two different PBRMs. Step (4) may be carried out after step (1) so that the modified polymer contains two different functional groups that can react with two different drugs or their derivatives. In this embodiment, the modified polymer containing two different functional group that can react with two different drugs or their derivatives can be further modified so that it contains a functional group that can react with a functional group of the PBRM or its derivative; prior to the reaction of the modified polymer with either the two different drugs (step (3) and step (5) or PBRM (step (6).

The biodegradable biocompatible conjugates of the invention can be prepared to meet desired requirements of biodegradability and hydrophilicity. For example, under physiological conditions, a balance between biodegradability and stability can be reached. For instance, it is known that molecules with molecular weights beyond a certain threshold (generally, above 40-100 kDa, depending on the physical shape of the molecule) are not excreted through kidneys, as small molecules are, and can be cleared from the body only through uptake by cells and degradation in intracellular compartments, most notably lysosomes. This observation exemplifies how functionally stable yet biodegradable materials may be designed by modulating their stability under general physiological conditions (pH=7.5±0.5) and at lysosomal pH (pH near 5). For example, hydrolysis of acetal and ketal groups is known to be catalyzed by acids, therefore polyals will be in general less stable in acidic lysosomal environment than, for example, in blood plasma. One can design a test to compare polymer degradation profile at, for example, pH=5 and pH=7.5 at 37° C. in aqueous media, and thus to determine the expected balance of polymer stability in normal physiological environment and in the "digestive" lysosomal compartment after uptake by cells. Polymer integrity in such tests can be measured, for example, by size exclusion HPLC. One skilled on the art can select other suitable methods for studying various fragments of the degraded conjugates of this invention.

In many cases, it will be preferable that at pH=7.5 the effective size of the polymer will not detectably change over 1 to 7 days, and remain within 50% from the original for at least several weeks. At pH=5, on the other hand, the polymer should preferably detectably degrade over 1 to 5 days, and be completely transformed into low molecular weight fragments within a two-week to several-month time frame. Although faster degradation may be in some cases preferable, in general it may be more desirable that the polymer degrades in cells with the rate that does not exceed the rate of metabolization or excretion of polymer fragments by the cells. Accordingly, in certain embodiments, the conjugates of the present invention are expected to be biodegradable, in particular upon uptake by cells, and relatively "inert" in relation to biological systems. The products of carrier degradation are preferably uncharged and do not significantly shift the pH of the environment. It is proposed that the abundance of alcohol groups may provide low rate of polymer recognition by cell receptors, particularly of phagocytes. The polymer backbones of the present invention generally contain few, if any, antigenic determinants (characteristic, for example, for some polysaccharides and polypeptides) and generally do not comprise rigid structures capable of engaging in "key-and-lock" type interactions in vivo unless the latter are desirable. Thus, the soluble, crosslinked and solid conjugates of this invention are predicted to have low toxicity and bioadhesivity, which makes them suitable for several biomedical applications.

In certain embodiments of the present invention, the biodegradable biocompatible conjugates can form linear or branched structures. For example, the biodegradable biocompatible polyal conjugates of the present invention can be chiral (optically active). Optionally, the biodegradable biocompatible polyal conjugates of the present invention can be scalemic.

In certain embodiments, the conjugates of the invention are water-soluble. In certain embodiments, the conjugates of the invention are water-insoluble. In certain embodiments, the inventive conjugate is in a solid form. In certain embodiments, the conjugates of the invention are colloids. In certain embodiments, the conjugates of the invention are in particle form. In certain embodiments, the conjugates of the invention are in gel form.

This invention also features a polymeric scaffold useful for conjugating with a PBRM to form a polymer-drug-PBRM conjugate described herein. The scaffold comprises a polymeric carrier of Formula (Ia) useful to conjugate with a protein based recognition-molecule (PBRM), e.g., PBRM with a molecular weight of about 40 kDa or greater:

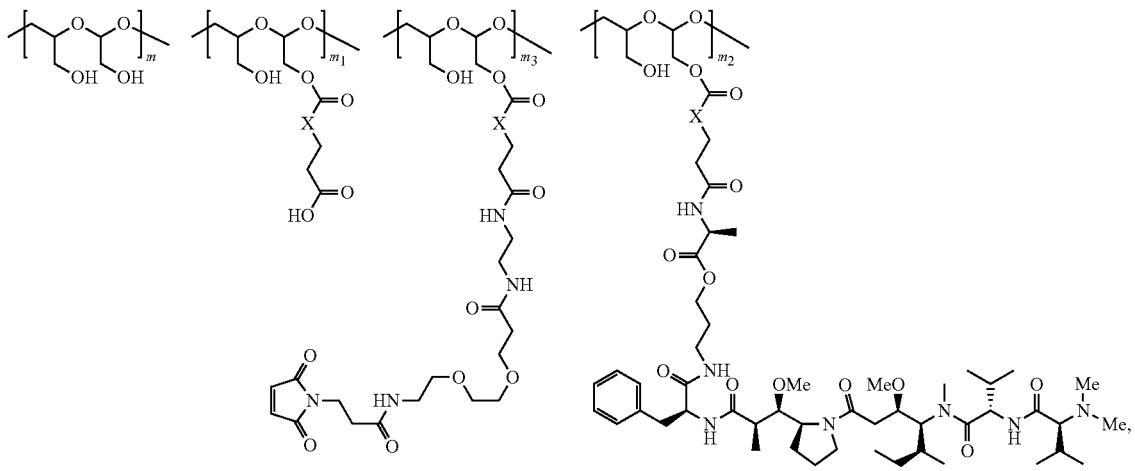

(Ia)

the scaffold comprises poly(1-hydroxymethylethylene hydroxymethyl-formal) (PHF) having a molecular weight ranging from about 2 kDa to about 40 kDa;

X is $CH_2$, O, or NH;

m is an integer from 1 to about 300, $m_1$ is an integer from 1 to about 140, $m_2$ is an integer from 1 to about 40, $m_3$ is an integer from 1 to about 18, and the sum of m, $m_1$, $m_2$ and $m_3$ ranges from about 15 to about 300.

For example, each occurrence of the maleimido moiety in the "$m_3$" unit of Formula (Ia) is yet to form a covalent bond with a functional group of the PBRM.

For example, for conjugating a PBRM having a molecular weight of 40 kDa or greater (e.g., 60 kDa or greater, 80 kDa or greater, 100 kDa or greater, 120 kDa or greater, 140 kDa or greater, 160 kDa or greater or 180 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, or 100-140 kDa), the polymeric carrier of the scaffold of the invention is a polyacetal, e.g., a PHF having a molecular weight (i.e., MW of the unmodified PHF) ranging from about 2 kDa to about 40 kDa (e.g., about 2-20 kDa or about 3-15 kDa or about 5-10 kDa).

For example, for conjugating a PBRM having a molecular weight of 40 kDa to 200 kDa, the polymeric carrier of the scaffold of the invention is a polyacetal, e.g., a PHF having a molecular weight (i.e., MW of the unmodified PHF) ranging from about 2 kDa to about 40 kDa (e.g., about 2-20 kDa or about 3-15 kDa or about 5-10 kDa).

For example, for conjugating a PBRM having a molecular weight of 40 kDa to 80 kDa, the polymeric carrier of the scaffold of the invention is a polyacetal, e.g., a PHF having a molecular weight (i.e., MW of the unmodified PHF) (i.e., MW of the unmodified PHF) ranging from about 2 kDa to about 40 kDa (e.g., about 2-20 kDa or about 3-15 kDa or about 5-10 kDa). For example the PHF has a molecular weight of about 5 kDa, 8 kDa, 10 kDa, 13 KDa or 15 kDa.

PBRMs in this molecular weight range include, but are not limited to, for example, antibody fragments, such as, for example, Fabs.

For example, for conjugating a PBRM having a molecular weight of 60 kDa to 120 kDa, the polymeric carrier of the scaffold of the invention is a polyacetal, e.g., a PHF having a molecular weight (i.e., MW of the unmodified PHF) ranging from about 5 kDa to about 40 kDa (e.g., about 5-30 kDa, about 5-20 kDa or about 5-15 kDa or about 5-10 kDa). For example the PHF has a molecular weight of about 10 kDa, 20 kDa, 30 kDa or 40 kDa.

PBRMs in this molecular weight range include, but are not limited to, for example, camelids, Fab2, scFcFv, and the like.

For example, for conjugating a PBRM having a molecular weight of 140 kDa to 180 kDa, the polymeric carrier of the scaffold of the invention is a polyacetal, e.g., a PHF having a molecular weight (i.e., MW of the unmodified PHF) ranging from about 2 kDa to about 40 kDa (e.g., about 2-20 kDa or about 3-15 kDa or about 5-10 kDa). For example the PHF has a molecular weight of about 5 kDa, 8 kDa, 10 kDa, 13 kDa or 15 kDa.

PBRMs in this molecular weight range include, but are not limited to, for example, full length antibodies, such as, IgG, IgM.

For example, when the PHF in Formula (Ia) has a molecular weight ranging from about 2 kDa to about 40 kDa (i.e., the sum of m, $m_1$, $m_2$, and $m_3$ ranging from about 1 to about 300), $m_2$ is an integer from 1 to about 40, $m_3$ is an integer from 1 to about 18, and/or $m_1$ is an integer from 1 to about 140 (e.g., $m_1$ being about 1-90).

For example, when the PHF in Formula (Ia) has a molecular weight ranging from about 2 kDa to about 20 kDa (i.e., the sum of m, $m_1$, $m_2$, and $m_3$ ranging from about 1 to about 150), $m_2$ is an integer from 1 to about 20, $m_3$ is an integer from 1 to about 10, and/or $m_1$ is an integer from 1 to about 70 (e.g., $m_1$ being about 4-45).

For example, when the PHF in Formula (Ia) has a molecular weight ranging from about 3 kDa to about 15 kDa (i.e., the sum of m, $m_1$, $m_2$, and $m_3$ ranging from about 1 to about 110), $m_2$ is an integer from 2 to about 15, $m_3$ is an integer from 1 to about 8, and/or $m_1$ is an integer from 2 to about 50 (e.g., $m_1$ being about 4-30).

For example, when the PHF in Formula (Ia) has a molecular weight ranging from about 5 kDa to about 10 kDa (i.e., the sum of m, $m_1$, $m_2$, and $m_3$ ranging from about 1 to about 75), $m_2$ is an integer from 3 to about 10, $m_3$ is an integer from 1 to about 5, and/or $m_1$ is an integer from 5 to about 35 (e.g., $m_1$ being about 10-25).

For example, one or more drug-carrying polymeric carriers are connected to one PBRM. For example, the scaffold (e.g., a PBRM-polymer-drug conjugate) comprises a PBRM with a molecular weight of about 40 kDa or greater and one or more D-carrying polymeric carriers connected to the PBRM.

For example, the scaffold further comprises a PBRM connected to the polymeric carrier via the maleimido group.

The invention also provides for polymeric scaffolds of Formula (Ic) of molecular weight ranging from about 2 kDa to about 40 kDa;

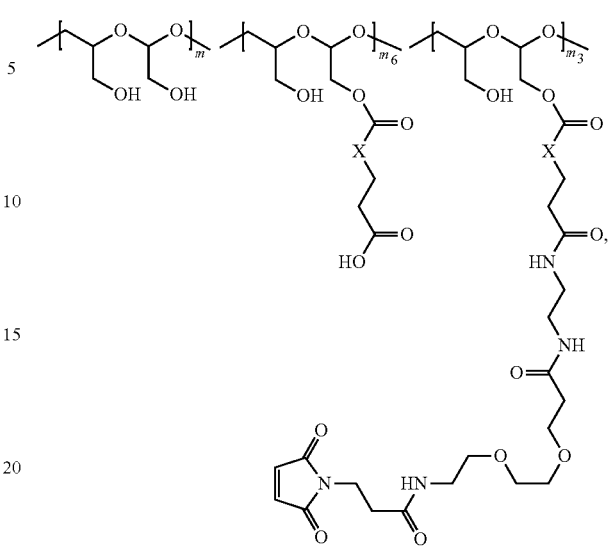

(Ic)

wherein:
X is $CH_2$, O, or NH;
m is an integer from 1 to about 300,
$m_6$ is an integer from 2 to about 180,
$m_3$ is an integer from 1 to about 18, and
the sum of m, $m_6$, and $m_3$ ranges from about 15 to about 300.

For example, each occurrence of the maleimido moiety in the "$m_3$" unit of Formula (Ic) is yet to form a covalent bond with a functional group of the PBRM.

For example, when the PHF in Formula (Ic) has a molecular weight ranging from about 2 kDa to about 20 kDa (i.e., the sum of m, $m_6$, and $m_3$ ranging from about 15 to about 150), $m_3$ is an integer from 1 to about 9, and/or $m_6$ is an integer from 2 to about 90 (e.g., $m_6$ being about 6-60).

For example, when the PHF in Formula (Ic) has a molecular weight ranging from about 3 kDa to about 15 kDa (i.e., the sum of m, $m_6$, and $m_3$ ranging from about 20 to about 110), $m_3$ is an integer from 1 to about 8, and/or $m_6$ is an integer from 4 to about 65 (e.g., $m_6$ being about 6-45).

For example, when the PHF in Formula (Ic) has a molecular weight ranging from about 5 kDa to about 10 kDa, the sum of m, $m_6$ and $m_3$ ranges from about 40 to about 75, $m_6$ is an integer from about 8 to about 45, and $m_3$ is an integer from 1 to about 5.

In some embodiments, the polymeric scaffold (e.g., a polyacetal polymer such as PHF) is conjugated with PBRMs by utilizing cysteine-based bioconjugation strategy. See, e.g., WO2010100430 and U.S. Pat. No. 7,595,292, the contents of which are hereby incorporated by reference in their entireties. In one embodiment, the polymeric scaffold (e.g., a polyacetal polymer such as PHF) conjugates with a PBRM (e.g., an antibody) via cysteines in the antibody hinge region. Without wishing to be bound by the theory, the resulting conjugate is stabilized through the formation of inter-chain bridge structures.

Accordingly, the invention also relates to a polymeric scaffold (e.g., a polyal polymer) comprising at least two moieties connected to the polymeric scaffold, in which each moiety is capable of conjugation to a thiol group from an amino acid (e.g., cysteine) in a PBRM so as to form a protein-polymer conjugate. In one embodiment, the at least two moieties connected to the polymeric scaffold are maleimide groups.

In embodiments, one or more free thiol groups of a PBRM are produced by reducing a protein. The one or more free thiol groups of the PBRM then react with the at least two moieties contained in the polymer scaffold that are capable of conjugation to a thiol group from an amino acid so as to conjugate the PBRM with the polymer scaffold. In one embodiment, the at least two moieties connected to the polymeric scaffold are maleimide groups.

In embodiments, the free thiol groups of the PBRM that are used for the conjugation are derived from a disulfide bridge of a native protein or a disulfide bridge of a protein complex consisting of two or more protein chains connected by the disulfide bridge. A disulfide bridge may be intrachain or interchain bridge. Alternatively, the free thiol groups of the PBRM are from cysteines or the unpaired thiol groups of the native protein that are not involved in inter or intra disulfide bridge formation.

Disulfide bonds can be reduced, for example, with dithiothreitol, mercaptoethanol, tris-carboxyethylphosphine, dehydroascorbic acid, copper sulfate, using conventional methods. A protein can contain one or more disulfide bridges. Reduction to give free thiol groups can be controlled to reduce one or more specific disulfide bridges in a protein. Depending on the extent of disulfide reduction and the stoichiometry of the moieties on the polymeric scaffold polymeric, it is possible to conjugate one or more polymer scaffolds to the protein. Immobilized reducing agents may be used if it is desired to reduce less than the total number of disulfides, as can partial reduction using different reaction conditions or the addition of denaturants.

Advantages of conjugating a polymer to a protein via a thiol include, but are not limited to optimized efficacy, improved dose to dose consistency and homogeneity (as the number of conjugated polymer molecules per protein is the substantially the same for each protein molecule), specific conjugation directed to a specific residue or residues on each protein, and easier purification. Also, the protein-polymer conjugates via the thiol conjugation exhibit substantially improved half-life, mean residence time, and/or clearance rate in circulation as compared to the unconjugated protein.

In some embodiments, the drug-polymer-PBRM conjugates, drug-polymer conjugates, drug carrying-polymeric scaffolds, or PBRM-carrying polymer scaffolds described herein each typically have a polydispersity index (PDI) of ≤1.5, e.g., <1.2.

PBRM-polymer-drug conjugates, drug carrying-polymeric scaffolds, or PBRM-carrying polymer scaffolds can be purified (i.e., removal of residual unreacted drug, PBRM, or polymeric starting materials) by extensive diafiltration. If necessary, additional purification by size exclusion chromatography can be conducted to remove any aggregated PBRM-polymer-drug conjugates. In general, the PBRM-polymer-drug conjugates as purified typically contain less than 5% (e.g., <2% w/w) aggregated PBRM-polymer-drug conjugates as determined by SEC; less than 0.5% (e.g., <0.1% w/w) free (unconjugated) drug as determined by RP-HPLC; less than 1% polymer-drug conjugate as determined by SEC and less than 2% (e.g., <1% w/w) unconjugated PBRM as determined by HIC-HPLC.

Tables C and D below provide examples of the drug-carrying polymeric scaffolds and the polymer-drug-protein conjugates of the invention respectively. In Table D, $m_5$ in the chemical structures is defined as in Formula (Ib) described herein.

TABLE C

| Ref # | Drug:Polymer Ratio | Structure |
|---|---|---|
| Ex 3 | 6:1 | 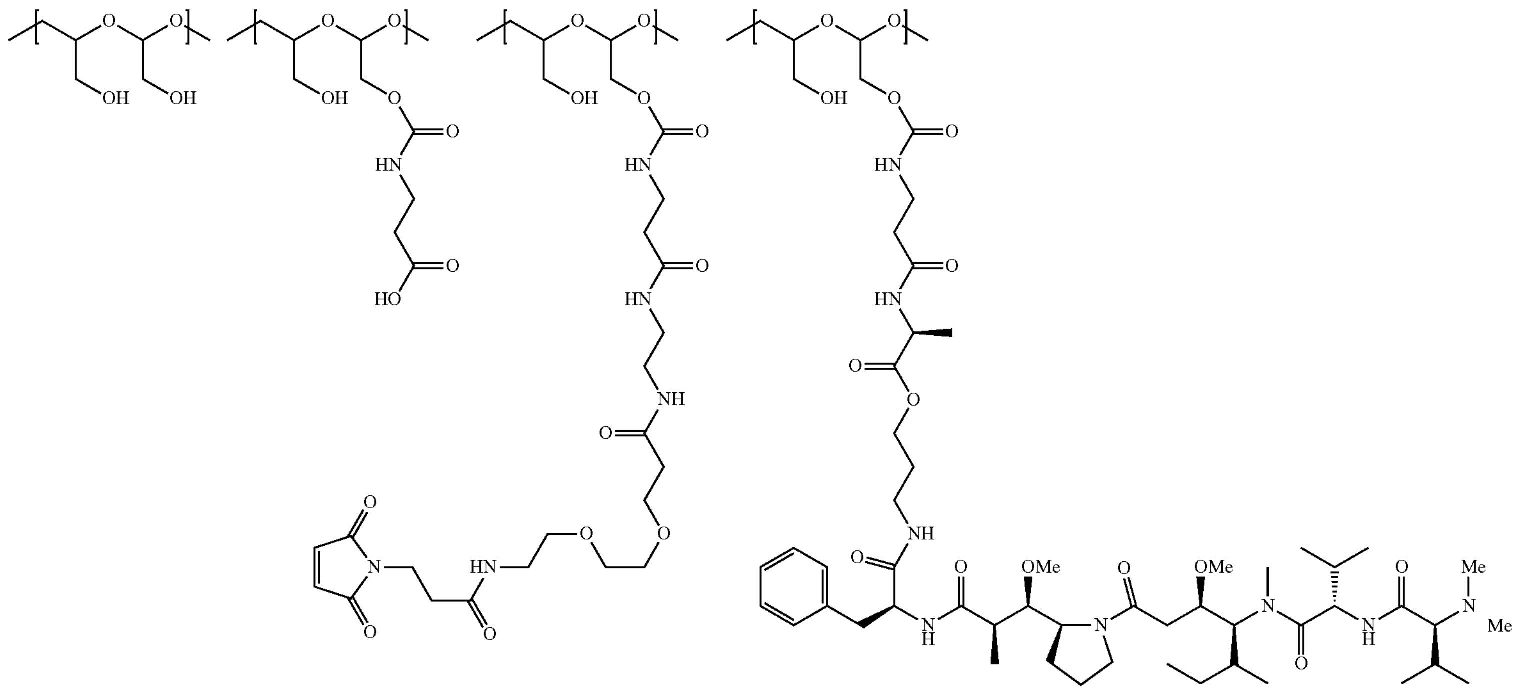 |

TABLE C-continued
| Ref # | Drug:Polymer Ratio | Structure |
|---|---|---|
| Ex 5 | 6:1 | 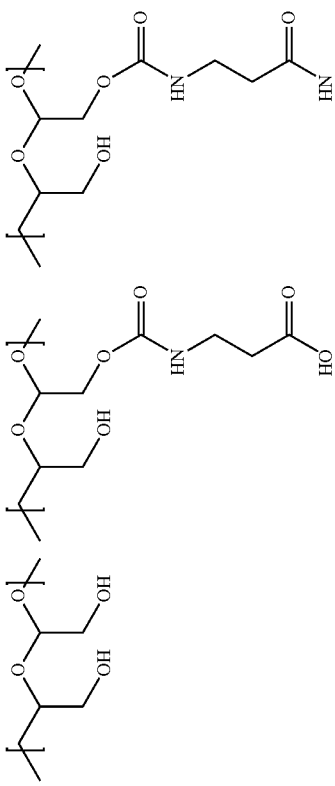 |

TABLE C-continued
| Ref # | Drug:Polymer Ratio | Structure |
|---|---|---|
| Ex 6 | 6:1 | 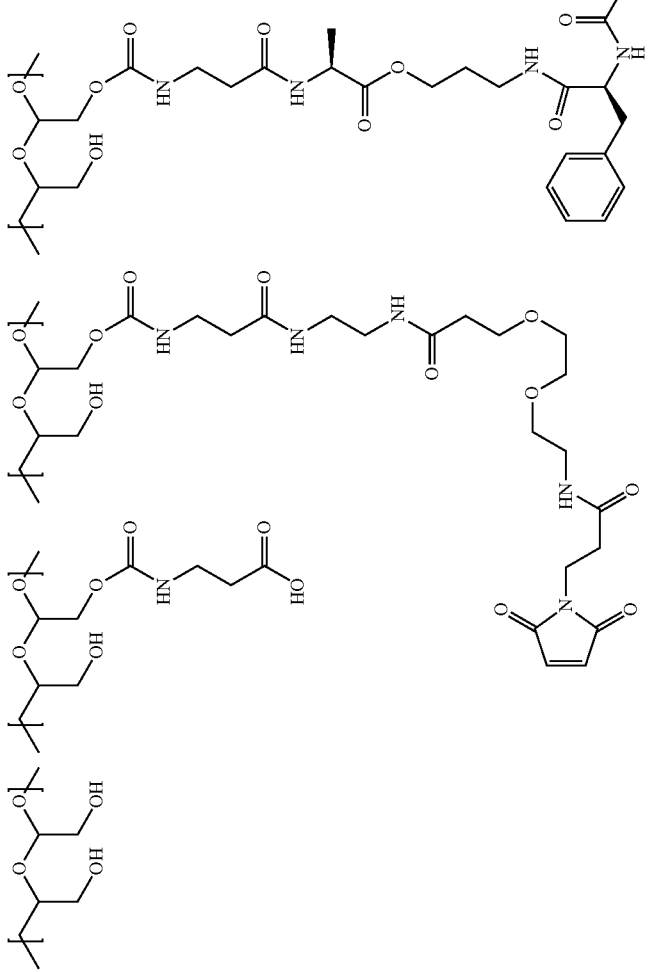 |

TABLE C-continued

| Ref # | Drug:Polymer Ratio | Structure |
|---|---|---|
| Ex 12 | 4.5:1 | 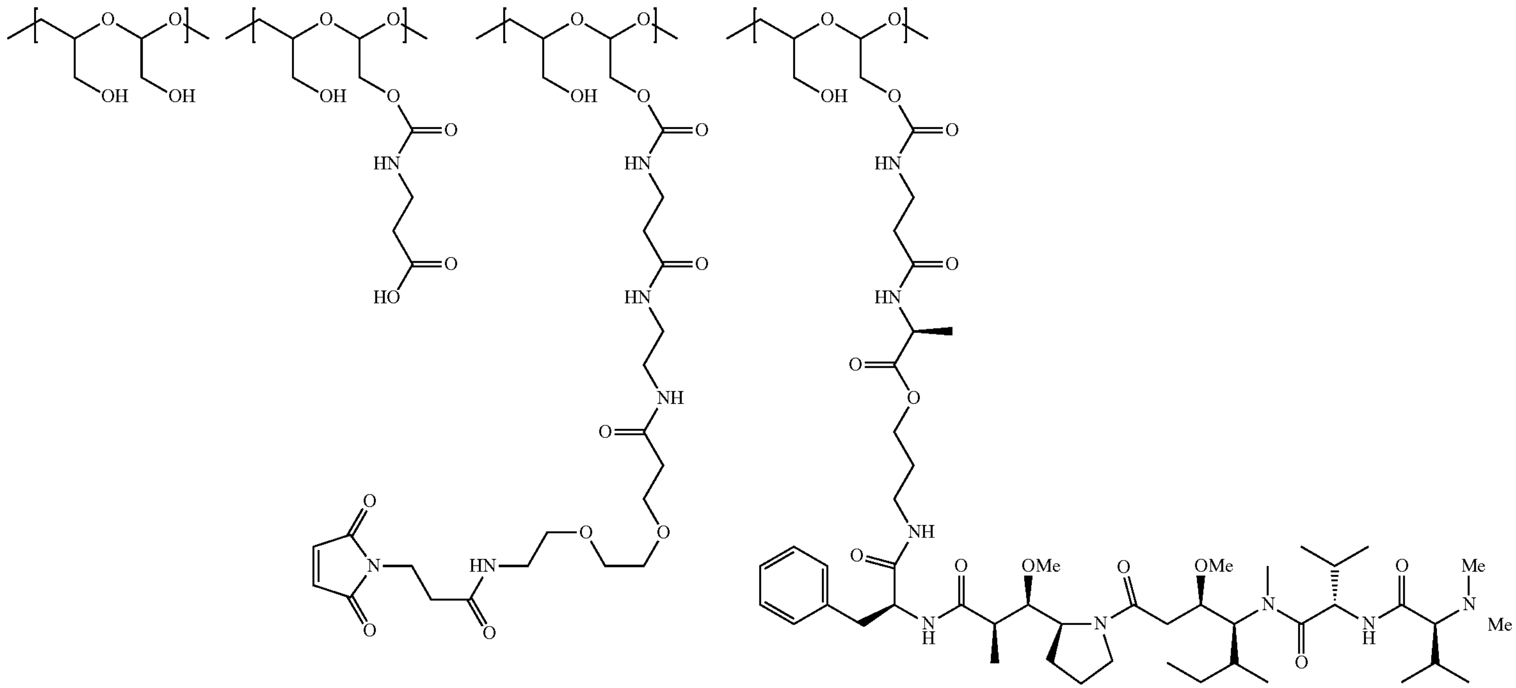 |

TABLE C-continued

| Ref # | Drug:Polymer Ratio | Structure |
|---|---|---|
| X = NH | | 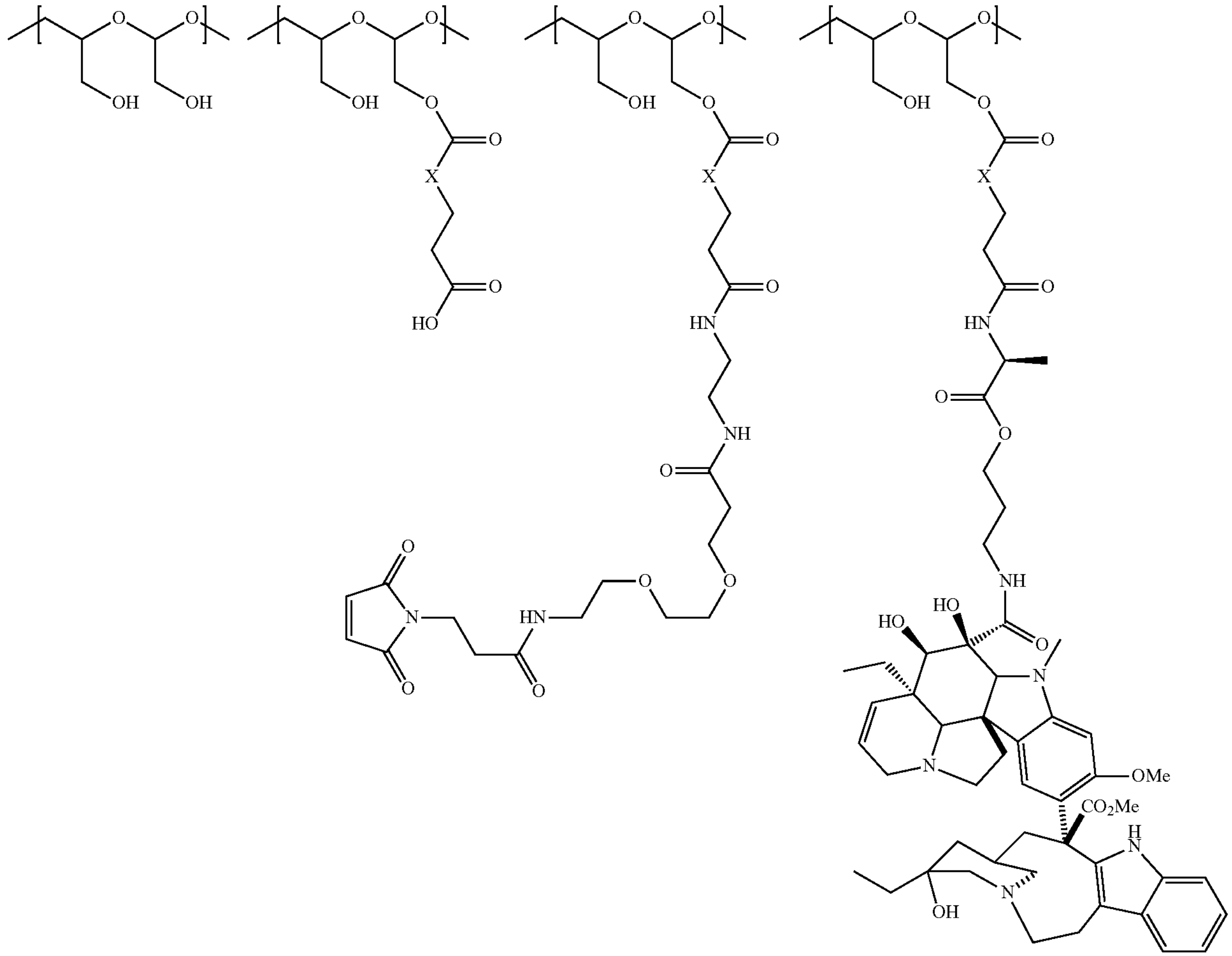 |
| Ex 19A | 2.4:1 | |
| Ex 19B | 4.6:1 | |
| Ex 19C | 2.6:1 | |

TABLE C-continued
| Ref # | Drug: Polymer Ratio | Structure |
|---|---|---|
| Ex 21 | 2.5:1 | 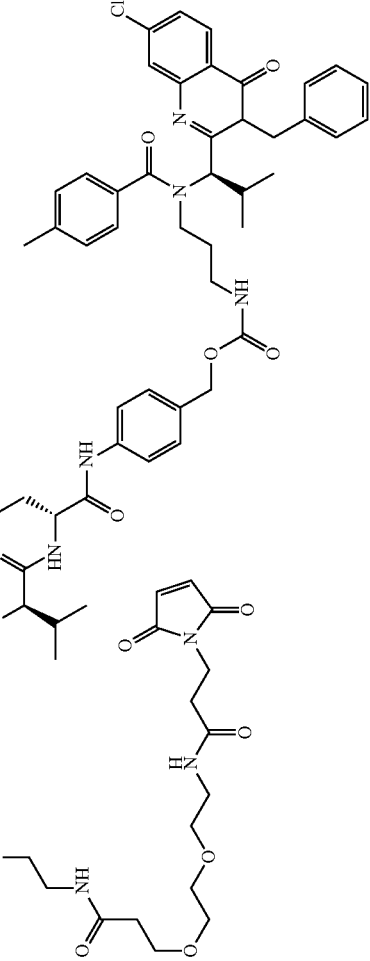 |

TABLE C-continued
| Ref # | Drug:Polymer Ratio | Structure |
|---|---|---|
| Ex 25 | 1.7:1 | 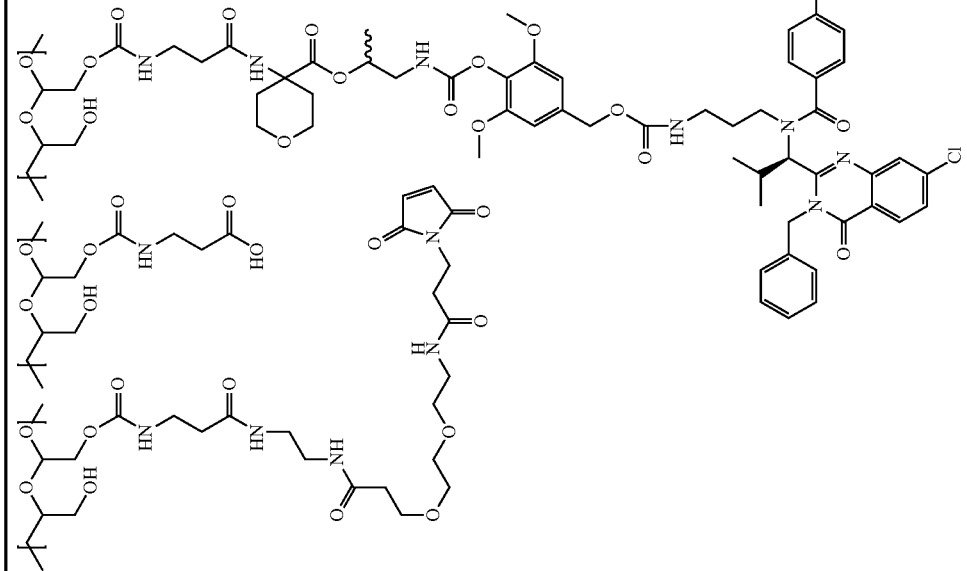 |

TABLE C-continued
| Ref # | Drug:Polymer Ratio | Structure |
|---|---|---|
| Ex 29 | 2.2:1 | 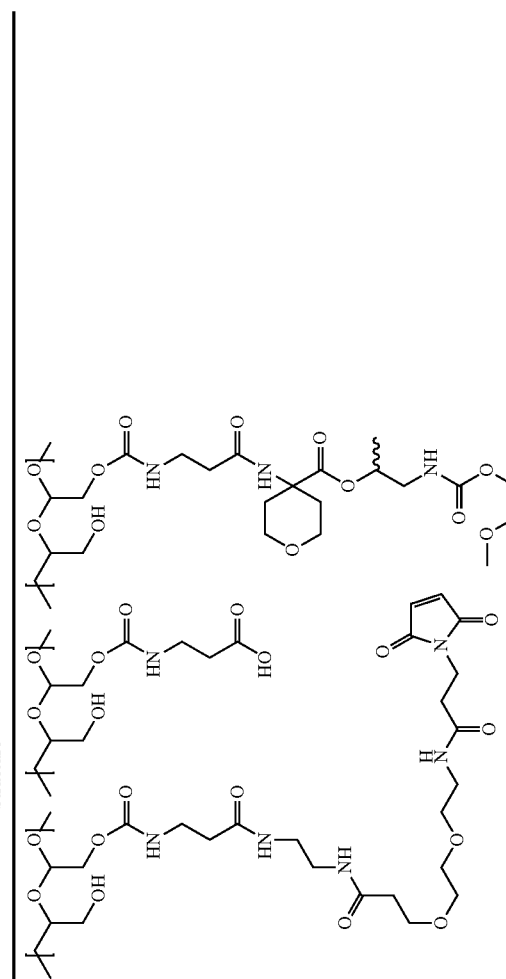 |

TABLE C-continued
| Ref # | Drug:Polymer Ratio | Structure |
|---|---|---|
| Ex 32 | 5.7:1 | 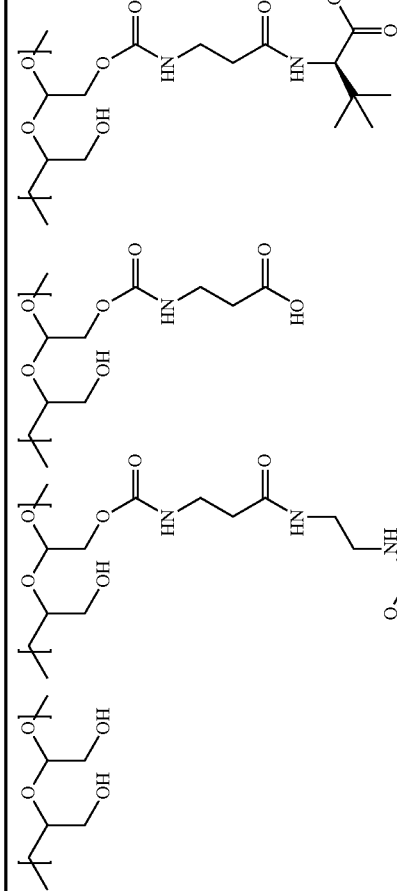 |

TABLE C-continued
| Ref # | Drug:Polymer Ratio | Structure |
|---|---|---|
| Ex 37 | 2.1:1 | 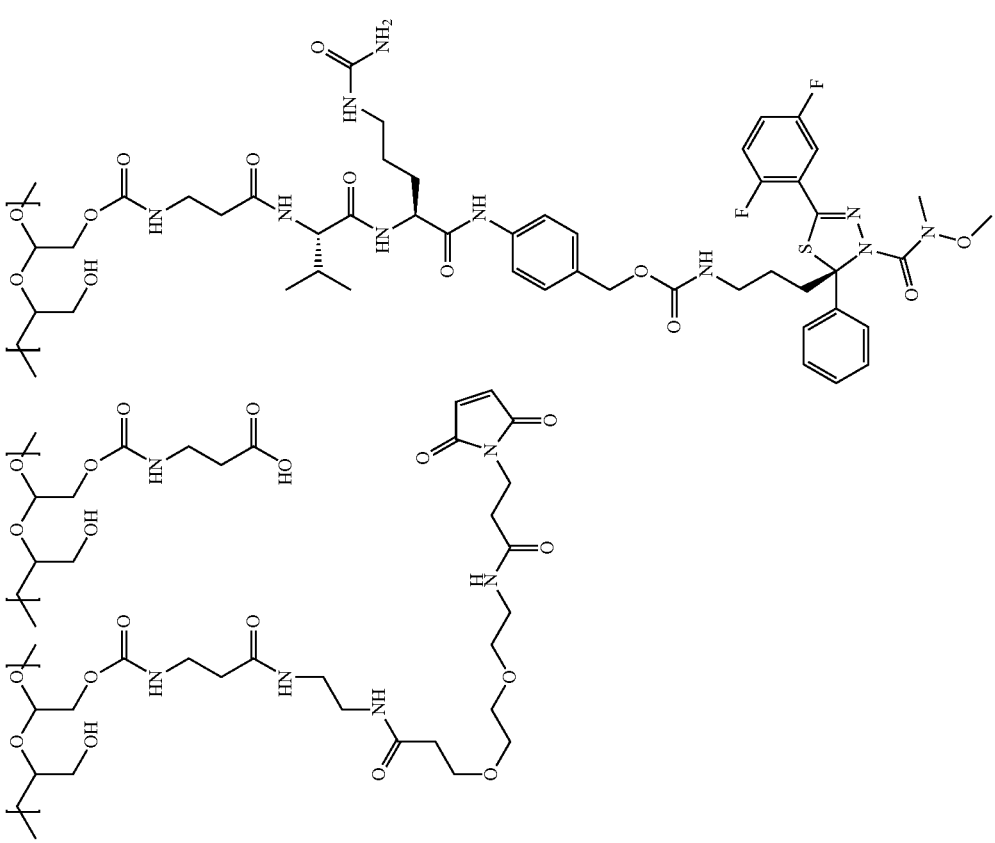 |

TABLE C-continued
| Ref # | Drug:Polymer Ratio | Structure |
|---|---|---|
| Ex 42 | 4.2:1 | 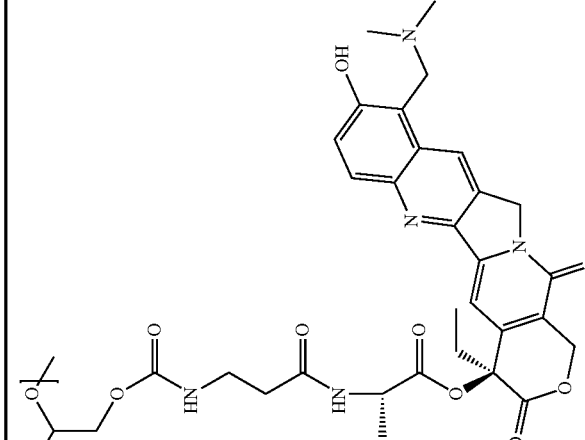 |

TABLE C-continued
| Ref # | Drug:Polymer Ratio | Structure |
|---|---|---|
| | | 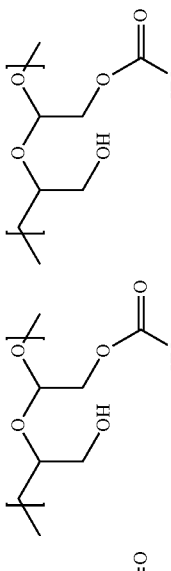 |

TABLE C-continued

| Ref # | Drug: Polymer Ratio | Structure |
|---|---|---|

TABLE D

| Ref # | Drug:PBRM Ratio | Structure |
|---|---|---|
| Ex 4 | 12:1 to 17:1 | |
| Ex 7 | 16:1 to 21:1 | |
| Ex 8 | 10:1 to 15:1 | |

TABLE D-continued

| Ref # | Drug:PBRM Ratio | Structure |
|---|---|---|
| Ex 9 | 13:1 to 18:1 | (structure with RITUXIMAB) |
| Ex 10 | 12:1 to 18:1 | (structure with ANTI-5T4) |

TABLE D-continued

| Ref # | Drug: PBRM Ratio | Structure |
|---|---|---|
| Ex 13 | 18:1 to 23:1 | 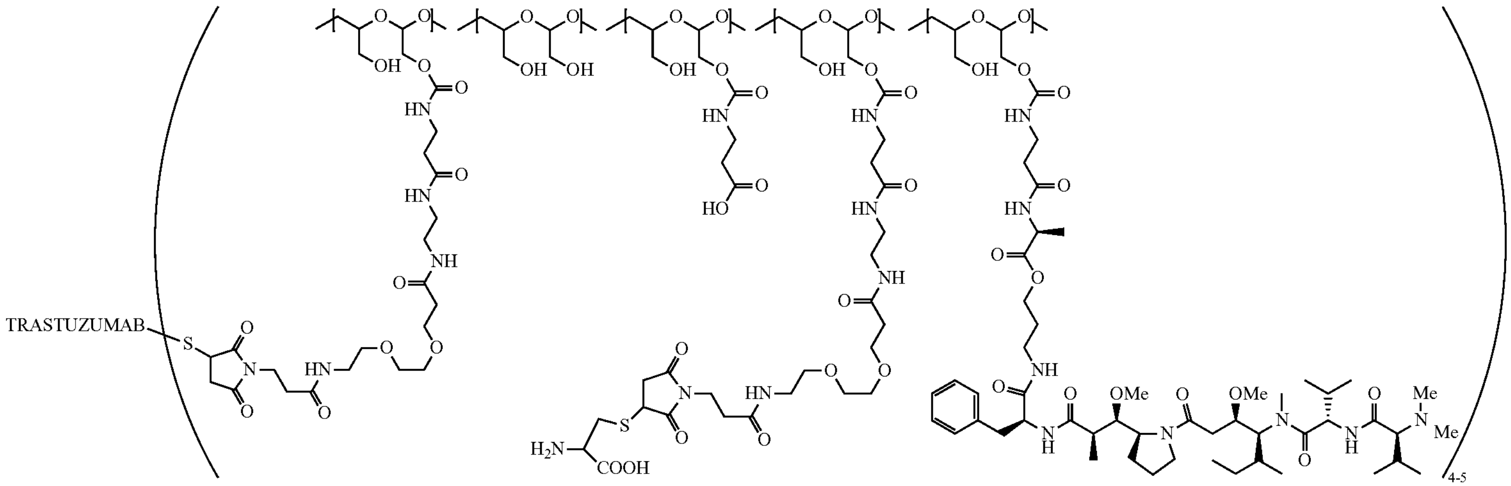 |

TABLE D-continued

| Ref # | Drug:PBRM Ratio | Structure |
|---|---|---|

TABLE D-continued

| Ref # | Drug:PBRM Ratio | Structure |
|---|---|---|
| Ex 14 | 10:1 to 15:1 | 191 |
| Ex 15 | 11:1 to 16:1 | 192 |

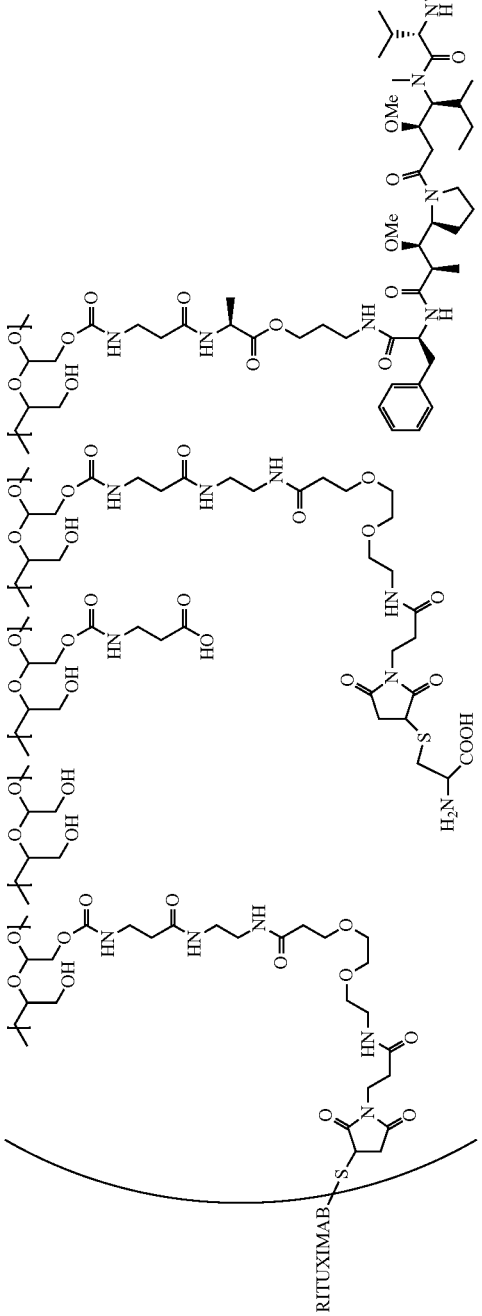

TABLE D-continued

| Ref # | Drug:PBRM Ratio | Structure |
|---|---|---|
| Ex 18 A | 19:1 to 24:1 | 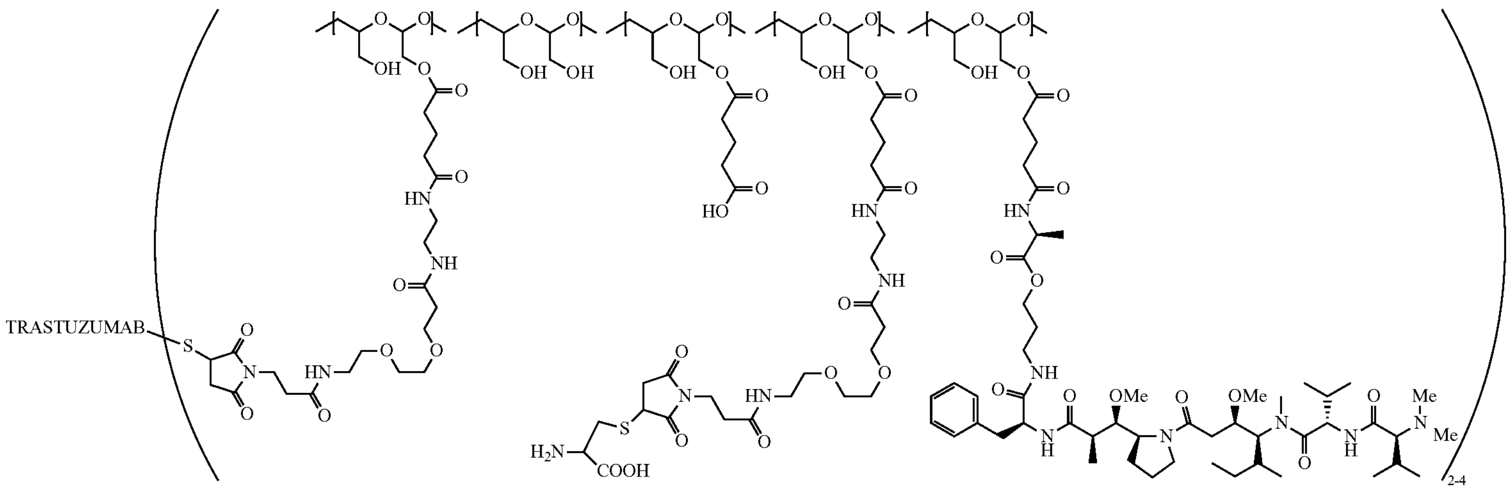 |
| Ex 18 B | 20:1 to 25:1 | 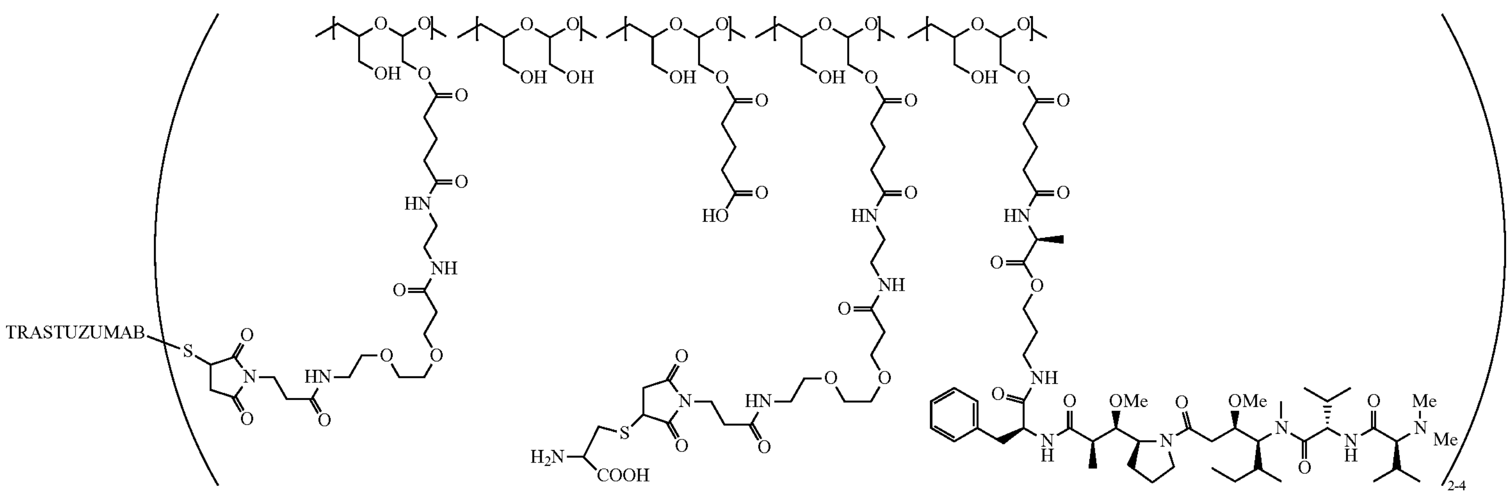 |

TABLE D-continued
| Ref # | Drug: PBRM Ratio | Structure |
|---|---|---|
| Ex 18 C | 23:1 to 28:1 | 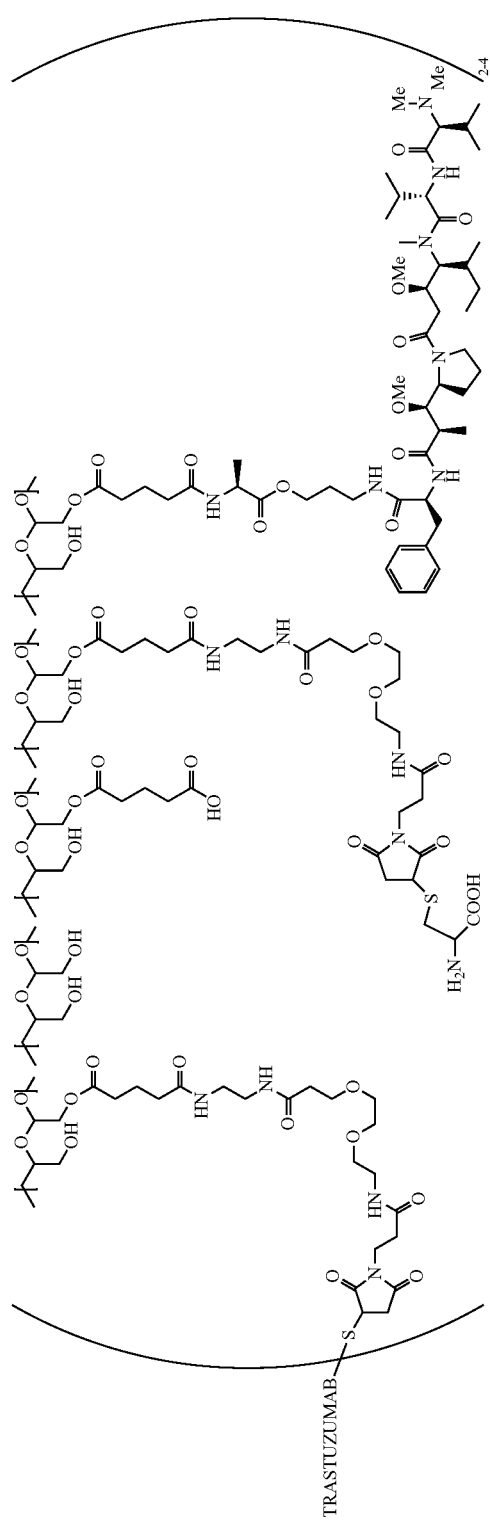 |

TABLE D-continued

| Ref # | Drug:PBRM Ratio | Structure |
|---|---|---|
| Ex 20A | 13:1 to 18:1 | 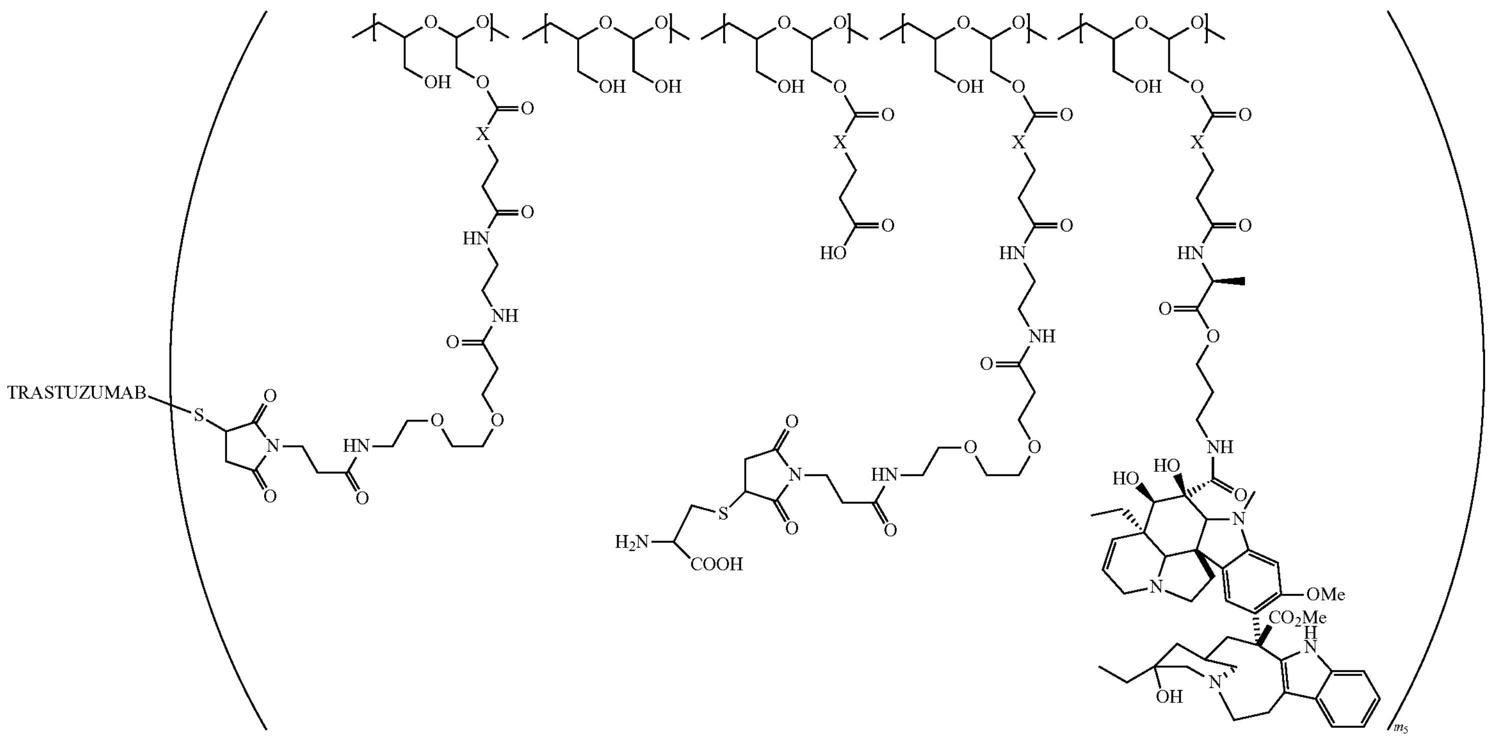 |
| Ex 20B | 10:1 to 14:1 | |
| Ex 20C | 8.5:1 to 12:1 | |

TABLE D-continued
| Ref # | Drug:PBRM Ratio | Structure |
|---|---|---|
| Ex 22 | 7.5:1 to 10:1 | 201 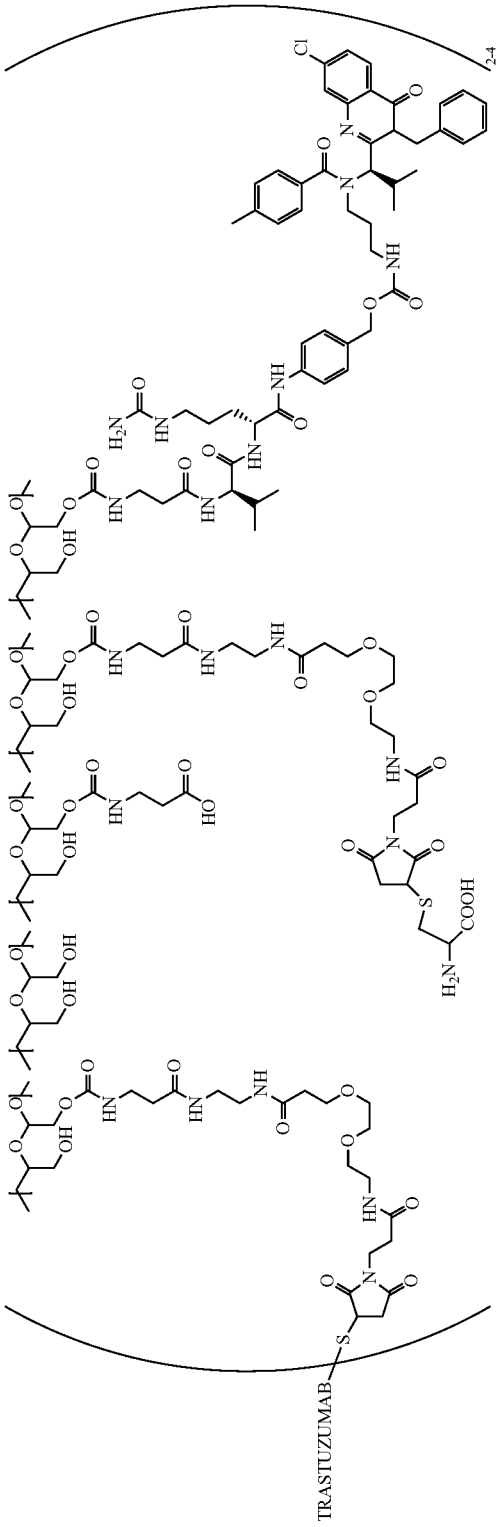 |
| Ex 23 | 6.5:1 to 10:1 | 202 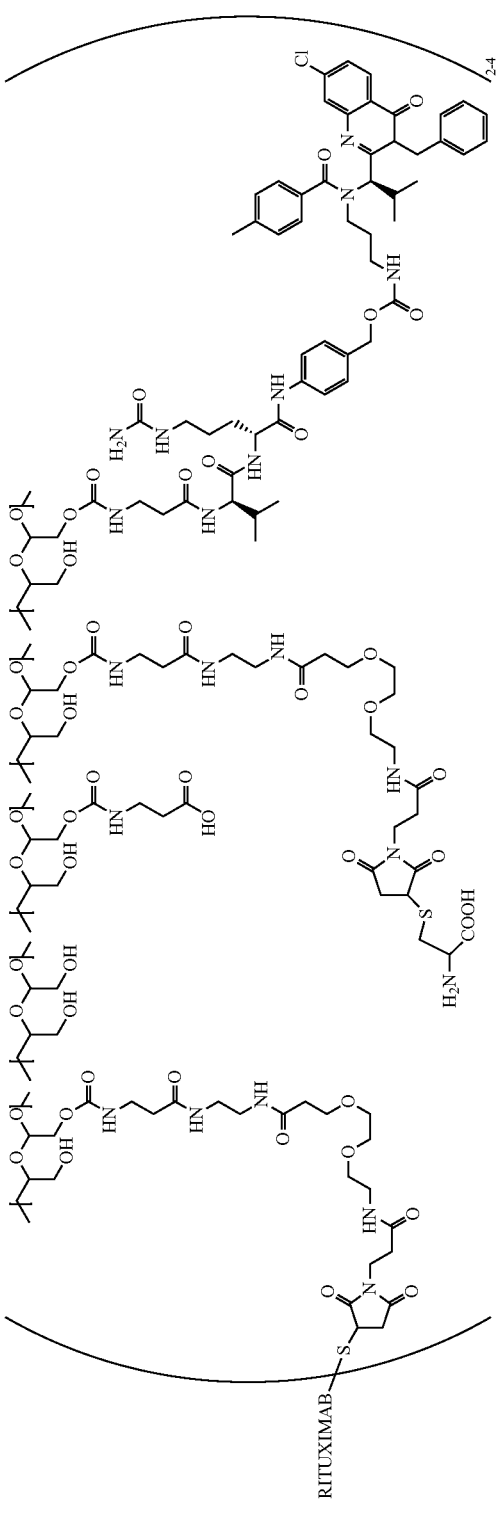 |

TABLE D-continued
| Ref # | Drug:PBRM Ratio | Structure |
|---|---|---|
| Ex 26 | 5:1 to 8:1 | 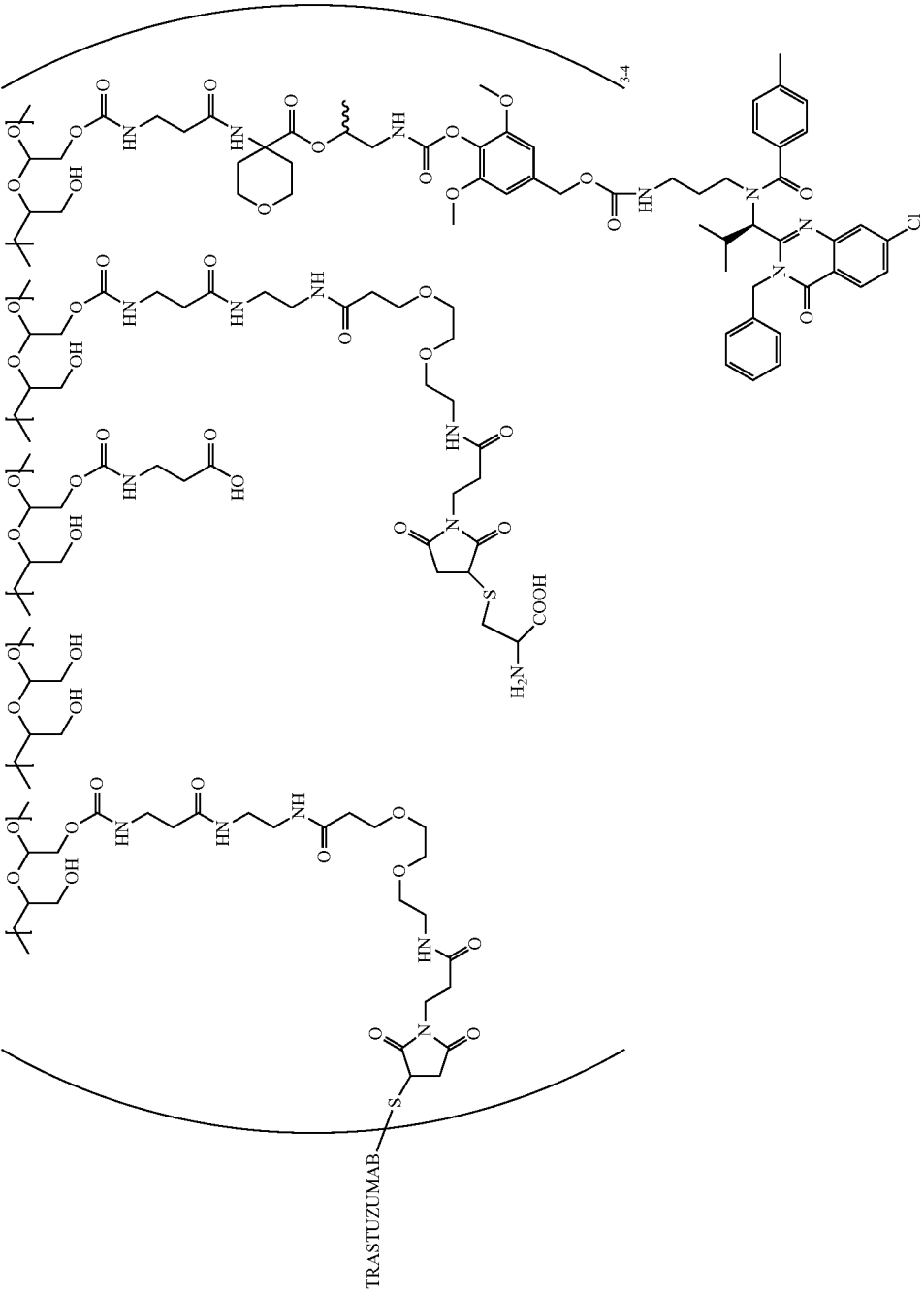 |

TABLE D-continued
| Ref # | Drug:PBRM Ratio | Structure |
|---|---|---|
| Ex 27 | 4.5:1 to 7:1 | 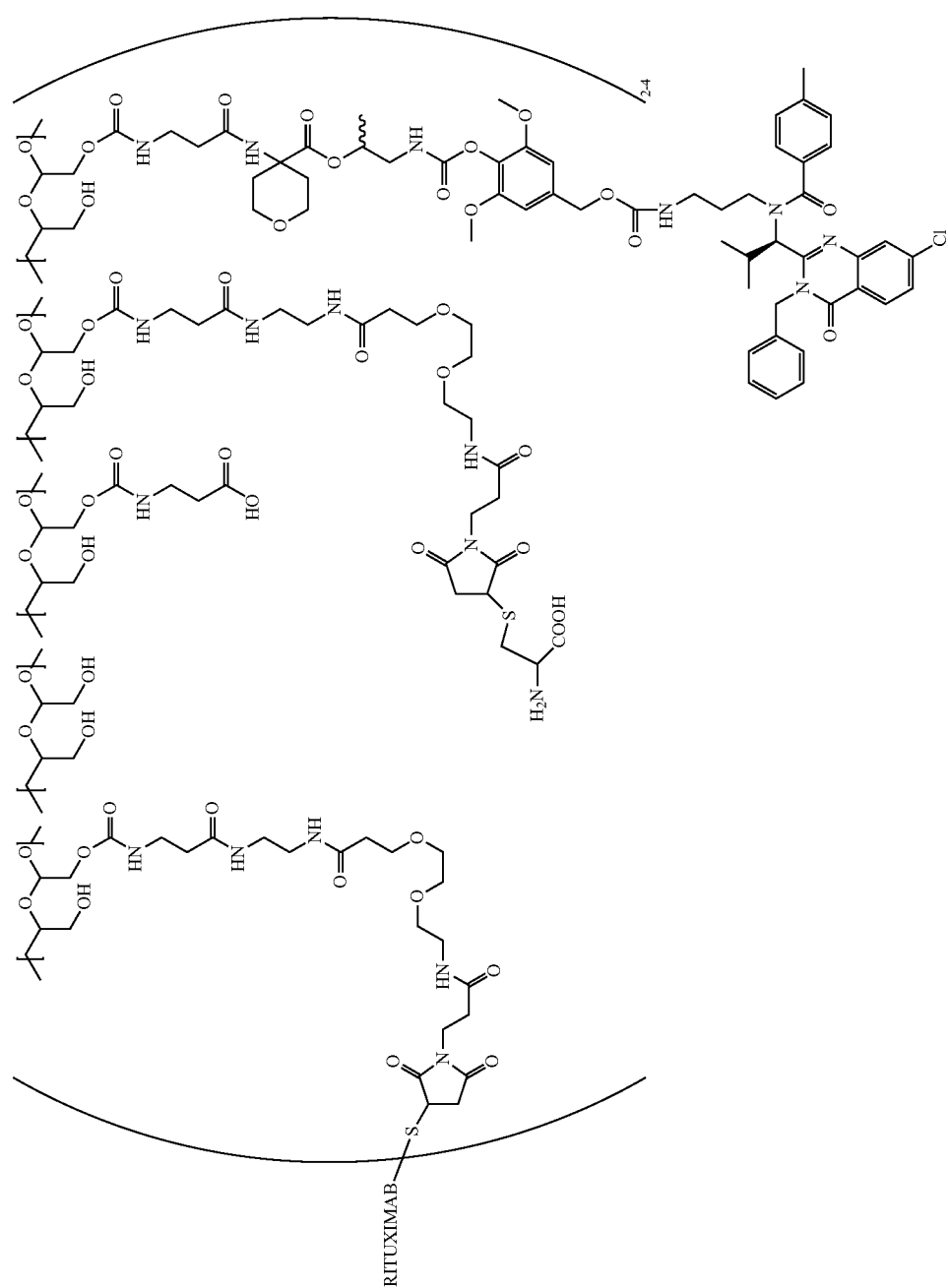 |

TABLE D-continued

| Ref # | Drug:PBRM Ratio | Structure |
|---|---|---|
| Ex 30A | 11:1 to 15:1 | 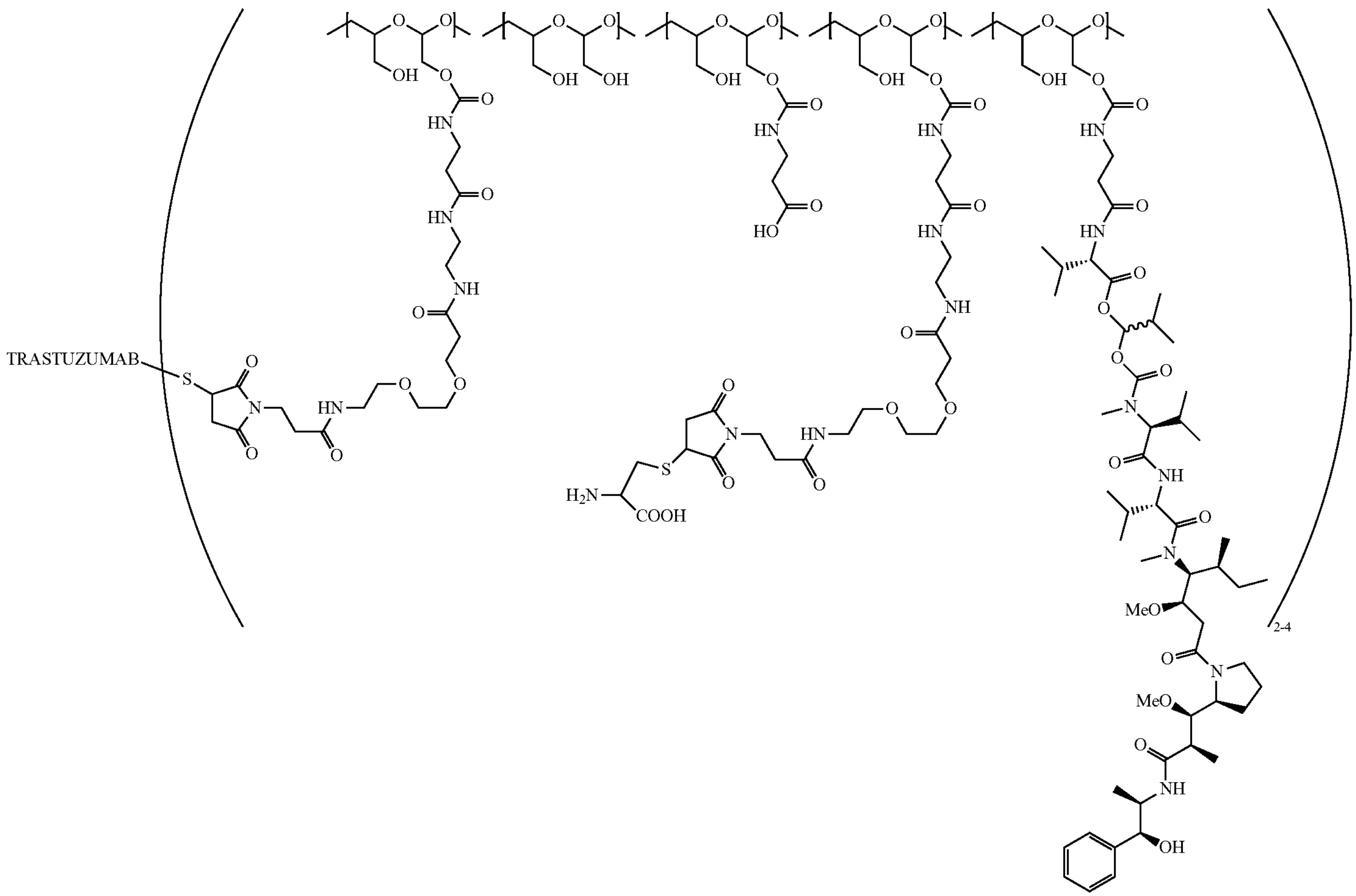 |
| Ex 30B | 12:1 to 16.5:1 | |

TABLE D-continued

| Ref # | Drug:PBRM Ratio | Structure |
|---|---|---|
| Ex 30C | 9.5:1 to 13:1 | |

TABLE D-continued

| Ref # | Drug:PBRM Ratio | Structure |
|---|---|---|
| Ex 33 | 4:1 to 6:1 | 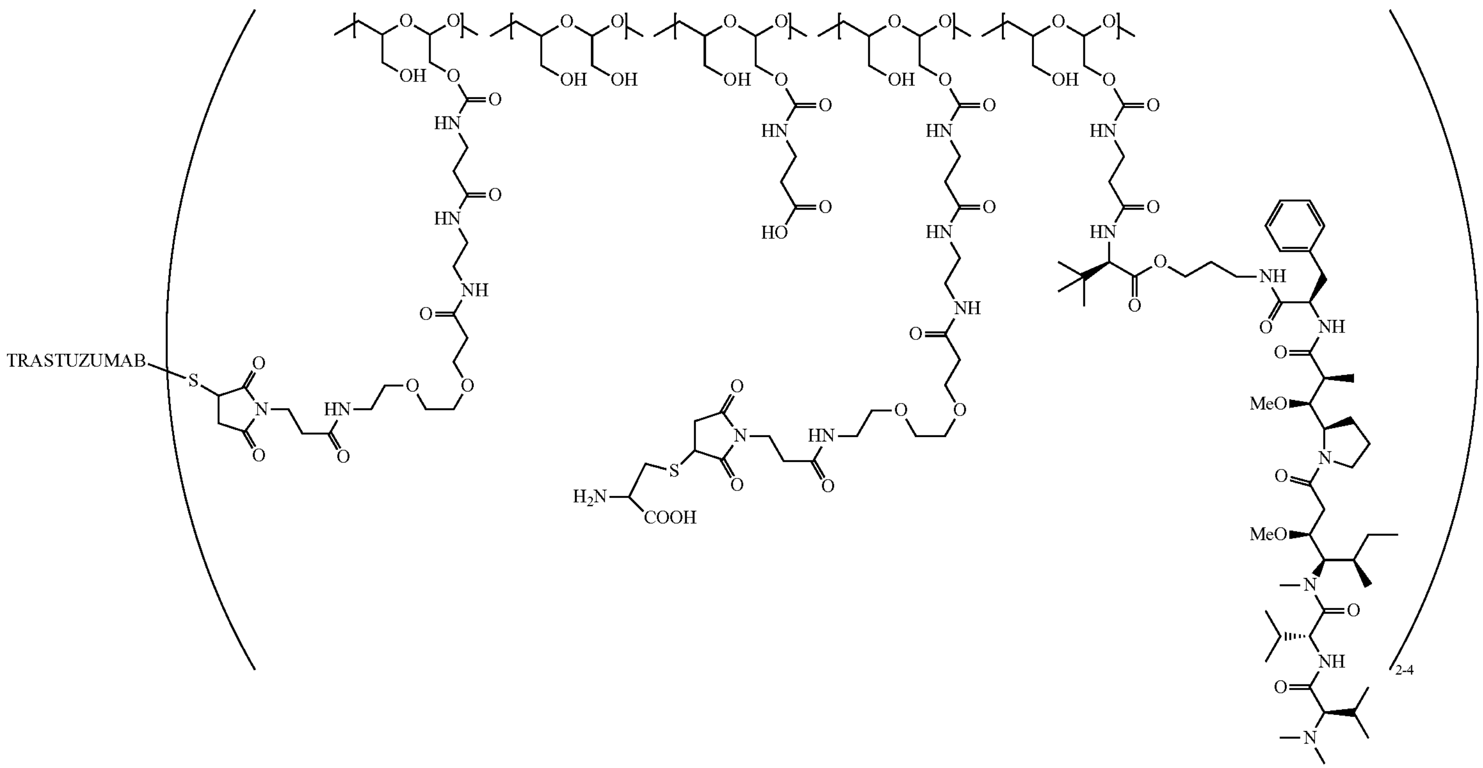 |

TABLE D-continued
| Ref # | Drug:PBRM Ratio | Structure |
|---|---|---|
| Ex 34 | 2.5:1 to about 3.5:1 | 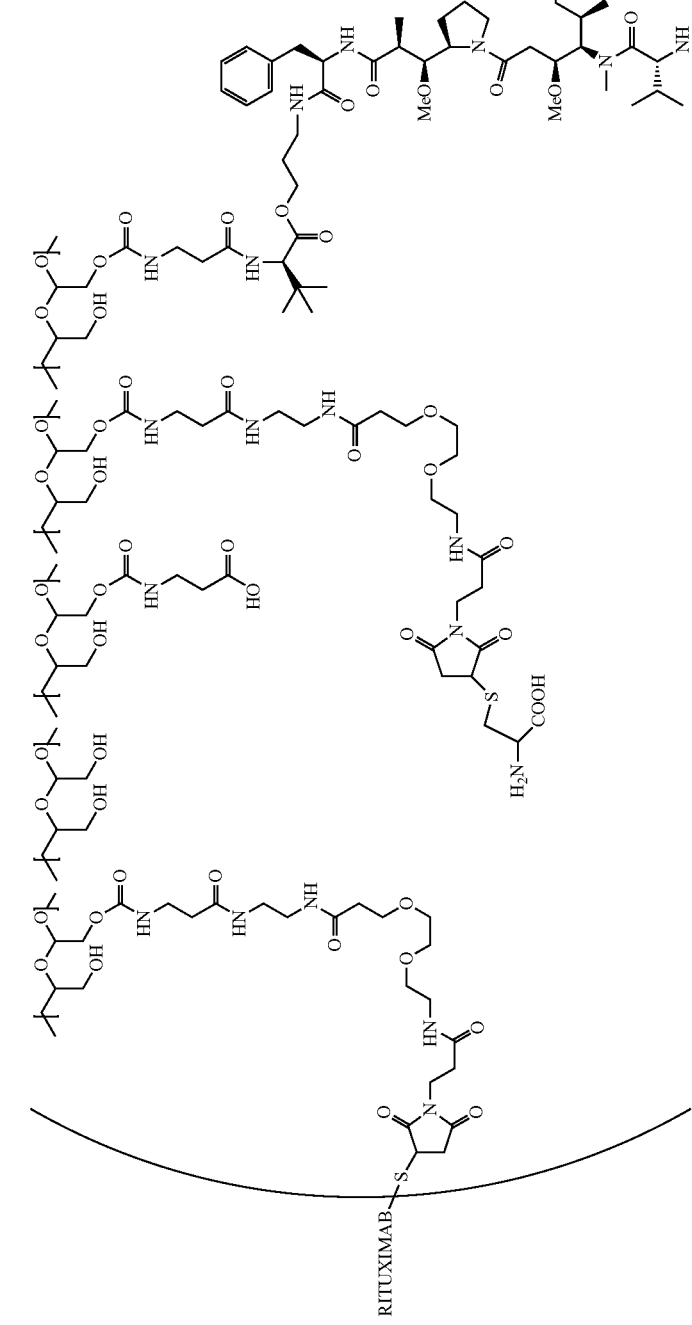 |

TABLE D-continued
| Ref # | Drug:PBRM Ratio | Structure |
|---|---|---|
| Ex 36 | 14.5:1 to 20:1 | 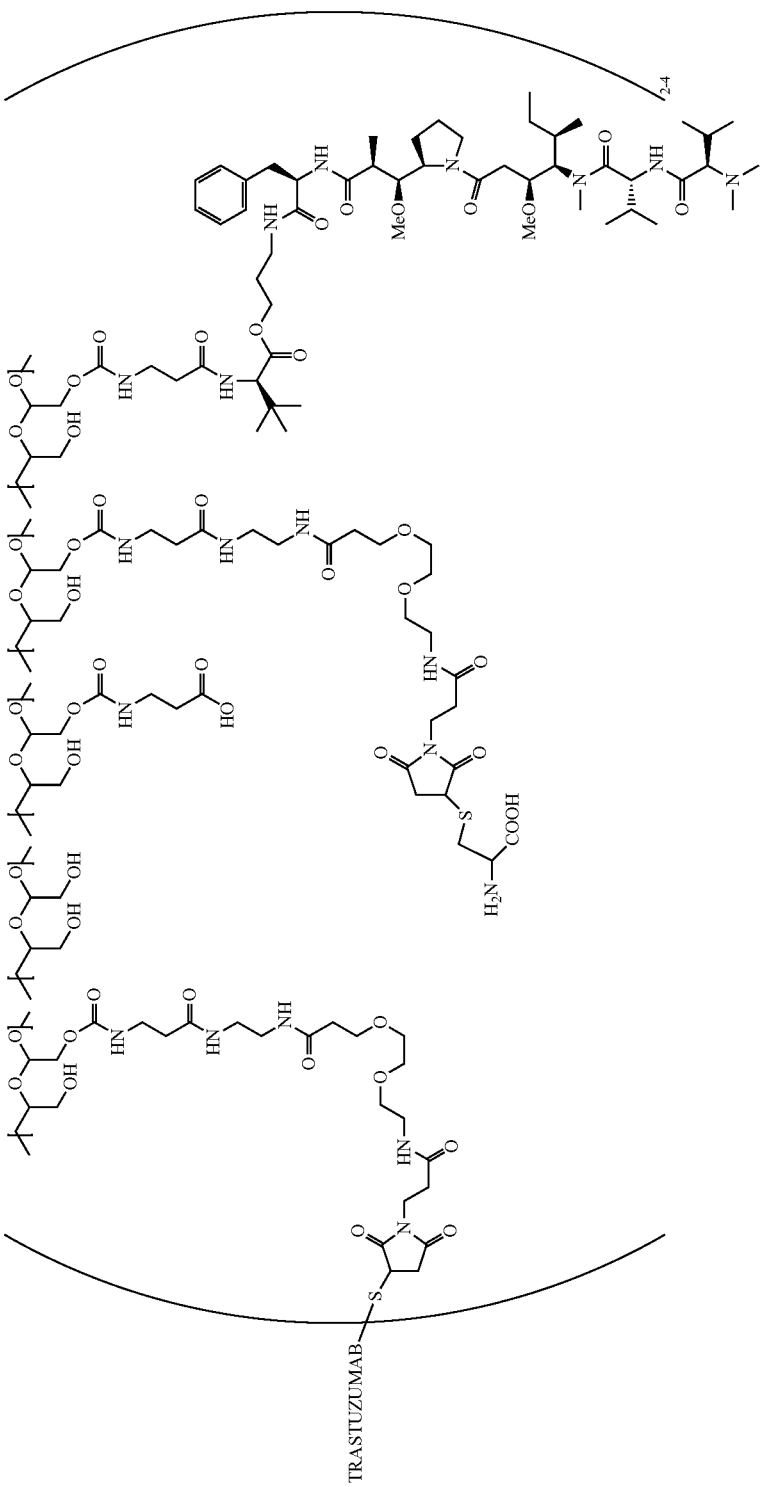 |

TABLE D-continued
| Ref # | Drug:PBRM Ratio | Structure |
|---|---|---|
| Ex 38 | 4:1 to 6:1 | 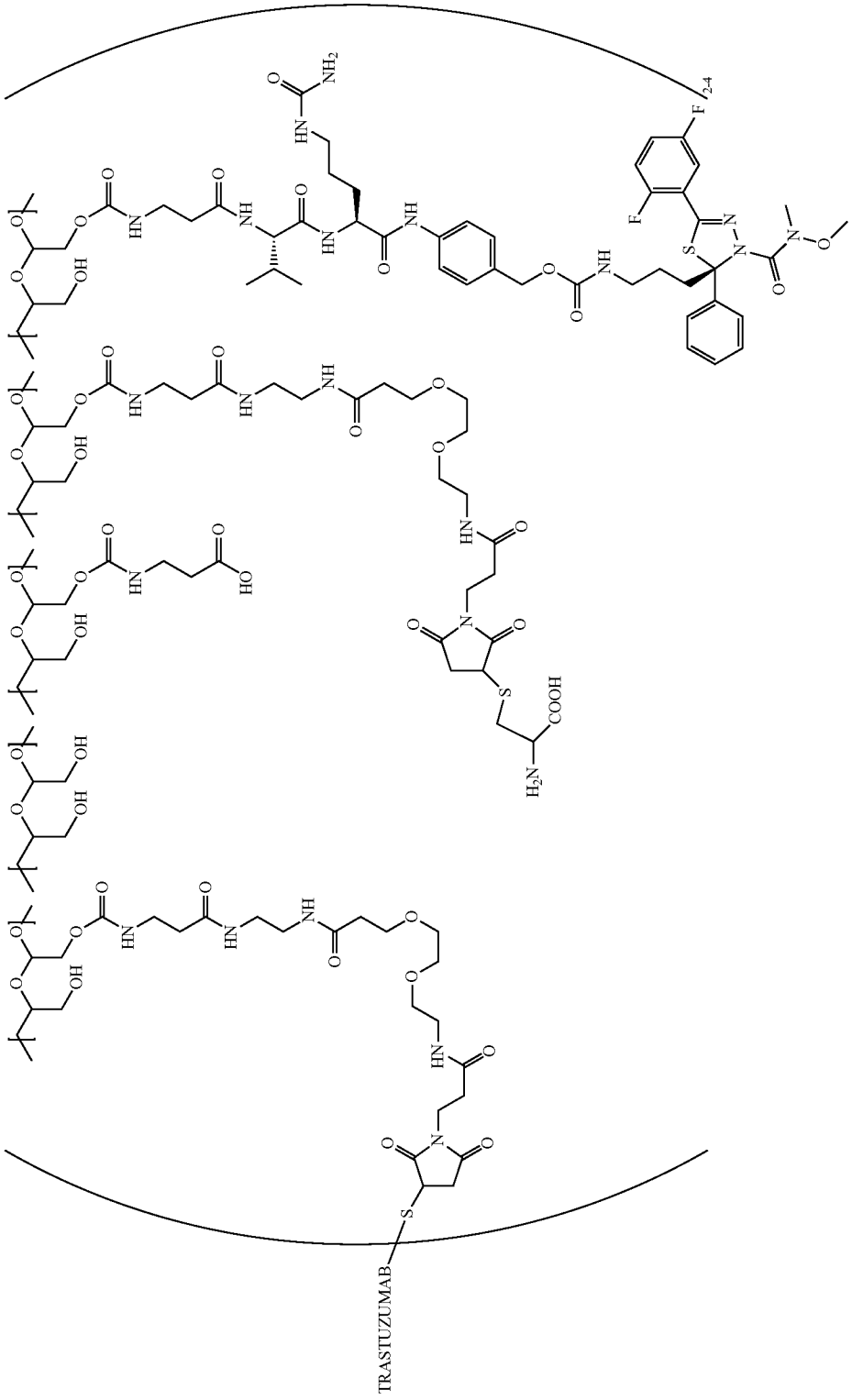 |

TABLE D-continued
| Ref # | Drug:PBRM Ratio | Structure |
|---|---|---|
| Ex 39 | 4:1 to 6:1 | 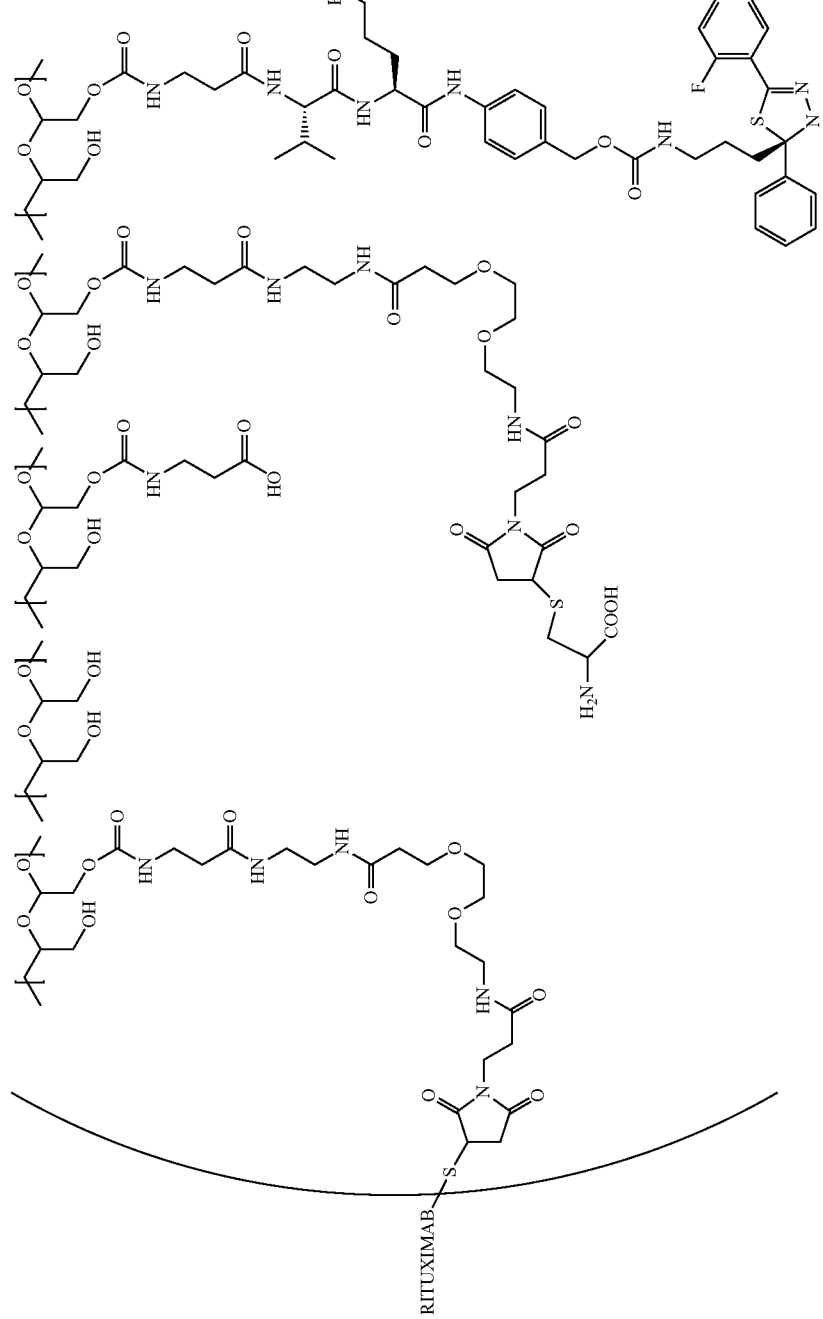 |

TABLE D-continued
| Ref # | Drug:PBRM Ratio | Structure |
|---|---|---|
| Ex 40 | 14:1 to 19:1 | 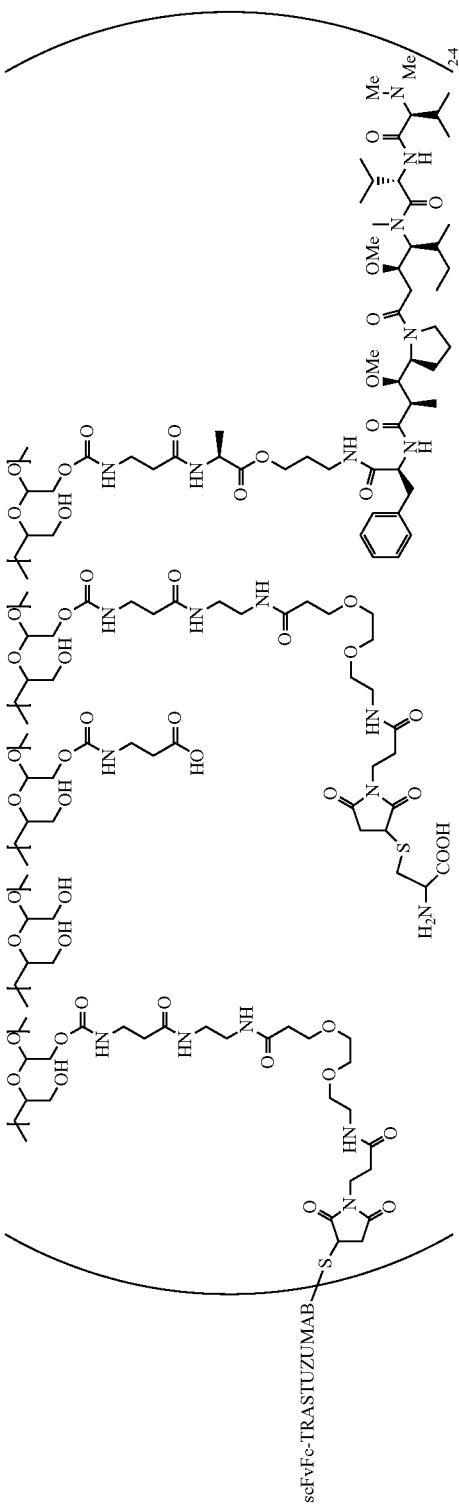 |

TABLE D-continued
| Ref # | Drug:PBRM Ratio | Structure |
|---|---|---|
| Ex 42A | 19:1 to 26:1 | 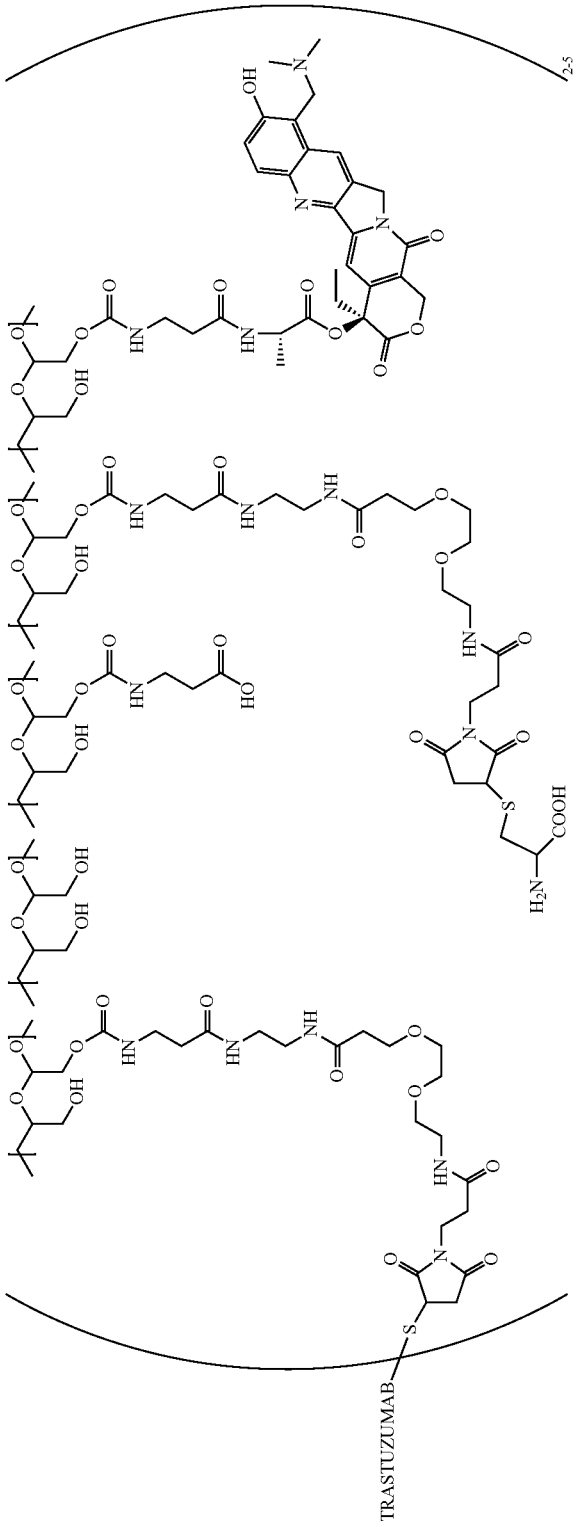 |

TABLE D-continued
| Ref # | Drug:PBRM Ratio | Structure |
|---|---|---|
| Ex 42B | 16:1 to 22:1 | 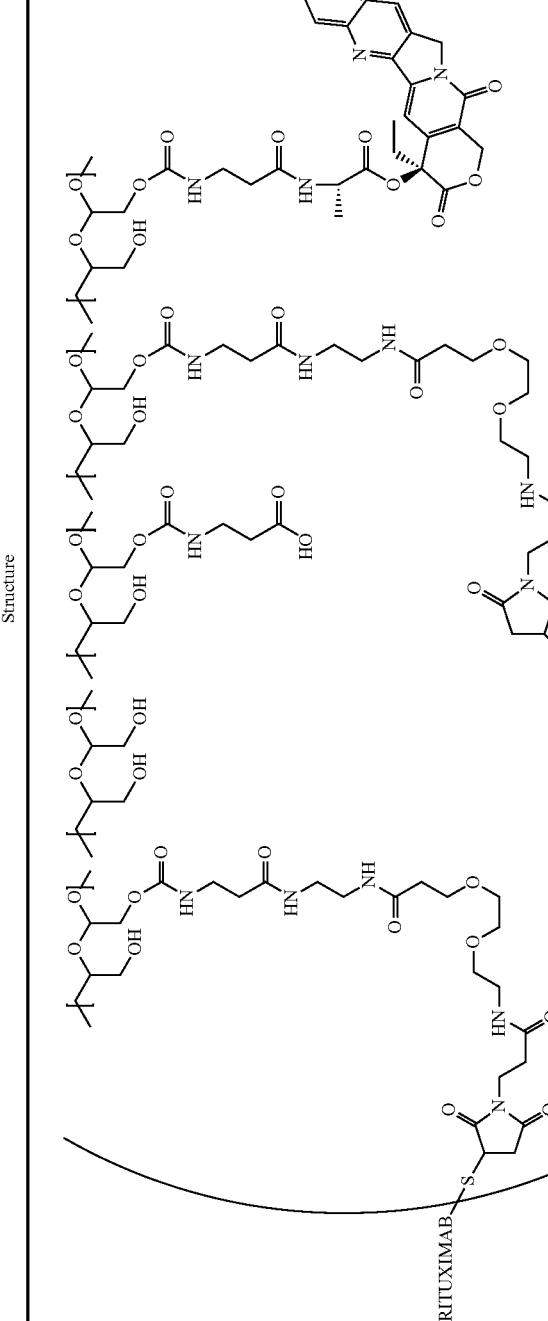 |

TABLE D-continued

| Ref # | Drug: PBRM Ratio | Structure |
|---|---|---|
| Ex 43A | 6:1 to 9:1 | 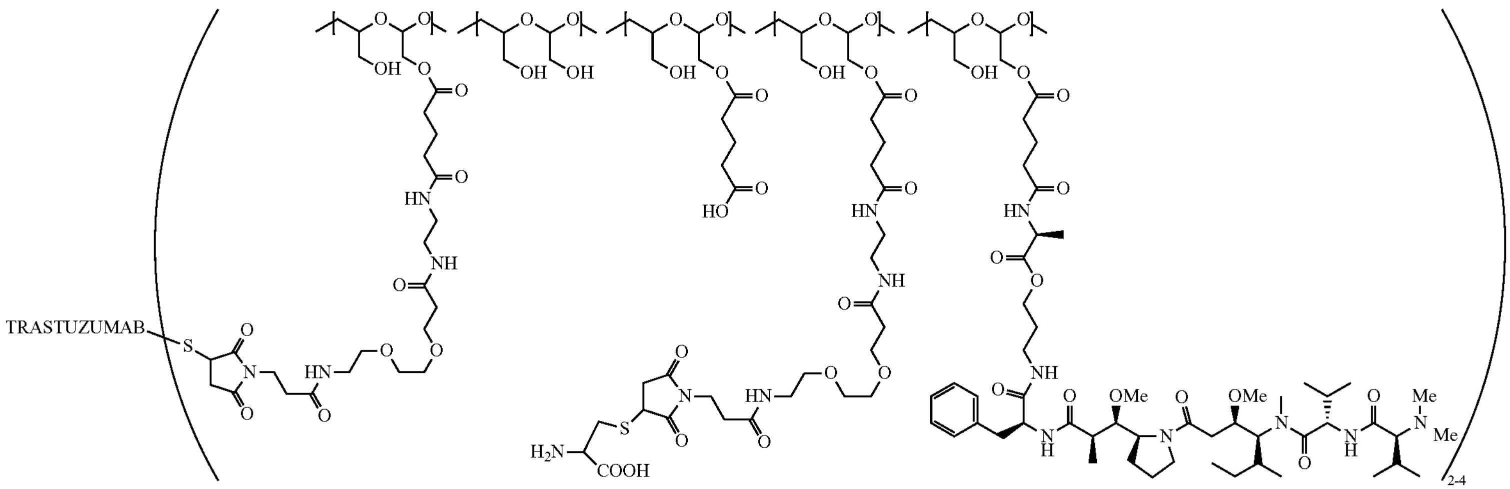 |
| Ex 43B | 12:1 to 17:1 | |
| Ex 43C | 12:1 to 16:1 | |

TABLE D-continued
| Ref # | Drug:PBRM Ratio | Structure |
|---|---|---|
| Ex 44 | | 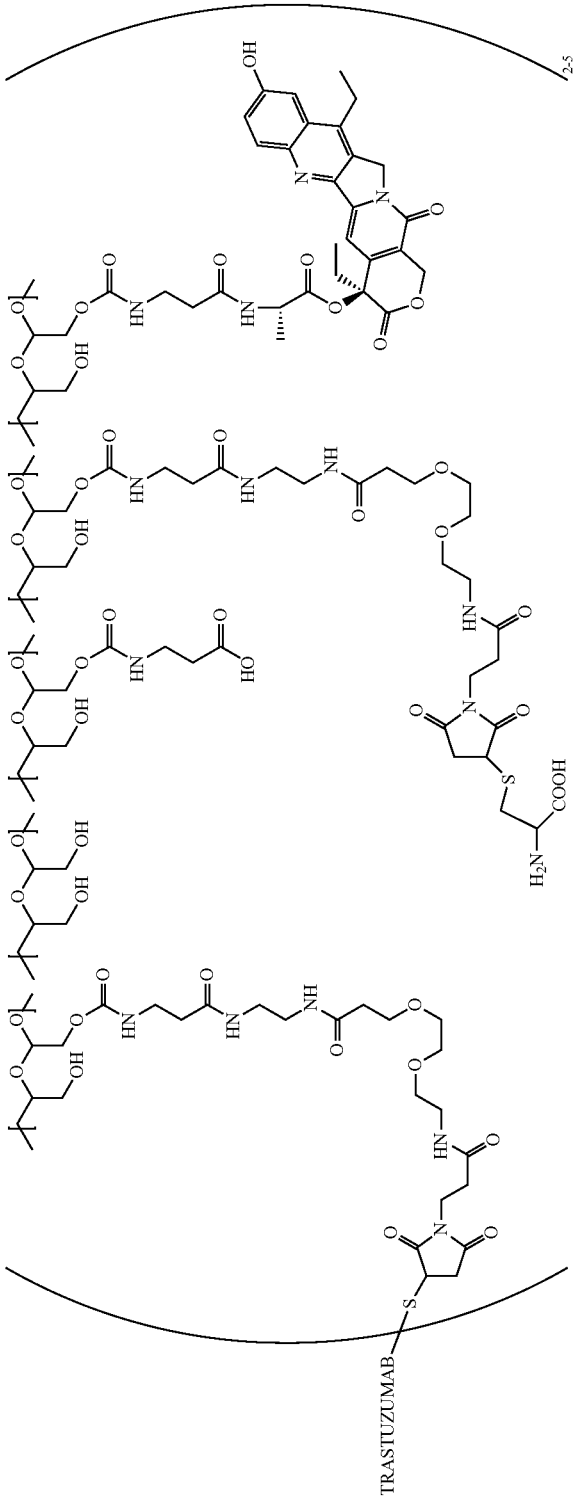 |

TABLE D-continued
| Ref # | Drug:PBRM Ratio | Structure |
|---|---|---|
| Ex 45 | | 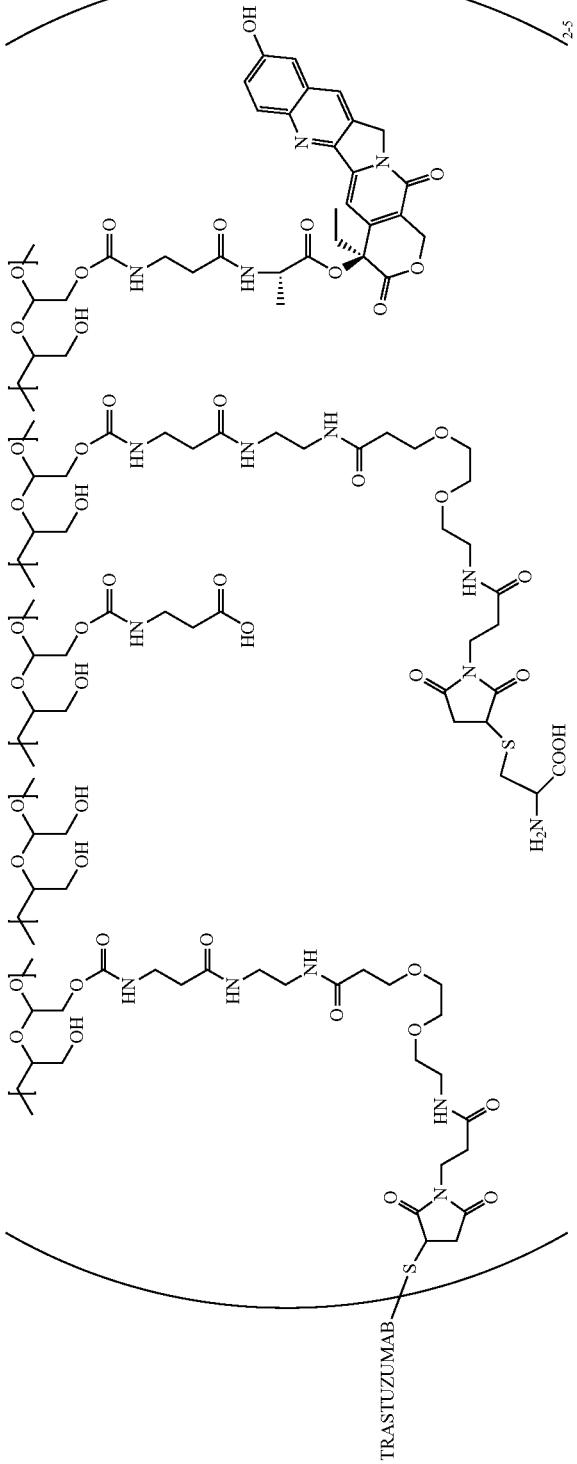 |

In a further example, an anti-5T4 therapeutic drug and targeting conjugate is provided. The conjugate comprises (a) a ligand (LG) which is an immunoglobulin or functional fragment thereof which targets human oncofetal protein 5T4, the ligand having a molecular weight of greater than about 40 kD and having bound thereto $m_5$ of polymeric scaffolds of (b), wherein $m_5$ is one to about ten and (b) the polymeric scaffold comprising poly(1-hydroxymethylethylene hydroxymethyl-formal) (PHF) which has a molecular weight ranging from about 2 kDa to about 40 kDa, wherein the polymeric scaffold comprises randomly arranged monomeric units m, $m_1$, $m_2$, $m_{3a}$, and $m_{3b}$, defined as follows: (i) $m_{3a}$:

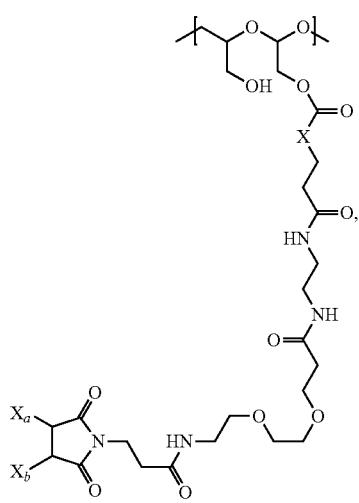

wherein $m_{3a}$ is absent or 1 to about 17 monomeric $m_{3a}$ units are present in the polymer scaffold, and in each unit, $X_a$ and $X_b$ are independently selected from (A) one is H and the other is a maleimido blocking moiety, or (B) $X_a$ and $X_b$, together with the carbon atoms to which they are attached form a carbon-carbon double bond; (ii) $m_{3b}$, wherein the sulfide bond forms the point of attachment to LG, and

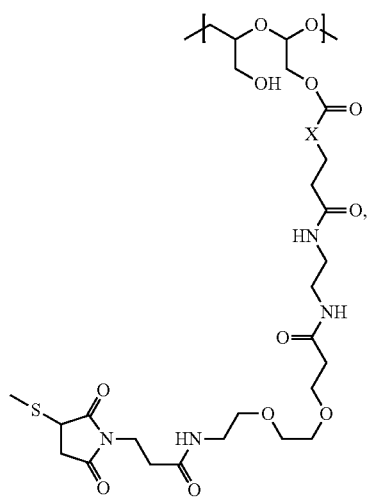

wherein 1 to about 8 monomer $m_{3b}$ units are present in the polymeric scaffold, wherein the sum of $m_{3a}$ and $m_{3b}$ is 1 to 18, and wherein the sulfur atom is part of LG; (iii) m:

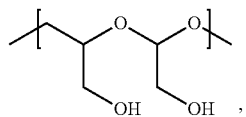

wherein 1 to about 300 monomer m units are present in the polymeric scaffold; (iv) $m_1$:

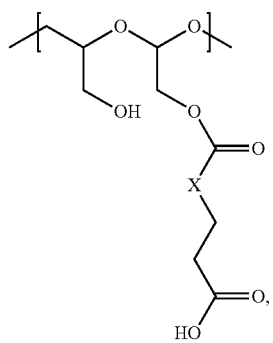

wherein 1 to about 140 monomeric $m_1$ units are present in the polymer scaffold; and
(v): $m_2$:

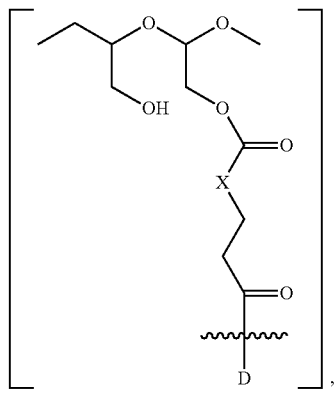

wherein 1 to about 40 monomeric m2 units are present in the polymer scaffold; wherein in each of the monomeric units m, $m_1$, $m_2$, $m_{3a}$, and $m_{3b}$, X is $CH_2$, O or NH and the sum of m, $m_1$, $m_2$, $m_{3a}$, and $m_{3b}$ ranges from about 15 to about 300, and wherein each occurrence of D independently is a therapeutic agent having a molecular weight of ≤5 kDa, and the $-\xi-$ between D and the carbonyl group denotes direct or indirect attachment of D to the carbonyl group. Suitably, the anti-5T4 ligand is an immunoglobulin or a functional fragment thereof as defined herein. For example, the immunoglobulin or functional fragment thereof is selected from the group consisting of a monoclonal antibody, a chimeric antibody, a humanized antibody, a human antibody, an immunoadhesin, a $F(Ab)_2$, a minibody, Fab', a single-domain antibody, a nanobody, a single chain Fv, a tandem/bis-scFv, a $F(ab)_3$, a scFv-Fc (or scFvFc), a dsFv, a diabody, a triabody, and a tetrabody.

In a further example, the therapeutic drug and targeting conjugate is characterized by the structures illustrated in Formula (E):

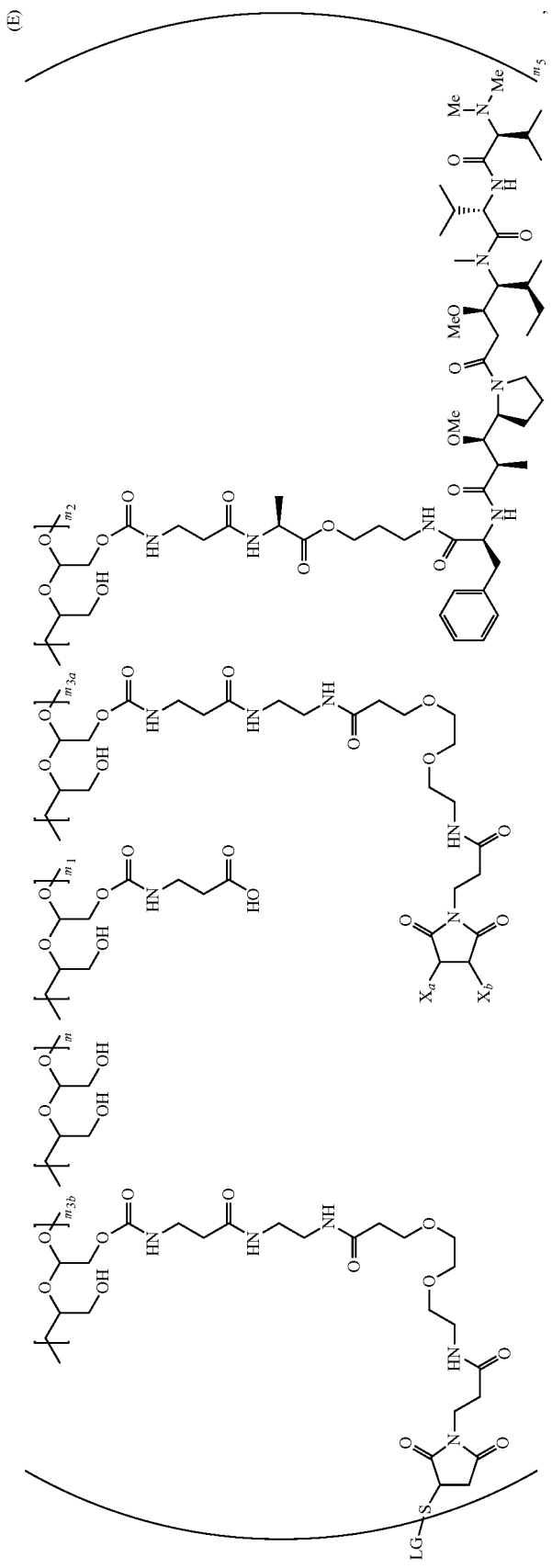

wherein: the PHF has a molecular weight ranging from about 5 kDa to about 10 kDa; m is 1 to 75, $m_1$ is about 5 to about 35, $m_2$ is about 3 to about 10, $m_{3a}$ is 0 to about 4, $m_{3b}$ is 1 to about 5, the sum of m, $m_1$, $m_2$, $m_{3a}$, and $m_{3b}$ is about 40 to about 75, and $m_5$ is 2 to about 4.

In a further embodiment, a therapeutic anti-5T4 drug targeting conjugate useful in anti-neoplastic therapies is provided, which comprises a polymeric scaffold comprising a PHF having a molecular weight from about 2 kDa to about 40 kDa, wherein the conjugate is of the following structure:

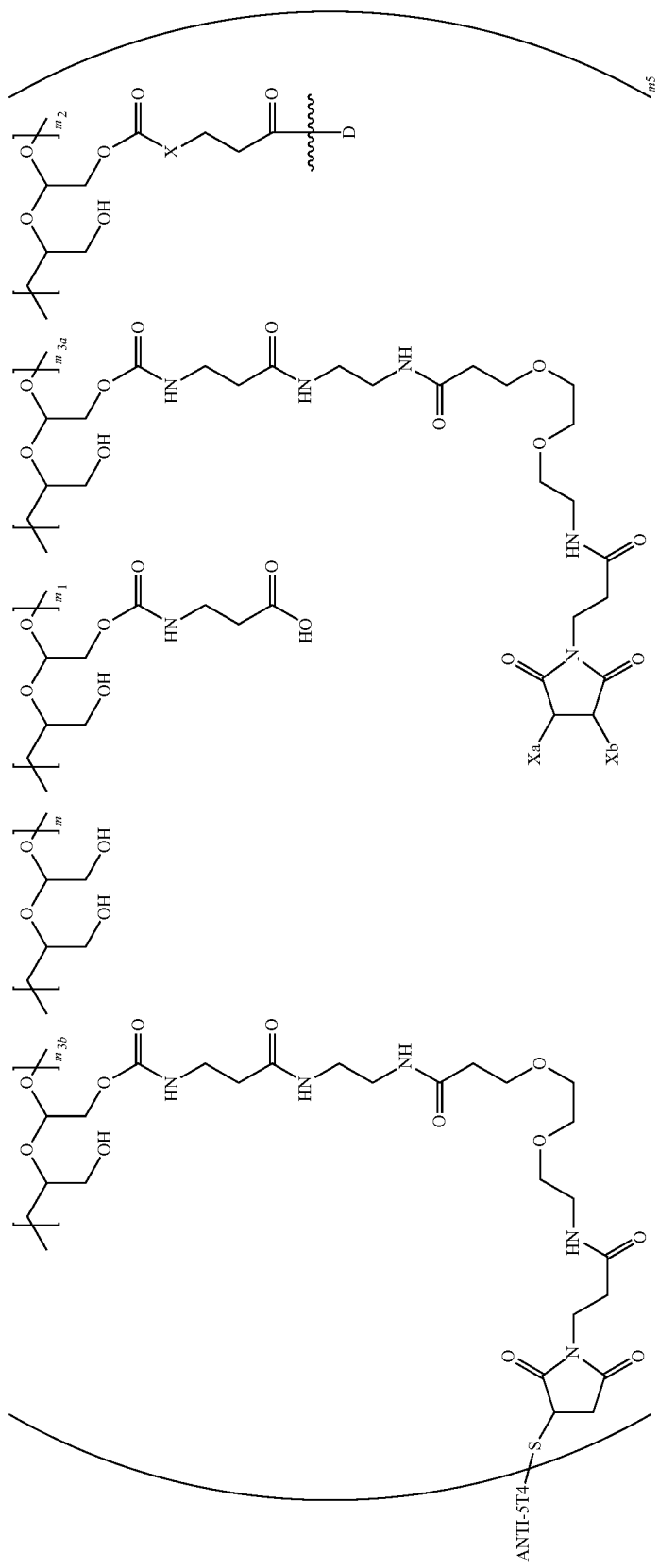

wherein $m_5$ is 1 to 10; m is an integer from 1 to about 300; $m_1$ is an integer from 1 to about 140; $m_2$ is an integer from 1 to about 40; $m_{3a}$ is an integer from 0 to about 17; $m_{3b}$ is an integer from 1 to about 8; wherein the sum of $m_{3a}$ and $m_{3b}$ is an integer from 1 to about 18; and the sum of m, $m_1$, $m_2$ and $m_3$ ranges from about 15 to about 300; X is NH; one of Xa or Xb is H and the other is a maleimido blocking moiety; and where each occurrence of D independently is a therapeutic agent having a molecular weight of ≤5 kDa, and the $-\xi-$ between D and the carbonyl group denotes direct or indirect attachment of D to the carbonyl group; wherein the ANTI-5T4 is an anti-5T4 ligand which comprises an immunoglobulin or a functional fragment thereof which is selective for human oncofetal antigen 5T4. For example, the molecular weight of the anti-5T4 is at least about 40 kDa. In one embodiment, D is an auristatin or analog thereof attached to the carbonyl moiety of $m_2$ via a hydroxypropylamide-L-alanine moiety. In one embodiment, the ratio of the drug to anti-5T4 is about 5:1 to about 30:1, or about 12:1 to about 18:1. In another embodiment, the average ratio of the PHF drug conjugate to anti-5T4 antibody is about 2:1 to about 4:1.

These conjugates may be further defined by molar percentages or molar fractions of the various units which form the conjugate. For example, the monomer unit comprising diethylene glycol maleimide (EG2-MI) moiety linked to the ligand has a molar fraction of about 2 molar % to about 5 molar %. In still a further example, monomer unit carrying the drug has a molar fraction of about 5 molar % to about 10 molar %. For example, the ratio of the drug to anti-5T4 is about 5:1 to about 30:1, or about 12:1 to about 18:1. In a further example, the average ratio of the PHF scaffold comprising the drug to anti-5T4 antibody is about 2:1 to about 3:1 or about 3:1 to about 4:1. In one embodiment, the conjugate is anti-5T4-((EG2-MI (3%)-(10 kDa PHF-BA (30%)-(AF-HPA-Ala (8%)). This conjugate may be prepared as described in Example 10, and more generally, in Scheme 5.

In still a further embodiment, therapeutic drug and targeting conjugate useful in anti-neoplastic therapies is provided, which comprises anti-5T4 and a PHF polymeric scaffold comprising the units shown below which may be randomly connected to each other,

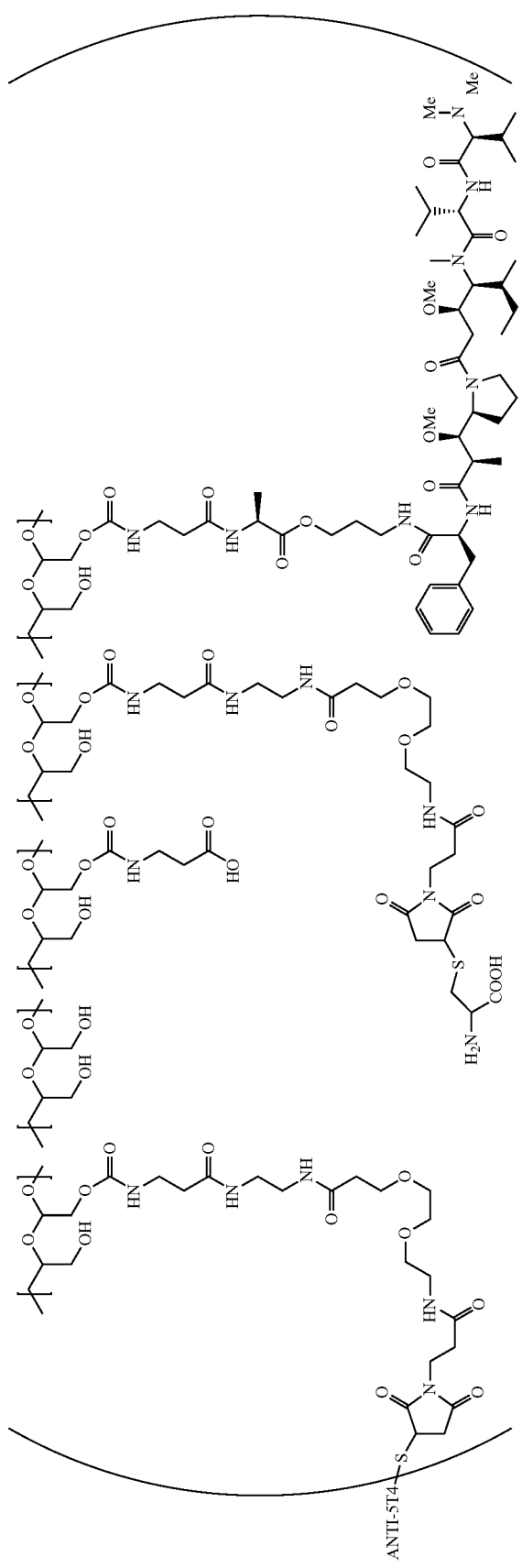

wherein:

anti-5T4 is a single chain antibody construct comprising the amino sequence of SEQ ID NO: 7; the PHF has a molecular weight ranging from about 2 kDa to about 40 kDa; the average polymeric scaffold to anti-5T4 antibody ratio is about 2:1 to about 3:1 or about 3:1 to about 4:1; and the AF-HPA to anti-5T4 antibody ratio is about 12:1 to about 18:1.

These conjugates may be prepared as described herein and combined with suitable carriers into compostions suitable for delivery to a subject. These compositions may contain blends of thes anti-5T4 drug targeting conjugates, i.e., a single composition may contain anti-5T4 drug targeting conjugates with different drugs and/or different polymeric scaffolds.

Synthetic Methods

According to the present invention, any available techniques can be used to make the inventive conjugates or compositions including them, and intermediates and components (e.g., carriers and modifiers) useful for making them. For example, semi-synthetic and fully synthetic methods may be used.

Carriers

Methods for preparing polymer carriers (e.g., biocompatible, biodegradable polymer carriers) suitable for conjugation to modifiers are known in the art. For example, synthetic guidance can be found in U.S. Pat. Nos. 5,811,510; 5,863,990; 5,958,398; 7,838,619; 7,790,150; 8,685,383; and 8,815,226, the contents of each of which are hereby incorporated by reference in their entireties. The skilled practitioner will know how to adapt these methods to make polymer carriers for use in the practice of the invention.

In one embodiment, a method for forming the biodegradable biocompatible polyal conjugates of the present invention comprises a process by which a suitable polysaccharide is combined with an efficient amount of a glycol-specific oxidizing agent to form an aldehyde intermediate. The aldehyde intermediate, which is a polyal itself, may then be reduced to the corresponding polyol, succinulated, and coupled with one or more suitable modifiers to form a biodegradable biocompatible polyal conjugate comprising succinamide-containing linkages.

In another preferred embodiment, fully synthetic biodegradable biocompatible polyals for used in the present invention can be prepared by reacting a suitable initiator with a suitable precursor compound.

For example, fully synthetic polyals may be prepared by condensation of vinyl ethers with protected substituted diols. Other methods, such as cycle opening polymerization, may be used, in which the method efficacy may depend on the degree of substitution and bulkiness of the protective groups.

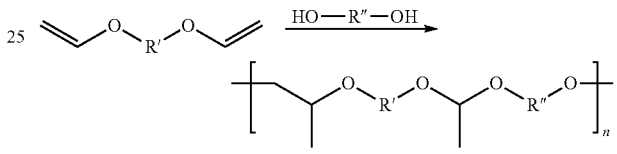

One of ordinary skill in the art will appreciate that solvent systems, catalysts and other factors may be optimized to obtain high molecular weight products.

In certain embodiments, the carrier is PHF.

In embodiments, the polymer carrier is PHF having a polydispersity index (PDI) of less than 1.5, e.g., <1.2.

Drugs and Drug Derivatives

In certain embodiments, the drug may be modified before conjugation to the polymeric carrier. Schemes 1 and 2 are illustrative methods for modifying a Vinca alkaloid. Scheme 3 shows a method for modifying a non-natural camptothecin derivative. Scheme 4 shows a method for modifying auristatin F. More modification methods are described in US 2010/0305149, which is hereby incorporated by reference.

Scheme 1

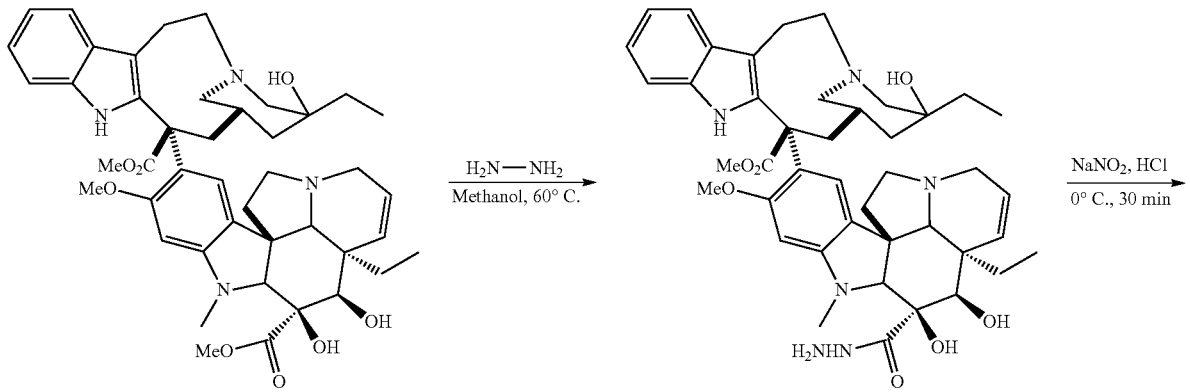

-continued

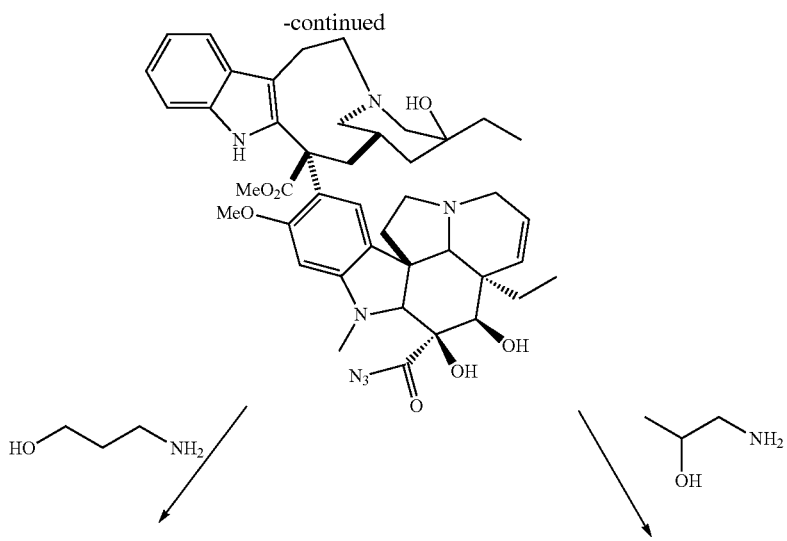

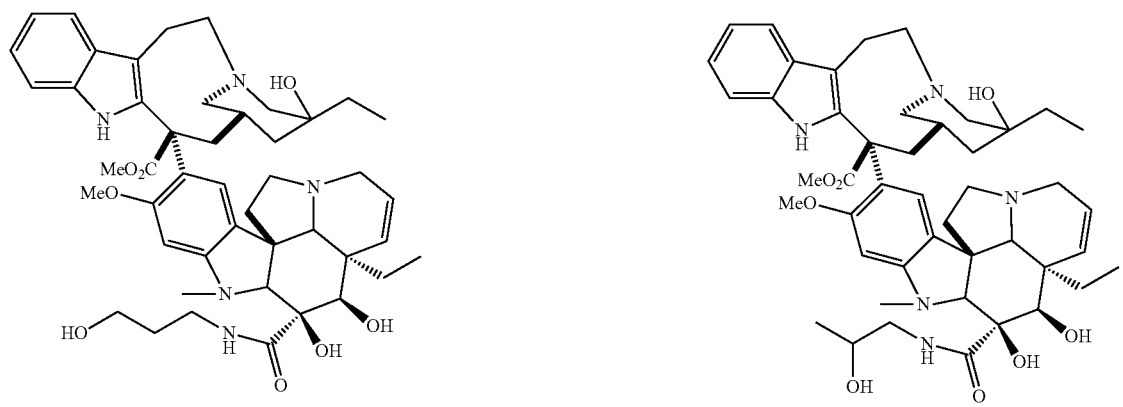

Reaction of the $C_{23}$ ester of a Vinca alkaloid with hydrazine followed by treatment with $NaNO_2$ results in an active azido ester. Reaction of the azido ester with an amino compound such as propanolamine or 1-aminopropan-2-ol results in a Vinca alkaloid derivative with a functionalized hydroxyl which can be further derivatized with amino containing compounds, such as, for example, alanine or methyl alanine derivates, for conjugation with polymers (see Scheme 1).

Scheme 2

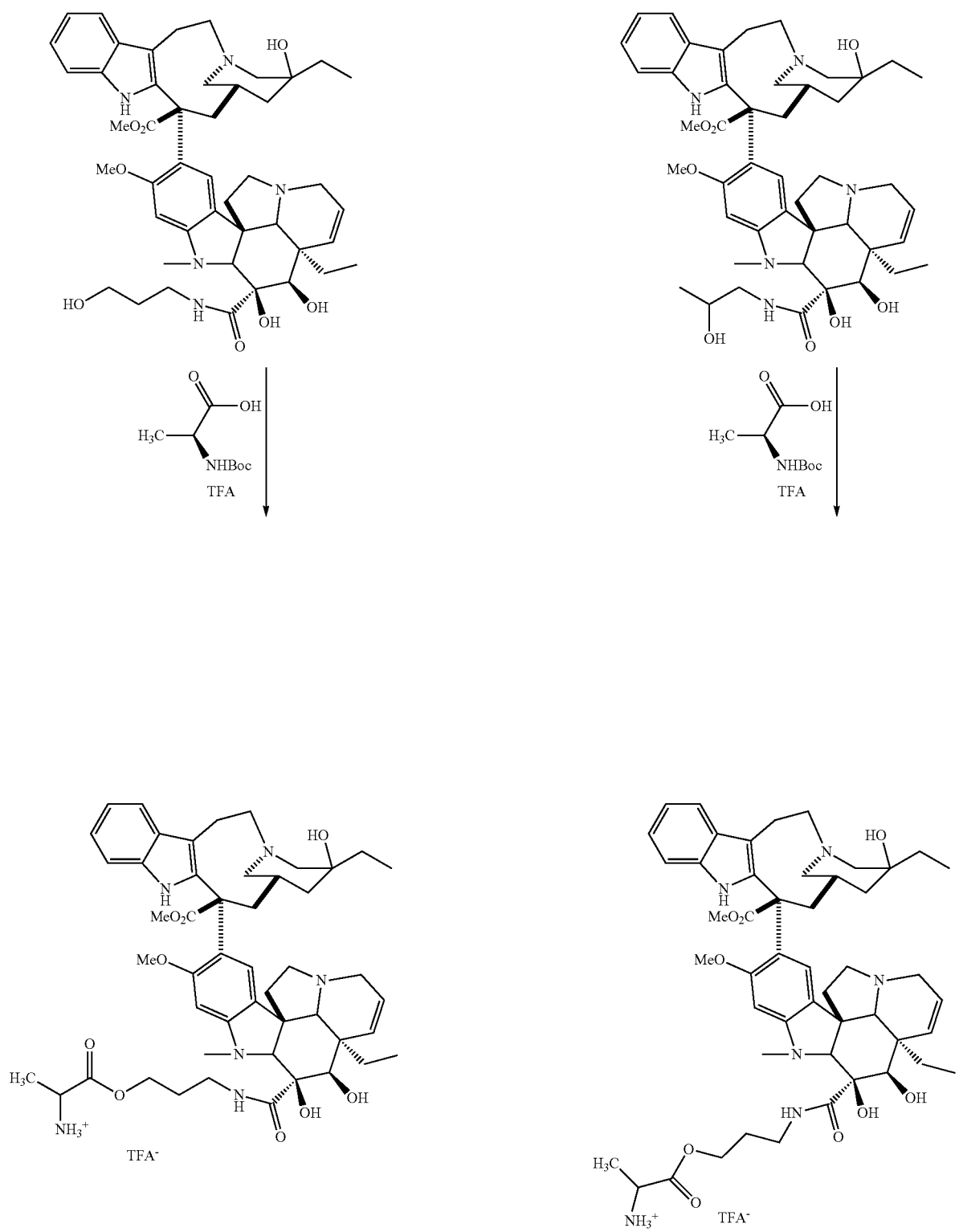

Treatment of the hydroxyl derivative of the Vinca alkaloid with a protected amino containing tether such as t-butoxy esterified amino acid followed by TFA hydrolysis of the ester gives the triflate salt of the vinca alkaloid. (Scheme 2)

Conjugation of the vinca alkaloid to functionalized polymers results in drug-polymer conjugates that can be further conjugated with a PBRM or its derivative to result in protein-polymer-drug conjugates.

Scheme 3

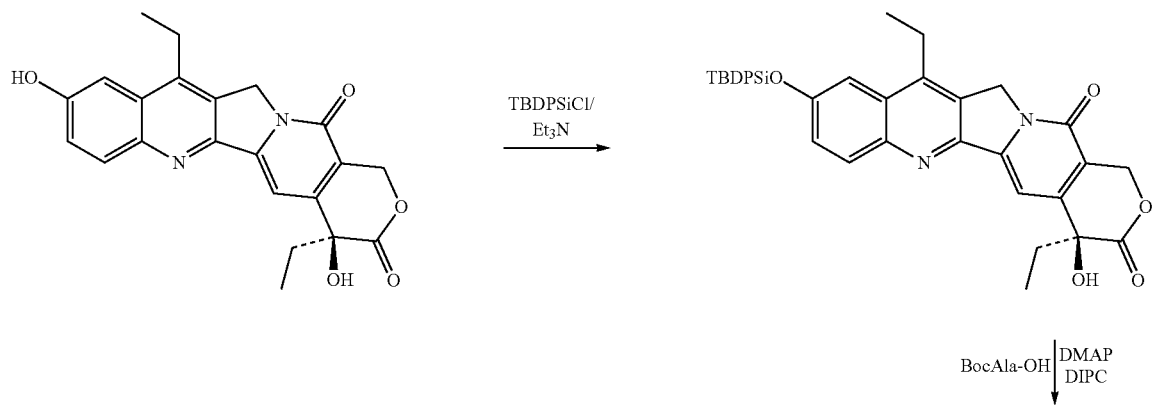

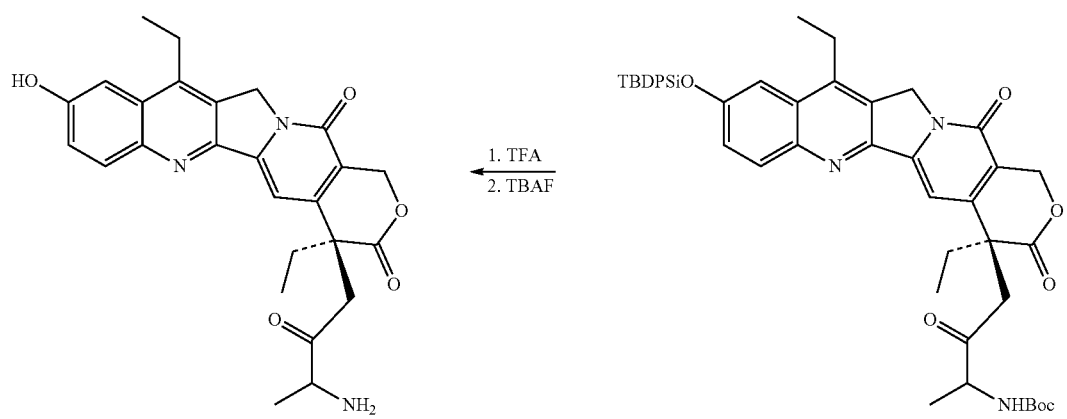

The 10-hydroxy group of non-natural camptothecin derivative, for example, SN38, is selectively protected by reacting the derivative with tert-butyldiphenylsilyl chloride (TBDPSiCl) in the presence of triethylamine. The 20-hydroxy group can be by reacted with t-butylcarbonyl-alanine to form the alanine derivative using the procedure described in Sapra, P. et al., Clin. Cancer Res., 14: 1888-1896 (2008).

Alternatively, other amino acids can be employed, e.g., glycine. The primary amine is unmasked by removing the Boc protecting group by treatment with trifluoroacetic acid, followed by removing the TBDPS protecting group with tetrabutylammonium fluoride (see Scheme 3). The resulting amino derivatized SN38 compound can be conjugated with a functionalized polymer to form a drug-polymer conjugate.

Scheme 4

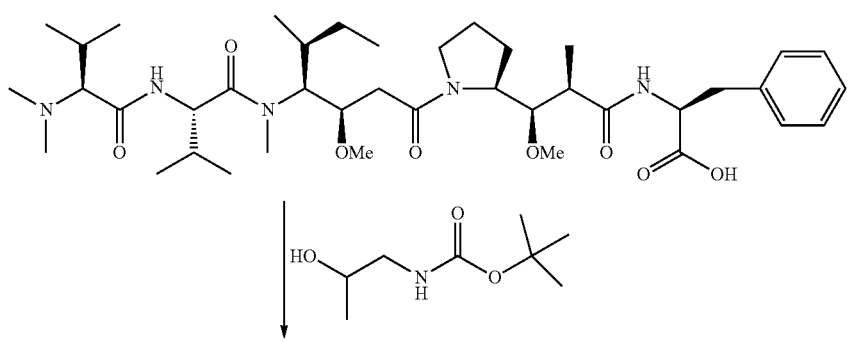

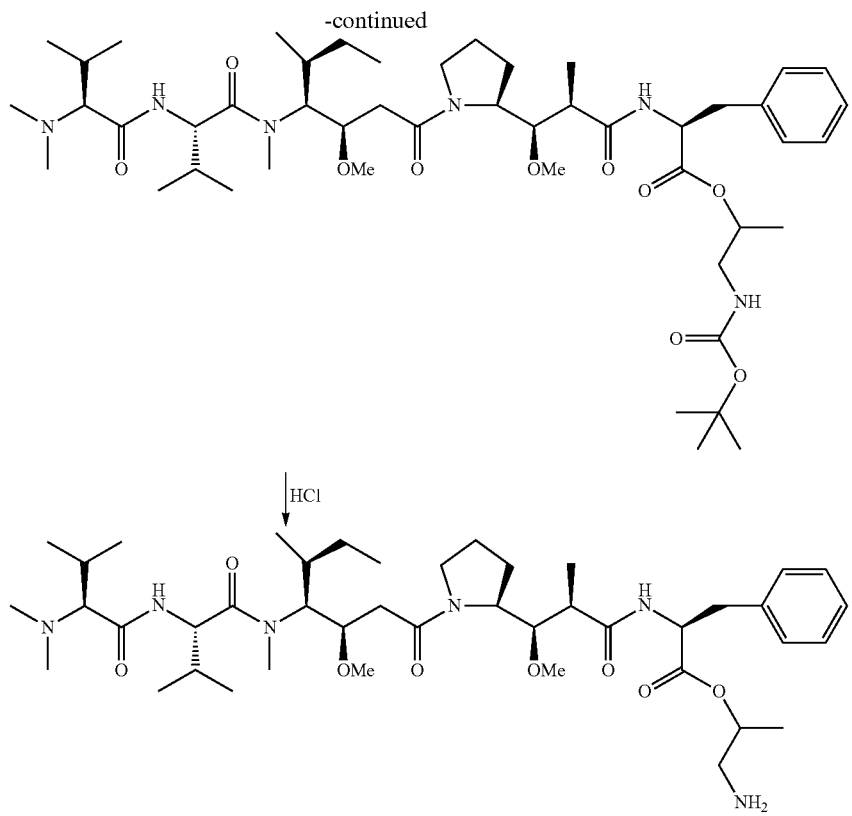

Treatment of auristatin F with a protected amino containing tether such as t-butoxy esterified 2-hydroxypropyl amine followed by HCl hydrolysis of the ester gives the 2-hydroxylpropyl amino derivative of auristatin F (see Scheme 4). Conjugation of the auristatin F derivative to functionalized polymers results in drug-polymer conjugates that can be further conjugated with a PBRM or its derivative to result in protein-polymer-drug conjugates.

Conjugates or Polymeric Scaffolds

Scheme 5 below shows a synthetic scheme of making the polymeric drug scaffolds of the invention. In one embodiment, the conjugates are formed in several steps: (1) the polymer, PHF is modified to contain a COOH moiety (e.g., —C(O)—X—(CH$_2$)$_2$—COOH); (2) the polymer is then further modified so that it contains a maleimido moiety (e.g., EG2-MI) that can react with a functional group of a PBRM; (3) the modified polymer, containing two different functional groups, is reacted with a functional group of a drug or its derivative (e.g., AF-HPA-Ala) to form a polymer-drug conjugate; (4) the disulfide bonds of a PBRM are reduced; (5) the reduced PBRM is then reacted with the polymer-drug conjugate to form the protein-polymer-drug conjugate; and (6) the remaining maleimido moieties are optionally reacted with a maleimido blocking compound (e.g., cysteine).

In another embodiment the order of steps (2) and (3) can be reversed as depicted in the right side route in Scheme 5 below.

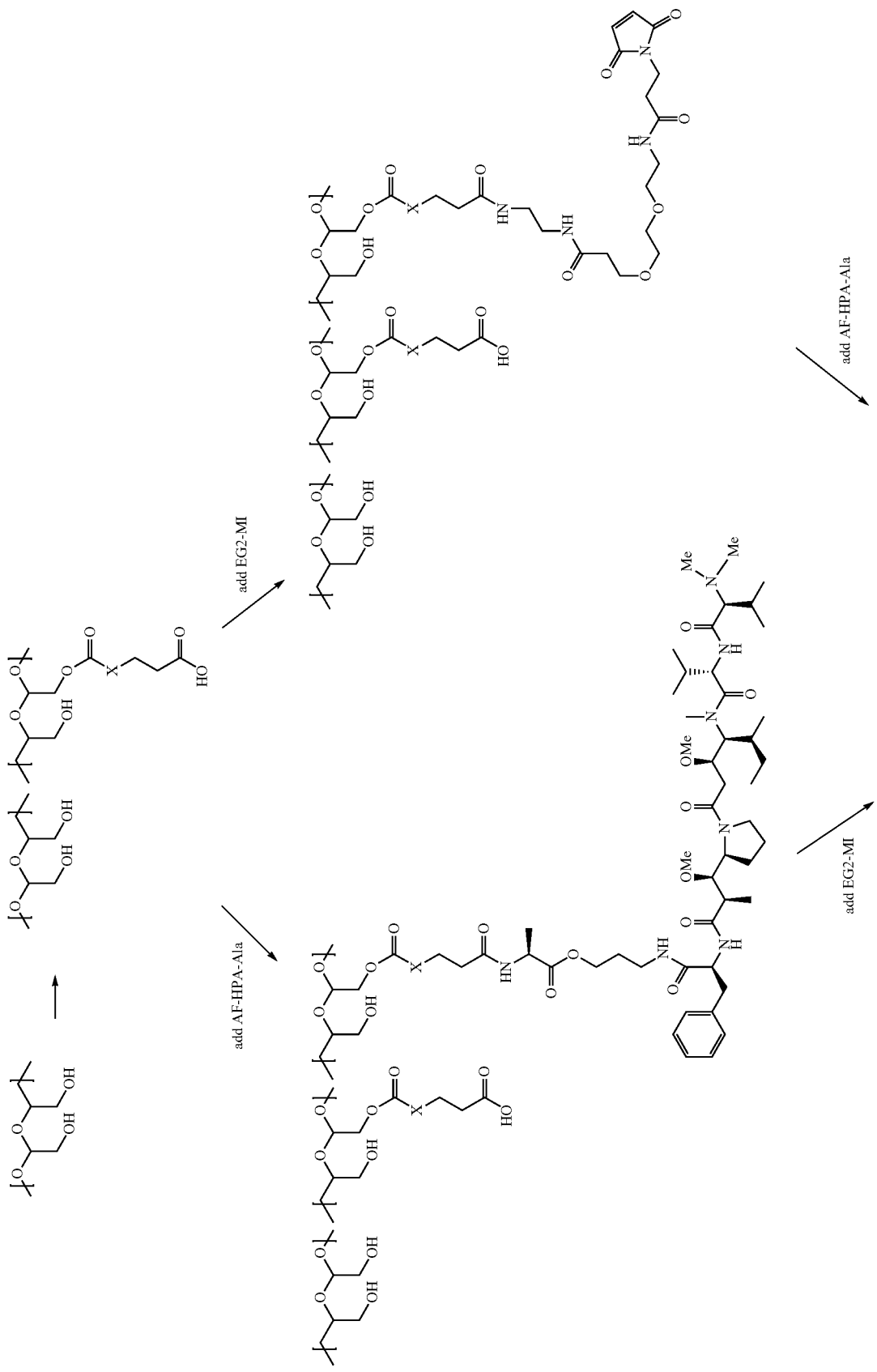

-continued
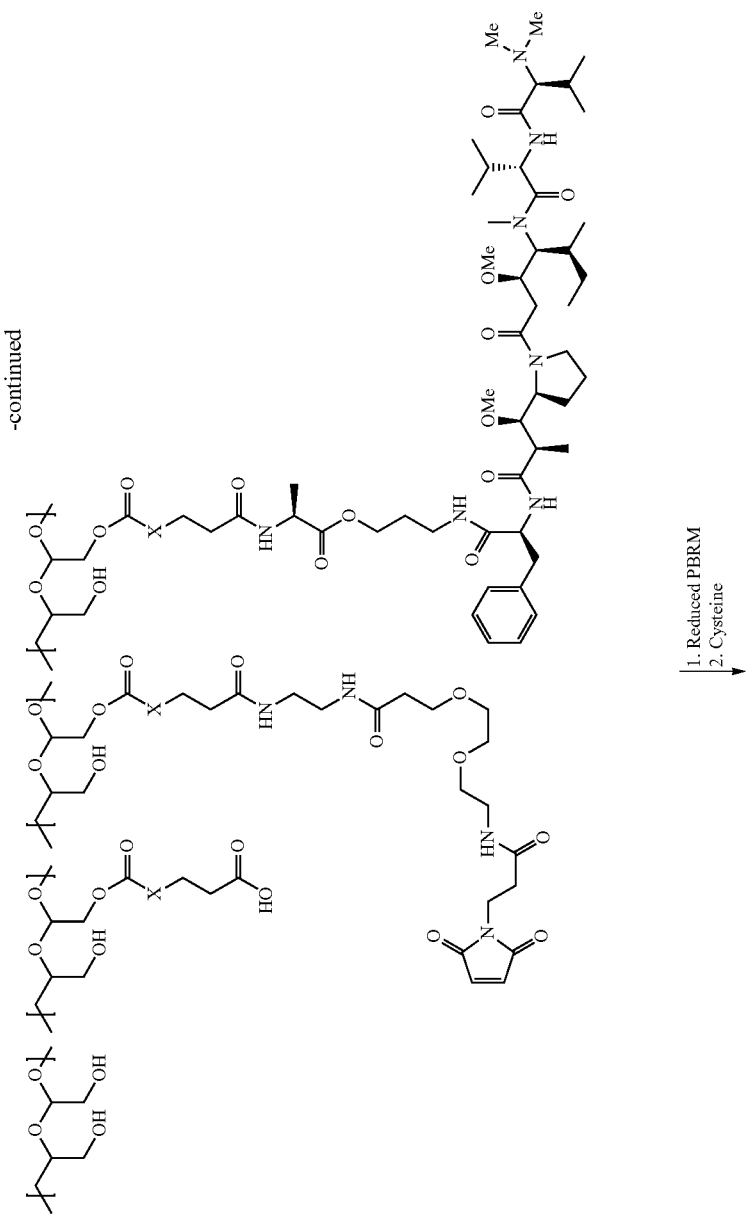

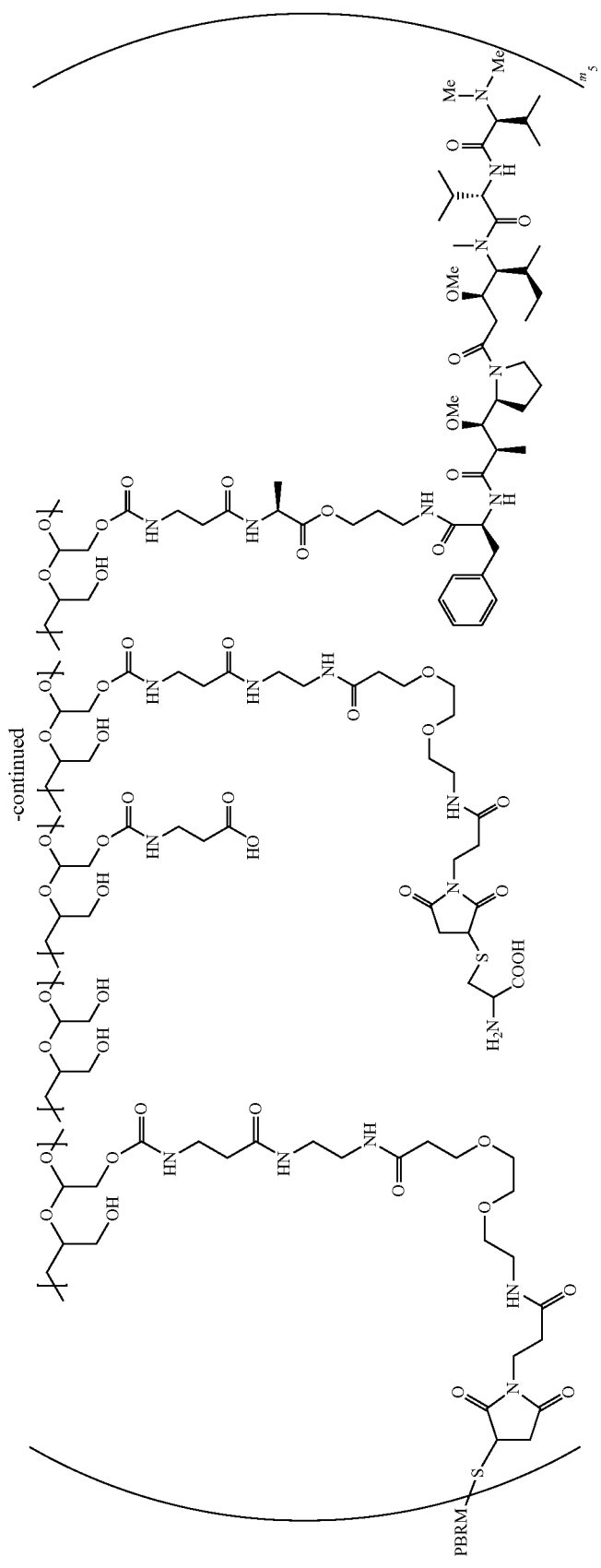

In yet another embodiment, steps (2) and (3) above are carried out simultaneously as depicted in Scheme 6 below.

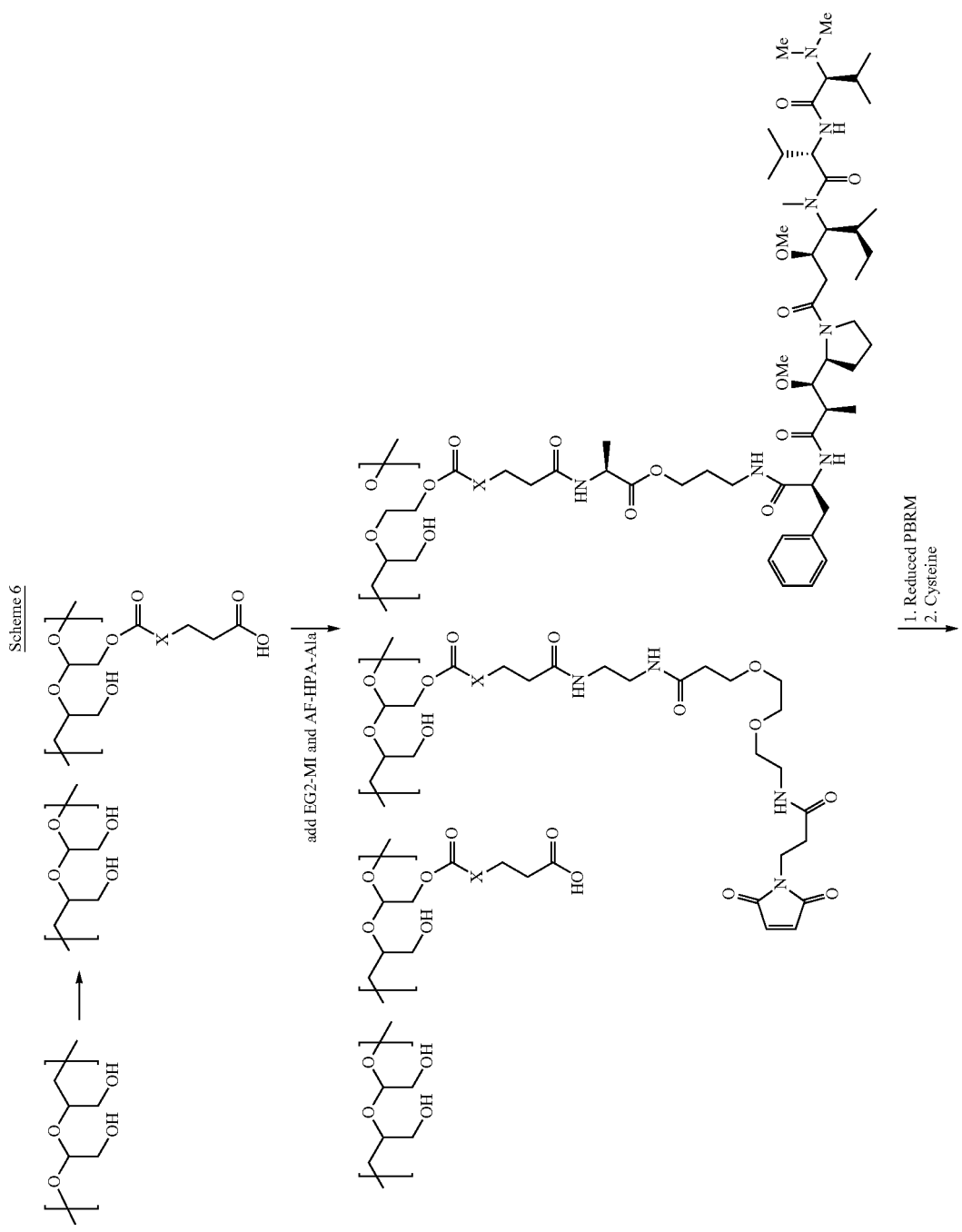

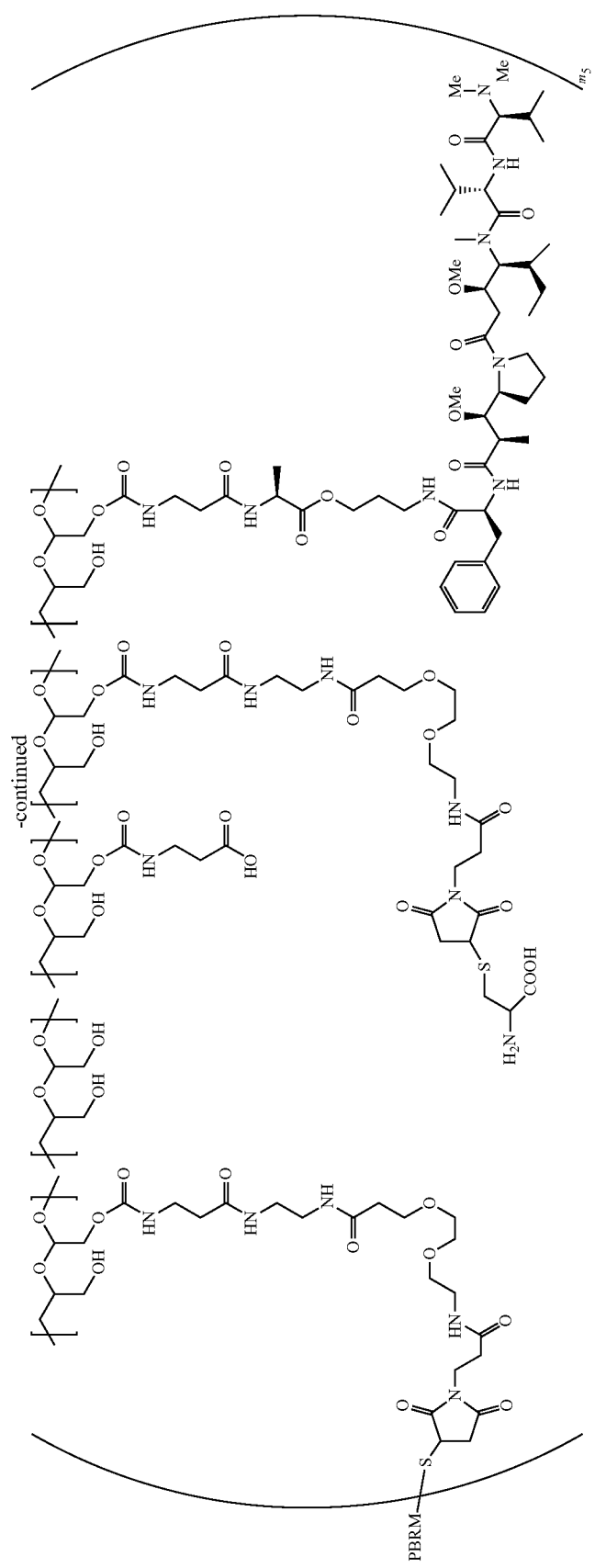

Pharmaceutical Compositions

Also included are pharmaceutical compositions comprising one or more protein-polymer-drug conjugates as disclosed herein in an acceptable carrier, such as a stabilizer, buffer, and the like. The conjugates can be administered and introduced into a subject by standard means, with or without stabilizers, buffers, and the like, to form a pharmaceutical composition. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal, oral or parenteral administration including intravenous, intraarterial, subcutaneous, intraperitoneal or intramuscular injection or infusion or intracranial, e.g., intrathecal or intraventricular, administration. The conjugates can be formulated and used as sterile solutions and/or suspensions for injectable administration; lyophilized powders for reconstitution prior to injection/infusion; topical compositions; as tablets, capsules, or elixirs for oral administration; or suppositories for rectal administration, and the other compositions known in the art.

A pharmacological composition or formulation refers to a composition or formulation in a form suitable for administration, e.g., systemic administration, into a cell or subject, including for example a human. Suitable forms, in part, depend upon the use or the route of entry, for example oral, inhaled, transdermal, or by injection/infusion. Such forms should not prevent the composition or formulation from reaching a target cell (i.e., a cell to which the drug is desirable for delivery). For example, pharmacological compositions injected into the blood stream should be soluble. Other factors are known in the art, and include considerations such as toxicity and forms that prevent the composition or formulation from exerting its effect.

By "systemic administration" is meant in vivo systemic absorption or accumulation of the modified polymer in the blood stream followed by distribution throughout the entire body. Administration routes that lead to systemic absorption include, without limitation: intravenous, subcutaneous, intraperitoneal, inhalation, oral, intrapulmonary, and intramuscular. Each of these administration routes exposes the modified polymers to an accessible diseased tissue. The rate of entry of an active agent into the circulation has been shown to be a function of molecular weight or size. The use of a conjugate of this invention can localize the drug delivery in certain cells, such as cancer cells via the specificity of PBRMs.

A "pharmaceutically acceptable formulation" means a composition or formulation that allows for the effective distribution of the conjugates in the physical location most suitable for their desired activity. In one embodiment, effective delivery occurs before clearance by the reticuloendothelial system or the production of off-target binding which can result in reduced efficacy or toxicity. Non-limiting examples of agents suitable for formulation with the conjugates include: P-glycoprotein inhibitors (such as Pluronic P85), which can enhance entry of active agents into the CNS; biodegradable polymers, such as poly (DL-lactide-coglycolide) microspheres for sustained release delivery after intracerebral implantation; and loaded nanoparticles, such as those made of polybutylcyanoacrylate, which can deliver active agents across the blood brain barrier and can alter neuronal uptake mechanisms.

Also included herein are pharmaceutical compositions prepared for storage or administration, which include a pharmaceutically effective amount of the desired conjugates in a pharmaceutically acceptable carrier or diluent. Acceptable carriers, diluents, and/or excipients for therapeutic use are well known in the pharmaceutical art. For example, buffers, preservatives, bulking agents, dispersants, stabilizers, dyes, can be provided. In addition, antioxidants and suspending agents can be used Examples of suitable carriers, diluents and/or excipients include, but are not limited to: (1) Dulbecco's phosphate buffered saline, pH about 6.5, which would contain about 1 mg/ml to 25 mg/ml human serum albumin, (2) 0.9% saline (0.9% w/v NaCl), and (3) 5% (w/v) dextrose.

The term "pharmaceutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Pharmaceutically effective amounts for a given situation can be determined by routine experimentation that is within the skill and judgment of the clinician. In a preferred aspect, the disease or condition to can be treated via gene silencing.

For any conjugate, the pharmaceutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

For example, a drug or its derivatives, drug-polymer conjugates or PBRM-polymer-drug conjugates can be evaluated for their ability to inhibit tumor growth in several cell lines using Cell titer Glo. Dose response curves can be generated using SoftMax Pro software and $IC_{50}$ values can be determined from four-parameter curve fitting. Cell lines employed can include those which are the targets of the PBRM and a control cell line that is not the target of the PBRM contained in the test conjugates.

In one embodiment, the conjugates are formulated for parenteral administration by injection including using conventional catheterization techniques or infusion. Formulations for injection may be presented in unit dosage form, e.g., in ampules or in multi-dose containers, with an added preservative. The conjugates can be administered parenterally in a sterile medium. The conjugate, depending on the vehicle and concentration used, can either be suspended or dissolved in the vehicle. Advantageously, adjuvants such as local anesthetics, preservatives, and buffering agents can be dissolved in the vehicle. The term "parenteral" as used herein includes percutaneous, subcutaneous, intravascular (e.g., intravenous), intramuscular, or intrathecal injection or infusion techniques and the like. In addition, there is provided a pharmaceutical formulation comprising conjugates and a pharmaceutical acceptable carrier. One or more of the conjugates can be present in association with one or more non-toxic pharmaceutically acceptable carriers and/or diluents and/or adjuvants, and if desired other active ingredients.

The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose, a bland fixed oil can be employed including synthetic mono- or diglycerides. In addition, fatty acids such as oleic acid find use in the preparation of injectables.

The conjugates and compositions described herein may be administered in appropriate form, preferably parenterally, more preferably intravenously. For parenteral administration, the conjugates or compositions can be aqueous or nonaqueous sterile solutions, suspensions or emulsions. Propylene glycol, vegetable oils and injectable organic esters, such as ethyl oleate, can be used as the solvent or vehicle. The compositions can also contain adjuvants, emulsifiers or dispersants.

Dosage levels of the order of from between about 0.001 mg and about 140 mg per kilogram of body weight per day are useful in the treatment of the above-indicated conditions (between about 0.05 mg and about 7 g per subject per day). In some embodiments, the dosage administered to a patient is between about 0.001 mg/kg to about 100 mg/kg of the subject's body weight. In some embodiments, the dosage administered to a patient is between about 0.01 mg/kg to about 15 mg/kg of the subject's body weight. In some embodiments, the dosage administered to a patient is between about 0.1 mg/kg and about 15 mg/kg of the subject's body weight. In some embodiments, the dosage administered to a patient is between about 0.1 mg/kg and about 20 mg/kg of the subject's body weight. In some embodiments, the dosage administered is between about 0.1 mg/kg to about 5 mg/kg or about 0.1 mg/kg to about 10 mg/kg of the subject's body weight. In some embodiments, the dosage administered is between about 1 mg/kg to about 15 mg/kg of the subject's body weight. In some embodiments, the dosage administered is between about 1 mg/kg to about 10 mg/kg of the subject's body weight. The amount of conjugate that can be combined with the carrier materials to produce a single dosage form varies depending upon the host treated and the particular mode of administration. Dosage unit forms can generally contain from between about 0.001 mg and about 100 mg; between about 0.01 mg and about 75 mg; or between about 0.01 mg and about 50 mg; or between about 0.01 mg and about 25 mg; of a conjugate.

For intravenous administration, the dosage levels can comprise ranges described in the preceding paragraphs, or from about 0.01 to about 200 mg of a conjugate per kg of the animal's body weight. In one aspect, the composition can include from about 1 to about 100 mg of a conjugate per kg of the animal's body weight. In another aspect, the amount administered will be in the range from about 0.1 to about 25 mg/kg of body weight of a compound.

In some embodiments, the conjugates can be administered are as follows. The conjugates can be given daily for about 5 days either as an i.v., bolus each day for about 5 days, or as a continuous infusion for about 5 days.

Alternatively, the conjugates can be administered once a week for six weeks or longer. As another alternative, the conjugates can be administered once every two or three weeks. Bolus doses are given in about 50 to about 400 ml of normal saline to which about 5 to about 10 ml of human serum albumin can be added. Continuous infusions are given in about 250 to about 500 ml of normal saline, to which about 25 to about 50 ml of human serum albumin can be added, per 24 hour period.

In some embodiments about one to about four weeks after treatment, the patient can receive a second course of treatment. Specific clinical protocols with regard to route of administration, excipients, diluents, dosages, and times can be determined by the skilled artisan as the clinical situation warrants.

In other embodiments, the therapeutically effective amount may be provided on another regular schedule, i.e., daily, weekly, monthly, or yearly basis or on an irregular schedule with varying administration days, weeks, months, etc. Alternatively, the therapeutically effective amount to be administered may vary. In one embodiment, the therapeutically effective amount for the first dose is higher than the therapeutically effective amount for one or more of the subsequent doses. In another embodiment, the therapeutically effective amount for the first dose is lower than the therapeutically effective amount for one or more of the subsequent doses. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy will be determined according to the recommendations of the relevant regulatory bodies and judgment of a health-care practitioner. The therapeutically effective amounts described herein refer to total amounts administered for a given time period; that is, if more than one different conjugate described herein is administered, the therapeutically effective amounts correspond to the total amount administered. It is understood that the specific dose level for a particular subject depends upon a variety of factors including the activity of the specific conjugate, the age, body weight, general health, sex, diet, time of administration, route of administration, and rate of excretion, combination with other active agents, and the severity of the particular disease undergoing therapy.

For administration to non-human animals, the conjugates can also be added to the animal feed or drinking water. It can be convenient to formulate the animal feed and drinking water so that the animal takes in a therapeutically appropriate quantity of the conjugates along with its diet. It can also be convenient to present the conjugates as a premix for addition to the feed or drinking water.

The conjugates can also be administered to a subject in combination with other therapeutic compounds to increase the overall therapeutic effect. The use of multiple compounds to treat an indication can increase the beneficial effects while reducing the presence of side effects. In some embodiment the conjugates are used in combination with chemotherapeutic agents, such as those disclosed in U.S. Pat. No. 7,303,749. In other embodiments the chemotherapeutic agents, include, but are not limited to letrozole, oxaliplatin, docetaxel, 5-FU, lapatinib, capecitabine, leucovorin, erlotinib, pertuzumab, bevacizumab, and gemcitabine. The present invention also provides pharmaceutical kits comprising one or more containers filled with one or more of the conjugates and/or compositions of the present invention, including, one or more chemotherapeutic agents.

Such kits can also include, for example, other compounds and/or compositions, a device(s) for administering the compounds and/or compositions, and written instructions in a form prescribed by a governmental agency regulating the manufacture, use or sale of pharmaceuticals or biological products. The compositions described herein can be packaged as a single dose or for continuous or periodic discontinuous administration. For continuous administration, a package or kit can include the conjugates in each dosage unit (e.g., solution or other unit described above or utilized in drug delivery), and optionally instructions for administering the doses daily, weekly, or monthly, for a predetermined length of time or as prescribed. If varying concentrations of a composition, of the components of the composition, or the relative ratios of the conjugates or agents within a composition over time is desired, a package or kit may contain a sequence of dosage units which provide the desired variability.

A number of packages or kits are known in the art for dispensing pharmaceutical agents for periodic oral use. In one embodiment, the package has indicators for each period. In another embodiment, the package is a labeled blister package, dial dispenser package, or bottle. The packaging means of a kit may itself be geared for administration, such as a syringe, pipette, eye dropper, or other such apparatus, from which the formulation may be applied to an affected area of the body, injected into a subject, or even applied to and mixed with the other components of the kit.

Methods of Use
Methods of Treating

In certain preferred embodiments of the invention, the protein-polymer-drug conjugate of the invention are used in methods of treating animals (preferably mammals, most preferably humans and includes males, females, infants, children and adults). In one embodiment, the conjugates of the present invention may be used in a method of treating animals which comprises administering to the animal a biodegradable biocompatible conjugate of the invention. For example, conjugates in accordance with the invention can be administered in the form of soluble linear polymers, copolymers, conjugates, colloids, particles, gels, solid items, fibers, films, etc. Biodegradable biocompatible conjugates of this invention can be used as drug carriers and drug carrier components, in systems of controlled drug release, preparations for low-invasive surgical procedures, etc. Pharmaceutical formulations can be injectable, implantable, etc.

In yet another aspect, the invention provides a method of treating a disease or disorder in a subject in need thereof, comprising administering to the subject an efficient amount of at least one conjugate of the invention; wherein said conjugate releases one or more therapeutic agents upon biodegradation.

In another embodiment the conjugates can be administered in vitro, in vivo and/or ex vivo to treat patients and/or to modulate the growth of selected cell populations including, for example, cancer. In some embodiments, the particular types of cancers that can be treated with the conjugates include, but are not limited to: (1) solid tumors, including but not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophogeal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma bile duct carcinoma, choriocarcinoma, seminoma, embryonal carcinoma, Wilms' tumor, cervical cancer, uterine cancer, testicular cancer, small cell lung carcinoma, non-small cell lung carcinoma, bladder carcinoma, lung cancer, epithelial carcinoma, glioma, glioblastoma, multiforme astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma; (2) blood-borne cancers, including but not limited to acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", hairy cell leukemia, multiple myeloma, acute and chronic leukemias, e.g., lymphoblastic myelogenous and lymphocytic myelocytic leukemias; and (3) lymphomas such as Hodgkin's disease, non-Hodgkin's Lymphoma, Multiple myeloma, Waldenstrom's macroglobulinemia, Heavy chain disease, and Polycythemia vera.

In another embodiment the conjugates can be administered in vitro, in vivo and/or ex vivo to treat patients and/or to modulate the growth of selected cell populations in patients having anal, astrocytoma, leukemia, lymphoma, head and neck, liver, testicular, cervical, sarcoma, hemangioma, esophageal, eye, laryngeal, mouth, mesothelioma, skin, myeloma, oral, rectal, throat, bladder, breast, uterus, ovary, prostate, lung, colon, pancreas, renal, or gastric cancer.

In another embodiment, the cancers are selected from the group consisting of breast cancer, gastric cancer, non-small cell lung cancer (NSCLC), and ovarian cancer.

In another embodiment, the conjugates can be administered in vitro, in vivo and/or ex vivo to treat, prevent, reduce the risk of developing and/or delay onset of certain pathologies, for example, a cancer. For example, the conjugates of the invention are useful in treating, preventing, delaying the progression of or otherwise ameliorating a symptom of a cancer selected from the group consisting of anal cancer, astrocytoma, leukemia, lymphoma, head and neck cancer, liver cancer, testicular cancer, cervical cancer, sarcoma, hemangioma, esophageal cancer, eye cancer, laryngeal cancer, mouth cancer, mesothelioma, skin cancer, myeloma, oral cancer, rectal cancer, throat cancer, bladder cancer, breast cancer, uterine cancer, ovarian cancer, prostate cancer, lung cancer, non-small cell lung cancer (NSCLC), colon cancer, pancreatic cancer, renal cancer, and gastric cancer.

In another embodiment the conjugates can be administered in vitro, in vivo and/or ex vivo to treat autoimmune diseases, such as systemic lupus, rheumatoid arthritis, psoriasis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, and AIDS; and parasite infections, such as giardiasis, amoebiasis, schistosomiasis, and the like.

In certain embodiments the conjugates can also be used for the manufacture of a medicament useful for treating or lessening the severity of disorders, such as, characterized by abnormal growth of cells (e.g., cancer).

In certain embodiments, the therapeutic agent is locally delivered to a specific target cell, tissue, or organ.

In certain embodiments, in practicing the method of the invention, the conjugate further comprises or is associated with a diagnostic label. In certain exemplary embodiments, the diagnostic label is selected from the group consisting of: radiopharmaceutical or radioactive isotopes for gamma scintigraphy and PET, contrast agent for Magnetic Resonance Imaging (MRI), contrast agent for computed tomography, contrast agent for X-ray imaging method, agent for ultrasound diagnostic method, agent for neutron activation, moiety which can reflect, scatter or affect X-rays, ultrasounds, radiowaves and microwaves and fluorophores. In certain exemplary embodiments, the conjugate is further monitored in vivo.

Examples of diagnostic labels include, but are not limited to, diagnostic radiopharmaceutical or radioactive isotopes for gamma scintigraphy and PET, contrast agent for Magnetic Resonance Imaging (MRI) (for example paramagnetic atoms and superparamagnetic nanocrystals), contrast agent for computed tomography, contrast agent for X-ray imaging method, agent for ultrasound diagnostic method, agent for neutron activation, and moiety which can reflect, scatter or affect X-rays, ultrasounds, radiowaves and microwaves, fluorophores in various optical procedures, etc. Diagnostic radiopharmaceuticals include -emitting radionuclides, e.g., indium-111, technetium-99m and iodine-131, etc. Contrast agents for MRI (Magnetic Resonance Imaging) include magnetic compounds, e.g., paramagnetic ions, iron, manganese, gadolinium, lanthanides, organic paramagnetic moieties and superparamagnetic, ferromagnetic and antiferromagnetic compounds, e.g., iron oxide colloids, ferrite colloids, etc. Contrast agents for computed tomography and other X-ray based imaging methods include compounds absorbing X-rays, e.g., iodine, barium, etc. Contrast agents for ultrasound based methods include compounds which can absorb, reflect and scatter ultrasound waves, e.g., emulsions, crystals, gas bubbles, etc. Still other examples include substances useful for neutron activation, such as boron and gadolinium. Further, labels can be employed which can reflect, refract, scatter, or otherwise affect X-rays, ultrasound, radiowaves, microwaves and other rays useful in diagnostic procedures. Fluorescent labels can be used for photoimaging. In certain embodiments a modifier comprises a paramagnetic ion or group.

In another aspect, the invention provides a method of treating a disease or disorder in a subject, comprising preparing an aqueous formulation of at least one conjugate of the invention and parenterally injecting said formulation in the subject.

In another aspect, the invention provides a method of treating a disease or disorder in a subject, comprising preparing an implant comprising at least one conjugate of the invention, and implanting said implant into the subject. In certain exemplary embodiments, the implant is a biodegradable gel matrix.

In another aspect, the invention provides a method for treating of an animal in need thereof, comprising administering a conjugate according to the methods described above.

In another aspect, the invention provides a method for eliciting an immune response in an animal, comprising administering a conjugate as in the methods described above.

In another aspect, the invention provides a method of diagnosing a disease in an animal, comprising steps of:
administering a conjugate as in the methods described above, wherein said conjugate comprises a detectable molecule; and
detecting the detectable molecule.

In certain exemplary embodiments, the step of detecting the detectable molecule is performed non-invasively. In certain exemplary embodiments, the step of detecting the detectable molecule is performed using suitable imaging equipment.

In one embodiment, a method for treating an animal comprises administering to the animal a biodegradable biocompatible conjugate of the invention as a packing for a surgical wound from which a tumor or growth has been removed. The biodegradable biocompatible conjugate packing will replace the tumor site during recovery and degrade and dissipate as the wound heals.

In certain embodiments, the conjugate is associated with a diagnostic label for in vivo monitoring.

The conjugates described above can be used for therapeutic, preventative, and analytical (diagnostic) treatment of animals. The conjugates are intended, generally, for parenteral administration, but in some cases may be administered by other routes.

In one embodiment, soluble or colloidal conjugates are administered intravenously. In another embodiment, soluble or colloidal conjugates are administered via local (e.g., subcutaneous, intramuscular) injection. In another embodiment, solid conjugates (e.g., particles, implants, drug delivery systems) are administered via implantation or injection.

In another embodiment, conjugates comprising a detectable label are administered to study the patterns and dynamics of label distribution in animal body.

In certain embodiments, any one or more of the conjugates disclosed herein may be used in practicing any of the methods described above. In certain exemplary embodiments, the conjugate is a Trastuzumab-PHF-, Rituximab-PHF-, Lintuzumab-PHF or anti-5T4-PHF-drug conjugate.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups; therefore various substituted starting materials can be used. The processes generally provide the desired final compound at or near the end of the overall process, although it may be desirable in certain instances to further convert the compound to a pharmaceutically acceptable salt, ester or prodrug thereof.

Drug compounds used for the conjugates of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001; and Greene, T. W., Wuts, P. G. M., *Protective Groups in Organic Synthesis*, 3$^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present invention.

Conjugates of the present invention and the drug compounds included therein can be conveniently prepared by a variety of methods familiar to those skilled in the art. The conjugates or compounds of this invention with each of the formulae described herein may be prepared according to the following procedures from commercially available starting materials or starting materials which can be prepared using literature procedures. These procedures show the preparation of representative conjugates of this invention.

Conjugates designed, selected and/or optimized by methods described above, once produced, can be characterized using a variety of assays known to those skilled in the art to determine whether the conjugates have biological activity. For example, the conjugates can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the conjugate molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

The following working examples are illustrative of the linkers, drug molecules and PBRM, and methods for preparing same. These are not intended to be limiting and it will be readily understood by one of skill in the art that other reagents or methods may be utilized.

Conjugates described herein can be prepared by the schemes generally outlined above and by methods described in the Examples below. The term "content" as used in certain examples below, unless otherwise specified, means the molar fraction or molar percentage of the polymer structural units that are substituted with the intended moiety, such as the linker, the drug molecule, or PBRM. Accordingly, the reported percentages for the various polymer units in the polymer-drug or PBRM-polymer-drug conjugates as used in the Examples below are molar percentages, unless otherwise specified.

Abbreviations

The following abbreviations are used in the reaction schemes and synthetic examples, which follow. This list is not meant to be an all-inclusive list of abbreviations used in the application as additional standard abbreviations, which are readily understood by those skilled in the art of organic synthesis, can also be used in the synthetic schemes and examples.

ACN Acetonitrile
AF-HPA Auristatin F-hydroxypropylamide
Ala Alanine
BA β-Alanine BOC tert-Butyloxycarbonyl
DCC N,N'-Dicyclohexylcarbodiimide
DCM Dichloromethane
DIEA N,N-Diisopropylethylamine
DMA Dimethylacetamide
DMAP N,N-Dimethylpyridin-4-amine
DMF Dimethylformamide
DMSO Dimethylsulfoxide
EDAC N1-((ethylimino)methylene)-N3,N3-dimethylpropane-1,3-diamine hydrochloride
EDC.HCl 1-Ethyl-3-[3-dimethylaminopropyl]carbodiimide hydrochloride
GA Glutaric acid
HIC-HPLC Hydrophobic interaction high pressure liquid chromatography
HOAt 1-Hydroxy-7-azabenzotriazole
HOBt 1-Hydroxybenzotriazole hydrate
HPLC High pressure liquid chromatography
HPSEC High performance size exclusion chromatography
HPV Hydroxypropylvindesine
2HPV 2-Hydroxypropylvindesine
MWCO Molecular Weight Cut-Off
NHS 1-Hydroxypyrrolidine-2,5-dione (i.e., N-hydroxysuccinimide)
NMP N-methyl-2-pyrrolidone
PBS Phosphate buffered saline, 0.9% NaCl
EG Ethylene glycol
EG2 Diethylene glycol
MI Maleimide or maleimido
HPA-Ala Hydroxypropylamide-L-alanine
PHF poly(1-hydroxymethylethylene hydroxylmethylformal), or
FLEXIMER®
RP-HPLC Reverse-phase high performance liquid chromatography
SEC Size exclusion chromatography
TBSCl tert-Butyldimethylsilyl ether chloride
TCEP Tris[2-carboxyethyl]phosphine
TEA Triethylamine
TEAA Triethylammonium acetate
TFA Trifluoroacetic acid
WCX Weak cation exchange chromatography General Information Maleimido-EG2-NHS ester was purchased from Biomatrik, China.

Boc-diaminoethane HCl was purchased from Chem-Impex International Inc., Wood Dale, Ill.

Kadcyla® (ado-trastuzumab emtansine) for injection manufactured by Genentech was purchased.

HPLC purification was performed on a Phenomenex Gemini 5 µm 110 Å, 250×10 mm, 5 micron, semi-preparation column.

SEC was performed on a Tosoh Biosciences TSK gel G5000 column (7.8 mm×30 cm, 10 um) or Superose 12 column (GE Healthcare).

WCX was performed on ProPac WCX-10 (94 mm×250 mm) column (ThermoFisher).

Whenever possible the drug content of the conjugates was determined spectrophotometrically otherwise LC/MS or $^1$H-NMR was performed for quantitative determination of the drug content.

The protein content of the protein-polymer-drug conjugates was determined spectrophotometrically at 280 nm or by ELISA.

The molecular weights of the polymer conjugates (reported as the apparent weight average molecular weights or peak molecular weights) were determined by SEC with either polysaccharide or protein molecular weight standards. More specifically, for the polymer or polymer-drug conjugates, polysaccharide molecular weights standard were used, and for protein-drug-polymer conjugates, protein standards are used. Unless specifically indicated the reported polymer carrier molecular weight is the weight average molecular weight of PHF; and the polymer-drug conjugate molecular weight and the protein-polymer-drug conjugates is the peak molecular weight. The PBRM-polymer-drug conjugates have a peak molecular weight of about 160 kDa to about 260 kDa. The polymer and polymer conjugates synthesized/measured typically have a polydispersity ≤1.5.

PBRM-polymer-drug conjugates were separated from residual unreacted drug-polymer conjugates by extensive diafiltration. If necessary, additional purification by size exclusion chromatography and/or WCX chromatography was conducted to remove any aggregated PBRM-polymer-drug conjugates. In general, the PBRM-polymer-drug conjugates typically contained <5% (w/w, e.g., <2% w/w) aggregated fraction as determined by SEC; <0.5% (w/w, e.g., <0.1% w/w) free (unconjugated) drug as determined by RP-HPLC or LC-MS/MS; <1% (w/w) of free polymer-drug conjugate as determined by SEC and/or RP-HPLC and <2% (w/w, e.g., <1% w/w) unconjugated PBRM as determined by HIC-HPLC and/or WCX HPLC. Reduced or partially reduced antibodies were prepared using procedures described in the literature, see, for example, Francisco et al., Blood 102 (4): 1458-1465 (2003). The total drug (conjugated and unconjugated) concentration was determined by LC-MS/MS;

To study the pharmacokinetic properties, i.e., time course of PBRM-polymer-drug conjugate absorption, distribution, metabolism, and excretion, assays were developed to measure the concentration of the PBRM-PHF-AF-HPA conjugate (i.e. conjugated AF-HPA) and concentration of the released, unconjugated AF-HPA and AF (free drug) in, e.g., plasma, tumor and tissue samples. To determine the concentration of the free drug in the sample, the acidified sample was treated with acetonitrile. The free drug was extracted from the supernatant and analyzed by LC-MS/MS. To determine the concentration of conjugated AF-HPA, the acidified plasma, tumor or tissue homogenate was subjected to basic hydrolysis followed by acidification and protein precipitation with acetonitrile. The acetonitrile supernatant containing the released AF-HPA and AF was analyzed by LC-MS/MS. The standard curves for the free drug and conjugated AF-HPA in plasma and tumor and tissue homogenates were linear over the concentration ranges of 0.3 to 3,000 ng/mL and 10 to 20,000 ng/mL, respectively. Total trastuzumab concentration was determined by ELISA.

In all the in vitro or in vivo experiments described herein, unless otherwise specified, the doses used were all based on the PBRM (e.g., antibody) of the PBRM-polymer-drug conjugates.

RP-HPLC, SDS-PAGE or capillary electrophorisis were used to characterize the specificity and distribution of the cysteine bioconjugation sites in the PBRM-polymer-drug conjugates. The results gave the positional distribution of the drug-polymer conjugates on the heavy (H) and light (L) chains of the PBRM and showed that conjugation to the PBRM occurred predominately at the heavy chain interchain cysteine hinge regions. Similar results were obtained with LC-MS PBRM peptide maps.

General Procedures

General Procedure A. Conjugation of Polymer with Linker or Drug

In general, the conjugation of the polymer (PHF-BA or PHF-GA) with an amine-containing linker, such as, for example, EG2-maleimide or an amine-containing linker drug, such as, for example, AF-HPA-Ala, HPV-Ala, is conducted in an aqueous or 10-90% organic/aqueous solvent mixture in the presence of an activating agent, such as, for example EDC.HCl. Typical organic solvents, include, but are not limited to, water miscible solvents, such as, for example, DMSO, DMF, DMA, NMP and ACN. To accelerate the coupling, a co-activator, such as, for example, NHS, is added. The polymer is first mixed with the amino-containing compound followed by addition of the co-activator (NHS) and then the addition of the activator (EDC.HCl). The reaction is conducted at 0-10° C., pH 4.5 to 7.5 for 1 h to 24 hours at ambient temperature. The resulting polymer conjugated product is purified by diafiltration or by SEC. The product is concentrated to 2-50 mg/mL, the pH is adjusted to 4.5 to 6.5 to insure drug-polymer linker stability and the conjugate is stored frozen at −20 to −80° C. until further use.

The conjugation of the polymer with the amine-containing linker or drug can conducted sequentially, in any order, or simultaneously.

General Procedure B. Partial Selective Reduction of Protein (PBRM)

The partial selective reduction of the inter-chain disulfide groups or unpaired disulfide in the relevant PBRM prior to conjugation with the polymer-drug conjugate is achieved by using a reducing agent, such as, for example, TCEP, DTT or β-mercaptoethanol. When the reduction is performed with an excess of the reducing agent, the reducing agent is removed prior to conjugation by SEC. The degree of conversion of the PBRM disulfide groups into reactive sulfhydryl groups depends on the stoichiometry of PBRM, reducing agent, pH, temperature and/or duration of the reaction. When some but not all of the disulfide groups in the PBRM are reduced, the reduced PBRM is a partially reduced PBRM.

General Procedure C. Conjugation of Partially Reduced PBRM with Polymer Drug Conjugate The conjugation of the partially reduced PBRM to the polymer-drug conjugate is conducted under neutral or slightly basic conditions (pH 6.5-8.5) at PBRM concentrations of 1-10 mg/mL and polymer-drug conjugate concentrations of 0.5-10 mg/mL. The polymer-drug conjugate is typically used in 1-5.0 fold excess relative to the desired protein-polymer-drug conjugate stoichiometry. When the PBRM is conjugated to the maleimido group of the polymer-drug conjugate, the conjugation is optionally terminated by the addition of a water-soluble maleimido blocking compound, such as, for example, N-acetyl cysteine, cysteine methyl ester, N-methyl cysteine, 2-mercaptoethanol, 3-mercaptopropanoic acid, 2-mercaptoacetic acid, mercaptomethanol (i.e., $HOCH_2SH$), benzyl thiol, and the like.

The resulting PBRM-polymer-drug conjugate is typically purified by diafiltration to remove any unconjugated polymer-drug conjugate, unconjugated drug and small molecule impurities. Alternatively or additionally, appropriate chromatographic separation procedures such as, for example, size-exclusion chromatography, hydrophobic interaction chromatography, ion chromatography such as, for example, WCX chromatography; reversed phase chromatography, hydroxyl apatite chromatography, affinity chromatography or combinations thereof may be used to purify the PBRM-polymer-drug conjugate. The resulting purified PBRM-polymer-drug conjugate is typically formulated in a buffer at pH 5.0-6.5.

Example 1

Synthesis of EG2-maleimide: (O—[N-(3-maleimidopropionyl)aminoethyl]-O'-[3-(N-(2-aminoethyl)amino)-3-oxopropyl]ethylene glycol)

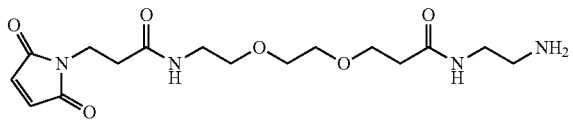

("EG2-maleimide" or "EG2-MI")

To an ice-cold suspension of maleimido-EG2-NHS ester (O—[N-(3-maleimidopropionyl)aminoethyl]-O'-[3-(N-succinimidyloxy)-3-oxopropyl]ethylene glycol, 1.2 g, 2.82 mmol) and Boc-diaminoethane hydrochloride (560 mg, 2.82 mmol) in ACN (15 mL) was added TEA (0.571 g, 5.64 mmol) drop-wise while stirring. The resulting mixture was brought to room temperature and the stirring continued overnight at room temperature. Additional BOC-diaminoethane hydrochloride was added (110 mg) to drive the reaction to completion. The reaction mixture was concentrated under vacuum and the residue purified on RP-HPLC (0-100% ACN in water) to give Boc-diaminoethane-EG2-maleimide as a colorless solid (1.18 g, 89% yield). ESI MS: calculated $C_{21}H_{35}N_4O_8$ [M+H$^+$] 471.3; found 471.2.

The Boc-diaminoethane-EG2-maleimide (1.18 g, 2.508 mmol) was dissolved in a 30% TFA solution in DCM (20 mL) at 0° C., the resulting solution was stirred for 2 hours at room temperature. The crude reaction mixture was concentrated under vacuum and then purified on RP-HPLC (0-10% ACN in water containing 0.1% TFA) to afford the title compound (EG2-maleimide) as a colorless oil (1.04 g, 86%).

$^1$H NMR (400 MHz, DMSO-d$_6$+D$_2$O): δ 6.95 (s, 2 H), 3.66-3.54 (m, 10 H), 3.34 (t, 2 H, J=5.6 Hz), 3.27 (t, 2 H, J=6.7 Hz), 3.18-3.10 (m, 2 H), 2.84 (t, 2 H, J=6.2 Hz), 2.33 (q, 4H, J=6.7 Hz); ESI MS: calculated for $C_{16}H_{27}N_4O_6$ [M+H$^+$] 371.2; found 371.2.

Example 2

Synthesis of 10K PHF-BA (30%)-EG2-MI (3%)

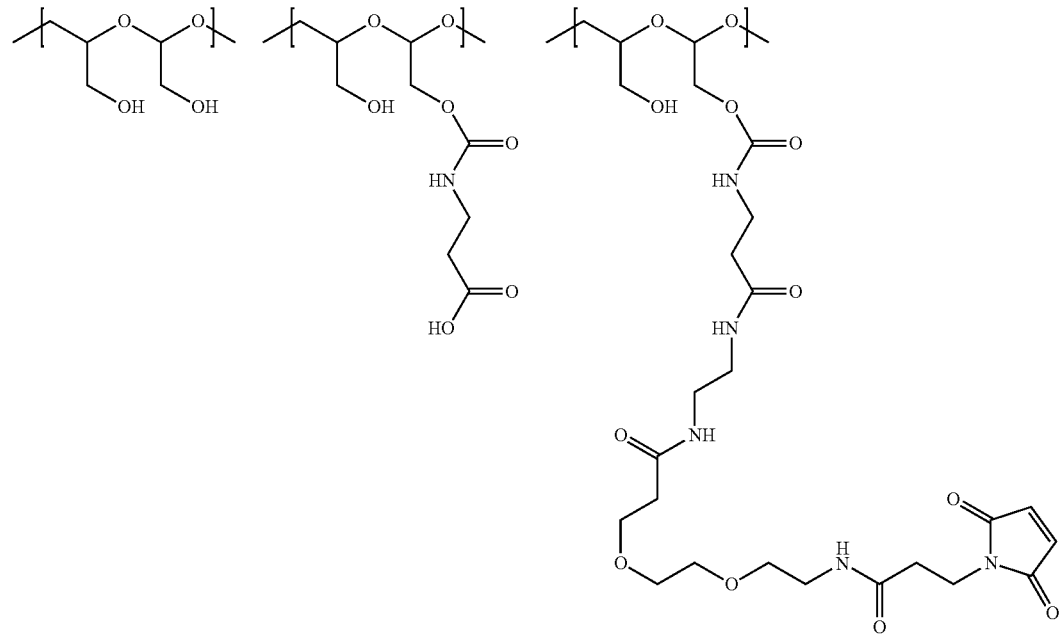

To a solution of 10K PHF-BA (30%) (588 mg, 3.46 mmol prepared in a fashion similar to that as described in U.S. Ser. No. 13/493,899, now U.S. Pat. No. 8,685,383, Example 1) in water (10 mL) was added a solution of EG2-maleimide (102 mg, 0.211 mmol, prepared in a fashion similar to that as described in Example 1) in water (5 mL) followed by the addition of N-hydroxy-succinimide (NHS, 25 mg, 0.211 mmol). The resulting mixture was cooled to 5-10° C., and the pH was adjusted to 5.8 (from 5.3) using 0.1N NaOH solution. Then EDC.HCl (94 mg, 0.486 mmol) in water (2 mL) was added to the reaction mixture over 40 minutes. The reaction mixture was brought to room temperature and the stirring continued at room temperature for 18 hours. The resulting product was purified by diafiltration on 3K MWCO membrane and lyophilzied to give the title compound as an off-white solid product (0.460 g, 71% yield).

$^1$H-NMR (400 MHz, D$_2$O): 6.9 ppm (broad singlet, MI), 5.0-4.7 ppm (m, 1H, O—CH—O—, acetal-proton polymer), 4.3-3.6 ppm (m, O—CH$_2$— polymer back bone and linker protons), 3.4-3.3 ppm (m, CH$_2$—NH—, beta-alanine and linker protons), 2.7-2.4 ppm (m, CH$_2$—COOH—, beta-alanine and linker protons). The EG2-MI linker loading (i.e., content of polymer units containing EG2-MI linker) determined by $^1$H-NMR was 3% mol of the polymer structural units.

Example 3

Synthesis of 10K PHF-BA (30%)-EG2-MI (3%)$^-$AF-HPA-Ala (8%)

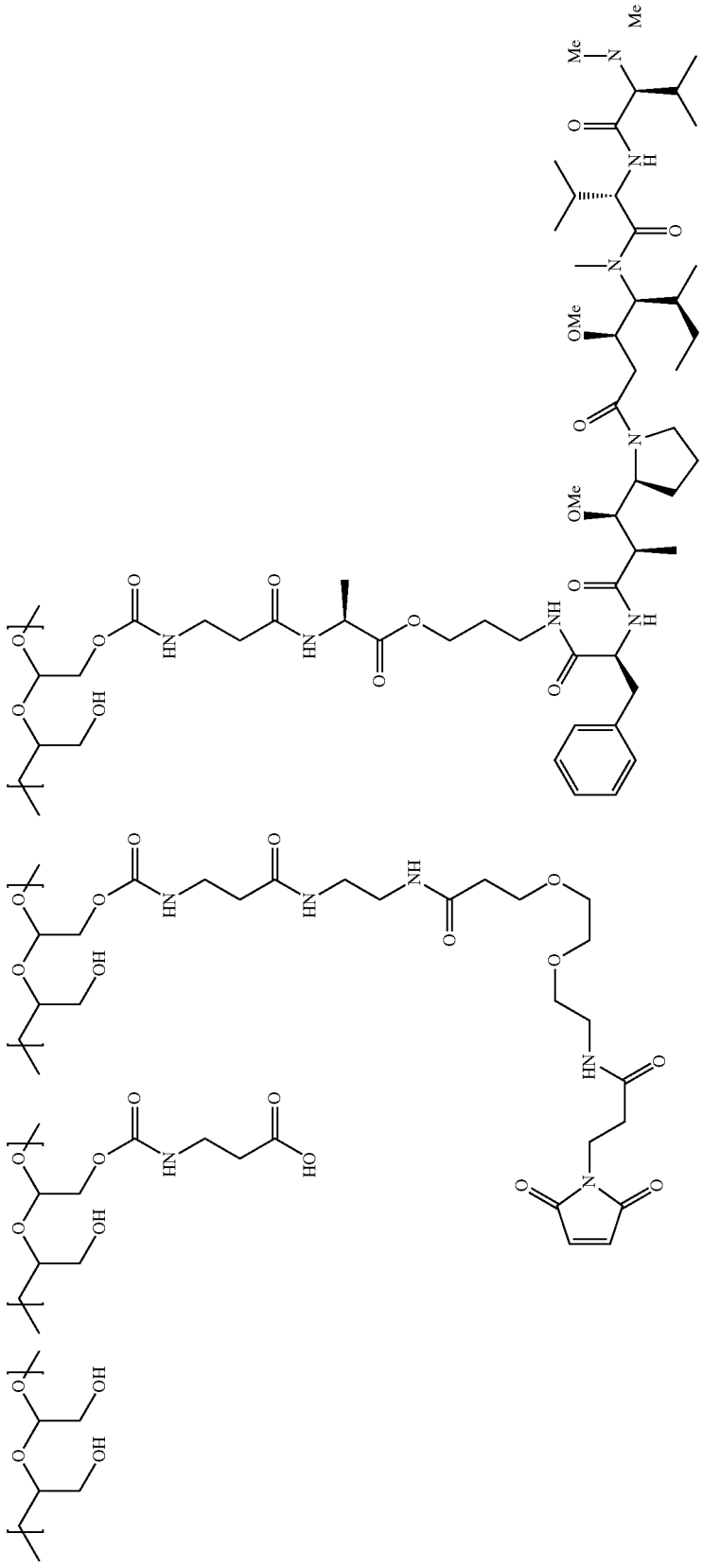

A homogeneous solution of 10K PHF-BA (30%) EG2-MI (3%) (144 mg, 11.08 μmol, prepared in a fashion similar to that as described in Example 2) in water (4.2 g) was chilled to 5-10° C. The pH of the solution was adjusted to 5.8 using 1N HCl, followed by addition of Auristatin F-hydroxypropylamide-L-Alanine.2TFA (AF-HPA-Ala.2TFA) (85 mg, 77.52 μmol, prepared in a fashion similar to that as described in U.S. Ser. No. 13/493,899, now U.S. Pat. No. 8,685,383, Example 50) dissolved in NMP (1.4 mL) and NHS (16 mg in 0.5 mL water). The mixture was stirred vigorously at 5-10° C. and the pH of the solution was adjusted to 5.8 with 0.1N NaOH. To the resulting mixture was added a freshly prepared aqueous solution of EDC.HCl (30 mg in 0.5 mL water). After 45 minutes additional EDC.HCl (30 mg in 0.5 mL water) was added and the resulting mixture was stirred for 18-24 hours while maintained the pH at 5.8. The RP-HPLC analysis of the reaction mixture indicated >95% consumption of the starting material auristatin compound. The product was purified by diafiltration on 3K MWCO membrane, followed by purification by HPLC and lyophilzation to give the title compound (143 mg, 78% yield).

$^1$H-NMR (400 MHz, D$_2$O): 7.15 ppm (broad singlet, AF-HPA aromatic protons), 6.9 ppm (broad singlet, MI), 5.0-4.8 ppm (m, 1H, O—CH—O-acetal-proton polymer), 4.4-3.6 ppm (m, O—CH$_2$— polymer back bone and drug/linker protons), 3.4-2.8 ppm (m, CH$_2$—NH—, beta-alanine and drug/linker protons), 2.2-1.8 ppm (m, CH$_2$—COOH—, beta-alanine and drug/linker protons) and 1.6-0.9 ppm (m, drug/linker protons).

The drug loading of the conjugated product (i.e., content of polymer units containing the drug) determined by $^1$H-NMR was 8% mol of the polymer structural units (or on average about 6 AF-HPA molecules per polymer chain). The molecular weight of the title conjugate was about 17 kDa.

Example 4

Synthesis of Trastuzumab-((EG2-MI (3%))-(10 kDa PHF-BA (30%)-(AF-HPA-Ala (8%))

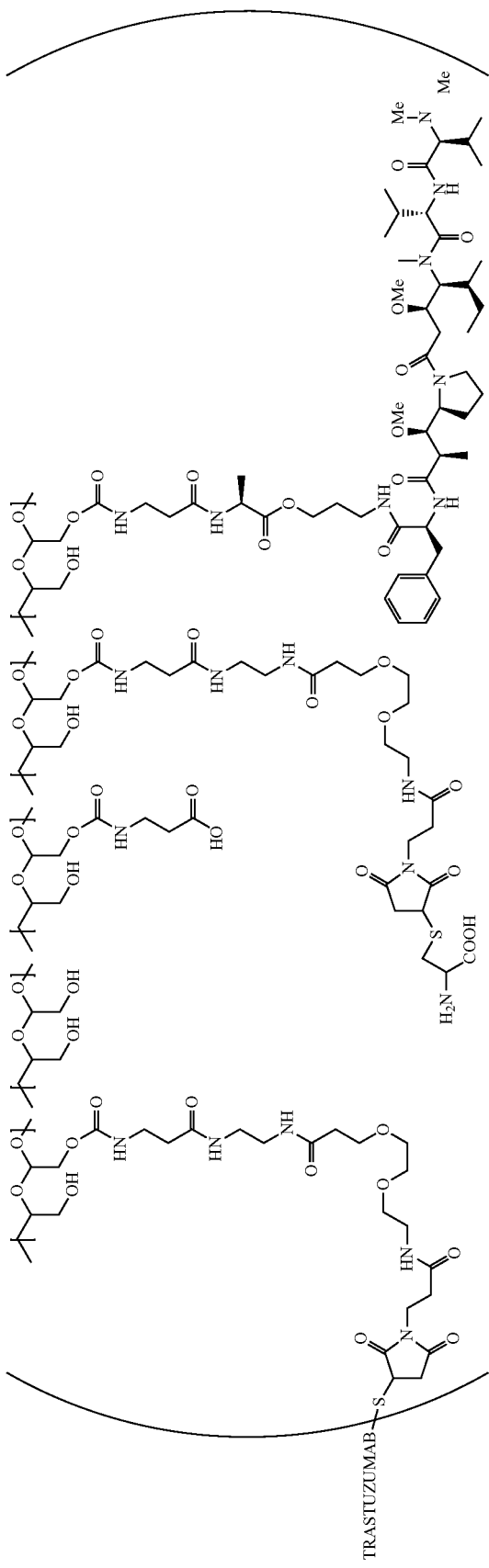

To a solution of trastuzumab (6.19 mL, 100 mg, 0.676 μmol) in TEAA buffer was added a solution of TCEP (0.6 mL, 2.36 μmol, 0.678 mg) while stirring. The mixture was incubated for 1 hour at 37° C., then cooled to ~0° C. The partially reduced trastuzumab was then added to a vigorously stirred solution of 10K PHF-BA (30%)-EG2-MI (3%)-AF-HPA-Ala (8%) (76 mg, prepared in a fashion similar to conjugates with varying ratios of drug to PBRM are obtained by varying the number of PBRM sulfhydryl groups and drug-polymer conjugate drug load.

Example 5

Synthesis of 10K PHF-BA (30%)-AF-HPA-Ala (9%)

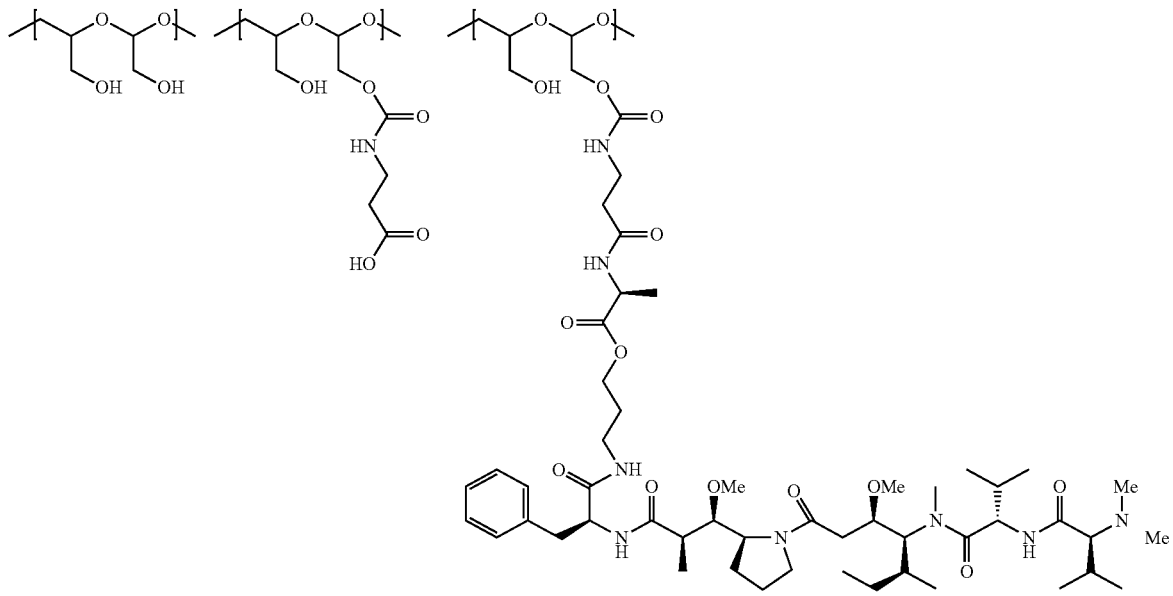

that as described in Example 3) in TEAA buffer, pH 7.4 (26.5 mL) at 0° C. The stirring was continued for 30 min at 0° C. The reaction was quenched with an aqueous solution of cysteine hydrochloride (65 mg, 371 μmol, 1.9 mL). After stirring for 1 h at ambient temperature at pH 7.0, the reaction mixture was acidified to pH 5.0. The crude product was purified by chromatography followed by SEC purification to give the title compound (61 mg, 61% yield).

The AF-HPA to trastuzumab ratio was about 12:1 to about 17:1. The molecular weight of the title conjugate was 180 kDa, PDI 1.15. The average PHF-drug conjugate to trastuzumab ratio was about 2:1 to about 3:1 or about 3:1 to about 4:1.

PBRM-polymer-drug conjugate, trastuzumab-((PEG2-MI (3%))-(10 kDa PHF-BA (30%)-(AF-HPA-Ala (8%)) (2.5 μg, prepared in a fashion similar to that as described above) was subjected to SDS-PAGE i.e., sodium dodecyl sulfate polyacrylamide gel electrophoresis) under non-reducing and reducing conditions and visualized with Odyssey IRDye® Blue Protein Stain Buffer. Under non-reducing conditions the conjugate was either heated at 70° C. for 10 minutes, or not heated prior to SDS-PAGE analysis.

The SGS-PAGE gels showed that the conjugate was stable and did not dissociate under non-reducing conditions, such as 70° C. for 10 minutes. Under reducing conditions the conjugate dissociated in to heavy and light chain fragments. Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies. Also PBRM-polymer-drug To a homogeneous solution of 10K PHF-BA (30%) (700 mg, prepared in a fashion similar to that as described in U.S. Ser. No. 13/493,899, now U.S. Pat. No. 8,685,383, Example 1) in water (20 mL) was added auristatin F-hydroxypropylamide-L-alanine.2TFA (AF-HPA-Ala.2TFA) (460 mg, 417 μmol, prepared in a fashion similar to that as described in U.S. Ser. No. 13/493,899, now U.S. Pat. No. 8,685,383, Example 50) dissolved in NMP (6.7 g). The resulting mixture was stirred vigorously while cooling to 5-10° C. The pH of the solution was adjusted to 5.8, followed by addition of NHS (129 mg in 1 mL water). To the resulting mixture was added a freshly prepared aqueous solution of EDC.HCl (223 mg in 1 mL water). After 30 minutes additional EDC.HCl (220 mg in 1 mL water) was added and the resulting mixture was stirred for 18 hours while maintained the pH at 5.8. The RP-HPLC analysis of the indicated >95% consumption of the starting material auristatin compound. The product was purified by HPLC and lyophilzation to give the title compound (859 mg, 83% yield).

$^1$H-NMR (400 MHz, D$_2$O): 7.7-7.2 ppm (broad singlet, AF-HPA aromatic protons), 5.0-4.8 ppm (m, 1H, O—C$\underline{H}$—O-acetal-proton polymer, partially buried under water signal), 4.4-3.6 ppm (m, O—CH$_2$— polymer back bone and drug/linker protons), 3.5-2.8 ppm (m, C$\underline{H}_2$—NH—, beta-alanine and drug/linker protons), 2.2-1.6 ppm (m, C$\underline{H}_2$—COOH—, beta-alanine and drug/linker protons) and 1.6-0.8 ppm (m, drug/linker protons).

The drug loading of the conjugated product determined by $^1$H-NMR was 8.7% mol of the polymer structural units (or on average about 6 AF-HPA molecules per polymer chain). Conjugate A: 10K PHF-BA (30%)-AF-HPA-Ala (9.5%) was prepared from 10K PHF-BA (30%) (100 mg) using the procedure described above.

Example 6

Synthesis of 10K PHF-BA (30%)-EG2-MI (2%)-AF-HPA-Ala (9%)

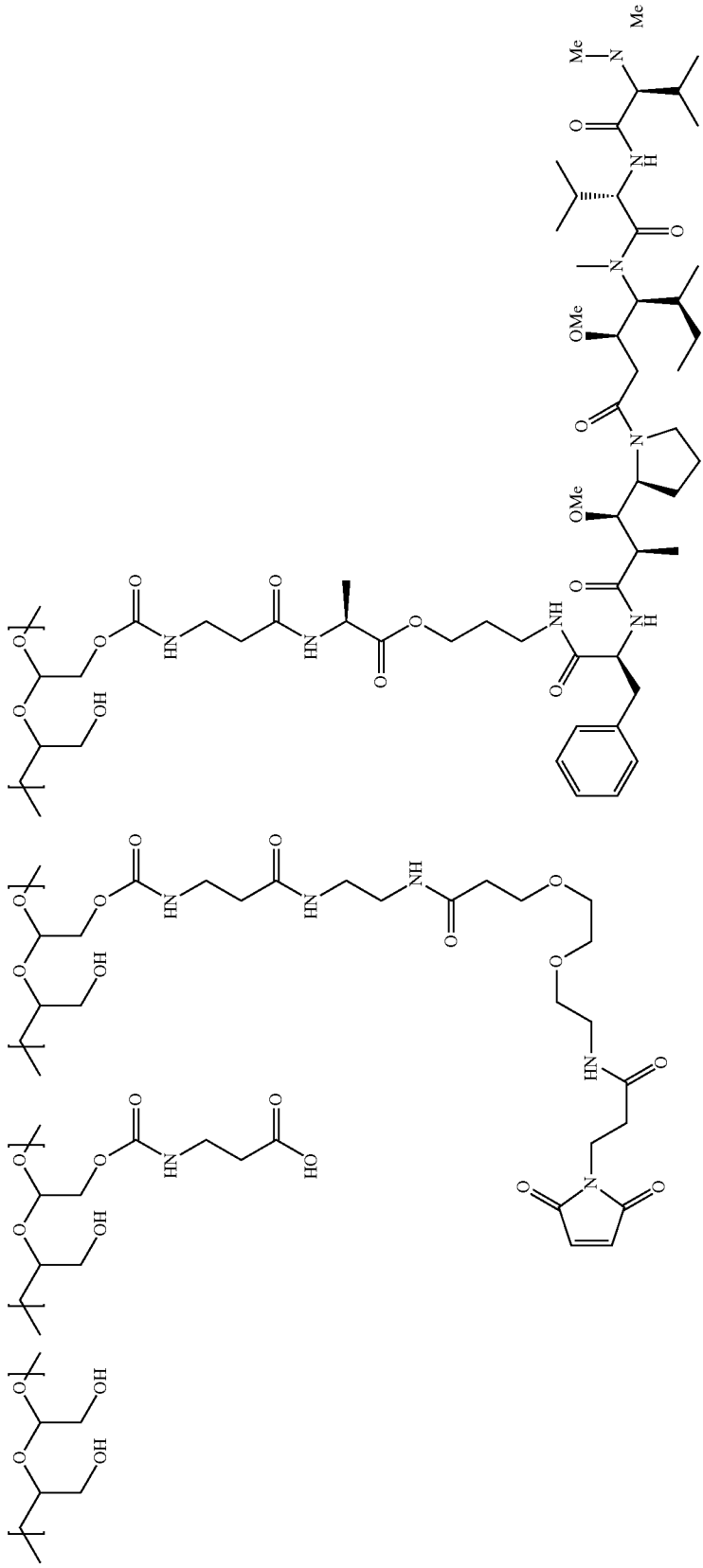

To a solution of 10K PHF-BA (30%)-AF-HPA-Ala (9%) (500 mg, 35 mmol. prepared in a fashion similar to that as described in Example 5) in water (13.7 mL) was added a solution of EG2-maleimide (83 mg, 0.139 mmol, prepared in a fashion similar to that as described in Example 1) followed N-hydroxy-succinimide (NHS, 40 mg, 0.348 mmol). The resulting mixture was cooled to 5-10° C., and the pH was adjusted to 5.8 (from 4.6) using 0.1N NaOH solution. Then EDC.HCl (174 mg, 0.91 mmol) in water (2 mL) was added to the reaction mixture over 40 minutes in two equal portions. The RP-HPLC analysis of the reaction mixture indicated >95% consumption of the EG2-maleimide. The reaction mixture was brought to room temperature and the stirring continued at room temperature for 18 hours. The resulting product was purified by diafiltration on 3K MWCO membrane and lyophilzied to give the title compound as an off-white solid product (0.57 g, 100% yield).

$^1$H-NMR (400 MHz, D$_2$O): 7.4-7.2 ppm (broad singlet, AF-HPA aromatic protons), 6.9 ppm (broad singlet, MI), 5.0-4.8 ppm (m, 1H, O—C$\underline{H}$—O-acetal-proton polymer, partially buried under water peak), 4.4-3.6 ppm (m, O—CH$_2$— polymer back bone and drug/linker protons), 3.5-2.8 ppm (m, C$\underline{H}_2$—NH—, beta-alanine and drug/linker protons), 2.2-1.6 ppm (m, C$\underline{H}_2$—COOH—, beta-alanine and drug/linker protons) and 1.6-0.8 ppm (m, drug/linker protons).

The EG2-MI linker loading determined by $^1$H-NMR was ~2% mol of the polymer structural units. The molecular weight of the title compound was about 20 kDa. On average, there were 6 AF-HPA molecules per polymer chain.

Example 7

Synthesis of Trastuzumab-((EG2-MI (2%)-(10 kDa PHF-BA (30%)-(AF-HPA-Ala (9%))

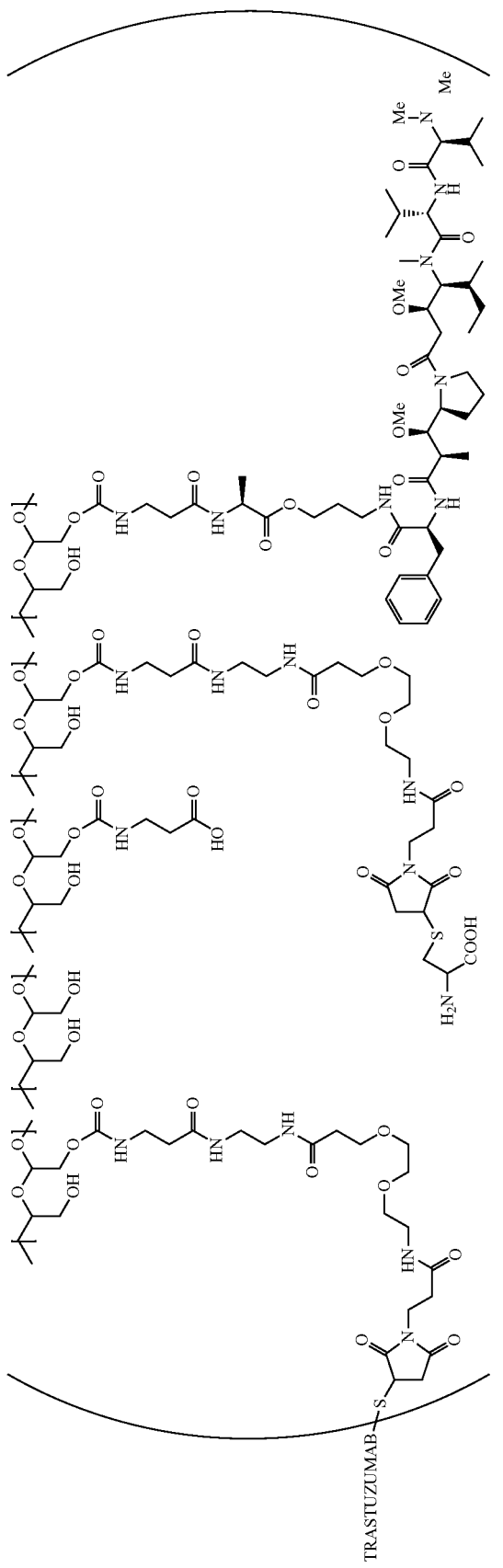

To a solution of trastuzumab (6.4 mL, 100 mg, 0.68 μmol) in TEAA buffer was added a solution of TCEP (0.993 mg, 3.4 μmol) while stirring. The mixture was incubated for 1.5 h at room temperature. The partially reduced trastuzumab was then added to a vigorously stirred solution of 10K PHF-BA (30%)-EG2-MI (2%)-AF-HPA-Ala (9%) (86 mg, 4.7 μmol, prepared in a fashion similar to that as described in Example 6) in TEAA buffer, pH 7.4 (26.5 mL) at 0° C. The stirring was continued for 45 minutes at room temperature. The reaction was quenched with an aqueous solution of cysteine in TEAA buffer, pH 6.8 (65 mg, 371 μmol, 1.9 mL). After stirring for 1 h at ambient temperature at pH 7.0, the reaction mixture was acidified to pH 5.8. The crude product was purified by SEC purification to give the title compound (35 mg, 35% yield).

The AF-HPA to trastuzumab ratio was about 16:1 to about 21:1. The molecular weight of the title conjugate was 210 kDa. The average PHF-drug conjugate to trastuzumab ratio was about 2:1 to about 3:1 or about 3:1 to about 4:1.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies. Also PBRM-polymer-drug conjugates with varying ratios of drug to PBRM are obtained by varying the number of PBRM sulfhydryl groups and drug-polymer conjugate drug load.

Example 8

Synthesis of Lintuzumab-((EG2-MI (2%)-(10 kDa PHF-BA (30%)-(AF-HPA-Ala (9%))

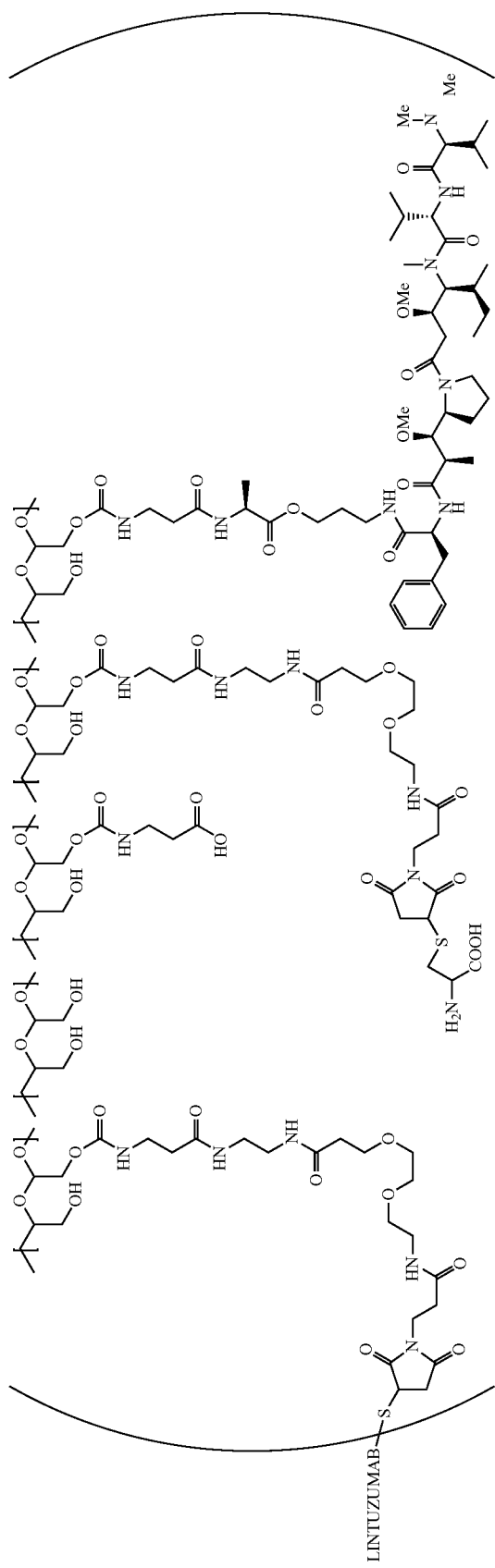

The title compound was prepared using the procedure described in Example 4 or Example 7 except 10K PHF-BA (30%)-EG2-MI (2%)-AF-HPA-Ala (9%) (prepared in a fashion similar to that as described in Example 3 or Example 6), lintuzumab and TCEP:lintuzumab 3.5:1 were used.

The AF-HPA to lintuzumab ratio was about 10:1 to about 15:1. The molecular weight of the title conjugate was 184 kDa. The average PHF-drug conjugate to lintuzumab ratio was about 2:1 to about 3:1 or about 3:1 to about 4:1.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies. Also PBRM-polymer-drug conjugates with varying ratios of drug to PBRM are obtained by varying the number of PBRM sulfhydryl groups and drug-polymer conjugate drug load.

Example 9

Synthesis of Rituximab-((EG2-MI (3%)-(10 kDa PHF-BA (30%)-(AF-HPA-Ala (8%))

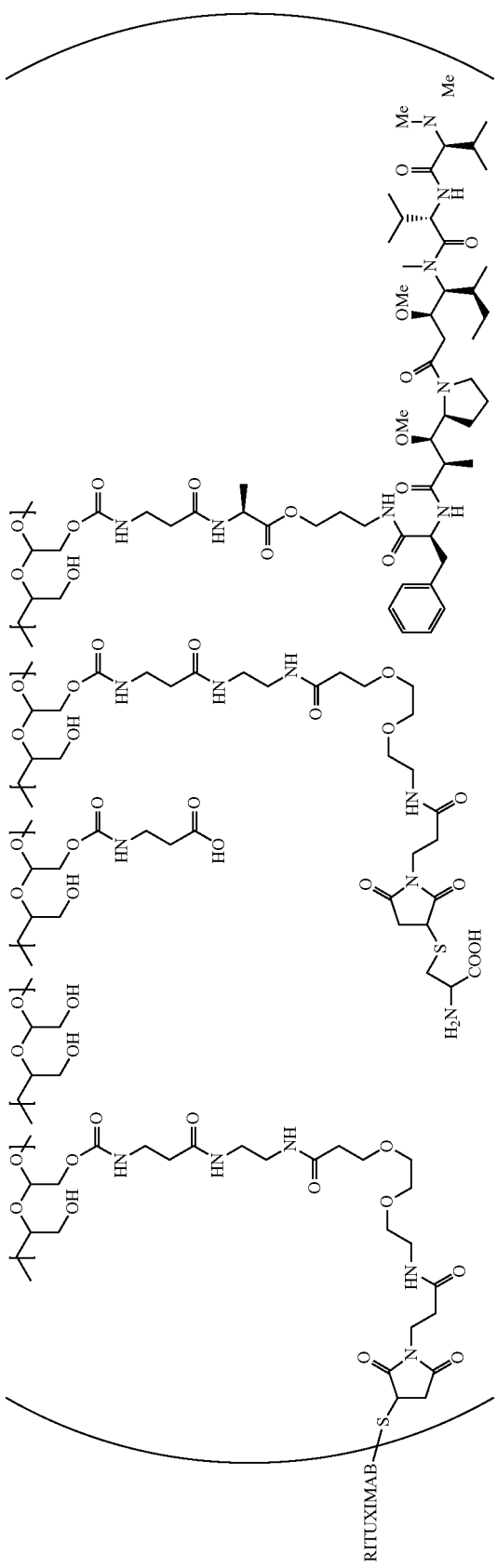

The title compound was prepared using the procedure described in Example 4 or Example 7 except 10K PHF-BA (30%)-EG2-MI (3%)-AF-HPA-Ala (8%) (prepared in a fashion similar to that as described in Example 3 or Example 6), rituximab and TCEP:rituximab 3.5:1 were used.

The AF-HPA to rituximab ratio was about 13:1 to about 18:1. The molecular weight of the title conjugate was 163 kDa. The average PHF-drug conjugate to rituximab ratio was about 2:1 to about 3:1 or about 3:1 to about 4:1.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies. Also PBRM-polymer-drug conjugates with varying ratios of drug to PBRM are obtained by varying the number of PBRM sulfhydryl groups and drug-polymer conjugate drug load.

Example 10

Synthesis of Anti-5T4-((EG2-MI (3%)-(10 kDa PHF-BA (30%)-(AF-HPA-Ala (8%))

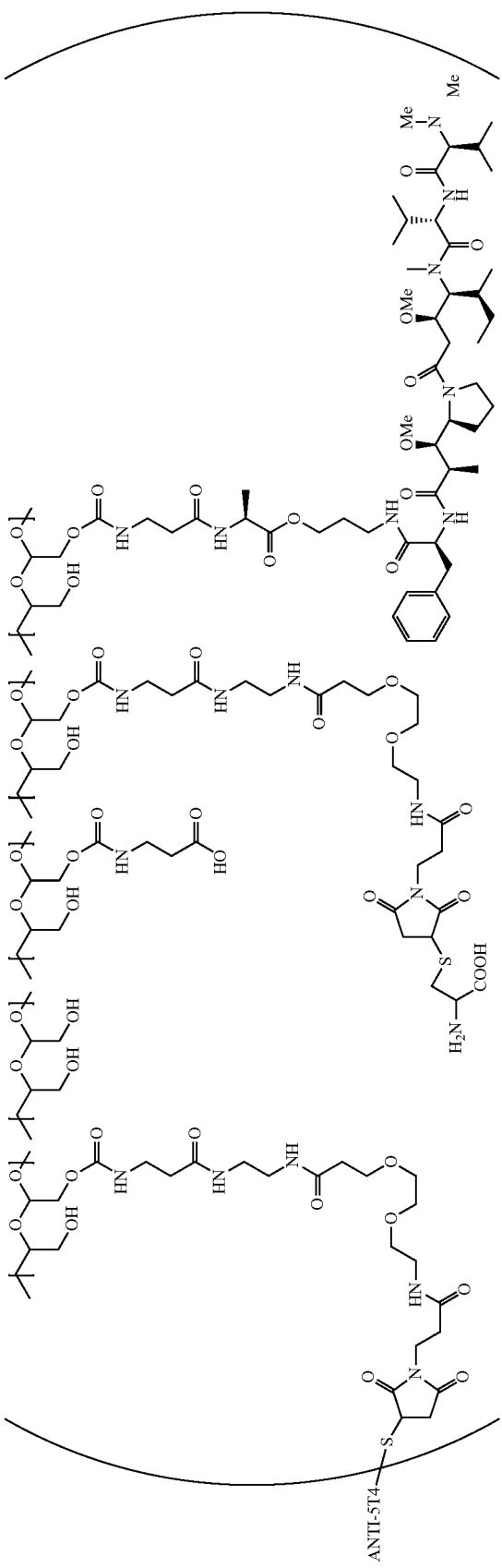

The title compound ("anti-5T4 scFvFc polymer drug conjugate", or "anti-5T4 scADC") was prepared in a fashion similar to that as described in Example 7 except 10K PHF-BA (30%)-EG2-MI (3%)-AF-HPA-Ala (8%) (prepared in a fashion similar to that as described in Example 3 or Example 6), and anti-5T4 scFvFc antibody and TCEP:anti-5T4 scFvFc antibody 3:1 were used. Anti-5T4 scFvFc antibody (anti-5T4 single chain antibody-Fc fusion protein) was prepared recombinantly in CHO DG44 cells, as disclosed in U.S. Provisional Application No. 61/835,858, filed Jun. 17, 2013, herein incorporated by reference.

The AF-HPA to anti-5T4 antibody ratio was about 12:1 to about 18:1. The molecular weight of the title conjugate was 200 kDa. The average PHF-drug conjugate to anti-5T4 antibody ratio was about 2:1 to about 3:1 or about 3:1 to about 4:1.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies. Also PBRM-polymer-drug conjugates with varying ratios of drug to PBRM are obtained by varying the number of PBRM sulfhydryl groups and drug-polymer conjugate drug load.

Example 11

Synthesis of 10K PHF-GA (29%)-EG2-MI (1%)

To a solution of 10K PHF-GA (29%) (1.7 g, 10.1 mmol, prepared in a fashion similar to that as described in U.S. Ser. No. 13/493,899, now U.S. Pat. No. 8,685,383, Example 2) in water (35 mL) was added a solution of EG2-maleimide (204 mg, 0.42 mmol, prepared in a fashion similar to that as described in Example 1) in DMA (3 mL) followed by the addition of N-hydroxy-succinimide (NHS, 70.3 mg, 0.611 mmol). The resulting mixture was cooled to 5-10° C. Then EDC.HCl (269 mg, 1.402 mmol) in water (2 mL) was added to the reaction mixture in two equal portions over 40 minutes. The reaction mixture was brought to room temperature and the stirring continued at room temperature for 18 hours. The resulting product was purified by diafiltration on 3K MWCO membrane and lyophilzied to give the title compound as an off-white solid product (1.7 g, 91% yield).

$^1$H-NMR (400 MHz, D$_2$O): 6.9 ppm (broad singlet, MI), 5.0-4.7 ppm (m, 1H, O—C$\underline{H}$—O—, acetal-proton polymer, partially buried under water peak), 4.4-3.6 ppm (m, O—CH$_2$-polymer back bone and linker protons), 3.3-2.6 ppm (m, linker protons), 2.5 ppm (m, C$\underline{H}_2$—CO—, glutaric protons), 2.3 ppm (broad singlet, C$\underline{H}_2$—COO—, glutaric protons), 1.9 ppm (broad singlet, —CH$_2$—C$\underline{H}_2$—CH$_2$—COO—, glutaric protons).

The EG2-MI linker loading determined by $^1$H-NMR was 1% mol of the polymer structural units.

Example 12

Synthesis of 10K PHF-GA (29%)-EG2-MI (1%)-AF-HPA-Ala (6%)

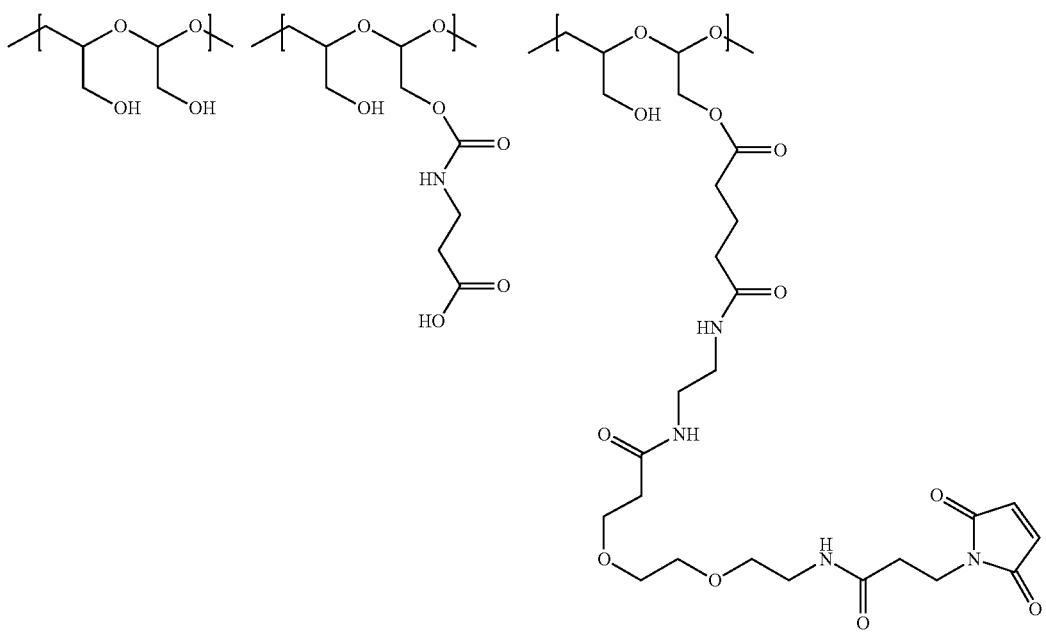

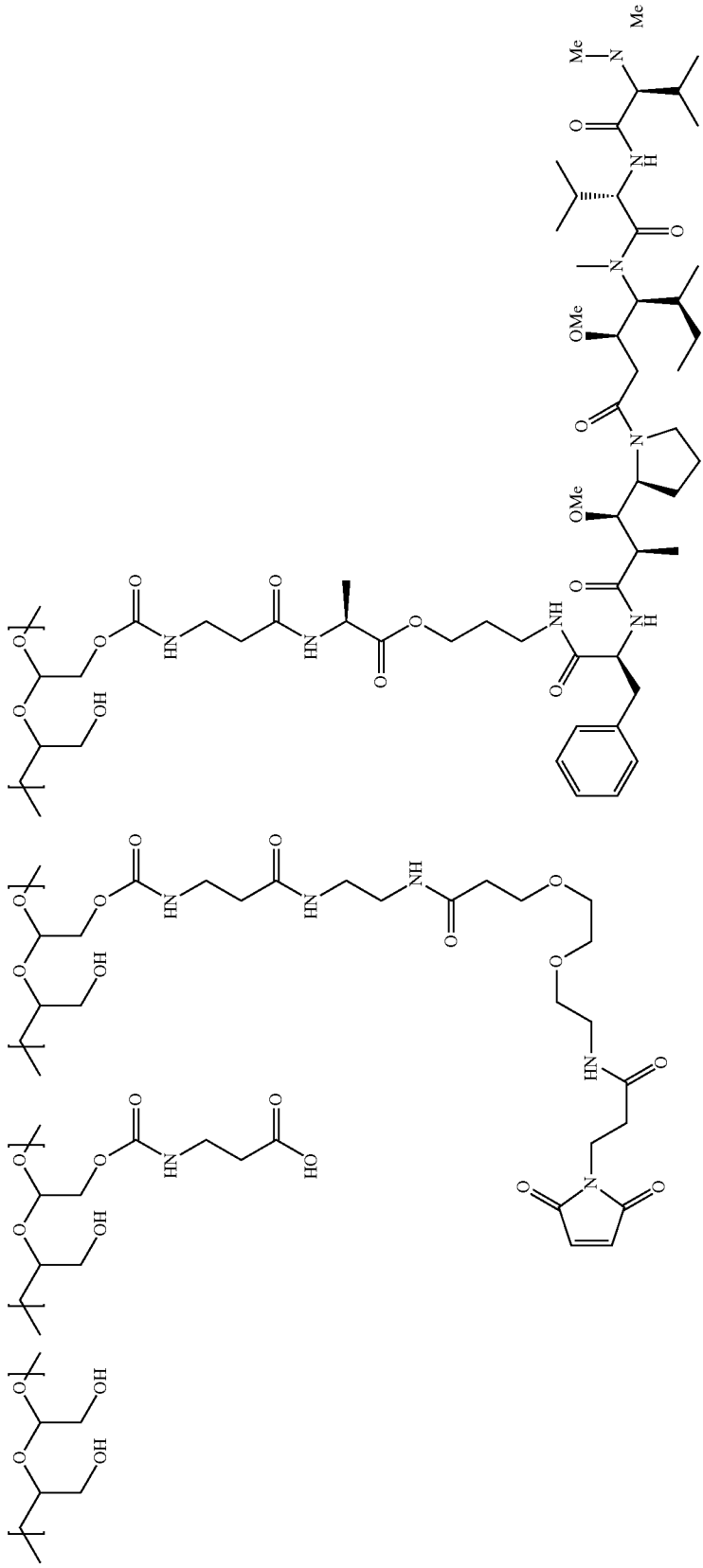

A homogeneous solution of 10K PHF-BA (29%)-EG2-MI (1%) (214 mg, 15 µmol, prepared in a fashion similar to that as described in Example 11) in water (5.4 g) was added AF-HPA-Ala.2TFA) (98 mg, 90 µmol, prepared in a fashion similar to that as described in U.S. Ser. No. 13/493,899, now U.S. Pat. No. 8,685,383, Example 50) dissolved in NMP (1.85 mL) and NHS (25 mg in 0.5 mL water). The mixture was stirred vigorously at 5-10° C. To the resulting mixture was added a freshly prepared aqueous solution of EDC.HCl (40 mg in 0.8 mL water). After 30 minutes additional EDC.HCl (44 mg in 0.8 mL water) was added and the resulting mixture was stirred for 18-24 hours while maintained the pH at 5.8. The RP-HPLC analysis of the indicated >95% consumption of the starting material auristatin compound. The product was purified by diafiltration on 3K MWCO membrane and concentrated to 10 mL to give the title compound (177 mg, 63% yield).

$^1$H-NMR (400 MHz, D$_2$O): 7.4-7.2 ppm (broad singlet, AF-HPA aromatic protons), 6.9 ppm (broad singlet, MI), 5.0-4.8 ppm (m, 1H, O—C$\underline{H}$—O—, acetal-proton polymer), 4.4-3.6 ppm (m, O—CH$_2$— polymer back bone and linker protons), 3.4-2.9 ppm (m, drug linker protons), 2.5 ppm (broad triplet, CO—C$\underline{H}_2$—, glutaric protons), 24-2.2 ppm (m, C$\underline{H}_2$—COO—, glutaric protons and drug/linker protons), 2.0-1.8 ppm (m, —CH$_2$—C$\underline{H}_2$—CH$_2$—CO—, glutaric protons), 1.5-0.8 (m, drug/linker protons).

The conjugated product drug loading determined by $^1$H-NMR was 5.9% mol of the polymer structural units (or on average about 4.5 AF-HPA molecules per polymer chain). The molecular weight of the title conjugate was about 17 kDa.

Example 13

Synthesis of Trastuzumab-((EG2-MI (1%))-(10 kDa PHF-GA (29%)-(AF-HPA-Ala (6%))

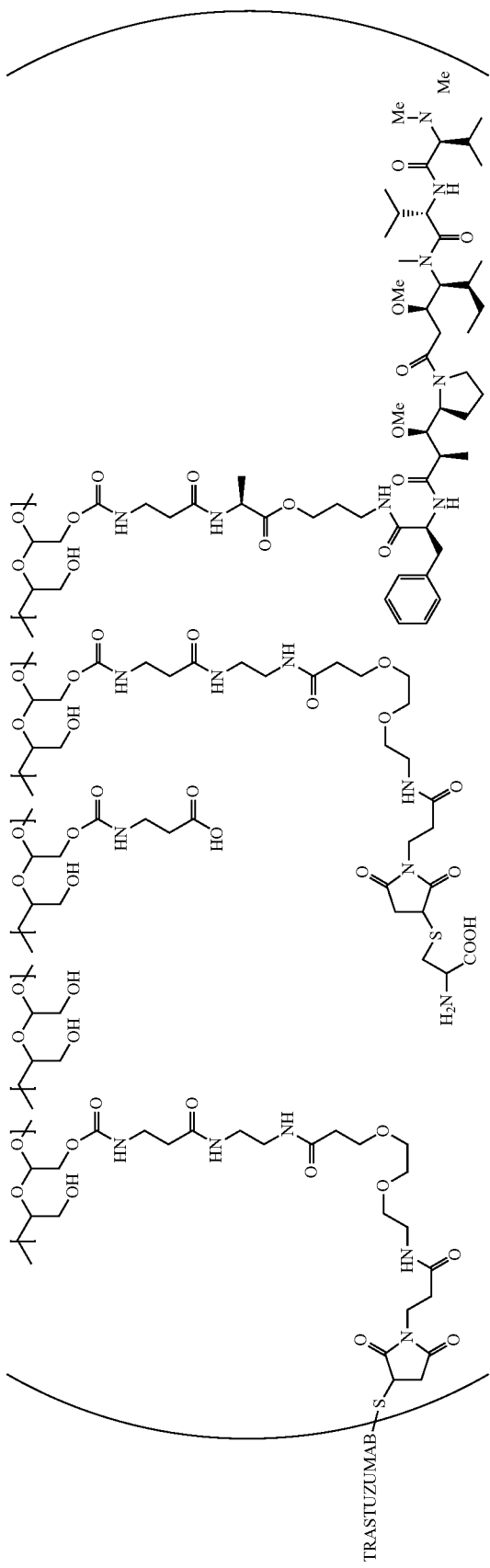

The title compound was prepared using the procedure described in Example 4 or Example 7 except 10K PHF-GA (29%)-EG2-MI (1%)-AF-HPA-Ala (6%) (78 mg, prepared in a fashion similar to that as described in Example 12) and trastuzumab (25 mg) and TCEP:trastuzumab 3.5:1 were used. The AF-HPA to trastuzumab ratio was about 18:1 to about 23:1. The molecular weight of the title conjugate was 200 kDa. The average PHF-drug conjugate to trastuzumab ratio was about 4:1 to about 5:1.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies. Also PBRM-polymer-drug conjugates with varying ratios of drug to PBRM are obtained by varying the number of PBRM sulfhydryl groups and drug-polymer conjugate drug load.

Example 14

Synthesis of Trastuzumab-((EG2-MI (2%)-(10 kDa PHF-BA (28%)-(AF-HPA-Ala (9%))

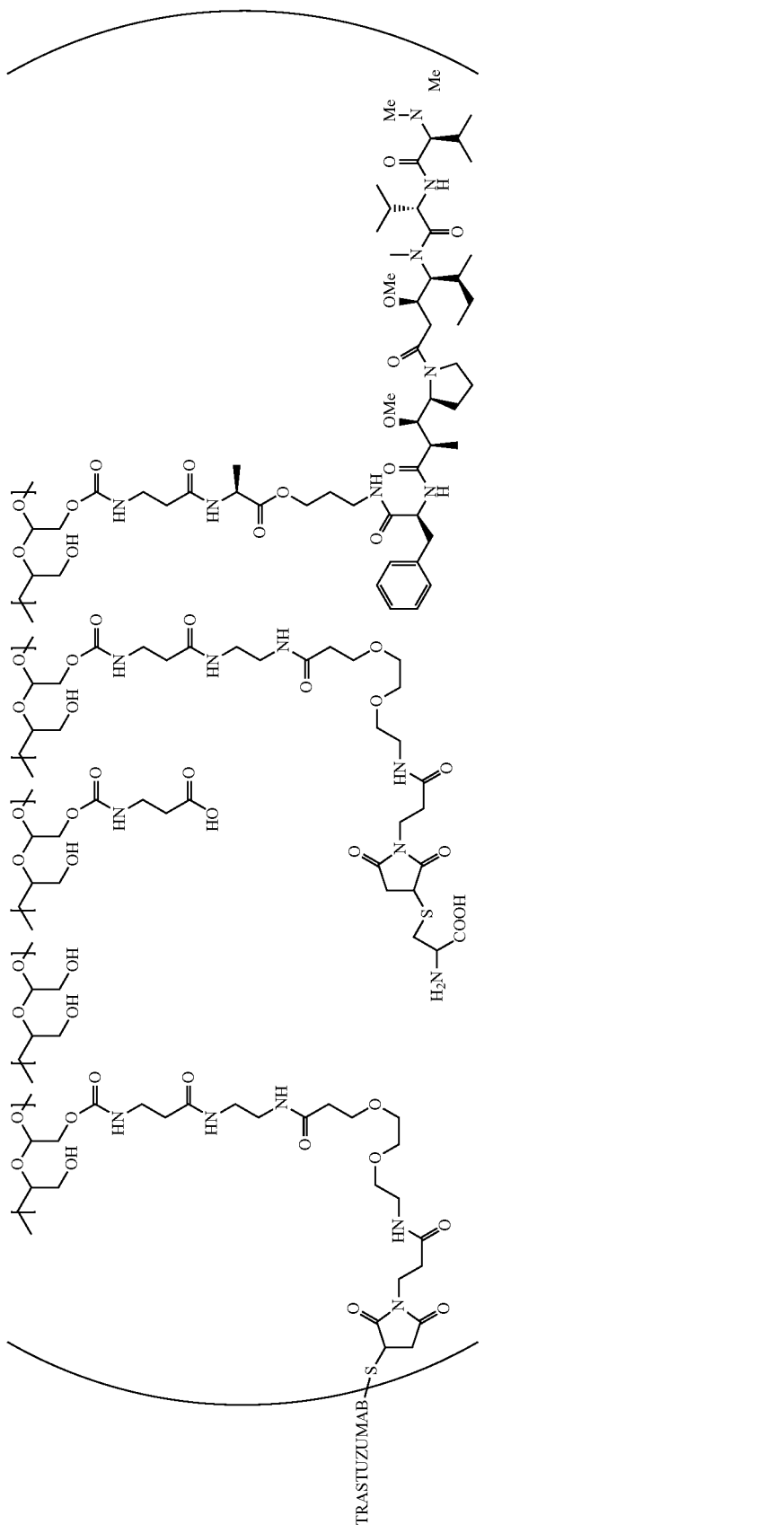

The title compound was prepared using the procedure described in Example 4 or Example 7 except 10K PHF-BA (28%)-EG2-MI (2%)-AF-HPA-Ala (9%) (11 mg, prepared using the procedure described in Example 3 or Example 6, trastuzumab (620 mg) and TCEP:trastuzumab 3.5:1 were used.

The AF-HPA to trastuzumab ratio was about 10:1 to about 15:1. The molecular weight of the title conjugate was 183 kDa. The average PHF-drug conjugate to trastuzumab ratio was about 2:1 to about 4:1.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies. Also PBRM-polymer-drug conjugates with varying ratios of drug to PBRM are obtained by varying the number of PBRM sulfhydryl groups and drug-polymer conjugate drug load.

Example 15

Synthesis of Trastuzumab-((EG2-MI (2%)-(10 kDa PHF-BA (28%)-(AF-HPA-Ala (9%))

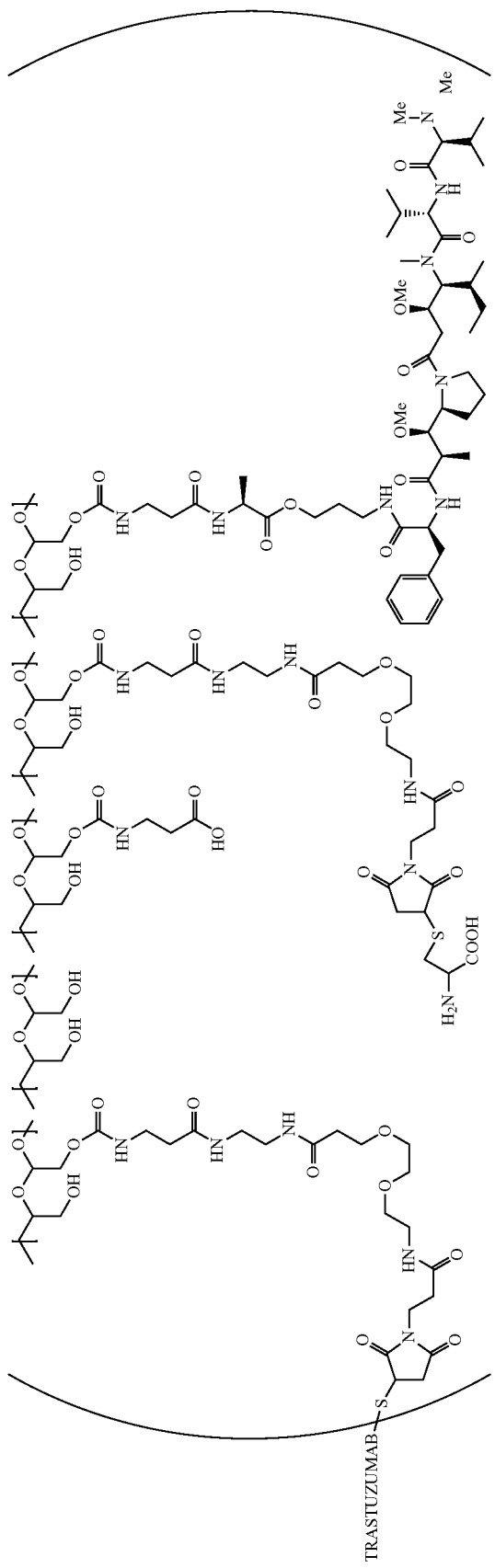

The title compound was prepared using the procedure described in Example 4 or Example 7 except 10K PHF-BA (28%)-EG2-MI (2%)-AF-HPA-Ala (9%) (243 mg, prepared using the procedure described in Example 3 or Example 6), trastuzumab (435 mg) and TCEP:trastuzumab 3:1 were used.

The AF-HPA to trastuzumab ratio was about 11:1 to about 16:1. The molecular weight of the title conjugate was 197 kDa. The average PHF-drug conjugate to trastuzumab ratio was about 2:1 to about 4:1.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies. Also PBRM-polymer-drug conjugates with varying ratios of drug to PBRM are obtained by varying the number of PBRM sulfhydryl groups and drug-polymer conjugate drug load.

Example 16

Synthesis of Rituximab-((EG2-MI (2%)-(10 kDa PHF-BA (28%)-(AF-HPA-Ala (9%))

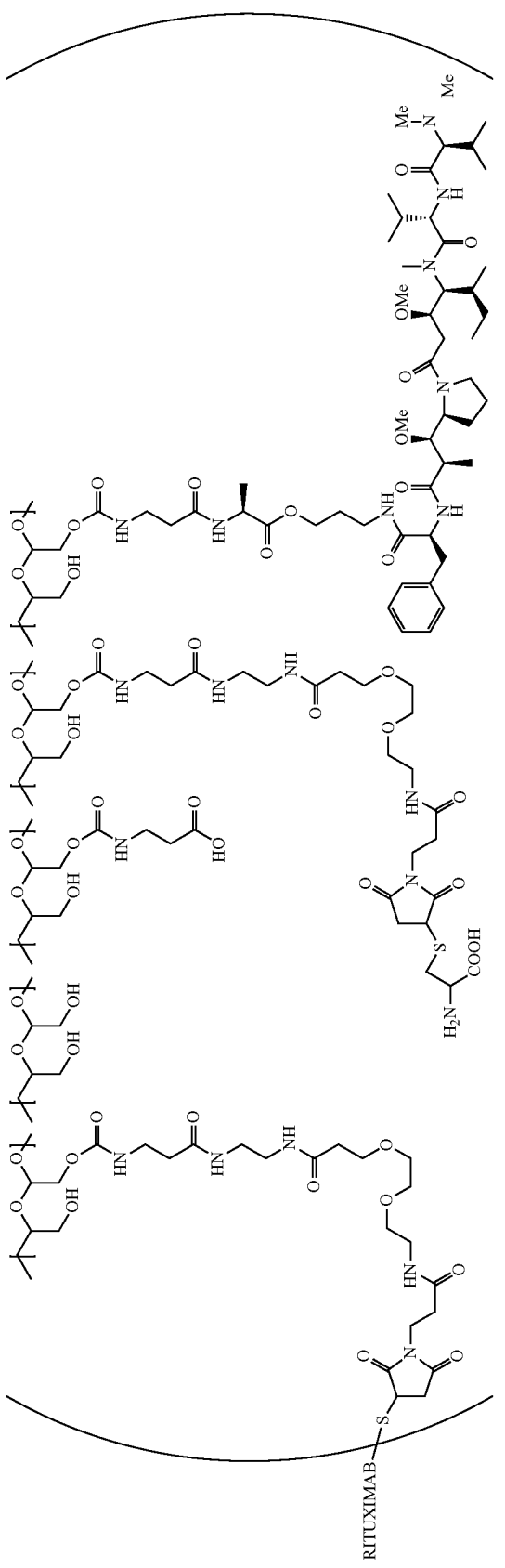

The title compound was prepared using the procedure described in Example 4 or Example 7 except 10K PHF-BA (28%)-EG2-MI (2%)-AF-HPA-Ala (9%) (170 mg, prepared using the procedure described in Example 3 or Example 6) 300 mg rituximab and TCEP:rituximab 3:1 were used.

The AF-HPA to rituximab ratio was about 13:1 to about 18:1. The molecular weight of the title conjugate was 180 kDa. The average PHF-drug conjugate to rituximab ratio was about 3:1 to about 4:1.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies. Also PBRM-polymer-drug conjugates with varying ratios of drug to PBRM are obtained by varying the number of PBRM sulfhydryl groups and drug-polymer conjugate drug load.

Example 17

Synthesis of Trastuzumab-((EG2-MI (2%)-(10 kDa PHF-BA (28%)-(AF-HPA-Ala (9%))

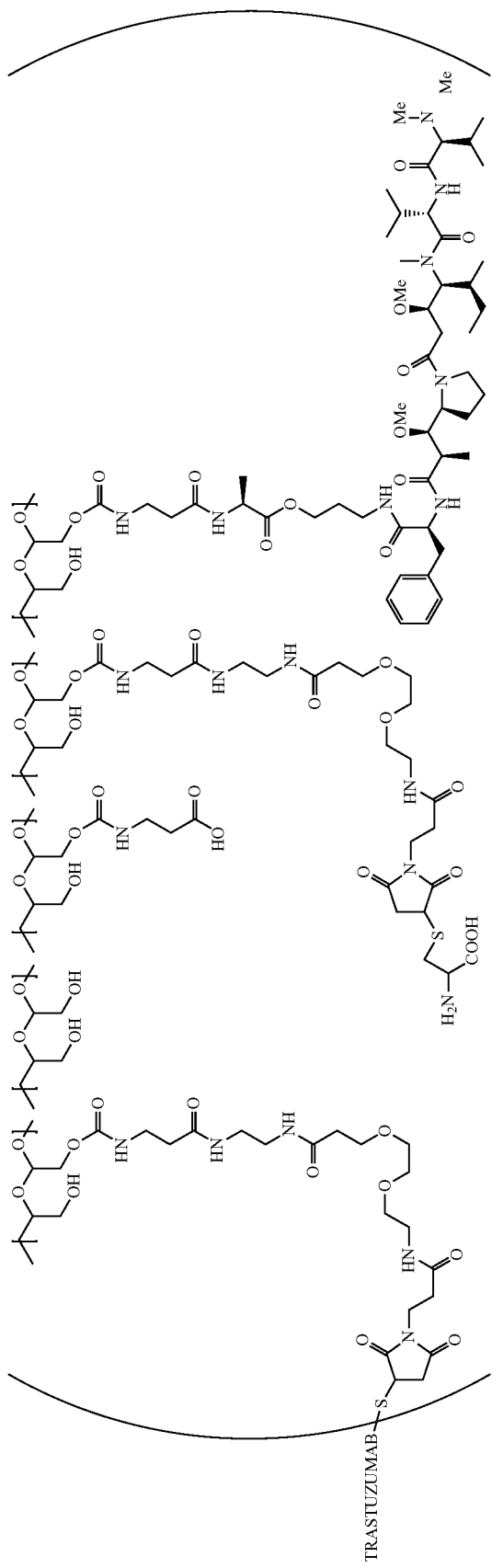

The title compound was prepared using the procedure described in Example 4 or Example 7 except 10K PHF-BA (28%)-EG2-MI (2%)-AF-HPA-Ala (9%) (8.4 mg, prepared using the procedure described in Example 3 or Example 6, trastuzumab (15 mg) and (TCEP:trastuzumab 3.5:1 were used. The AF-HPA to trastuzumab ratio was about 5:1 to about 10:1. The molecular weight of the title conjugate was 183 kDa. The average PHF-drug conjugate to trastuzumab ratio was about 2:1 to about 4:1.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies. Also PBRM-polymer-drug conjugates with varying ratios of drug to PBRM are obtained by varying the number of PBRM sulfhydryl groups and drug-polymer conjugate drug load.

Example 18

Synthesis of Trastuzumab-((EG2-MI (2%)-(10 kDa PHF-BA (28%)-(AF-HPA-Ala (9%))

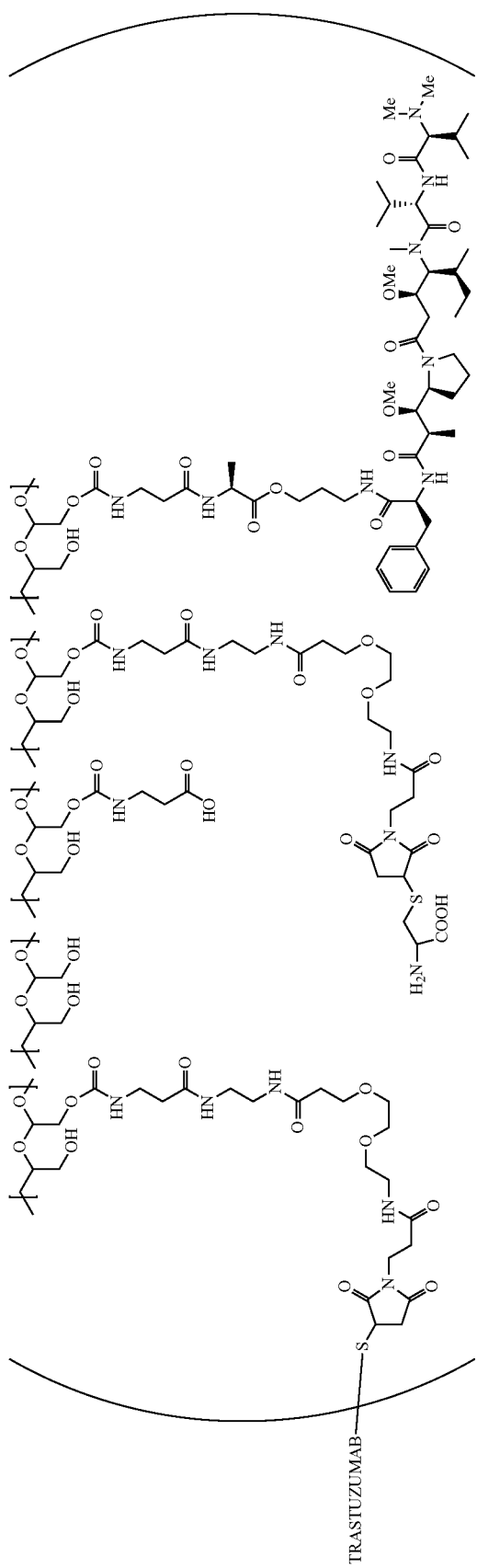

The title compound was prepared using the procedure described in Example 4 or Example 7.

Conjugate A—The AF-HPA to trastuzumab ratio was about 19:1 to about 24:1. The molecular weight of the title conjugate was 201 kDa. The average PHF-drug conjugate to trastuzumab ratio was about 2:1 to about 4:1.

Conjugate B—The AF-HPA to trastuzumab ratio was about 20:1 to about 25:1. The molecular weight of the title conjugate was 224 kDa. The average PHF-drug conjugate to trastuzumab ratio was about 2:1 to about 4:1.

Conjugate C—The AF-HPA to trastuzumab ratio was about 23:1 to about 28:1. The molecular weight of the title conjugate was 259 kDa. The average PHF-drug conjugate to trastuzumab ratio was about 2:1 to about 4:1.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies. Also PBRM-polymer-drug conjugates with varying ratios of drug to PBRM are obtained by varying the number of PBRM sulfhydryl groups and drug-polymer conjugate drug load.

Example 19

Synthesis of 10K PHF-BA (30%) EG2-MI (2.7%)-(HPV-Ala (14%)

A homogeneous solution of 10K PHF-BA (30%) EG2-MI (2.7%) (25.00 mg, 2.80 μmol, prepared in a fashion similar to that as described in Example 2) in water (0.612 mL and NMP (0.14 mL) was chilled to 0° C. 1-Hydroxypyrrolidine-2,5-dione (8.06 mg, 0.07 mmol) in NMP (0.14 mL) was added followed by HPV-Alanine (15.56 mg, 0.018 mmol, prepared in a fashion similar to that as described in U.S. Pat. No. 8,524,214, Example 1) in water (0.250 mL). The mixture was stirred vigorously until all materials had dissolved then a freshly prepared aqueous solution of EDC.HCl (6.71 mg in 0.125 mL water) was added. After 45 minutes additional EDC.HCl (6.71 mg in 0.125 mL water) was added and the resulting mixture was stirred for 18 hours while maintained the pH at 5.8. The RP-HPLC analysis of the reaction mixture indicated the reaction was incomplete. The mixture was cooled to 0° C. and EDC.HCl (12 mg in 0.250 mL) was added. The pH of the solution was adjusted to 5.9 with 0.1N NaOH and the mixture stirred for an additional 2 h at which time RP-HPLC analysis of the reaction mixture indicated complete consumption of the starting material The product was purified by column chromatography (Sephadex G25 Gel) followed by purification by HPLC and lyophilzation to give the title compound (10.18 mg, 24% yield).

Conjugate A: 10K PHF-BA (30%) EG2-MI (2.7%)-(HPV-Ala (14%) was prepared in a fashion similar to that as described above. The drug loading of the conjugated product (i.e., content of polymer units containing the drug) determined by $^1$H-NMR was 14% mol of the polymer structural units (i.e. on average 2.4 HPV-Ala molecules per polymer chain).

Conjugate B: 10K PHF-BA (30%) EG2-MI (2.7%)-(HPV-Ala (7.7%) was prepared using the procedure described above. The drug loading of the conjugated product (i.e., content of polymer units containing the drug) determined by $^1$H-NMR was 28.3% mol of the polymer structural units (i.e. on average 4.6 HPV-Ala molecules per polymer chain).

Conjugate C: 10K PHF-BA (30%) EG2-MI (3.5%)-(HPV-Ala (4.3%) was prepared using the procedure described above. The drug loading of the conjugated product (i.e., content of polymer units containing the drug) determined by HPLC was 4.3% mol of the polymer structural units (i.e. on average 2.6 HPV-Ala molecules per polymer chain).

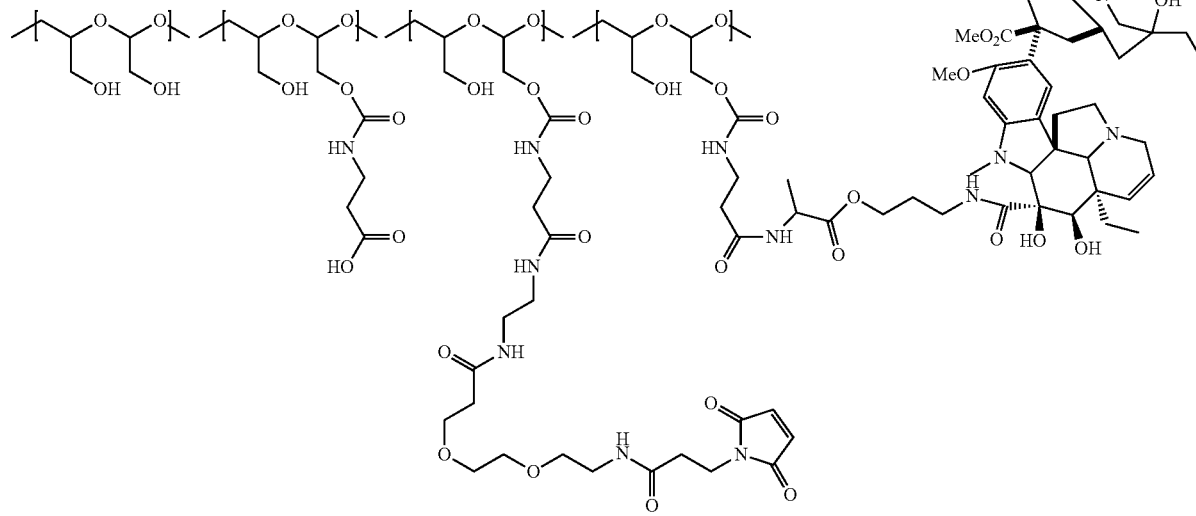

Example 20

Synthesis of Trastuzumab-((EG2-MI (2.7%)-(10 kDa PHF-BA (30%)-(HPV-Ala (14%))

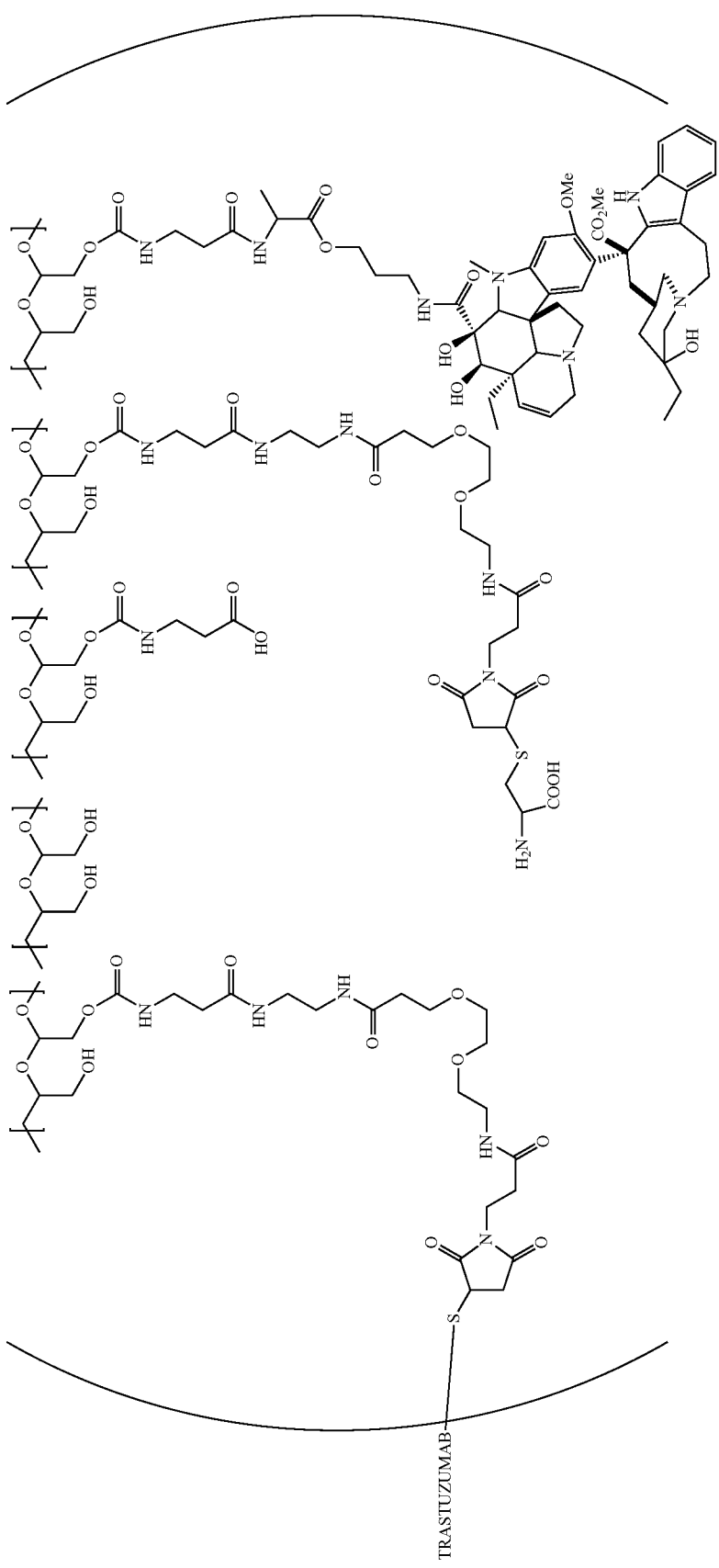

The title compound was prepared using the procedure described in Example 4 or Example 7 except 10K PHF-BA (30%) EG2-MI (2.7%)-(HPV-Ala (14%) (1.5 mg, prepared in a fashion similar to that as described in Example 19), trastuzumab and TCEP:trastuzumab 4:1 were used.

Conjugate A: Trastuzumab-((EG2-MI (2.7%)-(10 kDa PHF-BA (30%)-(HPV-Ala (14%)). The HPV-Ala to trastuzumab ratio was about 13:1 to about 18:1. The molecular weight of the title conjugate was about 168 kDa. The average PHF-drug conjugate to trastuzumab ratio was about 2:1 to about 4:1.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies. Also PBRM-polymer-drug conjugates with varying ratios of drug to PBRM are obtained by varying the number of PBRM sulfhydryl groups and drug-polymer conjugate drug load.

Example 21

Synthesis of 10K PHF-BA (28%) EG2-MI (2.7%)-(Ispinesib-PABA-Val-Cit (3.5%)

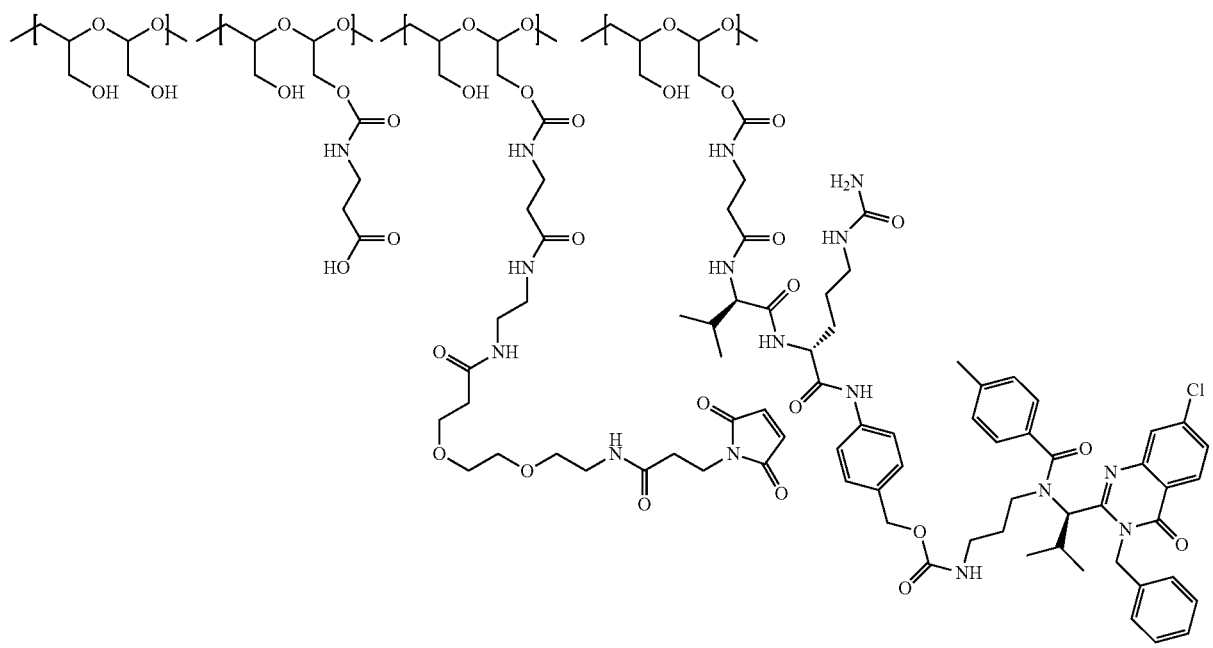

Conjugate B: Trastuzumab-((EG2-MI (2.7%)-(10 kDa PHF-BA (30%)-(HPV-Ala (7.7%)) was prepared using the procedure above except 10K PHF-BA (30%) EG2-MI (2.7%)-(HPV-Ala (7.7%) (5.7 mg, Example 19, conjugate B), trastuzumab and TCEP:trastuzumab 4:1 were used. The HPV-Ala to trastuzumab ratio was about 10:1 to about 14:1. The molecular weight of the title conjugate was about 180 kDa. The average PHF-drug conjugate to trastuzumab ratio was about 2:1 to about 4:1.

Conjugate C: Trastuzumab-((EG2-MI (3.5%)-(10 kDa PHF-BA (30%)-(HPV-Ala (4.3%)) was prepared in a fashion similar to that as described in this example except 10K PHF-BA (30%) EG2-MI (2.7%)-(HPV-Ala (4.3%) (4.2 mg, prepared in a fashion similar to that as described in Example 19 conjugate C), trastuzumab and TCEP:trastuzumab 4:1 were used. HPV-Ala to trastuzumab ratio was about 8.5:1 to about 12:1. The molecular weight of the title conjugate was about 181 kDa. The average PHF-drug conjugate to trastuzumab ratio was about 2:1 to about 4:1.

To a solution of 10K PHF-BA (28%) EG2-MI (2.7%) (60.8 mg, prepared in a fashion similar to that as described in Example 2) in 5 mL NMP was added Ispinesib-PABA-Val-Cit-NH$_2$ (TFA salt, 10.0 mg, prepared in a fashion similar to that as described in U.S. Pat. No. 8,815,226, Example 84) in NMP (0.5 mL). To this mixture was added HATU (5.5 mg) in NMP (0.5 mL) followed by DIEA (4.4 mg). The reaction mixture was stirred 5-10 min at room temperature. The crude mixture was purified by ultrafiltration to give the title compound (Yield: 64%, based on Ispinesib).

The drug loading of the conjugated product (i.e., content of polymer units containing the drug) determined by UV was 3.5% mol of the polymer structural units (or on average about 2.5 ispinesib-PABA-Val-Cit molecules per polymer chain).

Example 22

Synthesis of Trastuzumab-((EG2-MI (28%)-(10 kDa PHF-BA (2.7%)-(Ispinesib-PABA-Val-Cit-(3.5%))

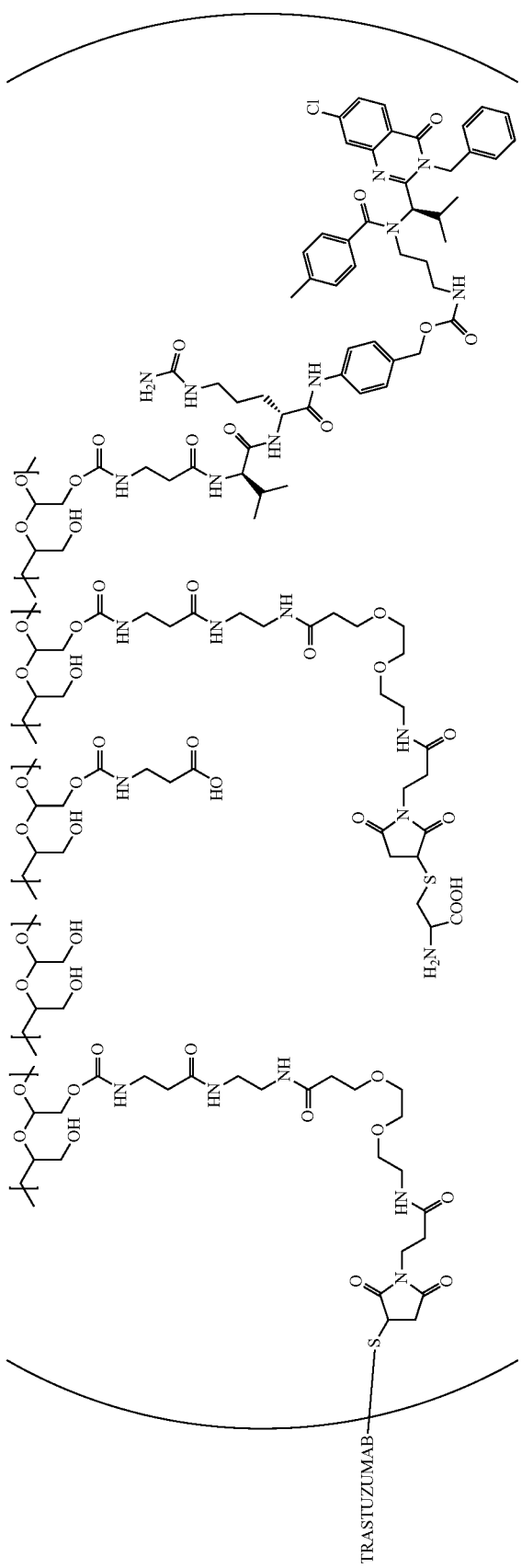

The title compound was prepared using the procedure described in Example 4 or Example 7 except 10K PHF-BA (28%) EG2-MI (2.7%)-(Ispinesib-PABA-Val-Cit (3.5%) (5.6 mg, prepared in a fashion similar to that as described in Example 21), trastuzumab and TCEP:trastuzumab 3.5:1 were used. The ispinesib to trastuzumab ratio was about 7.5:1 to about 10:1. The average PHF-drug conjugate to trastuzumab ratio was about 2:1 to about 4:1.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies as described above. Also PBRM-polymer-drug conjugates with varying ratios of drug to PBRM are obtained by varying the number of PBRM sulfhydryl groups and drug-polymer conjugate drug load.

Example 23

Synthesis of Rituximab-((EG2-MI (2.7%)-(10 kDa PHF-BA (28%)-(Ispinesib-PABA-Val-Cit-(3.5%))

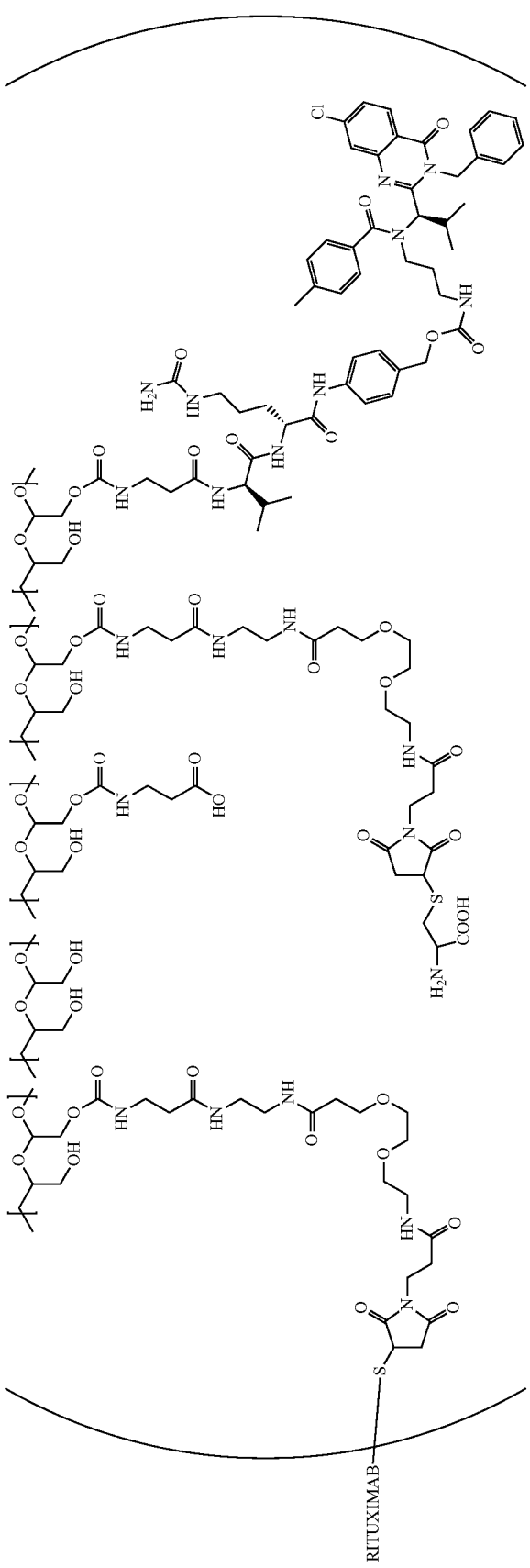

The title compound was prepared using the procedure described in Example 22, except rituximab and TCEP: rituximab 3.5:1 were used. The ispinesib to rituximab ratio was about 6.5:1 to about 10:1. The average PHF-drug conjugate to trastuzumab ratio was about 2:1 to about 4:1.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies as described above. Also PBRM-polymer-drug conjugates with varying ratios of drug to PBRM are obtained by varying the number of PBRM sulfhydryl groups and drug-polymer conjugate drug load.

Example 24

Synthesis of THP-2-methyl-Ispinesib

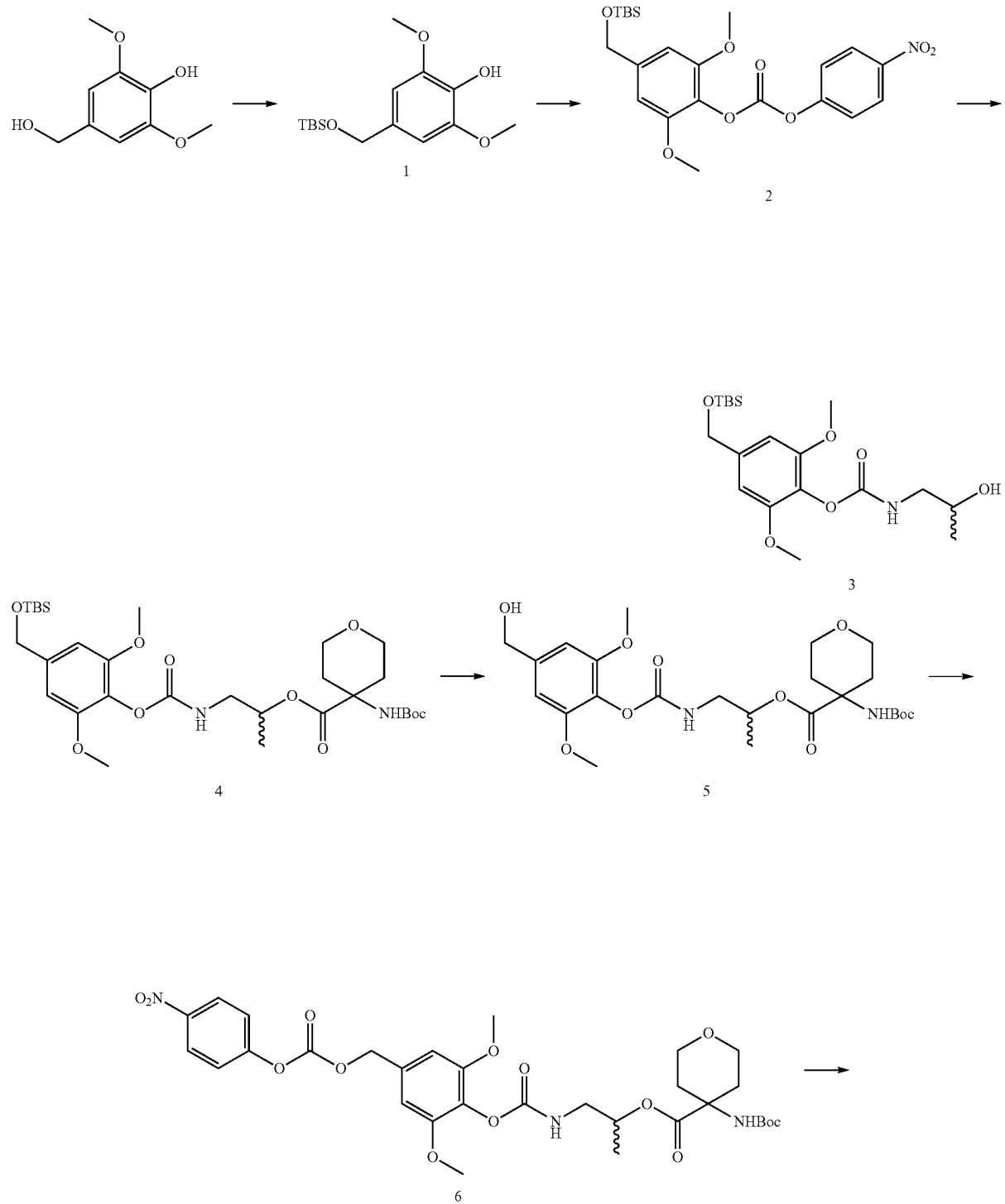

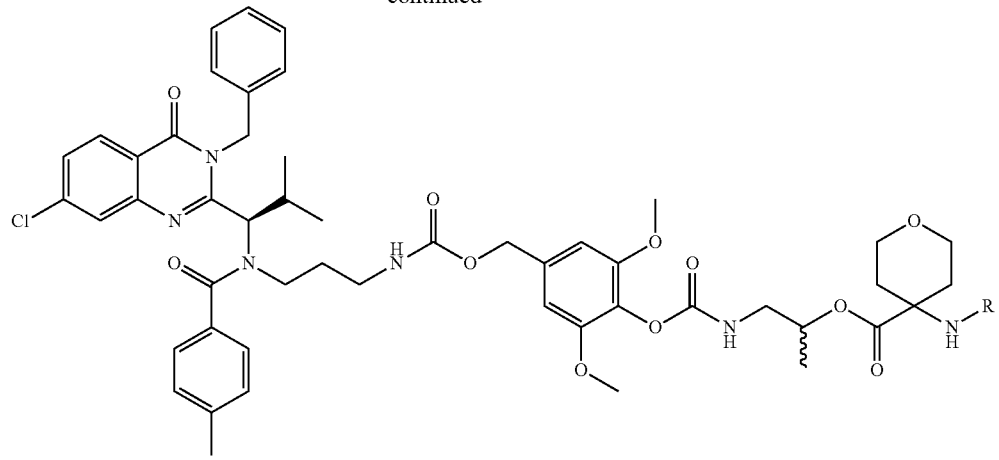

7, R = Boc
8, R = H (TFA salt)

Compound 1: To a solution of 4-(hydroxymethyl)-2,6-dimethoxyphenol (2.77 g) in 25 mL DMA was added imidazole (1.13 g). The mixture was cooled to 0° C. under argon and then TBSCl (2.49 g) was added. The reaction mixture was warmed to room temperature and stirred for 3 days under argon protected from light. The reaction mixture was diluted with DCM (300 mL) and washed with sat NH$_4$Cl (100 mL) then brine (100 mL). The organic phase was dried over Na$_2$SO$_4$ and concentrated to give the crude product that was purified by flash chromatography on silica gel (Hex/EtOAc, 0% B-30% B) to give a colorless oil (2.24 g, 50% yield). $^1$H NMR (400 MHz, DMSO-d$_6$) δ 8.17 (s, 1H), 6.54 (s, 2 H), 4.59 (s, 2 H), 3.72 (s, 6 H), 0.89 (s, 9 H), 0.05 (s, 6 H).

Compound 2: To an ice-cold solution of compound 1 (0.508 g), TEA (0.603 g) and DMAP (0.021 g) in 5 mL dry THF was added a solution of 4-nitrophenyl chloroformate (0.68 g) in ~3 mL THF. The ice bath was removed and stirring was continued at room temperature. The reaction was quenched with NH$_4$Cl (20 mL) and then extracted with ethyl acetate (60 mL). The organics were washed with brine (20 mL), dried over Na$_2$SO$_4$ then concentrated to give the crude product that was purified by flash chromatography on silica gel (Hex:Ethyl Acetate, 0% B-20% B) to afford compound 2 as a colorless solid (0.724 g, 92% yield). $^1$H NMR (400 MHz, CDCl$_3$) δ 8.32-8.28 (m, 2 H), 7.51-7.48 (m, 2 H), 7.12 (s, 1 H), 6.64 (s, 1 H), 4.75 (d, 2H, J=12.9 Hz), 3.93 (d, 3H, J=13.5 Hz), 3.88 (s, 3 H), 1.0-0.94 (m, 9 H), 0.15 (s, 3 H), 0.12 (s, 3 H).

Compound 3: To a solution of compound 2 (0.5 g) in 5 mL dry THF was added HOBt (0.291 g) and the resulting mixture was stirred for ~5 min To this mixture was added 2-aminopropanol (0.324 g) and TEA (0.546 g). The resulting mixture was stirred ~1 h at 0° C. at which point TLC indicated reaction was complete. The mixture was diluted with DCM (60 mL) and washed with sat NH$_4$Cl (20 mL) followed by brine (20 mL). The organics were dried (Na$_2$SO$_4$) and concentrated to give a yellow oil. The crude product was purified by flash chromatography on silica gel (Hex:Ethyl Acetate, 0% B-80% B) to afford compound 3 as a yellow solid (0.356 g, 83% yield). $^1$H NMR (400 MHz, DMSO-d$_6$) δ 7.50 (t, 1 H J=5.8 Hz), 6.64 (s, 2 H), 4.68 (s, 2 H), 4.64 (d, 1 H, J=4.8 Hz), 3.71 (s, 6 H), 3.70-3.61 (m, 1 H), 3.04-2.96 (m, 1 H), 2.96-2.86 (m, 1 H), 1.05 (d, 3 H, J=6.1 Hz), 0.10 (s, 6 H); ESI MS: theoretical C$_{19}$H$_{33}$NO$_6$Si (M+H) 400.2, found 400.2.

Compound 4: To an ice-cold solution of compound 3 (0.358 g) and DMAP (0.219 g) in 5 mL dry DCM was added a solution of DCC (0.369 g) in ~5 mL DCM under argon. The ice bath was removed and the mixture was stirred overnight at room temperature. The reaction mixture was filtered, diluted with DCM (~60 mL) and washed with sat NH$_4$Cl (2×20 mL) followed by brine (~20 mL). The organic phase was dried over Na$_2$SO$_4$ and concentrated to give the crude product that was purified by flash chromatography on silica gel to afford compound 4 as a colorless oil (0.422 g, 75% yield). $^1$H NMR (400 MHz, DMSO-d$_6$) δ 7.65 (s, 1 H), 7.39 (s, 1 H), 6.64 (s, 2 H), 4.93-4.84 (m, 1 H), 4.68 (s, 2 H), 3.71 (s, 6 H), 3.68-3.62 (m, 1 H), 3.62-3.47 (m, 4 H) 3.16 (t, 2H, J=5.9 Hz), 2.88 (s, 4 H), 2.01-1.93 (m, 2 H), 1.91-1.77 (m, 3 H), 1.75-1.66 (m, 1 H), 1.57-1.47 (m, 1H), 1.39 (s, 9 H), 1.35-1.29 (m, 1 H), 1.28-1.22 (m, 1 H), 1.15-1.10 (m, 3 H), 0.92 (s, 9 H); ESI MS: theoretical C$_{30}$H$_{50}$N$_2$O$_{10}$Si (M+H) 627.3, found 527.2 (M-Boc+H).

Compound 5: A solution of compound 4 (0.400 g) and SnCl$_2$ dihydrate (0.144 g) in a EtOH/water (7.25 mL, 9:1) was stirred at room temperature ~3 h under argon. Upon completion of the reaction (TLC) the reaction mixture was diluted with 60 mL EtOAc and then washed with sat NH$_4$Cl (20 mL) and brine (20 mL). The organic phase was dried over Na$_2$SO$_4$ and concentrated to give the crude product that was purified by flash chromatography on silica gel (Hex: Ethyl Acetate, 0% B-100% B) to afford compound 5 as a colorless oil (0.220 g, 67% yield). $^1$H NMR (400 MHz, CDCl$_3$) δ 6.61 (s, 2 H), 5.82 (brs, 1 H), 5.16 (brs, 1 H), 4.87 (m, 1 H), 4.64 (s, 2 H), 3.90-3.75 (m, 8 H), 3.75-3.62 (m, 2 H), 3.62-3.51 (m, 1 H), 3.41-3.18 (m, 1 H), 2.31-2.13 (m, 2 H), 1.93-1.81 (m, 2 H), 1.44 (s, 9 H), 1.29 (d, 3 H, J=6.6 Hz); ESI MS: theoretical C$_{24}$H$_{36}$N$_2$O$_{10}$ (M+H) 513.2, found 413.2 (M−Boc+H).

Compound 6: To a solution of compound 5 (0.220 g) in 2 mL dry THF was added TEA (0.152 g). The mixture was cooled to 0° C. and p-nitrophenyl chloroformate (0.087 g) was added as a solid. The mixture was warmed to room temperature and stirred ~4 h. Additional chloroformate (~0.05 g in ~1 mL THF) was added and the mixture was stirred overnight. The reaction mixture was diluted with 30 mL EtOAc and then washed with sat NH$_4$Cl (10 mL) followed by brine (10 mL). The organic phase was dried over Na$_2$SO$_4$ and concentrated to afford the crude product as an oil. The crude product was purified by flash chromatography on silica gel (Hexane: EtOAc 0% B to 90% B) to afford compound 6 as a colorless solid (0.257 g, 88% yield). ¹H NMR (400 MHz, CDCl₃) δ 8.28 (d, 2 H, J=9.3 Hz), 7.39 (d, 2 H, J=9.8 Hz), 6.67 (s, 2 H), 5.90 (brs, 1 H), 5.23 (s, 2 H), 5.21-5.13 (m, 1 H), 4.87 (brs, 1 H), 3.89-3.76 (m, 8 H), 3.75-3.64 (m, 2 H), 3.63-3.53 (m, 1 H), 2.30-2.19 (m, 1 H) 1.95-1.83 (m, 2 H), 1.44 (s, 9 H), 1.29 (d, 3 H, J=6.7 Hz); ESI MS: theoretical $C_{31}H_{39}N_3O_{14}$ (M+H) 678.2, found 578.2 (M-Boc+H).

Compound 7: To a solution of compound 6 (53.5 mg) in 0.5 mL dry DMA was added Ispinesib (37.1 mg), DIEA (9.27 mg), and HOAt (2.93 mg) in succession. The mixture was stirred at room temperature overnight under nitrogen. The crude reaction mixture was purified by preparative RP-HPLC (Hex:Ethyl Acetate 50% B-90% B over 25 min, 0.1% TFA in both mobile phases) to afford compound 7 as a colorless solid (64 mg, 84% yield). ESI MS: theoretical $C_{55}H_{67}ClN_6O_{13}$ (M+H) 1055.5, found 1055.4.

Compound 8: To an ice-cold solution of compound 7 (64 mg) in 2 mL dry DCM was added 1 mL TFA under nitrogen. The ice bath was removed and the mixture was stirred 1 h at room temperature at which point LC/MS indicated the reaction was complete. The solvent was removed via rotory evaporation and the residue was lyophillized to afford compound 8 as a colorless solid (64 mg, 99%). ESI MS: theoretical $C_{50}H_{59}ClN_6O_{11}$ (M+H) 955.4, found 955.3.

Example 25

Synthesis of 10K PHF-BA (28%) EG2-MI (2.7%)-(THP-2-methyl-Ispinesib) (2.4%)

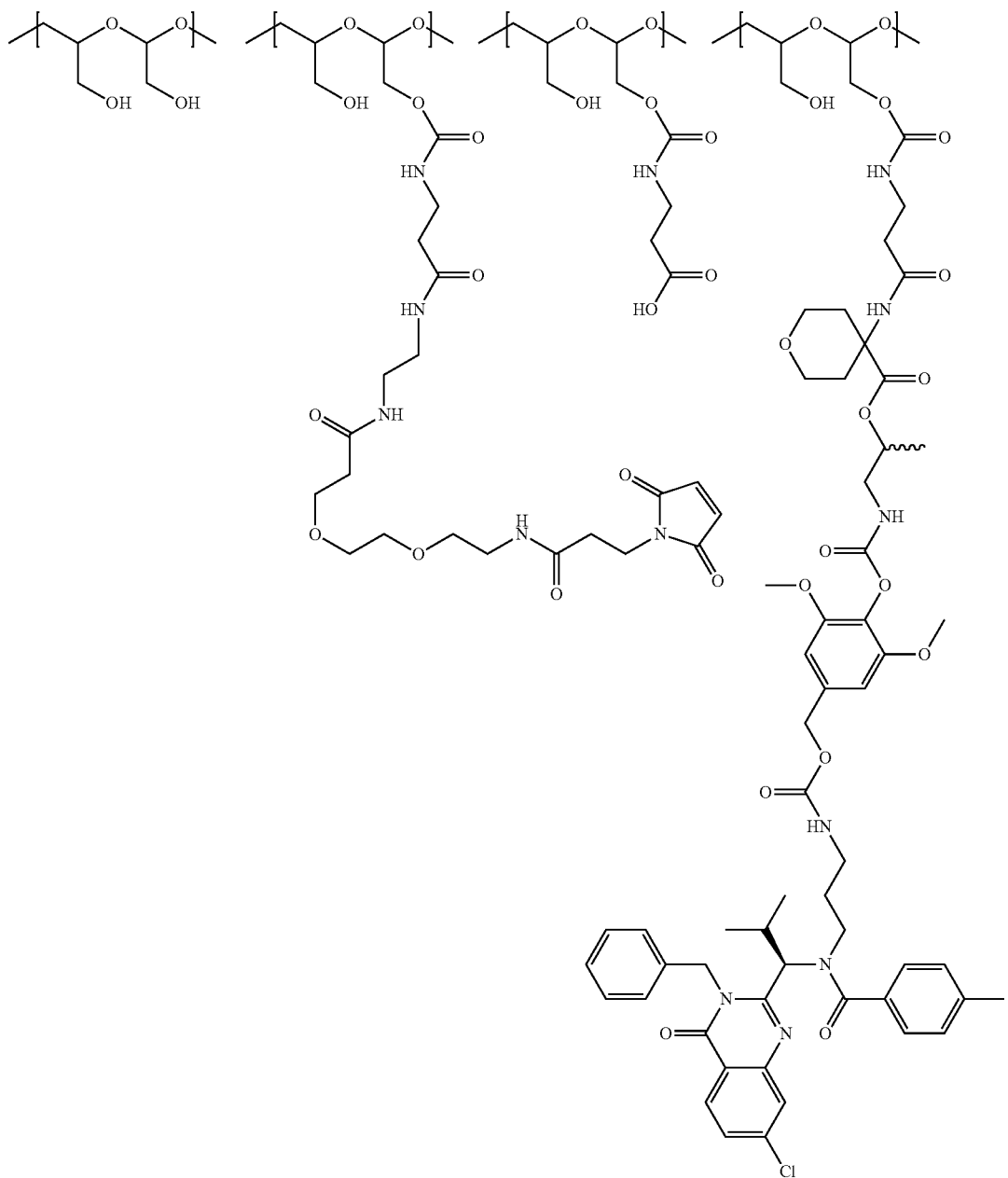

The title compound was prepared in a fashion similar to that as described in Example 21 using 10K PHF-BA (28%) EG2-MI (2.7%) (58.9 mg, prepared in a fashion similar to that as described in Example 2) and THP-2-methyl-Ispinesib (10.0 mg, prepared in a fashion similar to that as described in Example 24; 46% yield (based on Ispinesib).

The drug loading of the conjugated product (i.e., content of polymer units containing the drug) determined by UV was 2.4% mol of the polymer structural units (or on average about 1.7 THP-2-methyl-Ispinesib molecules per polymer chain).

Example 26

Synthesis of Trastuzumab-((EG2-MI (2.7%)-(10 kDa PHF-BA (28%)-(THP-2-methyl-Ispinesib) (2.4%))

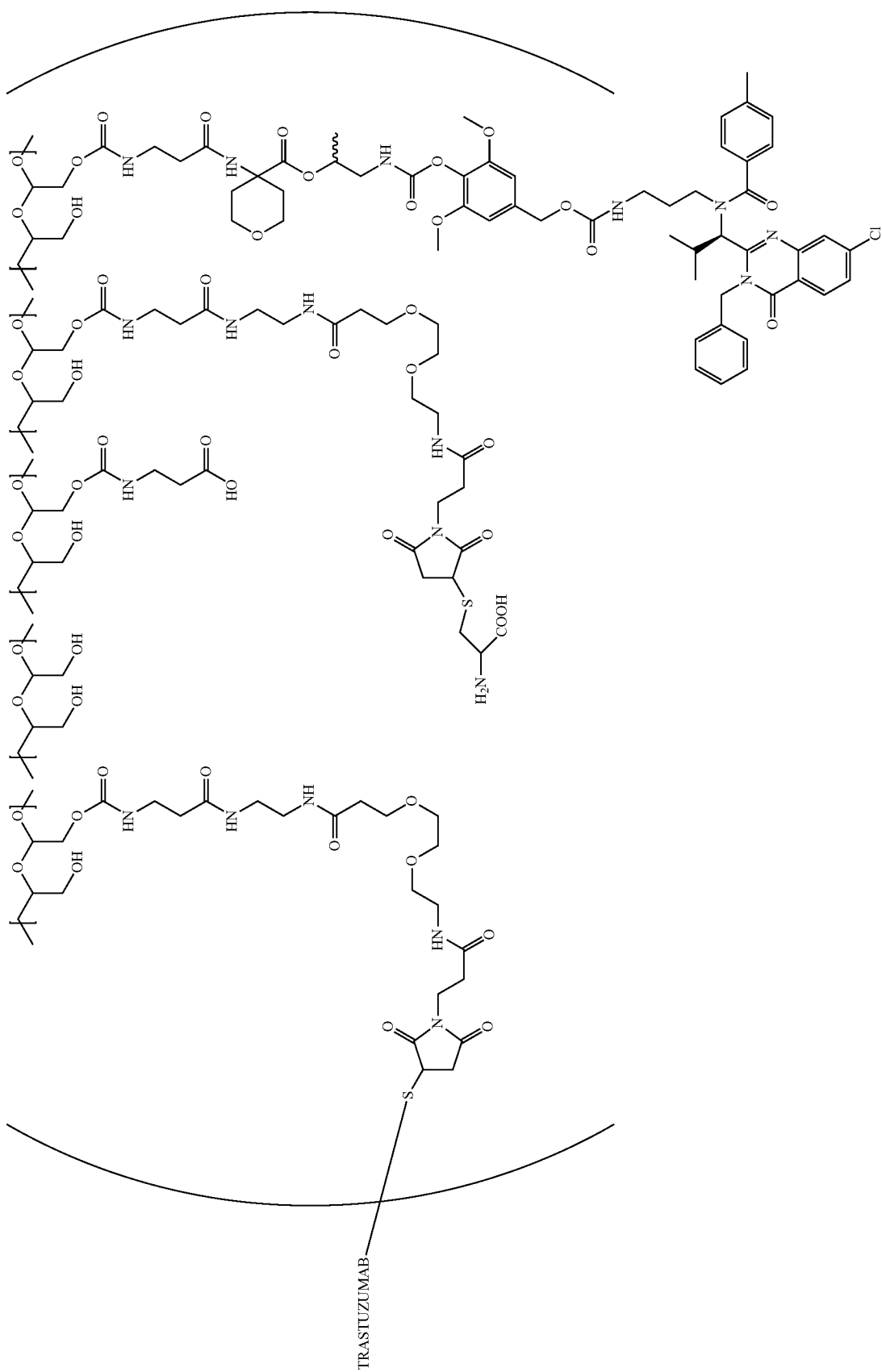

The title compound was prepared using the procedure described in Example 4 or Example 7 except 10K PHF-BA (28%) EG2-MI (2.7%)-(THP-2-methyl-Ispinesib) (2.4% mg, prepared in a fashion similar to that as described in Example 25), trastuzumab and TCEP:trastuzumab 3.5:1 were used. The ispinesib to trastuzumab ratio was about 5:1 to about 8:1. The average PHF-drug conjugate to trastuzumab ratio was about 3:1 to about 4:1.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies as described above. Also PBRM-polymer-drug conjugates with varying ratios of drug to PBRM are obtained by varying the number of PBRM sulfhydryl groups and drug-polymer conjugate drug load.

Example 27

Synthesis of Rituximab-((EG2-MI (2.7%)-(10 kDa PHF-BA (28%)-(THP-2-methyl-Ispinesib) (2.4%))

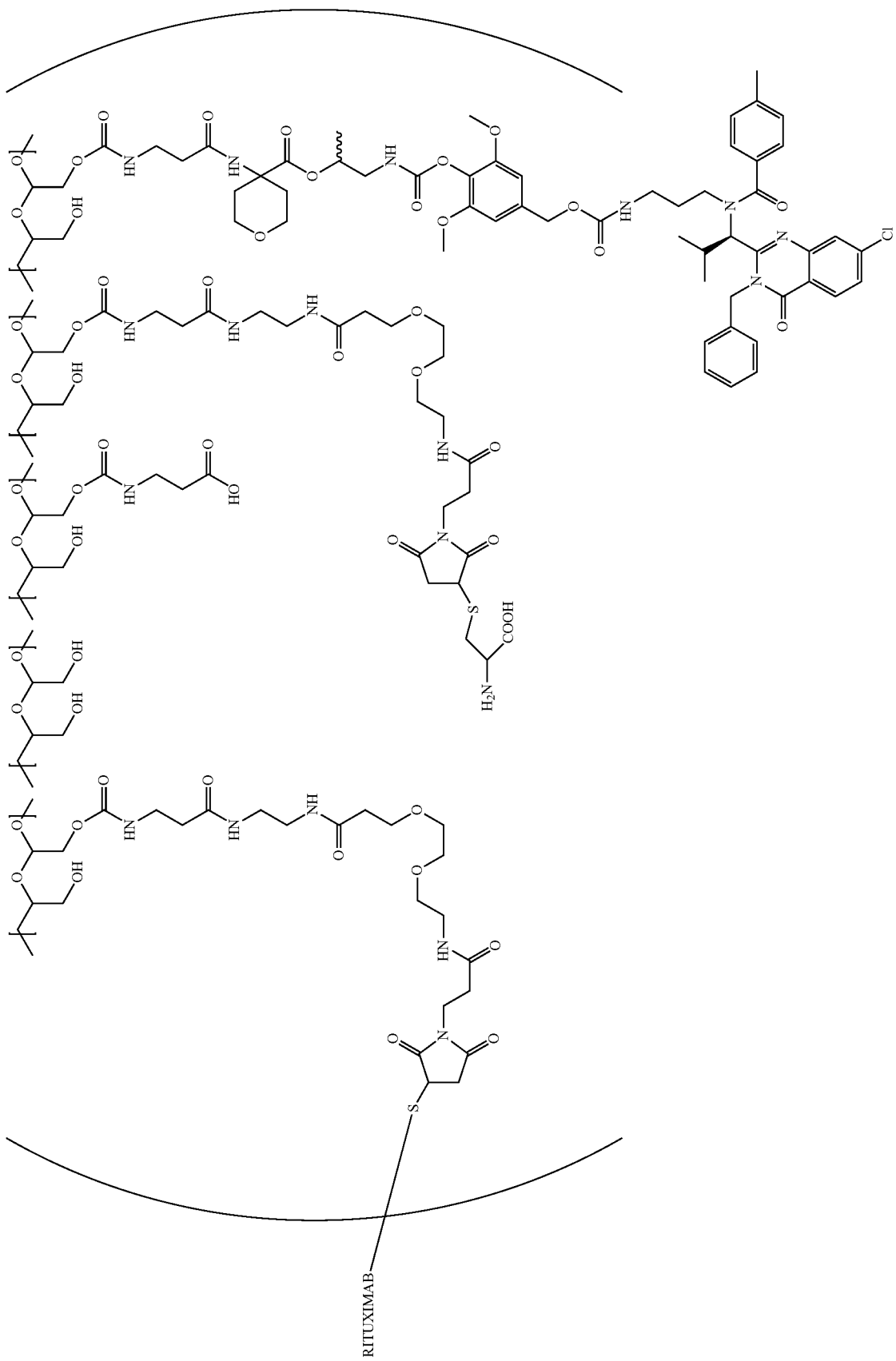

The title compound was prepared using the procedure described in Example 26 except rituximab and TCEP:rituximab 3.5:1 were used. The average ispinesib to rituximab ratio was about 4.5:1 to about 7:1. The average PHF-drug conjugate to trastuzumab ratio was about 2:1 to about 4:1.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies as described above. Also PBRM-polymer-drug conjugates with varying ratios of drug to PBRM are obtained by varying the number of PBRM sulfhydryl groups and drug-polymer conjugate drug load.

Example 28

Synthesis of valine-acyloxyisopropyloxy-MMAE

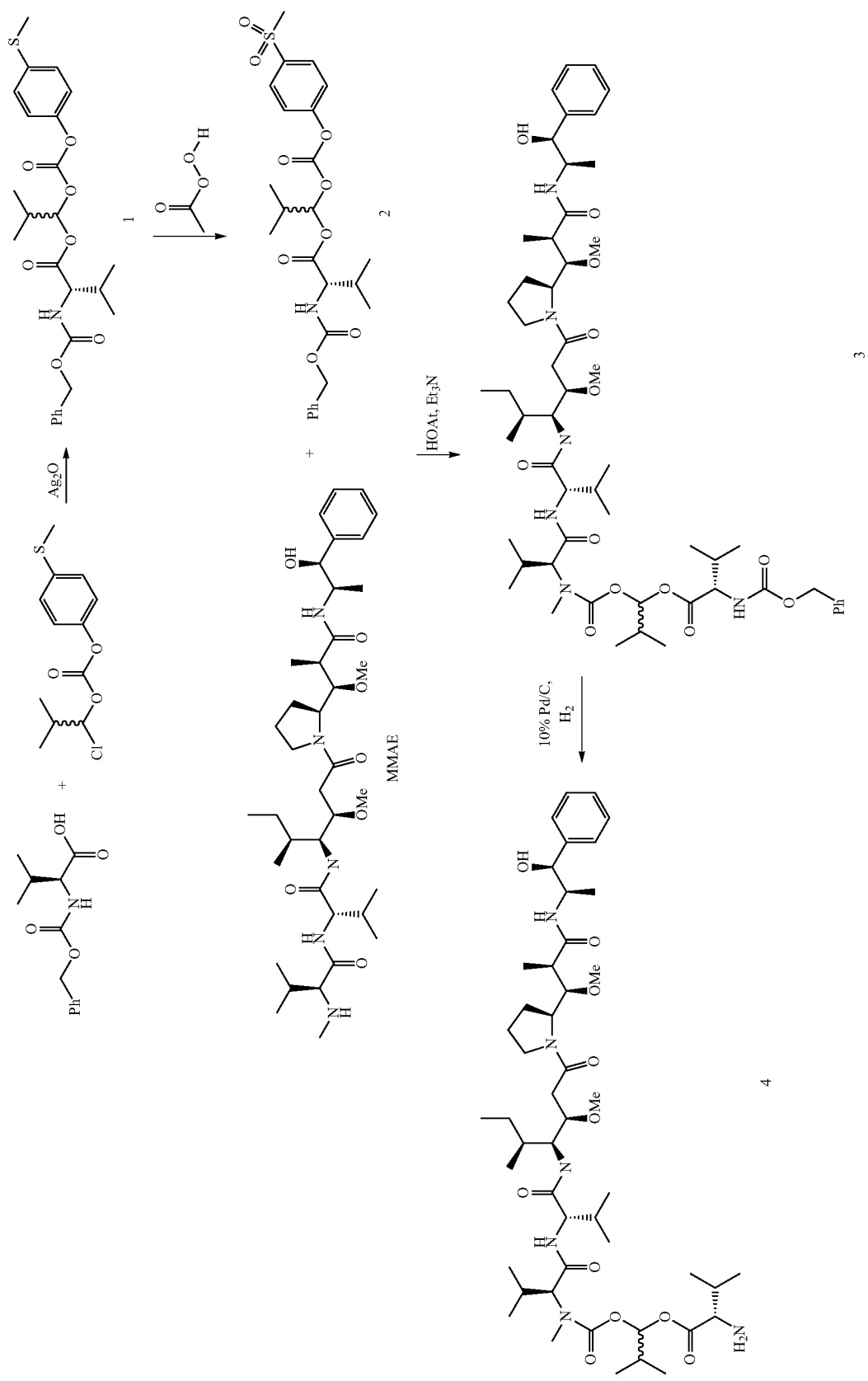

Compound 1: (S)-2-(benzyloxycarbonylamino)-3-methylbutanoic acid (4.76 g, 18.93 mmol), 1-chloro-2-methylpropyl 4-(methylthio)phenyl carbonate (2.6 g, 9.46 mmol) and monosilver(I) monosilver(III) monooxide (2.193 g, 9.46 mmol) were heated at 90° C. for 1 h. The reaction mixture was cooled to room temperature, the residue triturated with ethyl ether, and the solids were washed with ether. The organics were washed with water (4×), aqueous $NaHCO_3$, dried over $Na_2SO_4$ and concentrated to a straw colored oil. The crude oil in DCM was purified by flash chromatography on silica gel (Hexane: EtOAc 0% B to 20% B), followed by C-18 reversed phase HPLC using an acetonitrile/water gradient from 20-95% acetonitrile buffered with 0.1% TFA to give a colorless oil (2.78 g, 60% yield). The compound was characterized by 1H, $^{13}$C NMR and mass spec, M/z=490.3.

Compound 2: To an ice cold solution of compound 1, (2.5 g, 5.11 mmol) in DCM (20 ml) was added drop-wise a solution of peracetic acid in acetic acid (12.14 g, 51.1 mmol) and stirred for 2 h after the addition was complete. The reaction was monitored by LC/MS. After 2 h, to the reaction mixture was added 25 mL of water and stirred cold for 30 min, the organics diluted with 100 mL of DCM, washed with ice cold water (5×), aqueous $NaHCO_3$, dried over $Na_2SO_4$ and concentrated. The crude product was purified by flash chromatography on silica gel (Hexane: EtOAc 0% B to 50% B).

Compound 3: MMAE, (300 mg, 0.418 mmol), compound 2, (436 mg, 0.836 mmol), 3H-[1,2,3]-triazolo[4,5-b]pyridin-3-ol hydrate (129 mg, 0.836 mmol) and THF (25 ml) were combined and stirred in an ice bath. To the resulting mixture was added triethylamine (0.291 ml, 2.089 mmol) and stirred cold for 15 min then at 40° C. until the reaction was complete as indicated by LC/MS. After 4 h the reaction mixture was diluted with ethyl acetate, washed with aqueous $NaHCO_3$, 5% aqueous citric acid, dried over $Na_2SO_4$, concentrated and purified by reversed phase chromatography to give compound 3 as a white amorphous solid as the TFA salt. LC/MS, M/z=1067.6.

Compound 4: To compound 3 (150 mg, 0.141 mmol) in THF (10 ml) and EtOH (10.00 ml) was bubbled argon. To this mixture was added 10% palladium on carbon (29.9 mg, 0.028 mmol) followed by attaching a balloon of hydrogen (0.283 mg, 0.141 mmol) and the reaction monitored by LC/MS. When complete the reaction mixture was purified by reversed phase chromatography using a gradient of acetonitrile in water buffered with 0.1% TFA as mobile phase to give the title compound as a white amorphous solid as the TFA salt (56% yield). M/z=933.6

Example 29

Synthesis of 10K PHF-BA (28%) EG2-MI (2.7%)-(valine-acyloxyisopropyloxy-MMAE) (3%)

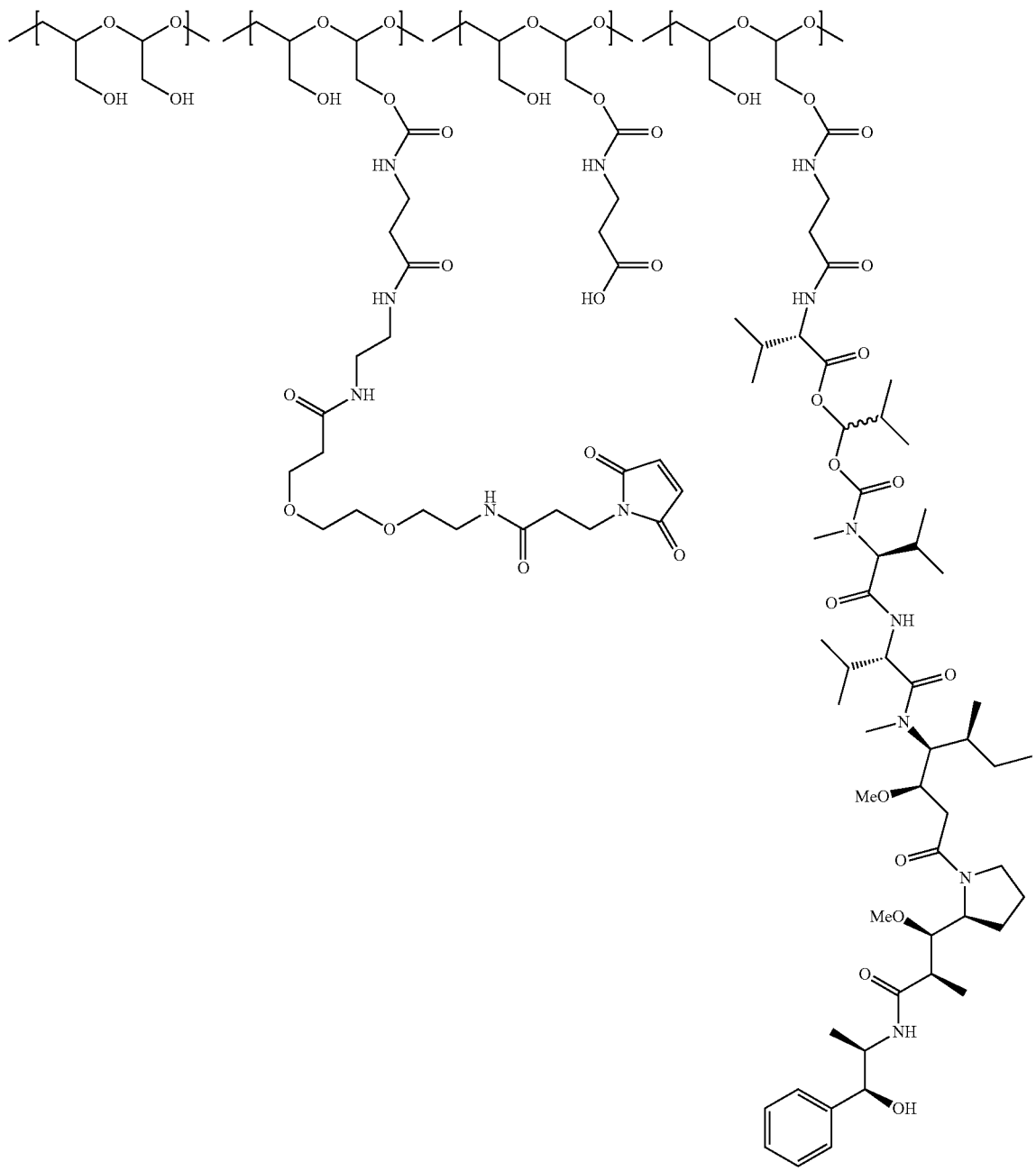

To a solution of 10K PHF-BA (28%) EG2-MI (2.7%) (20 mg, prepared in a fashion similar to that as described in Example 2) in 1 mL NMP was added valine-acyloxyisopropyloxy-MMAE (9.98 mg, prepared in a fashion similar to that as described in Example 28). To this mixture was added HOAt (5.41 mg), EDC.HCl (7.62 mg), and DIEA (3.1 mg) The reaction mixture was stirred overnight at room temperature and then added slowly to a stiffing aqueous solution of NaCl (1%, ~50 mL). The crude mixture was purified by diafiltration to give the title compound (21% yield based on MMAE).

The drug loading of the conjugated product (i.e. content of polymer units containing the drug) determined by LC/MS was 3.1% mol of the polymer structural units (or on average about 2.2 MMAE-val-isopropyl-acyloxyisopropyloxy molecules per polymer chain). The molecular weight of the title conjugate was about 8.3 kDa.

Example 30

Synthesis of Trastuzumab-((EG2-MI (2.7%)-(10 kDa PHF-BA (28%)-(valine-acyloxyisopropyloxy-MMAE) (3%))

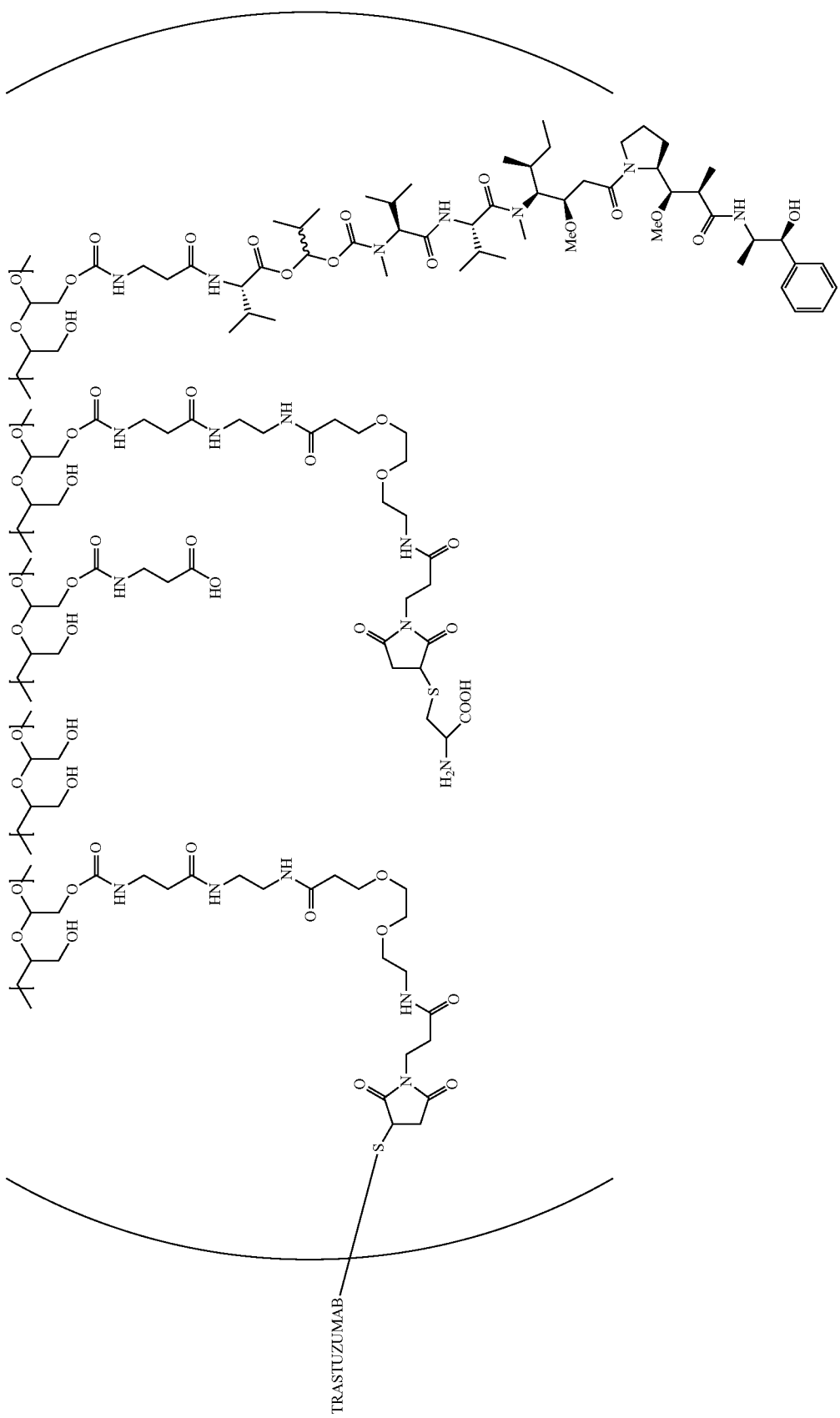

Conjugate A: Trastuzumab-((EG2-MI (2.7%)-(10 kDa PHF-BA (28%)-(valine-acyloxyisopropyloxy-MMAE) (3%)) was prepared using the procedure described in Example 4 or Example 7 except 10K PHF-BA (28%) EG2-MI (2.7%)-(valine-acyloxyisopropyloxy-MMAE (3%) (5.6 mg, prepared in a fashion similar to that as described in Example 29), and TCEP TCEP:trastuzumab 3.5:1 were used. The average MMAE to trastuzumab ratio was about 11:1 to about 15:1. The molecular weight of the title conjugate was about 171 kDa.

Conjugate B, Trastuzumab-((EG2-MI (2.7%)-(10 kDa PHF-BA (28%)-(valine-acyloxyisopropyloxy-MMAE) (9%)) was prepared using the procedure described in Example 4 or Example 7 except 10K PHF-BA (28%) EG2-MI (2.7%)-(valine-acyloxyisopropyloxy-MMAE) (9%) (31.7 mg, prepared using the procedure described in Example 30), trastuzumab (57 mg, TCEP:trastuzumab 3.5:1 were used. The average MMAE to trastuzumab ratio was about 12:1 to about 16.5:1. The molecular weight of the title conjugate was about 224 kDa.

Conjugate C: Rituximab-((EG2-MI (2.7%)-(10 kDa PHF-BA (28%)-(valine-acyloxyisopropyloxy-MMAE) (9%)) was prepared by substituting reduced rituximab in the procedure described above for Conjugate A. The MMAE to rituxiumab ratio was about 9.5:1 to about 13:1. The molecular weight of the title conjugate was about 202 kDa.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies as described above. Also PBRM-polymer-drug conjugates with varying ratios of drug to PBRM are obtained by varying the number of PBRM sulfhydryl groups and drug-polymer conjugate drug load.

Example 31

Synthesis of t-butylglycine AF-HPA trifluoroacetate

To ice cold solution of (R)-2-(tert-butoxycarbonylamino)-3,3-dimethylbutanoic acid (67.6 mg, 0.292 mmol) in DCM (5 ml) was added DCC (0.046 ml, 0.292 mmol) and the reaction mixture stirred cold for 15-20 min. Separately AF-HPA (134 mg, 0.146 mmol, prepared in a fashion similar to that as described in U.S. Pat. No. 8,685,383, Example 18) and DMAP (53.6 mg, 0.438 mmol) in DCM (5 ml) were cooled, the two reaction mixtures were combined and stirred cold for 20-30 min then at room temperature. The reaction mixture was monitored by LC/MS. After four hours LC/MS indicated the reaction was not complete. A second aliquot of activated the amino acid activated DCC ester (1 eq of each in DCM) was added and the reaction mix allowed to stir overnight at room temperature followed by HPLC purification using a gradient from 25-90% acetonitrile/water with the mobile phase buffered with 0.1% TFA. AF-HPA-Boc-t-Butyl Glycine was obtained as a white amorphous solid as the TFA salt (85% yield). M/z=1016.6.

To an ice cold solution of AF-HPA-Boc-t-Butyl Glycine, (140 mg, 0.124 mmol) in DCM (5 ml) was added TFA (0.477 ml, 6.19 mmol) and the reaction mixture stirred cold for 1 h then at room temperature until completion as indicated by LC/MS. The mixture was concentrated and the resulting residue purified by HPLC purification using a acetonitrile/water gradient from 10-90% acetonitrile buffered with 0.1% TFA used as mobile phase. The title compound was obtained as a white amorphous solid as the TFA salt. M/z=917.6

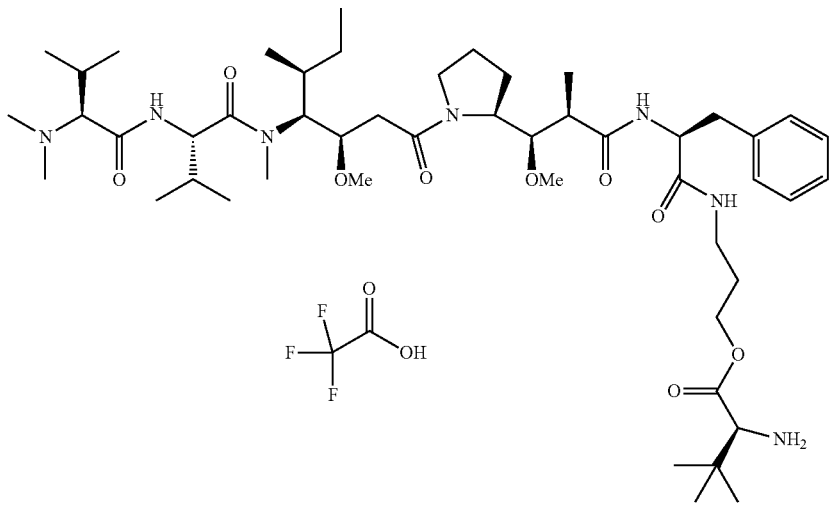 [SMILES: CC[C@H](C)[C@@H]([C@@H](CC(=O)N1CCC[C@H]1[C@H](OC)[C@@H](C)C(=O)N[C@@H](Cc1ccccc1)C(=O)NCCCOC(=O)[C@@H](N)C(C)(C)C)OC)N(C)C(=O)[C@@H](NC(=O)[C@H](C(C)C)N(C)C)C(C)C ; O=C(O)C(F)(F)F]

Example 32

Synthesis of 10K PHF-BA (28%) EG2-MI (2.7%)-
(t-butylglycine AF-HPA) (7.5%)

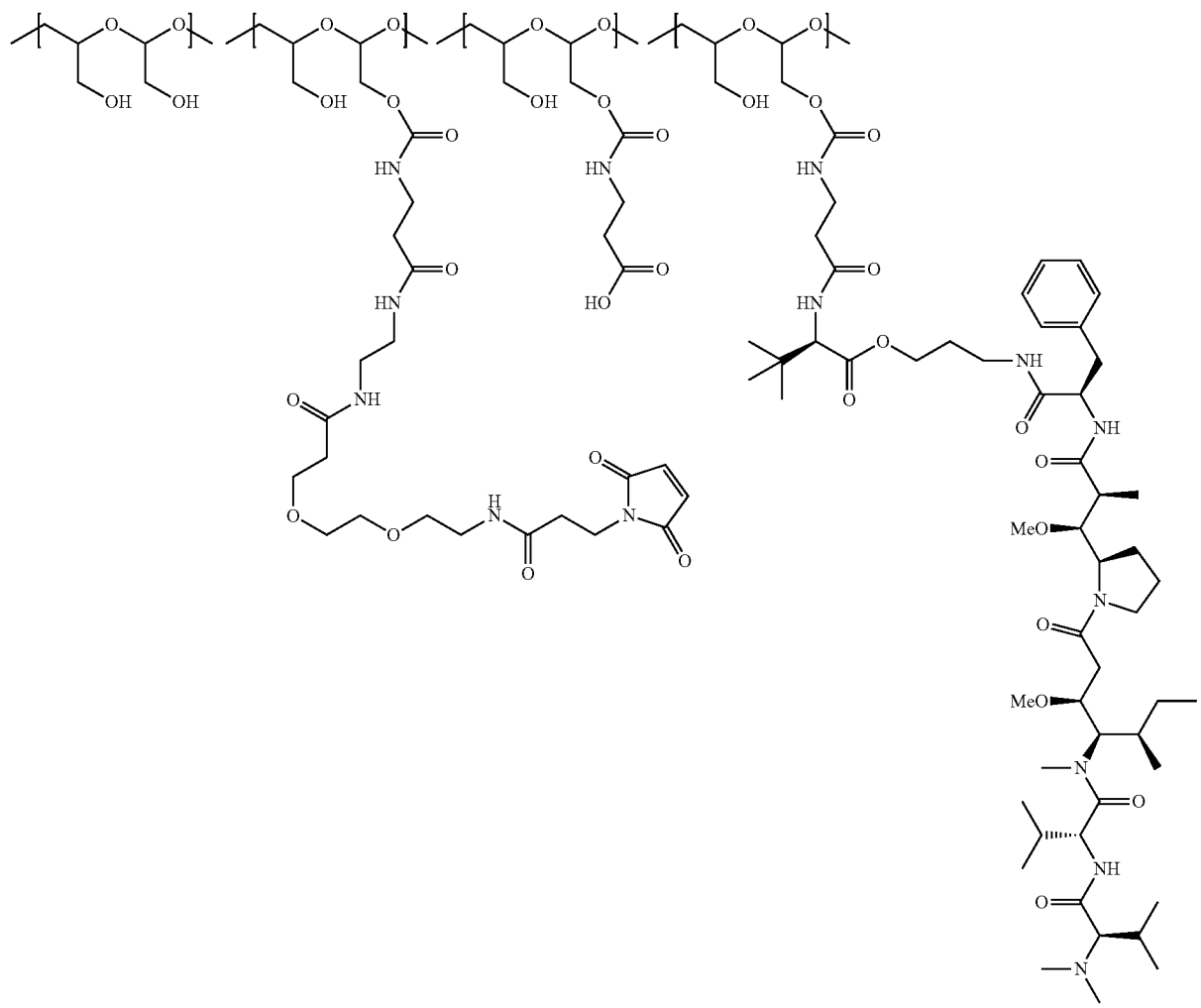

To an ice cold solution of 10K PHF-BA (28%)-PEG2-MI (2.7%) (137 mg, 10.84 µmol, prepared in a fashion similar to that as described in Example 2) in water (5.5 ml) and NMP (1.375 ml) was added AF-HPA-t-butylglycine, (67 mg, 0.065 mmol, prepared in a fashion similar to that as described in Example 31) and the resulting mixture stirred cold for 15 min followed by the addition of 1-hydroxypyrrolidine-2,5-dione (15.59 mg, 0.135 mmol). To the reaction mixture was added EDAC (51.9 mg, 0.271 mmol). After 30 min a second addition of the same amount of the reagent was added. After 4 h the pH was adjusted to 5.6 with 0.1N NaHCO₃, and an additional aliquot of EDAC (50 mg) was added and the reaction mixture was stirred overnight. The product was purified by gel filtration and reversed phase HPLC.

The drug loading of the conjugated product (i.e., content of polymer units containing the drug) determined by $^1$H-NMR was 7.5% mol of the polymer structural units (or on average about 5.7 t-butylglycine AF-HPA molecules per polymer chain). Example 33. Synthesis of Trastuzumab-((EG2-MI (2.7%)-(10 kDa PHF-BA (28%)-(t-butylglycine AF-HPA) (7.5%))

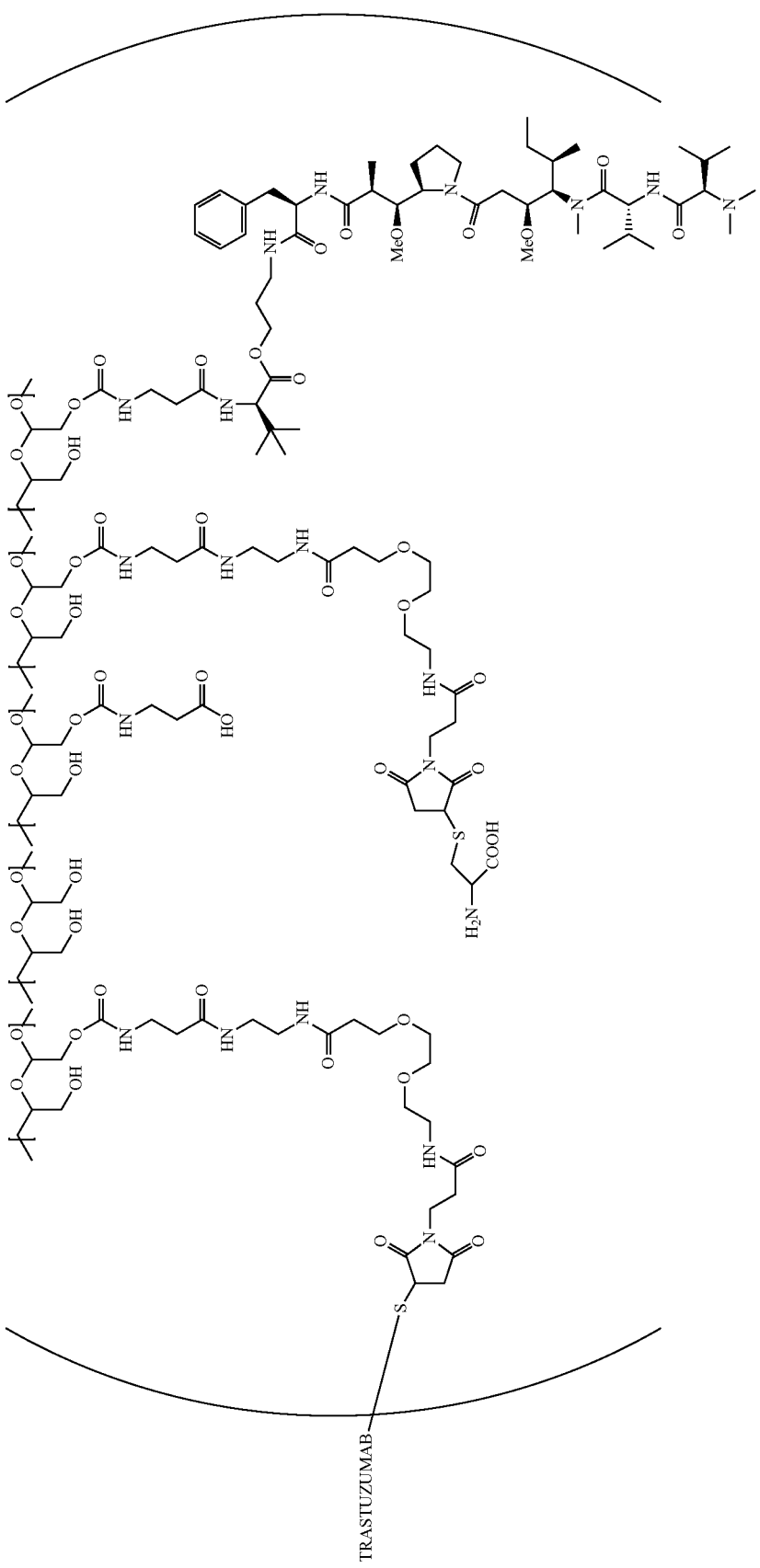

The title compound was prepared using the procedure described in Example 4 or Example 7 except 10K PHF-BA (28%) EG2-MI (2.7%)-(t-butylglycine AF-HPA) (7.5%) (45.7 mg, prepared in a fashion similar to that as described in Example 32), trastuzumab TCEP:trastuzumab 3.5:1 were used. The AF-HPA to trastuzumab ratio was about 4:1 to about 6:1. The average PHF-drug conjugate to trastuzumab ratio was about 2:1 to about 4:1. The molecular weight of the title conjugate was about 215 kDa.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies as described above. Also PBRM-polymer-drug conjugates with varying ratios of drug to PBRM are obtained by varying the number of PBRM sulfhydryl groups and drug-polymer conjugate drug load.

Example 34

Synthesis of Rituximab-((EG2-MI (2.7%)-(10 kDa PHF-BA (28%)-(t-butylglycine-AF-HPA) (7.5%))

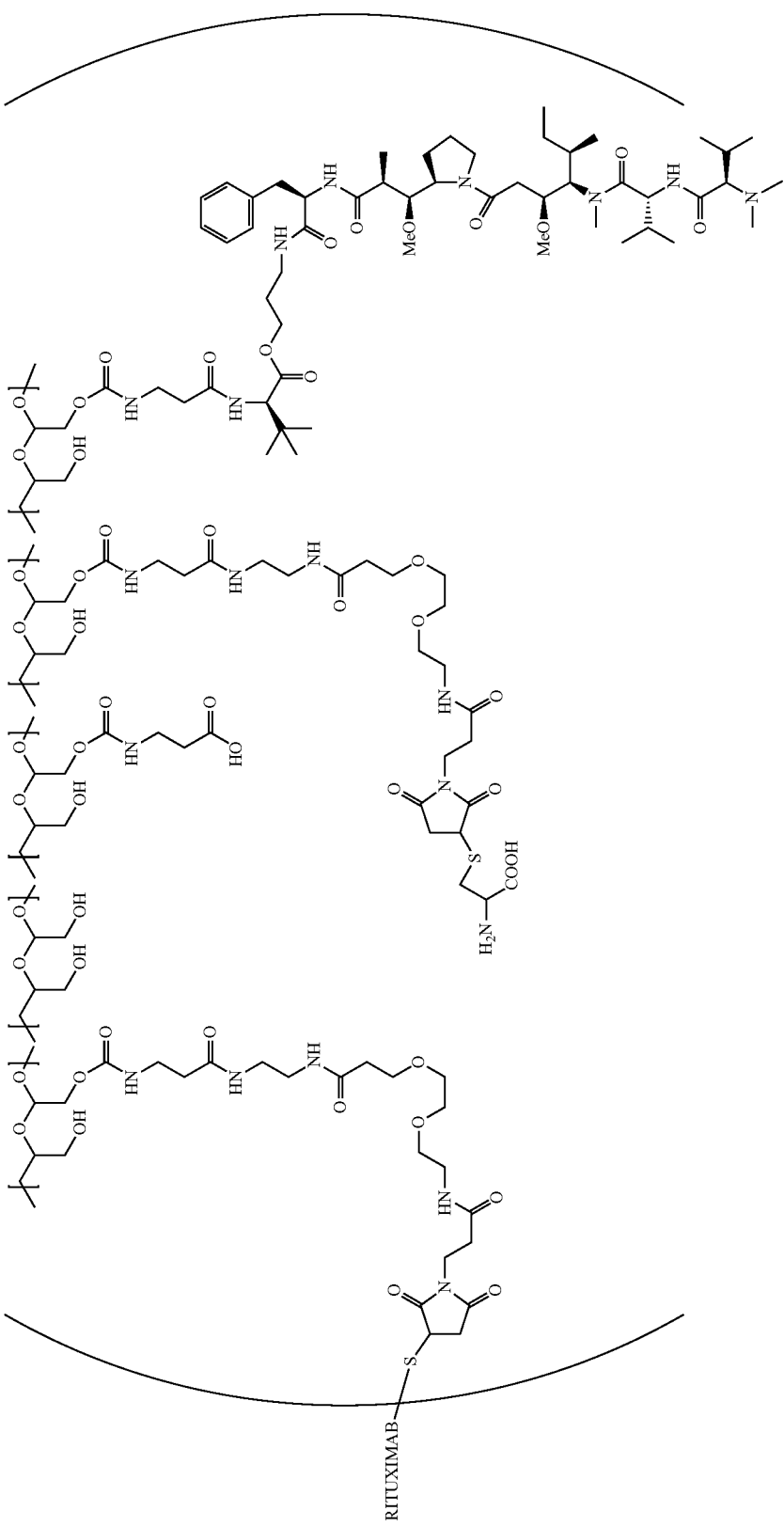

The title compound was prepared using the procedure described in Example 33 except rituximab and TCEP:rituximab 3.5:1 were used. The average AF-HPA to rituximab ratio was about 2.5:1 to about 3.5:1. The average PHF-drug conjugate to trastuzumab ratio was about 2:1 to about 4:1. The molecular weight of the title conjugate was about 202 kDa.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies as described above. Also PBRM-polymer-drug conjugates with varying ratios of drug to PBRM are obtained by varying the number of PBRM sulfhydryl groups and drug-polymer conjugate drug load.

Example 35

Synthesis of val-AF-HPA trifluoroacetate

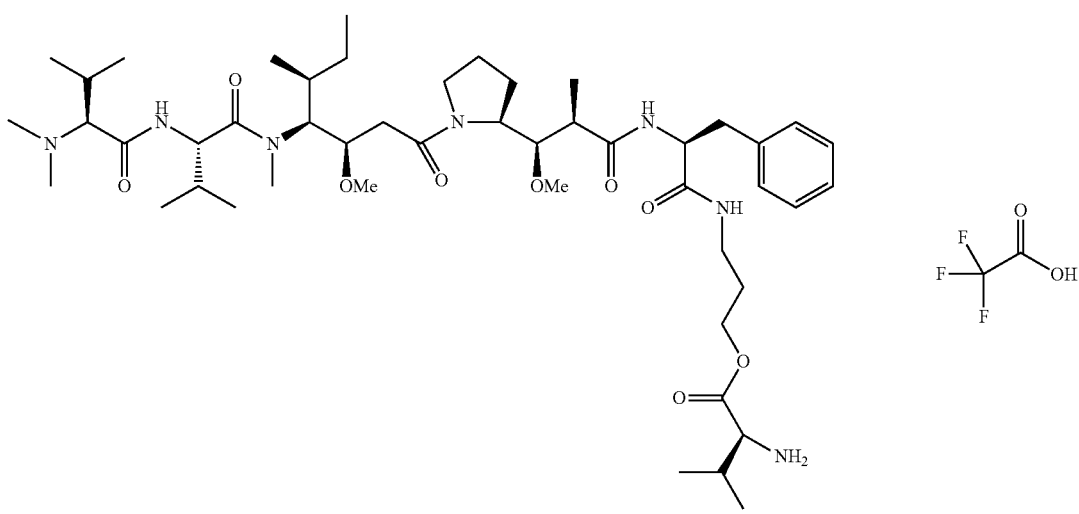 [SMILES: CC[C@H](C)[C@@H]([C@@H](CC(=O)N1CCC[C@H]1[C@H](OC)[C@@H](C)C(=O)N[C@@H](Cc1ccccc1)C(=O)NCCCOC(=O)[C@@H](N)C(C)C)OC)N(C)C(=O)[C@@H](NC(=O)[C@H](C(C)C)N(C)C)C(C)C ; O=C(O)C(F)(F)F]

AF-HPA-Boc-valine was prepared in a fashion similar to that as described in Example 31 except ((R)-2-(tert-butoxycarbonylamino)-3-methylbutanoic acid (63.5 mg, 0.292 mmol was used. AF-HPA-Boc-valine was obtained as a white amorphous solid as the TFA salt (85% yield). M/z=1002.6.

The title compound was prepared in a fashion similar to that as described in Example 31 except AF-HPA-Boc-valine (128 mg, 0.115 mmol) was used to give 106 mg, 91% yield. M/z=903.3

Example 36

Synthesis of Trastuzumab-((EG2-MI (2.7%)-(10 kDa PHF-BA (28%)-(val-AF-HPA) (7.2%))

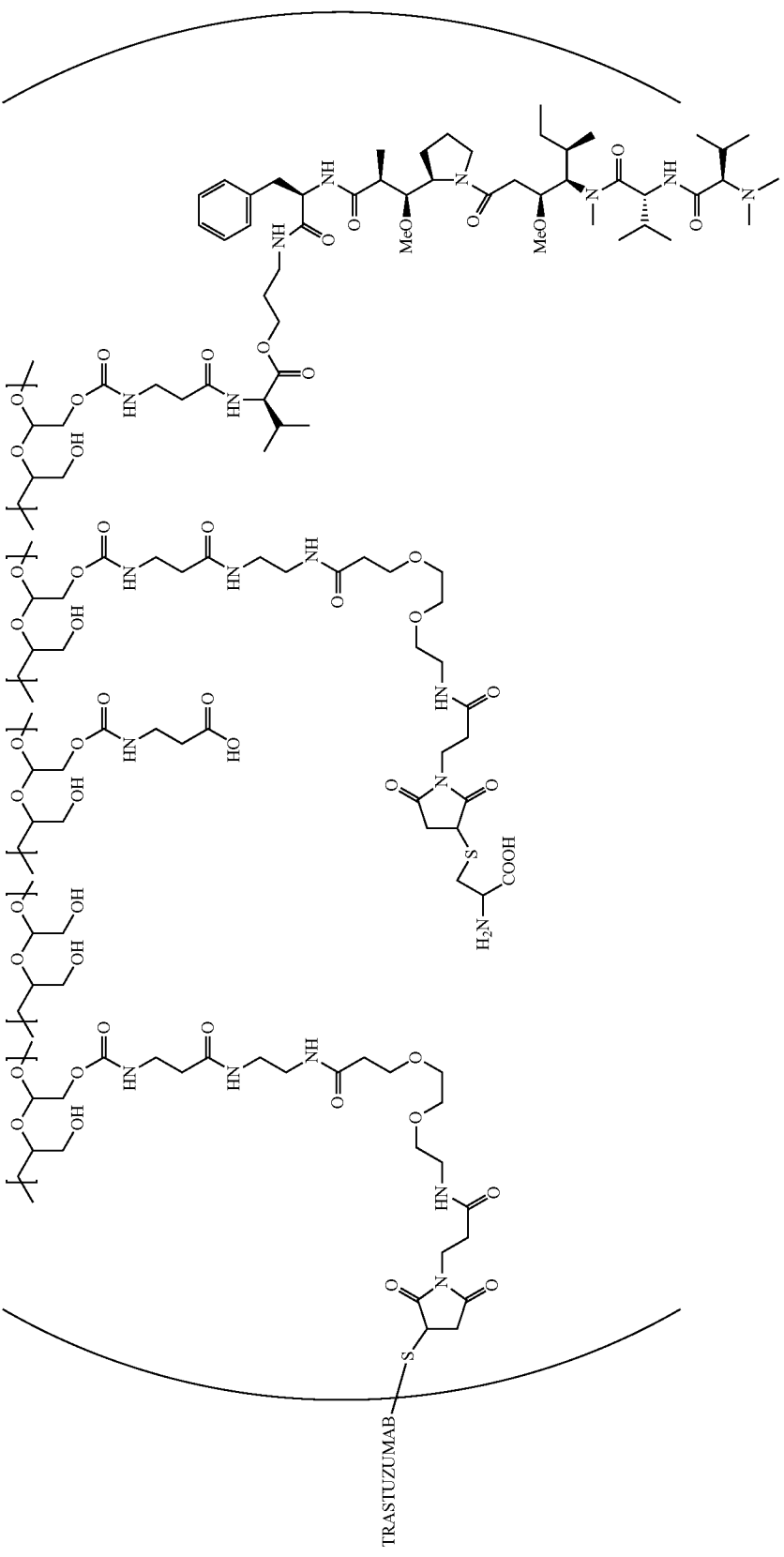

The title compound was prepared using the procedure described in Example 4 or Example 7 except 10K PHF-BA (28%) EG2-MI (2.7%)-(val AF-HPA) (7.2%) (52.3 mg, prepared using the procedure described in Example 32), trastuzumab and TCEP:trastuzumab 3.5:1 were used. The AF-HPA to trastuzumab ratio was about 14.5:1 to about 20:1. The average PHF-drug conjugate to trastuzumab ratio was about 2:1 to about 4:1. The molecular weight of the title conjugate was about 235 kDa.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies as described above. Also PBRM-polymer-drug conjugates with varying ratios of drug to PBRM are obtained by varying the number of PBRM sulfhydryl groups and drug-polymer conjugate drug load.

Example 37

Synthesis of 10K PHF-BA (28%) EG2-MI (2.7%)-(Val-Cit-PABA-Arry 520) (2.9%)

To a solution of 10K PHF-BA (28%) EG2-MI (2.7%)-(252 mg, prepared in a fashion similar to that as described in Example 2) in 23 mL NMP was added Any 520-PABA-Val-Cit-NH$_2$ (37.6 mg, prepared using the procedure described in U.S. Pat. No. 8,815,226, Example 84) in NMP (1 mL). To this mixture was added HATU (22.8 mg) in NMP (1 mL) followed by DIEA (20.7 mg). The reaction mixture was stirred 30 min at room temperature. The crude mixture was purified by diafiltration to give the title compound (47% yield based on Any 520).

The drug loading of the conjugated product (i.e., content of polymer units containing the drug) determined by UV was 2.9% mol of the polymer structural units (or on average about 2.1 Any 520-PABA-Val-Cit molecules per polymer chain). The molecular weight of the title conjugate was about 9.0 kDa.

Example 38

Synthesis of Trastuzumab-((EG2-MI (2.7%)-(10 kDa PHF-BA (28%)-(Val-Cit-PABA-Arry 520 (2.9%))

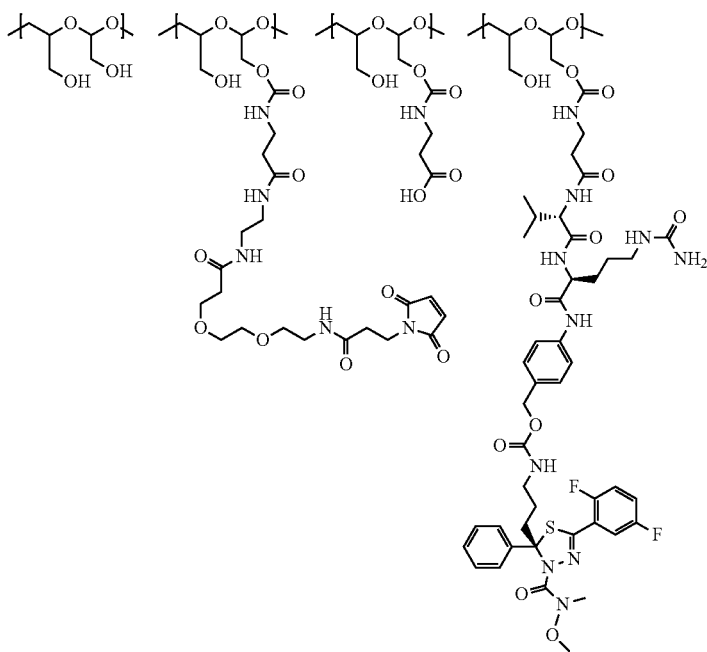

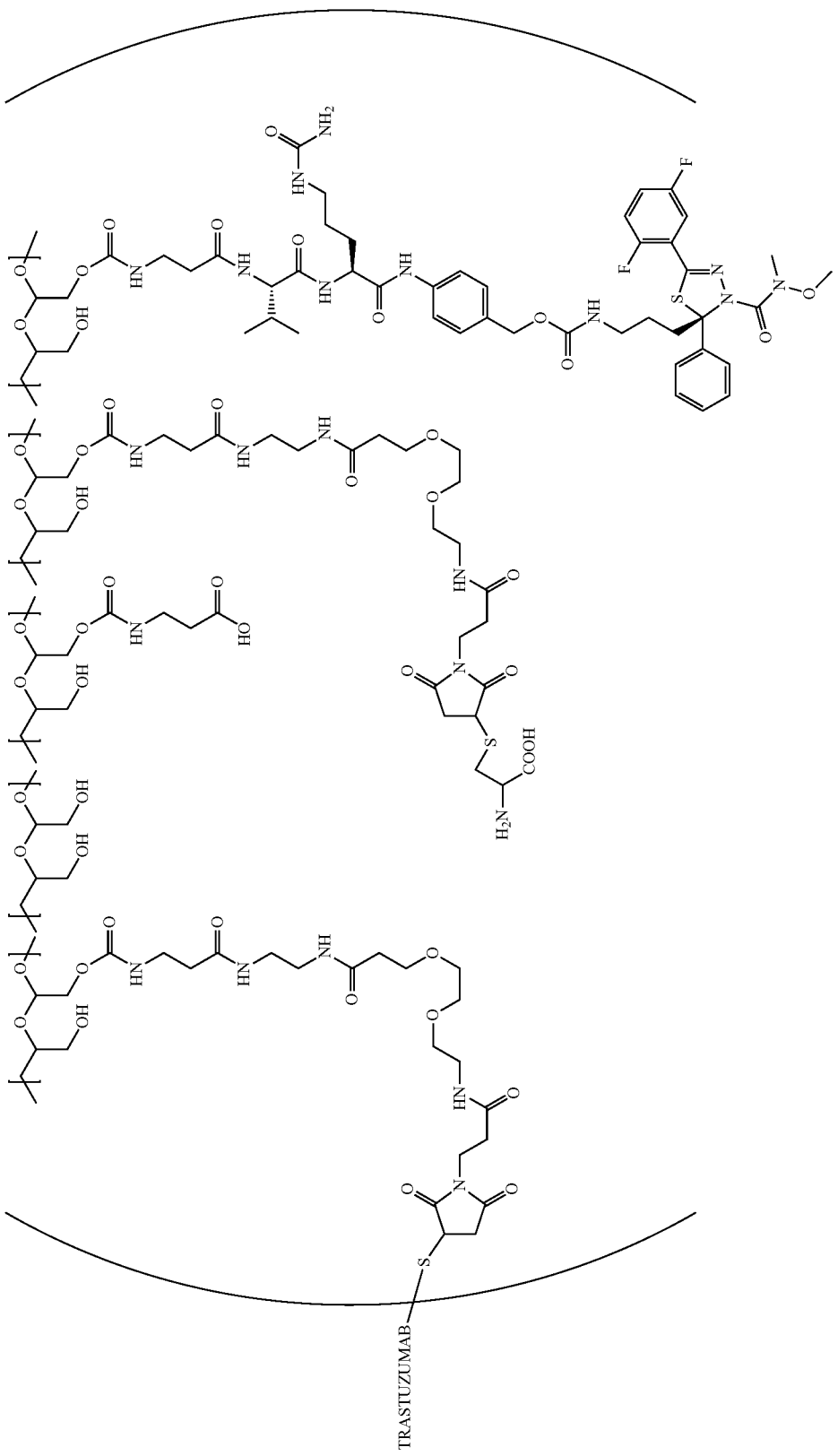

The title compound was prepared using the procedure described in Example 4 or Example 7 except 10K PHF-BA (28%) EG2-MI (2.7%)-(Val-Cit-PABA-Arry 520) (2.9%) (55.6 mg, prepared in a fashion similar to that as described in Example 38), trastuzumab and TCEP:trastuzumab 2.5:1 were used. The Arry 520 to trastuzumab ratio was about 4:1 to about 6:1. The molecular weight of the title conjugate was about 245 kDa. The average PHF-drug conjugate to trastuzumab ratio was about 2:1 to about 4:1.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies as described above. Also PBRM-polymer-drug conjugates with varying ratios of drug to PBRM are obtained by varying the number of PBRM sulfhydryl groups and drug-polymer conjugate drug load.

Example 39

Synthesis of Rituximab-((EG2-MI (2.7%)-(10 kDa PHF-BA (28%)-(Val-Cit-PABA-Arry 520 (2.9%))

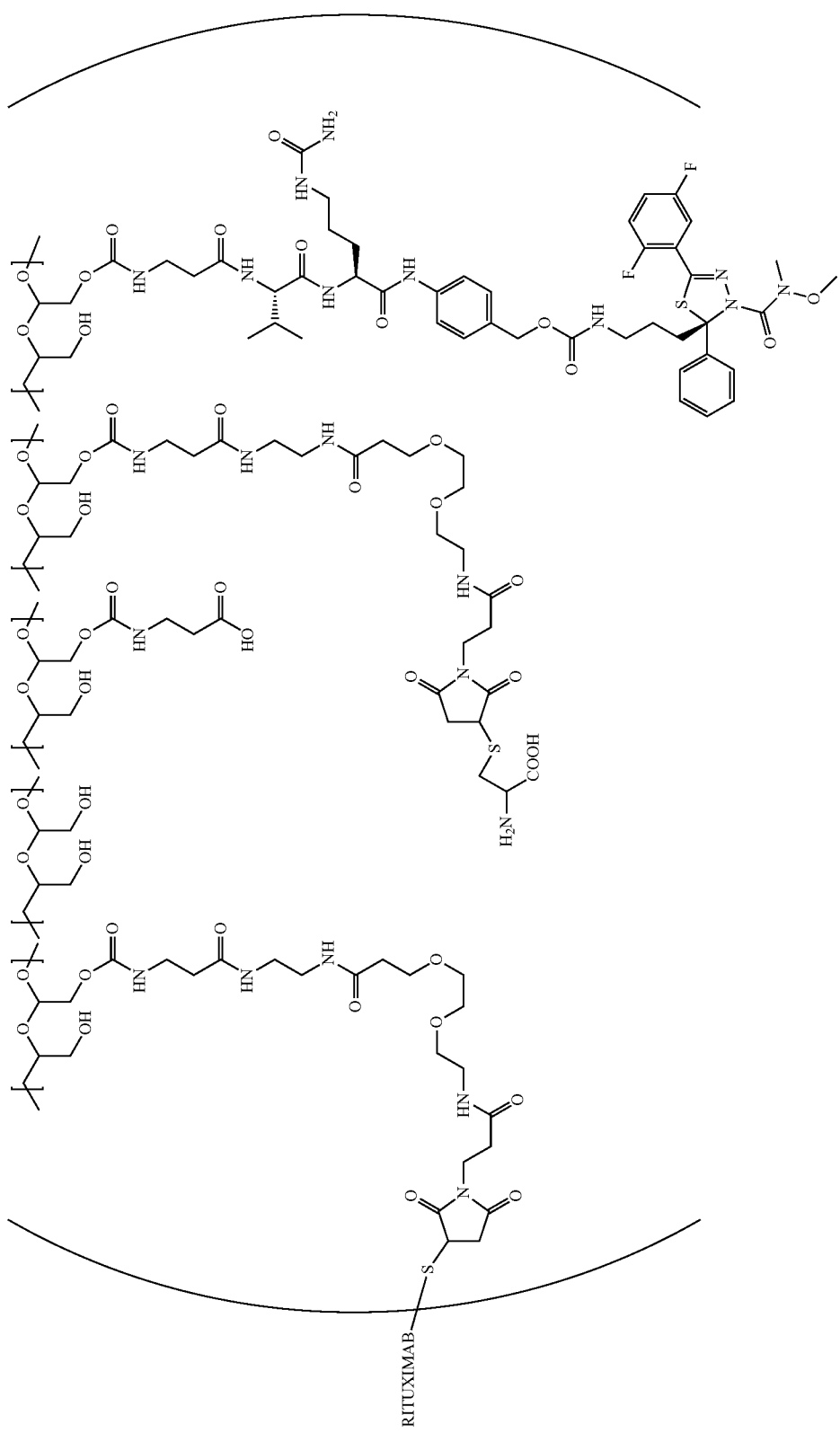

The title compound was prepared using the procedure described in Example 38, except rituximab and TCEP:rituximab 2.5:1 were used. The average Any 520 to rituximab ratio was about 4:1 to about 6:1. The molecular weight of the title conjugate was about 231 kDa. The average PHF-drug conjugate to trastuzumab ratio was about 2:1 to about 4:1.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies as described above. Also PBRM-polymer-drug conjugates with varying ratios of drug to PBRM are obtained by varying the number of PBRM sulfhydryl groups and drug-polymer conjugate drug load.

Example 40

Synthesis of sc-FvFc-Trastuzumab-((EG2-MI (2.8%)-(10 kDa PHF-BA (28%)-(AF-HPA-Ala (8%))

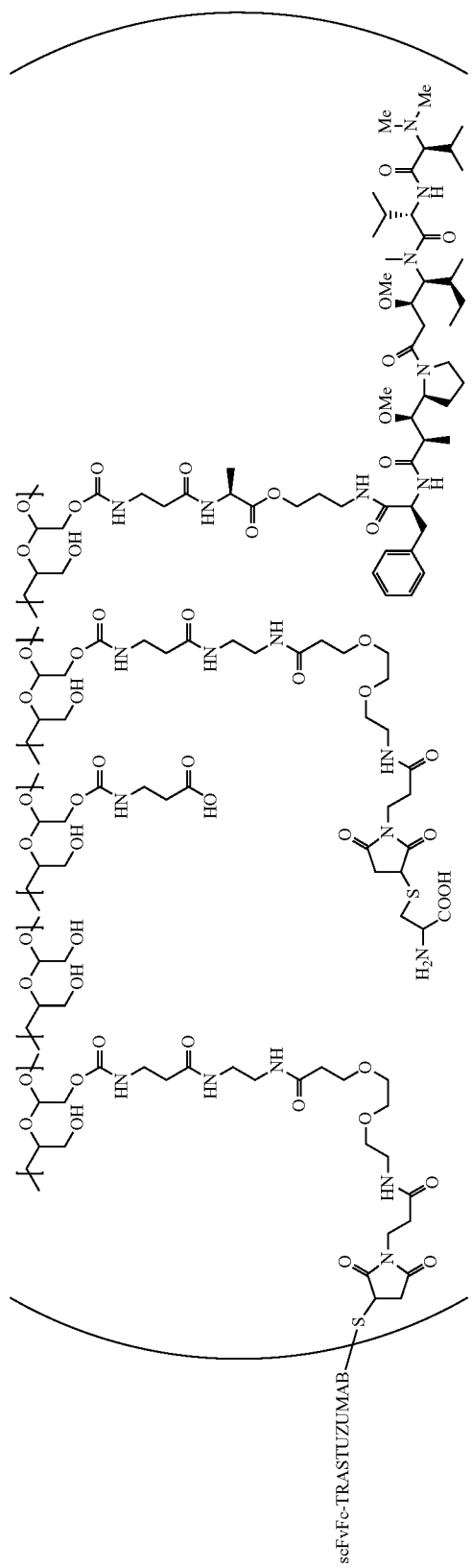

The title compound ("scFvFc-trastuzumab polymer drug conjugate", or "trastuzumab scADC") was prepared in a fashion similar to that as described in Example 4 or Example 7 except 10K PHF-BA (28%)-EG2-MI (2.8%)-AF-HPA-Ala (8%) (2.2 mg prepared in a fashion similar to that as described in Example 3 or Example 6) and scFvFc trastuzumab antibody and TCEP: scFvFc trastuzumab antibody 3:1 were used. The sequence of the scFvFc trastuzumab antibody (trastuzumab single chain antibody-Fc fusion protein) is as published in Olafsen et al (Cancer Res. 65(13): 5907-16, 2005) with three modifications in the constant regions: the hinge has one mutation (C->S) to eliminate the unpaired cysteine that usually bonds with the light chain constant (Yang and Rader, Cloning, Expression, and Purification of Monoclonal Antibody in scFv-Fc Format. Antibody Methods and Protocols. Ed. Proetzel and Ebersback, 2012). The two other modifications are also in the IgG1 sequence. Olafsen et al 2005, created Trastuzumab-scFv-Fc (H310A, H435Q) Double Mutant in order to shorten the half-life of the antibody fragment for improved imaging purposes. The modifications were reverted back to the canonical IgG1 sequence.

The AF-HPA to scFvFc trastuzumab antibody ratio was about 14:1 to about 19:1. The molecular weight of the title conjugate was about 182 kDa. The average PHF-drug conjugate to scFvFc trastuzumab antibody ratio was about 2:1 to about 4:1.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies. Also PBRM-polymer-drug conjugates with varying ratios of drug to PBRM are obtained by varying the number of PBRM sulfhydryl groups and drug-polymer conjugate drug load.

Example 41

Topotecan-alanine

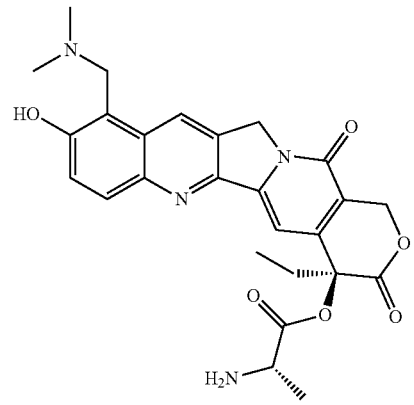 [SMILES: CC[C@@]1(OC(=O)[C@H](C)N)C(=O)OCc2c1cc1n(c2=O)Cc2cc3c(CN(C)C)c(O)ccc3nc2-1]

Topotecan (0.500 g, 1.19 mmol), BOC-ala-OH (0.449 g, 2.37 mmol), and N,N-dimethylpyridin-4-amine (0.145 g, 1.19 mmol) were dissolved in anhydrous $CH_2Cl_2$ (5.93 mL). N,N'-methanediylidenedicyclohexanamine (DCC) (0.580 g, 2.81 mmol) in anhydrous $CH_2Cl_2$ (1 mL) was added and the mixture stirred at room temperature for 18 hours. Additional DCC (300 mg, 1.45 mmol) was added and the mixture stirred for 48 hours. The solids were removed via filtration and the solution washed with 0.1N HCl (2×5 mL), water (5 mL), and brine (5 mL), then dried over $MgSO_4$, followed by RP-HPLC eluting with 0.1% $TFA/CH_3CN$: 0.1% TFA/water (combiflash, C18, 100 G column; 5 min 0% B, ramp to 100% B over 20 min) to give Topotecan-BOC-alanine as a solid (186.6 mg, 0.315 mmol, 26.5% yield).

Topotecan-BOC-alanine (186.6 mg, 0.315 mmol) was dissolved in anhydrous $CH_2Cl_2$ (1.5 mL). 2,2,2-trifluoroacetic acid (1.205 ml, 15.74 mmol) was added and the mixture stirred at room temperature for 1 hour followed by RP-HPLC (C18, HPLC eluting with 0.1% TFA:AcN/0.1% TFA; Water) to give the title compound as an orange/yellow solid (93.0 mg, 0.189 mmol, 60.0% yield).

Example 42

Synthesis of Trastuzumab-((EG2-MI (2.4%)-(10 kDa PHF-BA (22.3%)-(topotecan alanine) (6.5%))

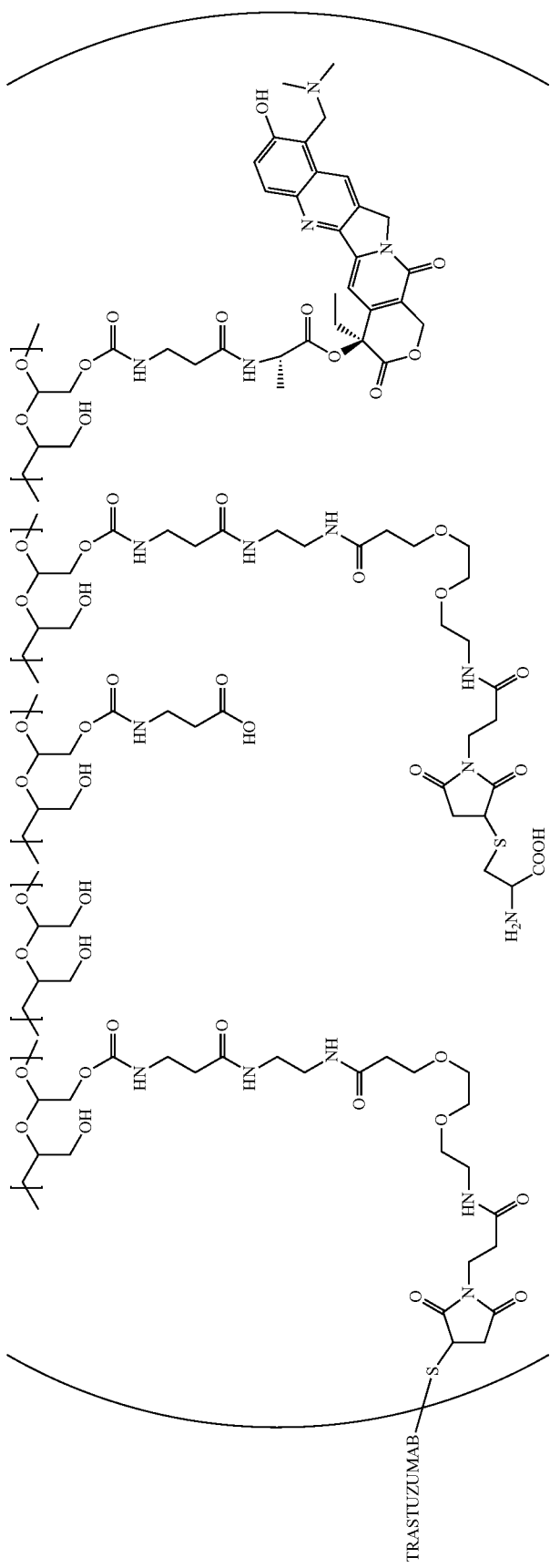

Conjugate A: Trastuzumab-((EG2-MI (2.4%)-(10 kDa PHF-BA (22.3%)-(topotecan alanine) (6.5%)) was prepared using the procedure described in Example 4 or Example 7 except 10K PHF-BA (22.3%) EG2-MI (2.4%)-(topotecan alanine) (6.5%) (19.3 mg, having on average about 4.2 topotecan molecules per polymer chain, prepared using the procedure described in Example 3 or Example 6), trastuzumab and TCEP:trastuzumab 3:1 were used. The molecular weight of the title conjugate was about 256 kDa. The average topotecan to trastuzumab ratio was about 19:1 to about 26:1. The average PHF-drug conjugate to trastuzumab ratio was about 2:1 to about 5:1.

Conjugate B: Rituximab-((EG2-MI (2.4%)-(10 kDa PHF-BA (22.3%)-(topotecan alanine) (13%)) was prepared by substituting reduced rituximab in the procedure described above. The molecular weight of the title conjugate was about 212 kDa. The average PHF-drug conjugate to rituxiumab ratio was about 16:1 to about 22:1.

Trastuzumab-((EG2-MI)-(10 kDa PHF-BA)-(topotecan valine) is prepared using the procedure described above except 10K PHF-BA EG2-MI-(topotecan valine), prepared using the procedure described in Example 41 is used.

Other PBRM-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies as described above. Also PBRM-drug conjugates with varying ratios of drug to PBRM are obtained by varying the number of PBRM sulfhydryl groups and drug load.

Example 43

Synthesis of Trastuzumab-((EG2-MI (2.8%)-(10 kDa PHF-BA (28%)-(AF-HPA-Ala (7.3%)))

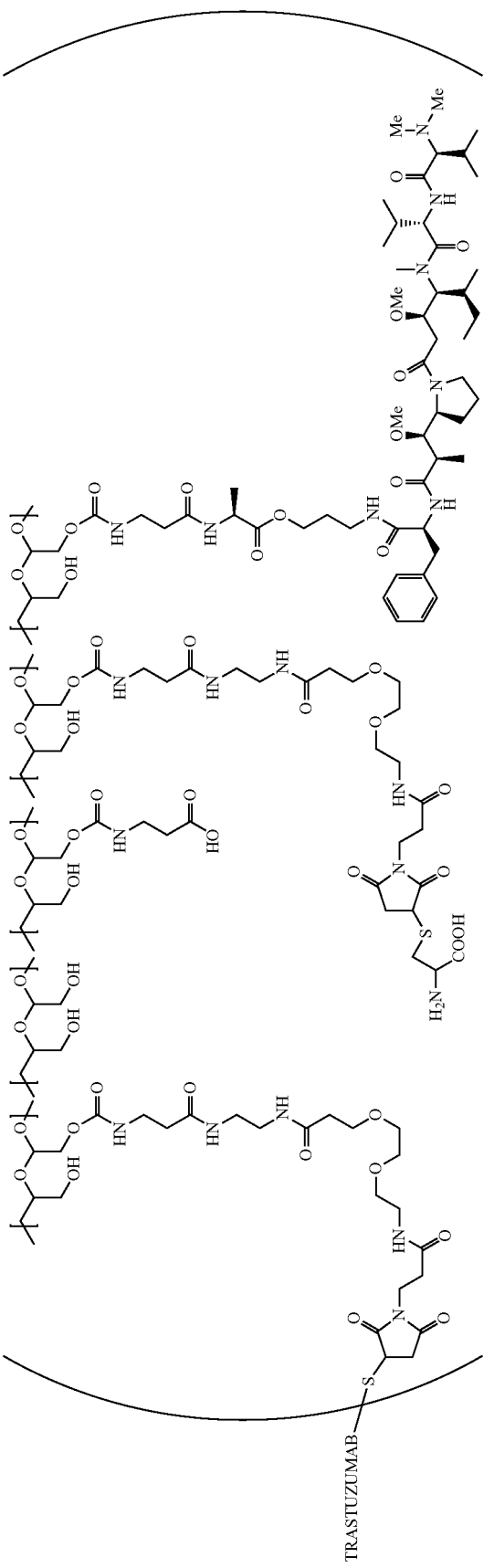

The title compound was prepared using the procedure described in Example 4 or Example 7 except 10K PHF-BA (28%) EG2-MI (2.8%)-(HPV-Ala (7.2%) (8.36 mg, prepared in a fashion similar to that as described in Example 3 or Example 6), trastuzumab and TCEP:trastuzumab 2.5:1 were used.

Conjugate A: Trastuzumab-((EG2-MI (2.8%)-(10 kDa PHF-BA (28%)-(AF-HPA-Ala (7.3%)). The AF-HPA to trastuzumab ratio was about 6:1 to about 9:1. The molecular weight of the title conjugate was about 183 kDa. The average PHF-drug conjugate to trastuzumab ratio was about 2:1 to about 4:1.

Conjugate B: Trastuzumab-((EG2-MI (2.5%)-(10 kDa PHF-BA (28%)-(AF-HPA-Ala (8.4%)) was prepared in a fashion similar to that as described in this example above except 10K PHF-BA (28%) EG2-MI (2.5%)-(HPV-Ala (8.4%) (prepared in a fashion similar to that as described in Example 3 or Example 6), trastuzumab and TCEP:trastuzumab 3.5:1 were used. The AF-HPA to trastuzumab ratio was about 12:1 to about 17:1. The molecular weight of the title conjugate was about 218 kDa. The average PHF-drug conjugate to trastuzumab ratio was about 2:1 to about 4:1.

Conjugate C: Trastuzumab-((EG2-MI (2.5%)-(10 kDa PHF-BA (28%)-(AF-HPA-Ala (8.4%)) was prepared in a fashion similar to that as described in this example except 10K PHF-BA (28%) EG2-MI (2.8%)-(HPV-Ala (8.4%) (prepared in a fashion similar to that as described in Example 3 or Example 6), trastuzumab and TCEP:trastuzumab 2.75:1 were used. AF-HPA to trastuzumab ratio was about 12:1 to about 16:1. The molecular weight of the title conjugate was about 247 kDa. The average PHF-drug conjugate to trastuzumab ratio was about 2:1 to about 4:1.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies. Also PBRM-polymer-drug conjugates with varying ratios of drug to PBRM are obtained by varying the number of PBRM sulfhydryl groups and drug-polymer conjugate drug load.

Example 44

Synthesis of Trastuzumab-((EG2-MI)-(10 kDa PHF-BA)-(SN38 alanine)

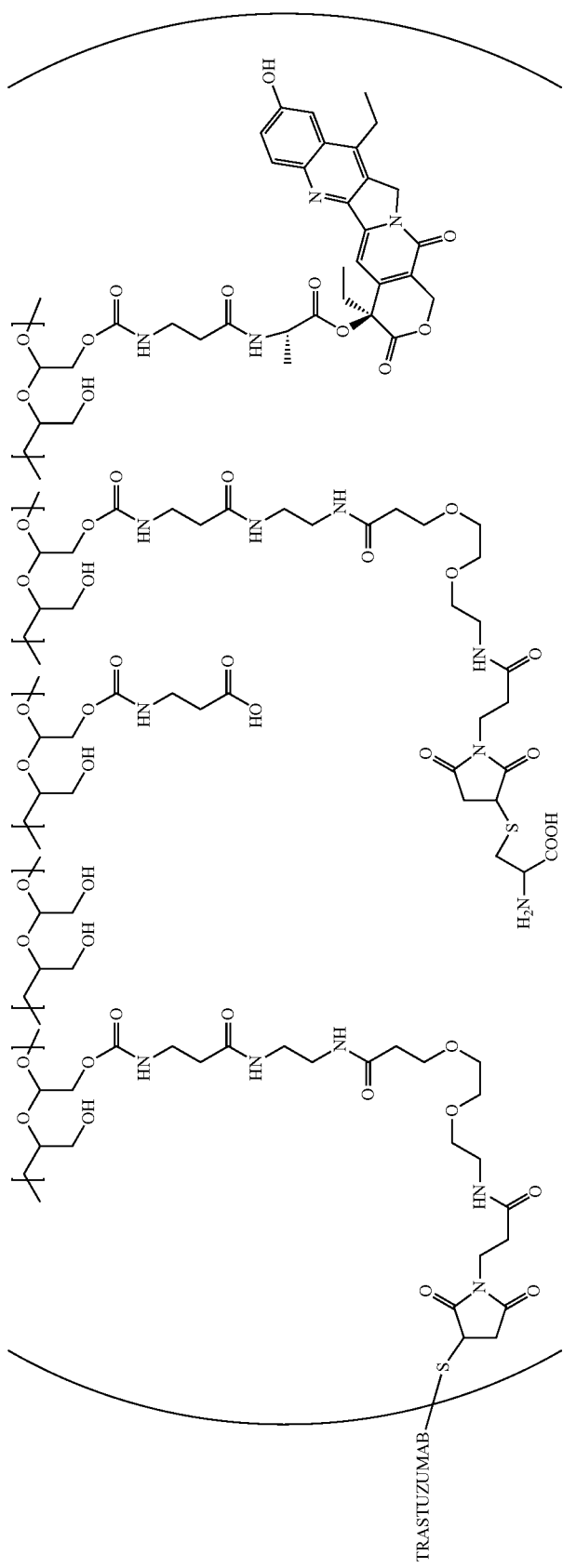

The title compound is prepared using the procedure described in Example 42 except 10K PHF-BA EG2-MI-(SN38 alanine), prepared using the procedure described in Examples 42 and 41 are used.

Trastuzumab-((EG2-MI)-(10 kDa PHF-BA)-(SN-38 valine) is prepared using the procedure described above except 10K PHF-BA EG2-MI-(SN-38 valine), prepared using the procedure described in Examples 41 and 42 are used.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies. Also PBRM-polymer-drug conjugates with varying ratios of drug to PBRM are obtained by varying the number of PBRM sulfhydryl groups and drug-polymer conjugate drug load.

Example 45

Synthesis of Trastuzumab-((EG2-MI)-(10 kDa PHF-BA)-(camptothecin-alanine)

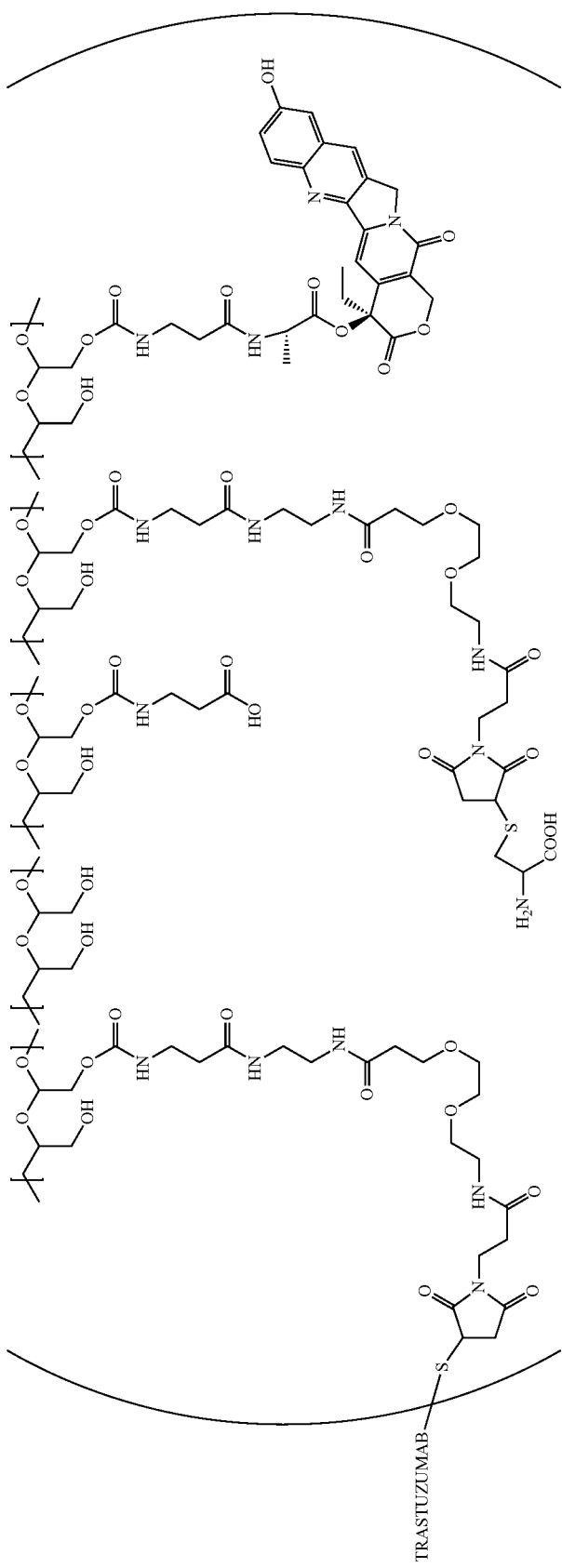

The title compound can be prepared using the procedure described in Example 42 except 10K PHF-BA EG2-MI-(camptothecin alanine), prepared using the procedure described in Examples 42 and 41 are used.

Trastuzumab-((EG2-MI)-(10 kDa PHF-BA)-(camptothecin valine) is prepared using the procedure described above except 10K PHF-BA EG2-MI-(camptothecin valine), prepared using the procedure described in Examples 41 and 42 are used.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies. Also PBRM-polymer-drug conjugates with varying ratios of drug to PBRM are obtained by varying the number of PBRM sulfhydryl groups and drug-polymer conjugate drug load.

Example 46

Cell Viability Assay for PBRM-polymer-drug Conjugates

PBRM-polymer-drug conjugates were evaluated for their antiproliferation properties in tumor cell lines in vitro using Cell Titer-Glo (Promega Corp). Cells were plated in black walled 96-well plate and allowed to adhere overnight at 37° C. in a humidified atmosphere of 5% $CO_2$. SKBR3, BT474, NCI-N87 cells (HER2 expressing cells), MCF7 cells (HER2 low expressing levels cells) and JIMT1 cells (HER2 medium expression level cells) were plated at a density of 5,000 cells per well. The next day the medium was replaced with 50 µL fresh medium and 50 µL of 2× stocks of PBRM-polymer-drug conjugate, drug polymer conjugate or drug were added to appropriate wells, mixed and incubated for 72 h. Cell Titer-Glo reagent was added to the wells at room temperature and the luminescent signal was measured after 10 min using a SpectraMax M5 plate reader (Molecular Devices). Dose response curves were generated using SoftMax Pro software. $IC_{50}$ values were determined from four-parameter curve fitting.

CD33 expressing cells HL-60 were passed at a density of 5,000 cells per well and treated with PBRM-polymer-drug conjugate on the same day. After 72 h incubation, the cells were analyzed using the same procedure described above.

OVCAR-3, TF-1α and HCT-15 expression cells were plated and analyzed using the same procedure described above.

5T4 expressing cell lines A431 (A431, an epidermoid carcinoma cell line available from the American Type Culture Collection (ATCC), Manassas Va. US, under accession number ATCC® CRL-1555); PC3 (a human prostate cell line, ATCC® CRL-1435), MDAMB231-5T4 OE and target negative control cell line LLC1 expression cells (lung cell carcinoma cells negative for 5T4 expression) were plated and analyzed using the same procedure described above. "MDAMB231-5T4 OE" means recombinant MDA-MB-231 cells over-expressing 5T4 (generated by stable transfection; disclosed in U.S. Provisional Application No. 61/835,858, filed Jun. 17, 2013, which is incorporated by reference herein).

Tables I to III are illustrative results for the antiproliferation properties of the PBRM-polymer-drug conjugate in either HER2 expressing cells (Tables I), CD33 expressing cells (Table II) or 5T4 expressing cells (Table III).

Table IV are illustrative results for the antiproliferation properties of the drug, AF-HPA in OVCAR-3 and TF-1α cell lines.

Table I lists the results for PBRM-polymer-drug conjugate Trastuzumab-((EG2-MI (3%))-(10 kDa PHF-BA (30%)-(AF-HPA-Ala (8%)), (AF-HPA:trastuzumab about 12:1 to 17:1), Example 4; Trastuzumab-((EG2-MI (2%)-(10 kDa PHF-BA (30%)-(AF-HPA-Ala (9%)), (AF-HPA:trastuzumab about 16:1 to about 21:1), Example 7; Trastuzumab-((EG2-MI (1%))-(10 kDa PHF-GA (29%)-(AF-HPA-Ala (6%)), (AF-HPA:trastuzumab about 18:1 to about 23:1), Example 13; Trastuzumab-((EG2-MI (2%))-(10 kDa PHF-BA (28%)-(AF-HPA-Ala (9%)), (AF-HPA:trastuzumab about 10:1 to about 15:1), Example 14; Trastuzumab-((EG2-MI (2%))-(10 kDa PHF-BA (28%)-(AF-HPA-Ala (9%)), (AF-HPA:trastuzumab about 11:1 to about 16:1), Example 15; and Rituximab-((EG2-MI (2%))-(10 kDa PHF-BA (28%)-(AF-HPA-Ala (9%)), (AF-HPA:trastuzumab about 13:1 to about 18:1), Example 16; Trastuzumab-((EG2-MI (2%)-(10 kDa PHF-BA (28%)-(AF-HPA-Ala (9%), (AF-HPA:trastuzumab about 5:1 to about 10:1), Example 17; Trastuzumab-((EG2-MI (2%)-(10 kDa PHF-BA (28%)-(AF-HPA-Ala (9%), (AF-HPA:trastuzumab about 19:1 to about 24:1), Example 18A; (AF-HPA:trastuzumab about 20:1 to about 25:1), Example 18B; (AF-HPA:trastuzumab about 23:1 to about 28:1), Example 18C; Trastuzumab-((EG2-MI (2.7%)-(10 kDa PHF-BA (30%)-(HPV-Ala (14%)), Example 20A; Trastuzumab-((EG2-MI (2.7%)-(10 kDa PHF-BA (30%)-(HPV-Ala (7.7%)), Example 20B; Trastuzumab-((EG2-MI (3.5%)-(10 kDa PHF-BA (30%)-(HPV-Ala (4.3%)), Example 20C; sc-FvFc-Trastuzumab-((EG2-MI (2.8%)-(10 kDa PHF-BA (28%)-(AF-HPA-Ala (8%)), Example 40; Trastuzumab-((EG2-MI (2.8%)-(10 kDa PHF-BA (28%)-(AF-HPA-Ala (7.3%) AF-HPA:trastuzumab about 6:1 to about 9:1), Example 43A; Trastuzumab-((EG2-MI (2.5%)-(10 kDa PHF-BA (28%)-(AF-HPA-Ala (8.4%), AF-HPA:trastuzumab about 12:1 to about 16:1), Example 43C; free drug (AF-HPA); and Kadcyla®.

TABLE I

| | BT474 $IC_{50}$ (nmol/L) | SKBR3 $IC_{50}$ (nmol/L) | N87 $IC_{50}$ (nmol/L) | MCF7 $IC_{50}$ (nmol/L) | JIMT1 $IC_{50}$ (nmol/L) |
|---|---|---|---|---|---|
| Example 4 | 0.05 | 0.02 | 0.03 | 40 | 0.14 |
| Example 7 | 0.03 | 0.01 | 0.05 | 3.6 | 0.11 |
| Example 13 | 0.12 | 0.03 | 0.05 | 7.7 | 0.28 |
| Example 14 | 0.07 | 0.02 | 0.11 | 28.9 | 0.13 |
| Example 15 | 0.05 | 0.01 | 0.11 | 23.5 | 0.12 |
| Example 16 | 3.04 | 1.44 | 5.23 | 27.9 | 1.88 |
| Example 17 | 0.03 | 0.03 | 0.43 | 28.8 | 0.06 |
| Example 18A | 0.04 | 0.02 | 0.06 | 9.6 | 0.16 |
| Example 18B | 0.05 | 0.01 | 0.04 | 33 | 0.12 |
| Example 18C | 0.03 | 0.02 | 0.06 | 3.8 | 0.18 |
| Example 20A | 0.01 | 0.07 | 0.31 | 2.86 | 0.67 |
| Example 20B | 0.15 | 0.79 | 4.07 | 100 | 6.51 |
| Example 20C | 0.76 | 0.79 | 4.49 | 10 | 9.73 |
| Example 40 | ND | 0.02 | 0.10 | >100 | 0.90 |
| Example 43A | 0.03 | 0.03 | 0.43 | 28.84 | 0.60 |
| Example 43C | 0.10 | 0.02 | 0.09 | >100 | 0.64 |
| AF-HPA (toxin equivalents) | 1.01 | 0.40 | 0.42 | 4.4 | 0.86 |
| Kadcyla ® | 2.40 | 0.23 | 0.09 | 38.6 | 18.0 |

ND = not determined

The results in Table I show that, for the HER2 expressing cell lines SKBR3, BT474, N87 and JIMT1, the PBRM-polymer-drug conjugates (Example 4, Example 7, Examples 13 to 15, Example 17, Examples 18A to 18C, Example 20A, Example 43A and Example 43C) exhibited higher antiproliferative activity as compared to the low HER2 expressing cell line MCF7 and as compared to the control PBRM-polymer-drug conjugate (Example 16) or Kadcyla®.

Table II lists the results for Lintuzumab-((EG2-MI (2%)-(10 kDa PHF-BA (30%)-(AF-HPA-Ala (9%)), (AF-HPA: lintuzumab about 10:1 to about 15:1), Example 8; and Rituximab-((EG2-MI (3%)-(10 kDa PHF-BA (30%)-(AF-HPA-Ala (8%)) (AF-HPA:rituximab about 13:1 to about 18:1), Example 9; and free drug (AF-HPA).

TABLE II

|  | HL-60 $IC_{50}$ (nmol/L) |
|---|---|
| Example 8 | 0.77 |
| Example 9 | 6.74 |
| AF-HPA | 4.8 |

The results in Table II show that, for the CD33 expressing cell line HL-60 the PBRM-polymer-drug conjugate (Examples 8) exhibited higher antiproliferative activity compared to control PBRM-polymer-drug conjugate (Example 9).

Table III lists the results for PBRM-polymer-drug conjugate Anti-5T4-((EG2-MI (3%)-(10 kDa PHF-BA (30%)-(AF-HPA-Ala (8%)), (AF-HPA:anti-5T4 about 12:1 to about 18:1), Example 10; and Rituximab-((EG2-MI (3%)-(10 kDa PHF-BA (30%)-(AF-HPA-Ala (8%))), (AF-HPA:rituximab about 13:1 to about 18:1), Example 9; and free drug (AF-HPA).

TABLE III

|  | A431 $IC_{50}$ (nmol/L) | PC3 $IC_{50}$ (nmol/L) | LLC1 $IC_{50}$ (nmol/L) | MDAMB231OE $IC_{50}$ (nmol/L) |
|---|---|---|---|---|
| Example 10 | 0.3, 0.3* | 0.6 | 16.9, >100* | 0.04 |
| Example 9 | 1.8, 0.9* | 9.3 | 5.3, 33* | ND |
| AF-HPA | 0.7, 0.9* | 2.5 | 1.6, >100* | ND |

ND: not determined.
*Results from two different experiments.

The results in Table III show that, for the 5T4 expressing cell lines A431, PC3 and MDAMB231OE the PBRM-polymer-drug conjugate (Example 10) exhibited higher antiproliferative activity relative to control PBRM-drug conjugate (Example 9) and the non-expressing target cells LLC1.

Table IV lists the results for free drug (AF-HPA).

TABLE IV

|  | OVCAR3 $IC_{50}$ (nmol/L) | TF-1 α $IC_{50}$ (nmol/L) |
|---|---|---|
| AF-HPA | 0.8 | 13.8 |

Example 47

Ligand Binding Studies by BIAcore Surface Plasmon Resonance (SPR)

The kinetic binding of the PBRM-polymer-drug conjugate to an immobilized receptor is determined by BIAcore SPR. The binding constants for the PBRM in the PBRM-polymer-drug conjugate and PBRM alone can be determined using standard BIAcore procedures.

Using standard amine coupling chemistry, hErbB2 is immobilized in three flow channels to the surface Plasmon resonance sensor chip surface at three similar densities. trastuzumab readily bound to the immobilized hErbB2 thereby demonstrating that both binding partners were active. The binding parameters $k_a$ (association or affinity rate constant) and $K_D$ (dissociation constant) are measured at 25° C. for the PBRM-polymer-drug conjugate and PBRM using a BioRad ProteOn XPR36 optical biosensor equipped with a GLC sensor chip and equilibrated with running buffer.

The results show that the PBRM in the PBRM-polymer-drug conjugate is recognized by the PBRM receptor and that the binding of the PBRM in the PBRM-polymer-drug conjugate is not significantly affected relative to the unconjugated PBRM.

Example 48

FACS Binding Assay

Cell surface binding of the PBRM-polymer-drug conjugate Trastuzumab-((EG2-MI (3%))-(10 kDa PHF-BA (30%)-(AF-HPA-Ala (8%)), (AF-HPA:trastuzumab about 12:1 to 17:1), Example 4, was evaluated using the MACSQuant® Analyzer 10 digital bench top flow cytometer in different human cancer cell lines. 100,000 cells were incubated in 6% goat serum on ice. PBRM polymer drug conjugate or unconjugated PBRM was added to the cells and incubated on ice for three hours, then cells were washed with ice cold PBS and incubated with the secondary fluorescently labeled antibodies in ice for one hour. Upon completion cells were washed with PBS, fixed with 1% paraformaldehyde and analyzed by flow cytometer. The cell surface binding of the PBRM polymer drug conjugate was determined by titration and compared to that of non-conjugated PBRM.

Table V gives the binding constant ($K_d$) of PBRM-polymer-drug conjugate Trastuzumab-((EG2-MI (3%))-(10 kDa PHF-BA (30%)-(AF-HPA-Ala (8%)), (AF-HPA:trastuzumab about 12:1 to 17:1), Example 4, and trastuzumab alone to JIMT-1 cells.

TABLE V

|  | $K_d$ (nM) |
|---|---|
| Example 4 | 2.16 |
| Trastuzumab | 0.92 |

The results show that the cell surface binding of the PBRM in the PBRM-polymer-drug conjugate was comparable to that of unconjugated PBRM.

The cell surface binding of the PBRM in other PBRM-polymer-drug conjugates to other human cancer cells can be determined and should be comparable to that of the unconjugated PBRM.

Example 49

Ligand Binding Studies by BIAcore Surface Plasmon Resonance (SPR)

The kinetic binding of the PBRM-polymer-drug conjugate to an immobilized receptor was determined by BIAcore SPR. The binding constants for the PBRM in the PBRMpolymer-drug conjugates such as Trastuzumab-((EG2-MI (3%))-(10 kDa PHF-BA (30%)-(AF-HPA-Ala (8%)), (AF-HPA:trastuzumab about 12:1 to 17:1), Example 4; Trastuzumab-((EG2-MI (2%)-(10 kDa PHF-BA (30%)-(AF-HPA-Ala (9%)), (AF-HPA:trastuzumab about 16:1 to about 21:1), Example 7, Trastuzumab-((EG2-MI (2%)-(10 kDa PHF-BA (28%)-(AF-HPA-Ala (9%)), (AF-HPA:trastuzumab about 5:1 to 10:1), Example 17; and Trastuzumab-((EG2-MI (2%)-(10 kDa PHF-BA (28%)-(AF-HPA-Ala (9%)), (AF-HPA:trastuzumab about 19:1 to 24:1), Example 18A; (AF-HPA:trastuzumab about 20:1 to 25:1), Example 18B; (AF-HPA:trastuzumab about 23:1 to 28:1), Example 18C; PBRM in PBRM-drug conjugate (i.e., Kadcyla®) and PBRM (i.e., trastuzumab) alone were determined using standard BIAcore procedures.

Using standard amine coupling chemistry, hErbB2 was immobilized in three flow channels to the surface Plasmon resonance sensor chip surface at three similar densities. trastuzumab readily bound to the immobilized hErbB2 thereby demonstrating that both binding partners were active. Table VI provides the binding parameters $k_a$ (association or affinity rate constant), $k_d$ (dissociation rate constant), and $K_D$ (dissociation constant) measured at 25° C. for the conjugates of Example 4 and Example 7 and trastuzumab using a BioRad ProteOn XPR36 optical biosensor equipped with a GLC sensor chip and equilibrated with running buffer.

TABLE VI

| | $k_a$ (M$^{-1}$s$^{-1}$) | $k_d$ (s$^{-1}$) | $K_D$ (pM) |
|---|---|---|---|
| Trastuzumab | 9.90 ± 0.1 × 10$^5$ | 2.60 ± 0.1 × 10$^{-5}$ | 26.2 ± 0.1 |
| Kadcyla® | 4.61 ± 0.2 × 10$^5$ | 3.17 ± 0.9 × 10$^{-5}$ | 68.7 ± 0.3 |
| Example 4 | 4.61 ± 0.3 × 10$^5$ | 2.60 ± 0.9 × 10$^{-5}$ | 56.3 ± 0.3 |
| Example 7 | 5.3 ± 0.3 × 10$^5$ | 2.43 ± 0.1 × 10$^{-5}$ | 45.9 ± 0.3 |
| Example 14 | 3.91 ± 0.3 × 10$^5$ | 2.56 ± 0.1 × 10$^{-5}$ | 65.5 ± 0.5 |
| Example 17 | 8.30 ± 0.2 × 10$^5$ | 2.32 ± 0.2 × 10$^{-5}$ | 28.0 ± 0.1 |
| Example 18A | 4.67 ± 0.7 × 10$^5$ | 2.07 ± 0.2 × 10$^{-5}$ | 44.4 ± 0.6 |
| Example 18B | 3.05 ± 0.2 × 10$^5$ | 2.46 ± 0.1 × 10$^{-5}$ | 80.7 ± 0.6 |
| Example 18C | 4.25 ± 0.5 × 10$^5$ | 2.03 ± 0.1 × 10$^{-5}$ | 47.7 ± 0.5 |

The results show that the PBRM in the PBRM-polymer-drug conjugate was recognized by the PBRM receptor.

Example 50

In Vivo Efficacy, Pharmacokinetic and Biodistribution Studies

In order to evaluate the efficacy and pharmacokinetics of the protein drug conjugate mouse and rat subcutaneous and orthotopic xenograft models are used.

Test articles, along with appropriate controls are administered intravenously (IV) via tail-vein injection or intraperitoneally. To assess circulating levels of test article blood sample is collected at designated times via terminal cardiacpuncture. Samples are kept at room temperature for 30 min to coagulate, then centrifuged for 10 min at 1,000×g at 4° C. and immediately frozen at −80° C. Total PBRM concentrations in serum samples are measured using ELISA. Circulating drug concentration (conjugated and free) is determined by LC/MS/MS methods.

To assess efficacy of the PBRM-polymer-drug conjugates the tumor size are measured using digital calipers. Tumor volume is calculated and used to determine the delay in tumor growth.

For the determination of drug biodistribution, tumor, and major organs such as, for example, liver, kidney, spleen, lung, heart, muscles, and brain are harvested, immediately frozen in liquid nitrogen, stored at −80° C. PBRM and/or drug levels are determined in tissue homogenates by standard methods, such as, for example, ELISA or LC/MS/MS methods respectively.

Example 51

Mouse Tissue Distribution after Administration of PBRM-polymer-drug Conjugates

Female CB-17 SCID mice were inoculated subcutaneously with BT474 tumors (n=4 for each group). Vehicle or PBRM-polymer-drug conjugates: Trastuzumab-((EG2-MI (3%))-(10 kDa PHF-BA (30%)-(AF-HPA-Ala (8%)), (AF-HPA:trastuzumab about 12:1 to about 17:1), Example 4, at 5 mg/kg; and Trastuzumab-((EG2-MI (1%))-(10 kDa PHF-GA (29%)-(AF-HPA-Ala (6%)), (AF-HPA:trastuzumab about 18:1 to about 23:1), Example 13, at 5 mg/kg were dosed IV as a single dose on day 1.

At 48 hours post administration, the mice were sacrificed and the blood was collected by terminal cardiac. The organs: kidney left, liver, lung, skeletal muscle, spleen and tumor were harvested, immediately frozen in liquid nitrogen and stored at −80° C. until analysis for conjugated, free AF-HPA and AF.

Tables VII, VIII and VIIIA give the concentration of the conjugated drug (conjugated AF-HPA, i.e., PBRM-PHF-AF-HPA); unconjugated (free) drug (i.e., AF-HPA and AF); free AF-HPA and free AF in different tissues. The concentrations are reported as ng AF-HPA (and/or AF) equivalent/g tissue as mean value±standard deviation.

TABLE VII

Conjugated AF-HPA concentration

| Tissue | Example 4 | Example 13 |
|---|---|---|
| Tumor | 476 ± 52 | 371 ± 16 |
| Liver | 200 ± 57 | 100 ± 17 |
| Spleen | 127 ± 97 | 77 ± 18 |
| Kidney | 190 ± 15 | 137 ± 4 |
| Muscle | 39 ± 22 | 16 ± 86 |
| Plasma | 2218 ± 182 | 1720 ± 501 |

TABLE VIII

Total concentrations of unconjugated AF-HPA and AF

| Tissue | Example 4 | Example 13 |
|---|---|---|
| Tumor | 93.6 ± 25.5 | 82.9 ± 23.9 |
| Liver | 11.0 ± 2.3 | 3.4 ± 1.1 |
| Spleen | 9.9 ± 2.2 | 6.6 ± 1.3 |
| Kidney | 9.0 ± 2.1 | 0.7 ± 0.0 |
| Muscle | 0.2 ± 0.0 | ND |
| Plasma | 0.4 ± 0.02 | 0.3 ± 0.02 |

TABLE VIIIA

Unconjugated AF-HPA and unconjugated AF concentrations

| | Example 4 | | Example 13 | |
|---|---|---|---|---|
| Tissue | AF | AF-HPA | AF | AF-HPA |
| Tumor | 67.3 ± 17.5 | 21.6 ± 6.8 | 56.3 ± 16.2 | 22.3 ± 6.8 |
| Liver | 8.4 ± 1.5 | 2.0 ± 0.7 | 5.0 ± 1.3 | 1.6 ± 1.2 |

TABLE VIIIA-continued

Unconjugated AF-HPA and unconjugated AF concentrations

| Tissue | Example 4 | | Example 13 | |
|---|---|---|---|---|
| | AF | AF-HPA | AF | AF-HPA |
| Lung | 2.4 ± 0.7 | 1.2 ± 0.1 | 1.5 ± 0.4 | 0.9 ± 0.2 |
| Spleen | 7.9 ± 1.9 | 1.4 ± 0.2 | 5.5 ± 1.0 | 0.9 ± 0.1 |
| Kidney | 7.9 ± 1.9 | 0.5 ± 0.1 | 0.7 ± 0.0 | ND |
| Muscle | 0.5 ± 0.1 | 0.1 ± 0.03 | ND | ND |
| Plasma | ND | 0.4 ± 0.02 | ND | 0.3 ± 0.02 |

ND = not determined

The results show that in tissue the released unconjugated AF-HPA is further metabolized to AF whereas in plasma the unconjugated AF-HPA is not converted to AF.

Example 52

Tumor Growth Response to Administration of PBRM-polymer-drug Conjugates

Female CB-17 SCID mice were inoculated subcutaneously with BT474 tumors (n=10 for each group) or JIMT-1 cells (n=10 for each group) or NCI-N87 cells (n=10 for each group). Female NCr nu/nu mice were inoculated subcutaneously with HL-60 cells (n=10 for each group). Test compounds or vehicle were dosed IV as a single dose on day 1. Tumor size was measured at the times indicated in FIGS. 1 to 9 using digital calipers. Tumor volume was calculated and was used to determine the delay in tumor growth. Mice were sacrificed when tumors reached a size of 1000 mm$^3$. Tumor volumes are reported as the mean±SEM for each group.

FIG. 1 provides the results for the tumor response in mice inoculated subcutaneously with BT474 tumors (n=10 for each group) after IV administration as a single dose on day 1 of vehicle; PBRM (trastuzumab) at 10 mg/kg; PBRM-polymer-drug conjugates Trastuzumab-((EG2-MI (3%))-(10 kDa PHF-BA (30%)-(AF-HPA-Ala (8%)), (AF-HPA:trastuzumab about 12:1 to about 17:1), Example 4, at 2.5 mg/kg and 5 mg/kg; or Trastuzumab-((EG2-MI (1%))-(10 kDa PHF-GA (29%)-(AF-HPA-Ala (6%)), (AF-HPA:trastuzumab about 18:1 to about 23:1), Example 13, at 2.5 mg/kg and 5 mg/kg. The results show reduction of tumor volume for Examples 4 and 13 with 100% regressions at 5 mg/kg dose and 100% and 80% tumor free survival respectively. The vehicle and trastuzumab alone, showed an increase of tumor volume. The conjugation of a PBRM specific for HER2 (trastuzumab) to a drug polymer conjugate was necessary for the reduction of tumor volume as the PBRM alone did not show reduction in tumor volume).

Figure 2:
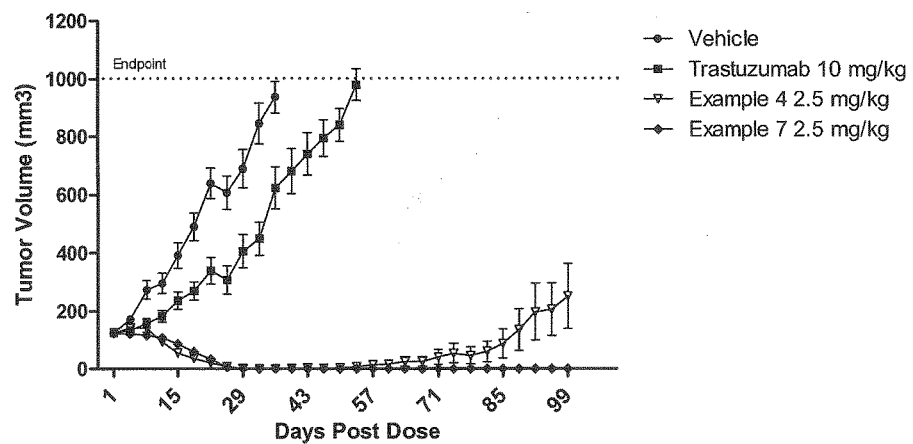
FIG. 2 shows the tumor response in mice inoculated subcutaneously with JIMT-1 cells (n=10 for each group) after IV administration as a single dose on day 1 of vehicle; PBRM (trastuzumab) at 10 mg/kg; PBRM-polymer-drug conjugates described in Example 4 or Example 7, at 2.5 mg/kg.

FIG. 2 provides the results for the tumor response in mice inoculated subcutaneously with JIMT-1 cells (n=10 for each group) after IV administration of vehicle; PBRM (trastuzumab) at 10 mg/kg; PBRM-polymer-drug conjugates Trastuzumab-((EG2-MI (3%))-(10 kDa PHF-BA (30%)-(AF-HPA-Ala (8%)), (AF-HPA:trastuzumab about 12:1 to about 17:1), Example 4, at 2.5 mg/kg; or Trastuzumab-((EG2-MI (2%)-(10 kDa PHF-BA (30%)-(AF-HPA-Ala (9%)), (AF-HPA:trastuzumab about 16:1 to about 21:1), Example 7, at 2.5 mg/kg. The results show reduction of tumor volume for both Examples 4 and 7. Specifically, in the tested group administered with the conjugate described in Example 4, there were 100% regressions at 2.5 dose consisting of nine complete regressions (one animal died due to non-treatment-related death) and three tumor free survivors. In the tested group administered with the conjugate described in Example 7, there were 100% regressions, consisting of complete regressions, all remained tumor free (two animals died tumor free at the end of the study due to non-treatment-related death). The vehicle, and trastuzumab alone, showed an increase of tumor volume. The conjugation of a PBRM specific for HER2 (trastuzumab) to a drug polymer conjugate was necessary for the reduction of tumor volume as the PBRM alone did not show reduction in tumor volume).

Female NCr nu/nu mice were inoculated subcutaneously with HL-60 cells (n=10 for each group). Test compounds or vehicle were dosed IV as a single dose on day 1. Tumor size was measured at the times indicated in FIG. 3 using digital calipers. Tumor volume was calculated and was used to determine the delay in tumor growth. Mice were sacrificed when tumors reached a size of 2000 mm$^3$. Tumor volumes are reported as the mean±SEM for each group.

Figure 3:
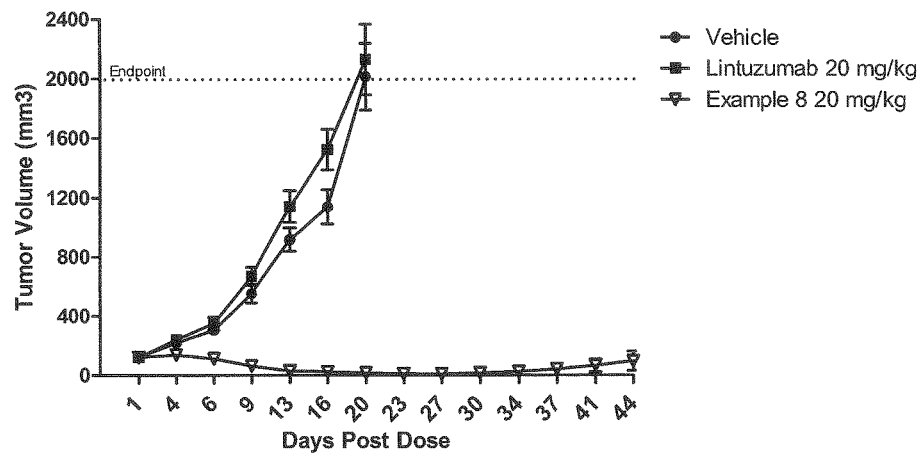
FIG. 3 shows the tumor response in mice inoculated subcutaneously with HL-60 cells (n=10 for each group) after IV administration as a single dose on day 1 of vehicle; PBRM (lintuzumab) at 20 mg/kg; or PBRM-polymer-drug conjugates described in Example 8 at 20 mg/kg.

FIG. 3 provides the results for the tumor response in mice inoculated subcutaneously with HL-60 cells (n=10 for each group) after IV administration as a single dose on day 1 of vehicle; PBRM (lintuzumab) at 20 mg/kg; or PBRM-polymer-drug conjugates Lintuzumab-((EG2-MI (2%)-(10 kDa PHF-BA (30%)-(AF-HPA-Ala (9%)), (AF-HPA:lintuzumab about 10:1 to about 15:1), Example 8, 20 mg/kg. The results show reduction of tumor volume for Example 8 with 100% regressions and 70% tumor free survival on day 44. The vehicle, and lintuzumab alone, showed an increase of tumor volume. The conjugation of a PBRM specific for CD33 (lintuzumab) to a drug polymer conjugate was necessary for the reduction of tumor volume as the PBRM alone did not show reduction in tumor volume.

Figure 4:
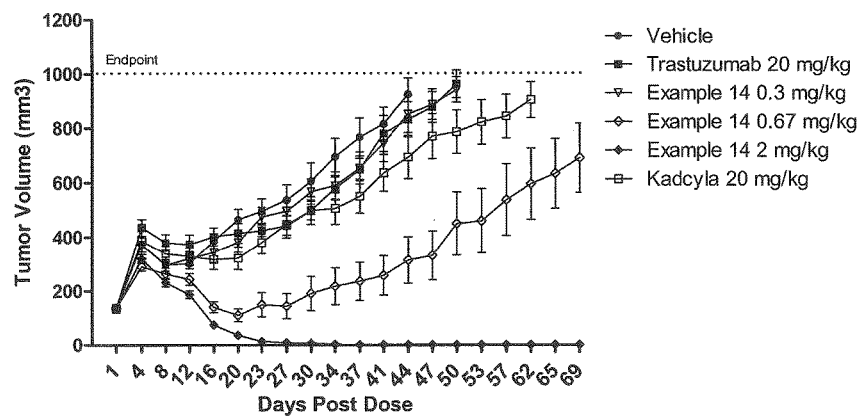
FIG. 4 shows the tumor response in mice inoculated subcutaneously with JIMT-1 cells (n=10 for each group) after IV administration as a single dose on day 1 of vehicle; PBRM (trastuzumab) at 20 mg/kg; Kadcyla® at 20 mg/kg; or PBRM-polymer-drug conjugate described in Example 14, at 2 mg/kg, 0.67 mg/kg or 0.3 mg/kg.

FIG. 4 provides the results for the tumor response in mice inoculated subcutaneously with JIMT-1 cells (n=10 for each group) after IV administration as a single dose on day 1 of vehicle; PBRM (trastuzumab) at 20 mg/kg; Kadcyla® (a PBRM-drug conjugate) at 20 mg/kg; or PBRM-polymer-drug conjugate Trastuzumab-((EG2-MI (2%))-(10 kDa PHF-BA (28%)-(AF-HPA-Ala (9%)), (AF-HPA:trastuzumab about 10:1 to about 15:1), Example 14, at 2 mg/kg, 0.67 mg/kg or 0.3 mg/kg. The results show reduction of tumor volume for Example 14 with 100% regressions at 2.0 dose and 100% tumor free survival. The vehicle, Kadcyla® and trastuzumab alone, showed an increase of tumor volume. The conjugation of a PBRM specific for HER2 (trastuzumab) to a drug polymer conjugate was necessary for the reduction of tumor volume as the PBRM alone did not show reduction in tumor volume.

Figure 5:
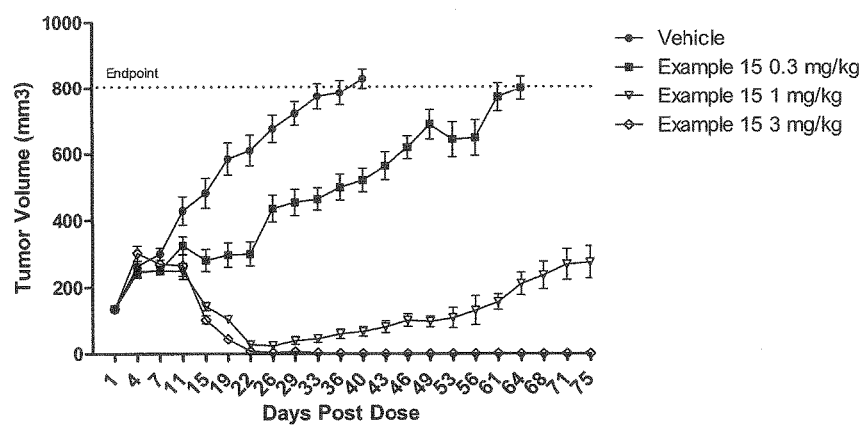
FIG. 5 shows the tumor response in mice inoculated subcutaneously with NCI-N87 cells (n=10 for each group) after IV administration as a single dose on day 1 of vehicle, or PBRM-polymer-drug conjugate described in Example 15, at 3 mg/kg, 1 mg/kg or 0.3 mg/kg.

FIG. 5 provides the results for the tumor response in mice inoculated subcutaneously with NCI-N87 cells (n=10 for each group) after IV administration as a single dose on day 1 of vehicle, or PBRM-polymer-drug conjugate Trastuzumab-((EG2-MI (2%))-(10 kDa PHF-BA (28%)-(AF-HPA-Ala (9%)), (AF-HPA:trastuzumab about 11:1 to about 16:1), Example 15, at 3 mg/kg, 1 mg/kg or 0.3 mg/kg. The results show a dose response for PBRM-polymer-drug conjugate (Example 15) with the highest dose of 3 mg/kg showing complete regression of tumor volume with 100 complete responses. At the middle dose 1 mg/kg there were 7 partial and 1 complete regression out of 10 animals.

Figure 6:
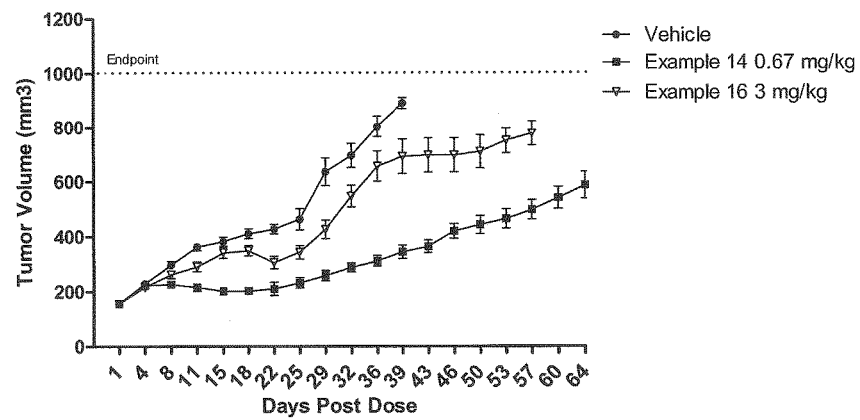
FIG. 6 shows the tumor response in mice inoculated subcutaneously with NCI-N87 cells (n=10 for each group) after IV administration as a single dose on day 1 of vehicle, PBRM-polymer-drug conjugates described is Example 14, at 0.67 mg/kg or Example 16, at 3 mg/kg.

FIG. 6 provides the results for the tumor response in mice inoculated subcutaneously with NCI-N87 cells (n=10 for each group) after IV administration as a single dose on day 1 of vehicle, PBRM-polymer-drug conjugates Trastuzumab-((EG2-MI (2%))-(10 kDa PHF-BA (28%)-(AF-HPA-Ala (9%)), (AF-HPA:trastuzumab about 11:1 to about 16:1), Example 14, at 0.67 mg/kg or Rituximab-((EG2-MI (2%))-(10 kDa PHF-BA (28%)-(AF-HPA-Ala (9%)), (AF-HPA:

trastuzumab about 13.7 to about 18.7), Example 16, at 3 mg/kg. The results show a tumor growth delay response for PBRM-polymer-drug conjugate (Example 14). The vehicle or Rituximab-drug polymer conjugate (Example 16) at the dose of 3 mg/kg has no effect on tumor growth.

Figure 7:
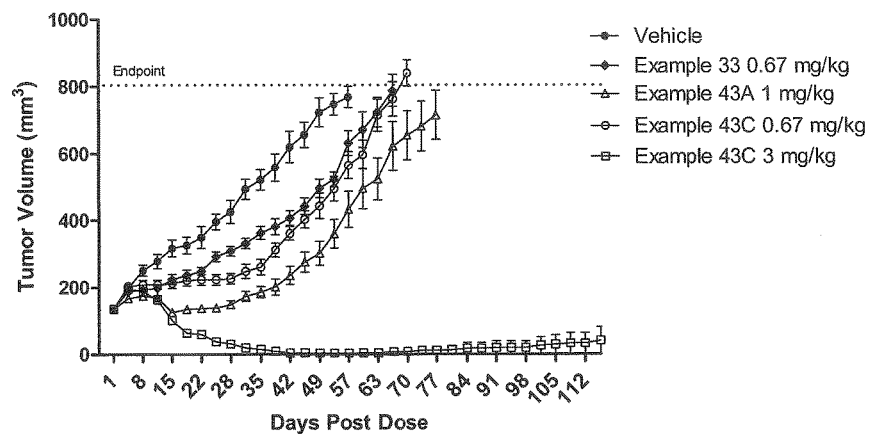
FIG. 7 shows the tumor response in mice inoculated subcutaneously with NCI-N87 cells (n=10 for each group) after IV administration as a single dose on day 1 of vehicle, PBRM-polymer-drug conjugate described in Example 33 at 0.67 mg/kg; Example 43A at 1 mg/kg or Example 43C at 0.67 mg/kg or 3 mg/kg.

FIG. 7 provides the results for the tumor response in mice inoculated subcutaneously with NCI-N87 cells (n=10 for each group) after IV administration as a single dose on day 1 of vehicle, PBRM-polymer-drug conjugates Trastuzumab-((EG2-MI (2.7%)-(10 kDa PHF-BA (28%)-(t-butylglycine AF-HPA) (7.5%)), (AF-HPA:trastuzumab about 4:1 to about 6:1) Example 33, at 0.67 mg/kg; Trastuzumab-((EG2-MI (2.8%)-(10 kDa PHF-BA (28%)-(AF-HPA-Ala (7.3%)) (AF-HPA:trastuzumab about 6:1 to about 9:1), Example 43A at 1 mg/kg; or Trastuzumab-((EG2-MI (2.5%)-(10 kDa PHF-BA (28%)-(AF-HPA-Ala (8.4%)), (AF-HPA:trastuzumab about 12:1 to about 16:1), Example 43C at 0.67 mg/kg or 3 mg/kg. The results show a tumor growth delay response for PBRM-polymer-drug conjugate Example 43C at the 0.67 mg/kg dose and the 3 mg/kg dose showed 90% tumor free survival on day 115.

Figure 8:
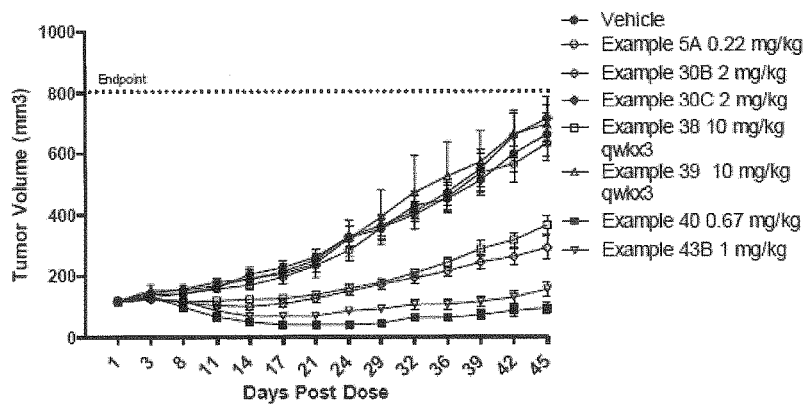
FIG. 8 shows the tumor response in mice inoculated subcutaneously with NCI-N87 cells (n=10 for each group) after IV administration as a single dose on day 1 of vehicle, polymer-drug conjugate described in Example 5A at 0.22 mg/kg; or PBRM-polymer-drug conjugates described in Example 30B or Example 30C each at 2 mg/kg; Example 40 at 0.67 mg/kg, or Example 43B at 1 mg/kg; or Example 38 at 10 mg/kg; or Example 39 at 10 mg/kg; each administered once weekly for 3 weeks.

FIG. 8 provides the results for the tumor response in mice inoculated subcutaneously with NCI-N87 cells (n=10 for each group) after IV administration as a single dose on day 1 of vehicle, polymer-drug conjugate 10K PHF-BA (30%)-AF-HPA-Ala (9.5%), Example 5A at 0.22 mg/kg; or PBRM-polymer-drug conjugates Trastuzumab-((EG2-MI (2.7%)-(10 kDa PHF-BA (28%)-(valine-acyloxyisopropyloxy-MMAE) (9%)), (MMAE:trastuzumab about 12:1 to about 16.5:1) Example 30B, at 2 mg/kg; Rituximab-((EG2-MI (2.7%)-(10 kDa PHF-BA (28%)-(valine-acyloxyisopropyloxy-MMAE) (9%)) (MMAE:rituximab about 9.5:1 to about 13:1), Example 30C at 2 mg/kg; sc-FvFc-Trastuzumab-((EG2-MI (2.8%)-(10 kDa PHF-BA (28%)-(AF-HPA-Ala (8.1%)), (AF-HPA: scFvFc trastuzumab antibody about 14:1 to about 19:1), Example 40 at 0.67 mg/kg; or Trastuzumab-((EG2-MI (2.5%)-(10 kDa PHF-BA (28%)-(AF-HPA-Ala (8.4%), (AF-HPA:trastuzumab about 12:1 to about 17:1), Example 43B at 1 mg/kg; or dosed weekly for 3 weeks with Trastuzumab-((EG2-MI (2.65%)-(10 kDa PHF-BA (28%)-(Val-Cit-PABA-Arry 520 (2.9%)), (Any 520:trastuzumab about 4:1 to about 6:1), Example 38 at 10 mg/kg; or dosed weekly for 3 weeks with Rituximab-((EG2-MI (2.65%)-(10 kDa PHF-BA (28%)-(Val-Cit-PABA-Arry 520 (2.9%)), (Any 520:trastuzumab about 4:1 to about 6:1), Example 39 at 10 mg/kg; The results show a tumor growth delay response for PBRM-polymer-drug conjugate (Example 40 and Example 43B).

Figure 9:
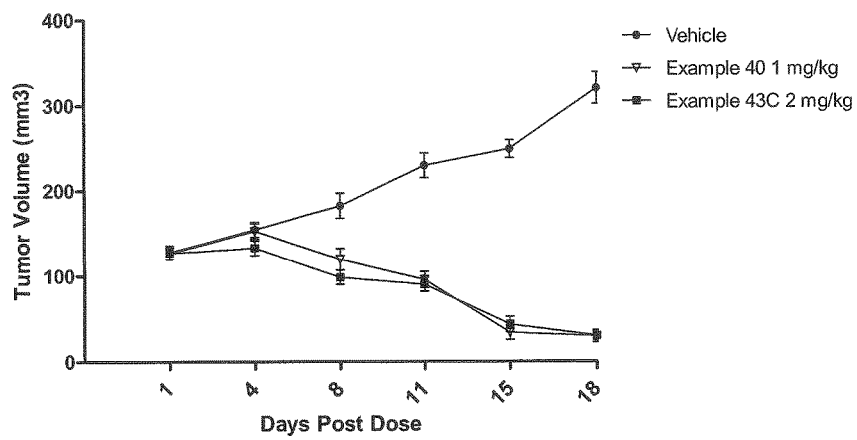
FIG. 9 shows the tumor response in mice inoculated subcutaneously with JIMT-1 cells (n=10 for each group) after IV administration as a single dose on day 1 of vehicle; Example 40 at 1 mg/kg and Example 43C at 2 mg/kg.

FIG. 9 provides the results for the tumor response in mice inoculated subcutaneously with JIMT-1 cells (n=10 for each group) after IV administration as a single dose on day 1 of vehicle, or sc-FvFc-Trastuzumab-((EG2-MI (2.8%)-(10 kDa PHF-BA (28%)-(AF-HPA-Ala (8.1%)), (AF-HPA: scFvFc trastuzumab antibody about 14:1 to about 19:1), Example 40 at 1 mg/kg; or Trastuzumab-((EG2-MI (2.5%)-(10 kDa PHF-BA (28%)-(AF-HPA-Ala (8.4%)), (AF-HPA:trastuzumab about 12:1 to about 16:1), Example 43C at 2 mg/kg.

Example 53

Mouse Plasma PK after Administration of PBRM-polymer-drug Conjugates

Female CD-1 mice were allowed to acclimate for at least 4 days prior to initial dosing. All mice were given regular chow and water ad libitum and were not fasted prior to compound administration. Test compounds or vehicle were dosed IV as a single dose on day 1.

The mice were injected intravenously with vehicle (n=3) or with PBRM-polymer-drug conjugate, Trastuzumab-((EG2-MI (3%))-(10 kDa PHF-BA (30%)-(AF-HPA-Ala (8%))), (AF-HPA:trastuzumab about 12:1 to about 17:1), Example 4, at 5 mg/kg, n=3 for each group). Plasma was collected at 5 min, 1 h, 3 h, 6 h, 24 h, 48 h, 72 h, day 7 and day 14 post dosing. Body weight was measured prior to dosing on day 1 and on days 1, 7 and 14. All animals were observed throughout the fourteen day period for mortality or morbidity.

The conjugated AF-HPA and unconjugated (free) drug (such as AF-HPA and AF) concentrations were determined by LC/MS analysis. Total trastuzumab concentration was determined by ELISA.

Figure 10:
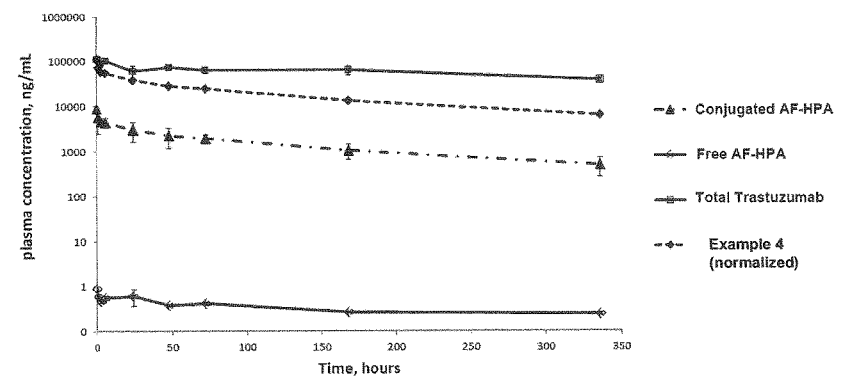
FIG. 10 shows the plasma PK for the conjugated AF HPA (total), unconjugated AF HPA and AF (denoted as "Free AF-HPA"), and trastuzumab in mice inoculated subcutaneously with BT474 tumors after IV bolus administration of PBRM-polymer-drug conjugate described in Example 4, at 5 mg/kg, 3 animals/time point.

The results in FIG. 10 showed that the trastuzumab had a plasma concentration of ~100 μg/mL and a half-life of ~12 days whereas unconjugated AF-HPA and AF had a total plasma concentration of <1 ng/mL. The PBRM-polymer-drug conjugate had a half-life of >5 days with an $AUC_{0\ to\ inf}$ of ~300 ug·day/mL.

Example 54

Mouse Plasma PK after Administration of PBRM-polymer-drug Conjugates

Female CD-1 mice were allowed to acclimate for at least 4 days prior to initial dosing. All mice were given regular chow and water ad libitum and were not fasted prior to compound administration. Test compounds or vehicle were dosed IV as a single dose on day 1.

The mice were injected intravenously with vehicle (n=3) or with PBRM-polymer-drug conjugates, as described in Examples 4, 7, 18A, 18B and 18C. Plasma was collected at 5 min, 1 h, 3 h, 6 h, 24 h, 48 h, 72 h, day 7 and day 14 post dosing. Body weight was measured prior to dosing on day 1 and on days 1, 7 and 14. All animals were observed throughout the fourteen day period for mortality or morbidity.

The total AF-HPA (conjugated AF-HPA and unconjugated (free) drug (such as AF-HPA and AF) concentrations were determined by LC-MS/MS analysis.

TABLE IX

| | Plasma PK | | |
| --- | --- | --- | --- |
| Test Sample | AF-HPA to trastuzumab ratio | $T_{1/2}$ (hr) | $AUC_{0\ to\ 336}$ (μg · hr/mL) |
| Example 4 | about 12:1 to about 17:1 | 125 | 20.1 |
| Example 7 | about 16:1 to about 21:1 | 136 | 22.9 |
| Example 18A | about 19:1 to about 24:1. | 154 | 19.4 |
| Example 18B | about 20:1 to about 25:1. | 139 | 22.7 |
| Example 18C | about 23:1 to about 28:1 | 119 | 25.1 |

The results in Table IX showed that the PBRM-polymer-drug conjugates had a half-life of ~120-154 hours (~5-6.4 days) with an $AUC_{0\ to\ 336}$ of ~19 to 25 μg·hr/mL and were independent of the AF-HPA to trastuzumab ratio of the PBRM-polymer-drug conjugates.

Example 55

Tolerability of the PBRM-polymer Drug Conjugate (MTD Study)

Tolerability of the PBRM-polymer drug conjugate was estimated in CD-1 female mice. The PBRM-polymer-drug conjugate, Example 4, was administered as a single IV dose at a dose of 20 mg/kg, 40 mg/kg, 60 mg/kg (n=6 for each group). The vehicle control group received physiological saline Animals were monitored for clinical signs over a twenty-one day period. Individual body weights of all study animals were recorded on day zero (baseline), every day for the first five days and approximately every other day thereafter. The results are summarized in Table X.

TABLE X

| Group | Dose (mg/kg) | % Change vs its Own Baseline on Day 7 | % Change vs its Own Baseline on Day 21 | Mortality or morbidity |
|---|---|---|---|---|
| 1 | Vehicle | −1% | +7.3% | None |
| 2 | 20 | +3.7% | +14.8% | None |
| 3 | 40 | −20% | +10.8% | 1 animal died on day 7 at 12% body weight loss |
| 4 | 60 | −28% | NA | 4 animals were moribund and sacrificed on Day 9 |

The 20 mg/kg dose was tolerated well, no body weight loss was observed in any of the mice in this group. At the 40 mg/kg dose the maximum body weight loss of ~20% was observe red on Day 7. One animal in this group was found dead on day 7 and had ~12% body weight loss on the previous day. By the end of the study (Day 21) all surviving animals (5 out of 6) in this study group gained weight relative to the control group. The 60 mg/kg dose clearly exceeded the maximum tolerated dose as all the animals in this group had significant body weight loss on Day 7 and were moribund and were sacrificed on Day 9.

The result show that the maximum tolerated dose for the mouse was between 20 and 40 mg/kg.

Example 56

Tolerability of the Auristatin F-hydroxypropylamide (MTD Study)

Tolerability of the Auristatin F-hydroxypropylamide (AF-HPA) was estimated in CD-1 female mice. The AF-HPA, (prepared in a fashion similar to that as described in U.S. Ser. No. 13/493,899, now U.S. Pat. No. 8,685,383, Example 48), was administered as a single IV dose at a dose of 1.6 mg/kg, 3.2 mg/kg, 4.7 mg/kg (n=6 for each group). The vehicle control group received physiological saline. Animals were monitored for clinical signs over a twenty-one day period. Individual body weights of all study animals were recorded on day zero (baseline), every day for the first five days and approximately every other day thereafter. The results are summarized in Table XI.

TABLE XI

| Group | Dose (mg/kg) | % Change vs its Own Baseline on Day 7 | % Change vs its Own Baseline on Day 21 | Mortality or morbidity |
|---|---|---|---|---|
| 1 | Vehicle | −1% | +7.3% | None |
| 2 | 1.6 | 11.6% | +5.5% | None |
| 3 | 3.2 | −20% | +10.8% | 1 animal died on day 7, 3 animals were moribund and sacrificed on Day 7. Two survivors |
| 4 | 4.7 | −28% | NA | 1 animal died on Day 3, 1 was moribund and sacrificed on Day 3, 3 animals were moribund and sacrificed on Day 4 and 1 animal on day 5. No survivors |

The 1.6 mg/kg dose was acceptably tolerated, with 11.6% body weight loss observed on Day 7. Animals fully recovered by Day 21 with 5.5% body weight increase relative to its group baseline. At the 3.2 mg/kg dose, 1 animal died on Day 7, 3 animals were moribund and sacrificed on Day 7. By the end of the study (Day 21) 2 out of 6 animals survived. The 4.7 mg/kg dose clearly exceeded the maximum tolerated dose as all the animals in this group either died, or were moribund and sacrificed.

Example 57

Estimation of Affinity and Kinetics of the Anti-5T4 scFvFc Polymer Drug Conjugate Binding to Human 5T4 (Extracellular Domain) by Surface Plasmon Resonance The affinity and kinetics parameters for binding of the anti-5T4 scFvFc polymer drug conjugate prepared in a fashion similar to that as described in Example 10 to the 5T4 antigen were measured by surface plasmon resonance using a BIAcore T200 instrument from GE Healthcare. The 5T4-ECD-Fc antigen (human 5T4 extracellular domain fused to Fc domain of human IgG1 subtype) was covalently immobilized on a BIAcore CM5 sensor chip by amine coupling method using reagents provided as a kit (GE Healthcare). In the binding study, anti-5T4 scFvFc polymer drug conjugate or control proteins were serially diluted to a concentration series in BIAcore running buffer HBS-EP+ (HEPES Buffered Saline supplemented with EDTA and P20) and flowed over the immobilized antigen for a fixed period of time to allow binding, followed by flow of running buffer only to dissociate the antigen and finally, regeneration of the surface using a low pH solution (10 mM Glycine-HCl, pH 2). All BIAcore reagents were procured from GE Healthcare. The resulting data curves are referred to as sensorgrams and constitute the raw binding data. The data were fit to a 1:1 Langmuir binding model using the BIAevaluation software (GE Healthcare) and the affinity/kinetics parameters such as association rate, dissociation rate and affinity were estimated. The affinity estimates are average of multiple measurements.

Figure 11:
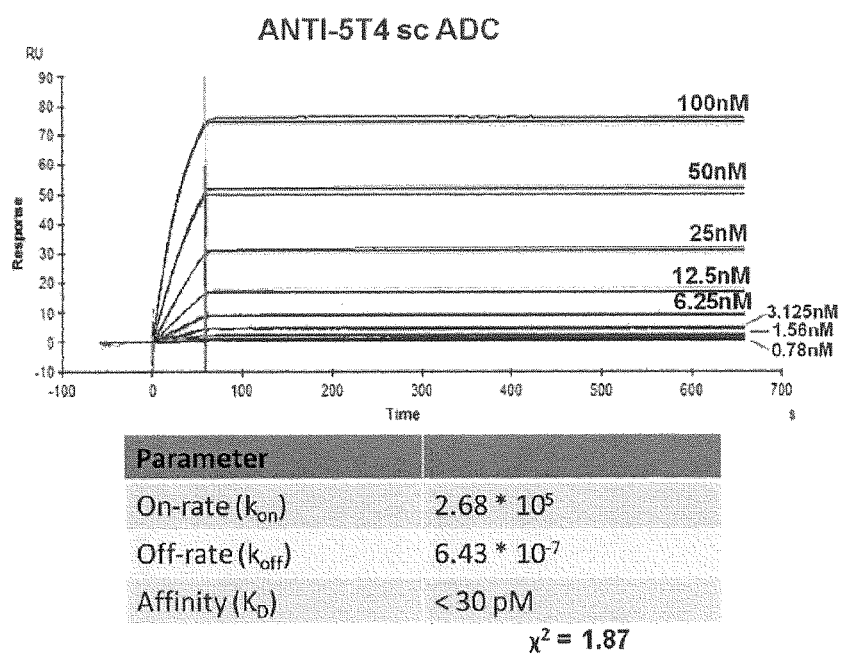
FIG. 11 illustrates the affinity and kinetics of a 5T4-specific scADC to human 5T4 extracellular domain, measured by surface plasmon resonance. The binding affinity ($K_D$ of <30 pM) is similar to that of the non-conjugated anti-5T4 scFvFc.

As illustrated in FIG. 11, the anti-5T4 scFvFc polymer drug conjugate (Example 10) bound to human 5T4 extracellular domain with high affinity ($K_D$ of <30 pM). This value is similar that determined for the non-conjugated anti-5T4 scFvFc.

Example 58

Binding of the Anti-5T4 scFvFc Polymer Drug Conjugate to Cell Surface 5T4 Antigen Cell surface binding of the anti-5T4 scFvFc polymer drug conjugate (anti-5T4 scADC) (Example 10) was evaluated using a FACS Calibre flow cytometer (Beckton Dickinson) in various human cancer cell lines. The cell surface binding of the anti-5T4 scFvFc polymer drug conjugate was determined by titration and compared to the cell surface binding measured for non-conjugated anti-5T4 scFvFc antibody.

5T4 over-expressing recombinant MDA-MB-231 (MDA-MB-231-5T4 OE), MDA-MB-231 (negative for 5T4; available from the American Type Culture Collection, Manassas Va. US, under accession number HTB-26) and A431 (naturally expressing 5T4) cells (A431, available from the American Type Culture Collection, Manassas Va. US, under accession number CRL-1555) were used for the titration of anti-5T4 scFvFc polymer drug conjugate and non-conjugated anti-5T4 scFvFc. Exponentially growing cells were detached from culture flask using 0.5 mM PBS/EDTA buffer. The cells were washed twice with PBS and incubated with anti-5T4 scFvFc, anti-5T4 scADC, or non-binding scFvFc fusion protein (0.01 to 10 µg/mL) in 1% BSA-PBS for 1 h at room temperature. The cells were washed three times with PBS and incubated with anti-Fc specific-FITC antibody for 45 mM at 4° C. After the incubation of anti-Fc specific FITC antibody, cells were washed three times with PBS and analyzed using flow cytometry (FACS Calibre, Becton Dickinson). Median fluorescence intensities (MFI) were determined for the samples.

Specific dose-dependent cell surface binding for anti-5T4 scFvFc polymer drug conjugate (Example 10) was comparable to that of non-conjugated anti-5T4 scFvFc in both A431 and 5T4 over-expressing MDA-MB-231 cells. Binding of an unrelated scFvFc fusion protein was 200-fold less at 5 µg/mL. In addition, MDA-MB-231 cells, which are negative for 5T4 expression, did not show any cell surface binding to either anti-5T4 scFvFc or the conjugated anti-5T4 scFvFc ADC.

Example 59

In Vivo Efficacy of the Anti-5T4 scFvFc Polymer Drug Conjugate

Materials: BD 1 mL syringes (271/2 Gauge), Sterile Culture medium, Sterile Phosphate Buffered Saline, Matrigel—BD Biosciences (catalog No. 354248), Sterile cotton plugs, Sterile Eppendrof tubes (1.5 mL, 2 mL), Pipettes, Filter paper, 70% Alcohol/Isopropyl alcohol, Vernier Caliper (Mitutoyo). All other essential items used were of analytical grade.

Animals: Athymic female nude mice (Hsd: Athymic Nude-Foxn1$^{nu}$) 5-6 weeks old, weighing 20-22 g were obtained from Harlan, Netherlands. Animals were taken care as per the Regulations of Committee for the Purpose of Control and Supervision of Experiments on Animals (CPCSEA), Government of India and Association for Assessment and Accreditation of Laboratory Animal Care (AAALAC) compliance. The 'Form B' for carrying out animal experimentation was reviewed and approved by the Institutional Animal Ethics Committee.

Housing and Feeding: Animals were maintained in a controlled environment with 22±3° C. temperature, 50±20% humidity, a light/dark cycle of 12 hours each and 15-20 fresh air changes per hour. Animals were housed group wise and autoclaved corncob was used as a bedding material. The animals were fed, ad libitum, with certified Irradiated Laboratory Rodent Diet during the study period.

Preparation of Animals & Animal Identification: The animals were kept under acclimatization in the experimental room for a period of at least 5 days Animals were individually numbered and the cage cards indicating the experiment, study number, date of tumor implantation, date of randomization, tumor type, mouse strain, gender, and individual mouse number were displayed to corresponding cages. After randomization, group identity, test compound, dosage, schedule and route of administration were added.

Preparation of tumor cells: All procedures were performed in laminar flow hood following sterile techniques. Cancer cells (a) A431 (Epidermoid), (b) recombinant MDA-MB-231 (breast) over-expressing 5T4 (MDA-MB-231 5T4++) (5T4 OE), and (c) H1975 (non small cell lung carcinoma) with 70-80% confluent and viability of >90% were chosen for the study. $5 \times 10^6$ cells were resuspended in 200 µl of PBS or serum free media containing 50% of matrigel kept in ice.

Subcutaneous injection of cells: Nude mice (Hsd: Athymic Nude-Foxn1$^{nu}$) housed in Individual Ventilated Cages (IVCs) were used. Cancer cell lines were propagated in the animals by injecting subcutaneously in the flanks or back of the animals. The implanted area was monitored for growth of tumor. Once the tumors were palpable and of required volume (TV≈150 mm$^3$), animals were randomized based on tumor volume and dosing was initiated. The tumor volume was determined by two-dimensional measurement with a caliper on the day of randomization (Day 0) and then once every three days (i.e. on the same days on which mice were weighed). Using a vernier caliper the length (L) and width (W) of the tumor was measured. Tumor volume (TV) was calculated using the following formula:

$$\text{Tumor Volume(mm}^3\text{)}=L \times W^2/2,$$

Where, L=Length (mm); W=Width (mm)

The anti-5T4 scFvFc polymer drug conjugate (Example 10) was dissolved in sterile 1×PBS which resulted in clear solutions at all prepared concentrations and was administered intravenously via tail vein. The test item was freshly prepared on the days of administration and the dose volume was kept at 5 mL/kg body weight. For each group separate new syringe and needles were used.

Body weight: Cage side observations, body weight were measured once every three days during the study period. The % change in body weights of individual mice was calculated.

Antitumor Activity: Antitumor activity was evaluated as maximum tumor volume inhibition versus the vehicle control group. Data evaluation was performed using statistical software Graph pad version.5.

Test/Control Value in % (% T/C): Tumor inhibition on a particular day (T/C in %) was calculated from the ratio of the mean TV values of the test versus control groups multiplied by 100%, as follows: T/C (Day X)=(Mean TV of the test group on Day X−Mean TV of the test group on Day 0)/(Mean TV of the control group on Day X−Mean TV of the control group on Day 0)×100%

The minimum (or optimum) % T/C value recorded for a particular test group during an experiment represents the maximum antitumor activity for the respective treatment. TV=Tumor volume (mm$^3$)

Tumor growth inhibition (TGI): TGI was calculated using the following formula:

TGI=(1−T/C)×100

Where, T=(Mean TV of the test group on Day X−Mean TV of the test group on Day 0) and C=(Mean TV of the control group on Day X−Mean TV of the control group on Day 0)

Clinical Signs: Morbidity & Mortality: Animals were observed individually for visible general clinical signs once every three days during the study period. All the animals were checked for morbidity and mortality.

Statistical Analysis: For the evaluation of the statistical significance of tumor inhibition, Two way ANOVA followed by Bonferroni posttest was performed using GraphPad Prism v5. p values <0.05 indicate statistically significant differences between groups.

Figure 12:
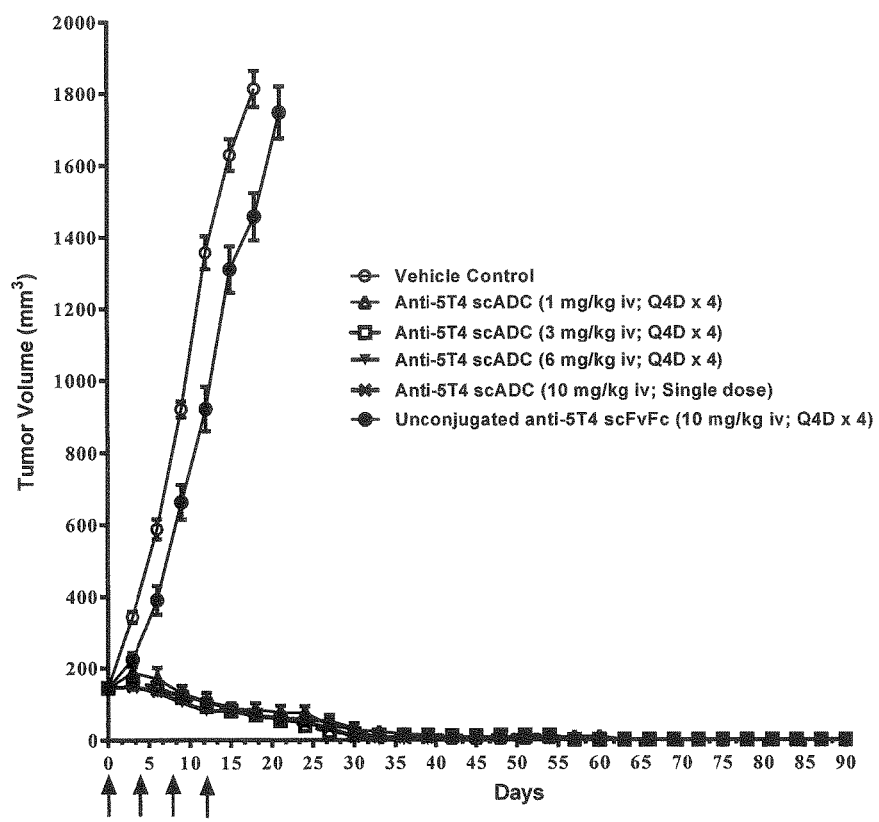
FIG. 12 illustrates the anti-tumor efficacy of a 5T4-specific scADC, as measured in an A431 tumor xenograft model. Tumor volume is determined on the days specified. Values are expressed as Mean±SEM. Statistical analysis carried out by Two-way ANOVA followed by Bonferroni post tests using Graph Pad Prism (Version. 5).

Results:

A431—Subcutaneous Xenograft Antitumor Activity:

In xenograft experiments with the A431 cell line ["Characterization of the A431 tumor xenograft as an in vivo model for testing epidermal growth factor-receptor antagonists", S. Robinson et al., Int. J. Oncol. 1992, 1(3):293-81, anti-5T4 scADC prepared in a fashion similar to that as described in Example 10 was administered IV to the tumor-bearing mice at the following doses: 10 mg/kg, single dose; 1 mg/kg, Q4D×4; 3 mg/kg, Q4D×4; and 6 mg/kg, Q4D×4. "Q4D×4" means dosing once every 4 days, for a total of 4 doses. A separate group of tumor-bearing mice was administered with unconjugated anti-5T4 scFvFc (10 mg/kg IV, Q4D×4). In this study, anti-5T4 scADC therapy demonstrated strong antitumor activity against A431 carcinoma xenografts when administered as a single dose or repeated doses at the above-mentioned dose levels (FIG. 12). Treatment with anti-5T4 scADC at a single dose (10 mg/kg IV) resulted in an optimal T/C value of −4% on Day 24. The % tumor growth inhibition (TGI) for 10 mg/kg IV single dose group was found to be 104% (Day 24, p<0.001). The optimal T/C value in repeat dose groups (1 mg/kg, 3 mg/kg and 6 mg/kg IV, Q4D×4) was found to be −2%, −4% & −3% on day 24, respectively. Further the % tumor growth inhibition (TGI) for repeat dose groups (1 mg/kg, 3 mg/kg and 6 mg/kg IV, Q4D×4) was found to be 102% (Day 24, p<0.001), 104% (Day 24, p<0.001) and 103% (Day 24, p<0.001), respectively. There was no significant difference between the single dose and repeat dose anti-5T4 scADC treatment groups. Administration of non-conjugated anti-5T4 scFvFc at the dose of 10 mg/kg IV, Q4D×4 did not cause any significant % reduction in tumor volume of A431 xenografts. The % T/C value of on Day 24 was found to be 87%. The difference in tumor sizes between the vehicle-treated group and the anti-5T4 ScFvFc-treated group was not statistically significant and the % tumor growth inhibition (TGI) at this dose was found to be 13% (Day 24). Post treatment regimen, animals in the anti-5T4 scADC test groups were observed until day 90, at which time the study was terminated. In the anti-5T4 scADC repeat-dose group treated at 6 mpk, i.v, Q4D×4 there was treatment-related severe body weight loss and mortality (7/10 animals) by Day 24; the surviving animals in this dose group were observed until day 90. Complete tumor growth regression was observed in all of the anti-5T4 scADC treated groups and there were no signs of tumor re-growth up to the end of the study period (including 3/10 in the 6 mpk, i.v., Q4D×4 dose group).

Figure 13:
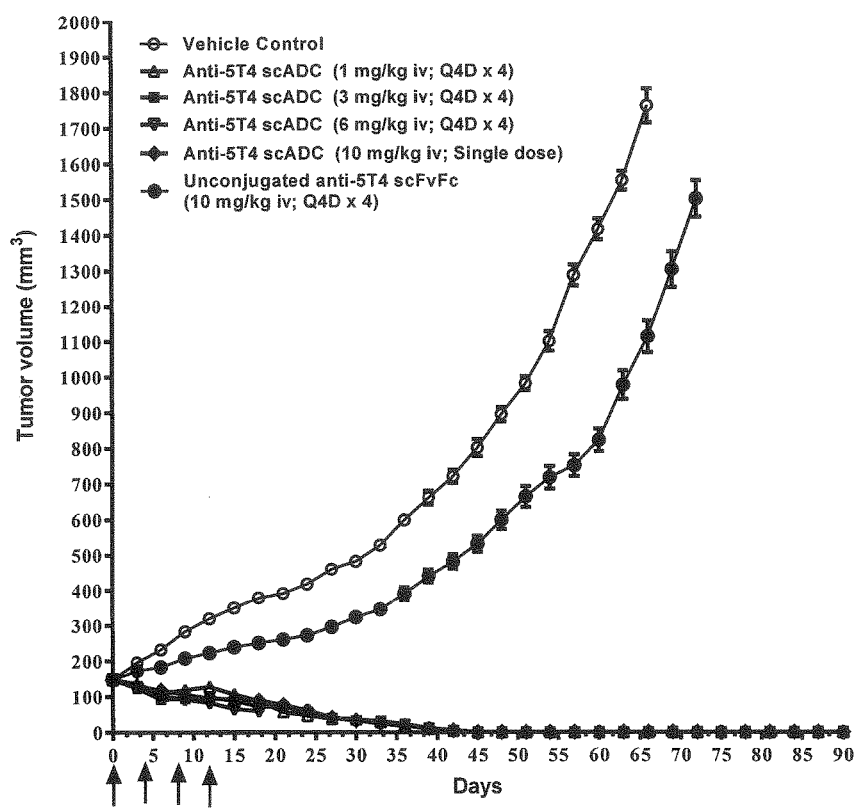
FIG. 13 illustrates the antitumor efficacy of a 5T4-specific scADC in nude mice bearing MDA-MB-231 5T4 overexpressing transfectant tumor xenograft. Values are expressed as Mean±SEM. Statistical analysis carried out by Two-way ANOVA followed by Bonferroni post tests using Graph Pad Prism (Version. 5).

MDA-MB-231 5T4++—Subcutaneous Xenograft Antitumor Activity:

In an experiment with the xenografts of MDA-MB-231-5T4 OE, anti-5T4 scADC prepared in a fashion similar to that as described in Example 10 was administered to the tumor-bearing mice at the following doses: 10 mg/kg IV, single dose; 1 mg/kg IV, Q4D×4; 3 mg/kg IV, Q4D×4; and 6 mg/kg IV, Q4D×4. A separate group was administered with unconjugated anti-5T4 scFvFc (10 mg/kg IV, Q4D×4). In this study, anti-5T4 scADC therapy demonstrated strong antitumor activity against MDA-MB-231-5T4 OE xenografts when administered as a single dose or repeated doses at the above-mentioned dose levels (FIG. 13). Treatment with anti-5T4 scADC at single dose (10 mg/kg IV) resulted in an optimal T/C value of −25% on Day 18. The % tumor growth inhibition (TGI) for 10 mg/kg IV single dose group was found to be 125% (Day 18, p<0.001). The optimal T/C value in repeat dose groups (1 mg/kg, 3 mg/kg and 6 mg/kg IV, Q4D×4) was found to be −26%, −32% & −38% on day 18 respectively. Further the % tumor growth inhibition (TGI) for repeat dose groups (1 mg/kg, 3 mg/kg and 6 mg/kg IV, Q4D×4) was found to be 126% (Day 18, p<0.001), 132% (Day 18, p<0.001) and 138% (Day 18, p<0.001) respectively. There was no significant difference between the single dose and repeat dose anti-5T4 scADC treatment groups. Non-conjugated anti-5T4 scFvFc therapy at the dose of 10 mg/kg IV, Q4D×4 showed moderate antitumor activity against MDA-MB-231 5T4OE xenografts. The % T/C value of on Day 18 was found to be 45% and the tumor growth inhibition (TGI) at this dose was 55% (Day 18, p<0.001). Furthermore, the mean tumor volume on Day 66 for the Vehicle control group was found to be 1763 mm$^3$. In anti-5T4 scADC repeat dose groups (1 mpk, 3 mpk, i.v; Q4D×4) and single dose group (10 mpk, i.v), there was complete tumor growth regression from Day 45 until Day 90, at which time the study was terminated. There were no signs of tumor re-growth in the above-mentioned anti-5T4 scADC treated groups up to the end of the study period. However, in the anti-5T4 scADC repeat-dose group treated at 6 mpk, i.v, Q4D×4 there was treatment-related severe body weight loss and mortality (10/10) by Day 21. The mean tumor volume for unconjugated anti-5T4 scFvFc antibody treated group on Day 72 was found to be 1502 mm$^3$. The % T/C value of on Day 66 for this antibody-treated group was found to be 60% and the tumor growth inhibition (TGI) at this dose was 40% (Day 66, p<0.001).

H1975—Subcutaneous Xenograft Antitumor Activity:

In xenograft experiments conducted in a similar manner with the H1975 lung carcinoma cell line, anti-5T4 scADC prepared in a similar manner as described in Example 10 was administered IV to the tumor-bearing mice (n=5 mice per group, initial tumor volume ~150 mm$^3$) at the following doses: 0.3 mg/kg, Q4D×4; 1 mg/kg, Q4D×4; and 3 mg/kg, Q4D×4. A separate group was administered with unconjugated anti-5T4 scFvFc antibody at 3 mg/kg IV, Q4D×4. Treatment with anti-5T4 scADC (0.3 & 1 mg/kg, i.v; Q4D×4) resulted in partial remission (on Day 39) of H1975 tumor xenografts when administered as repeated dose at the above mentioned dose levels. Treatment with anti-5T4 scADC at 3 mg/kg, i.v; Q4D×4, resulted in complete remission (on Day 39) of H1975 tumor xenografts. Treatment with anti-5T4 scADC at 0.3, 1 & 3 mpk, i.v; Q4D×4 resulted in an optimal T/C value of −0.7%, −4% & −5% on Day 39 respectively and the % tumor growth inhibition (TGI) was found to be 101%, 104% & Complete remission (CR) (Day 39, p<0.001). Treatment with unconjugated anti-5T4 scFvFc antibody resulted in poor antitumor activity with a % T/C value of 88% on Day 39 with the % TGI being 12%. Post treatment regimen, animals in the test groups were observed until Day 81, at which time the study was terminated. On Day 60, anti-5T4 scADC therapy (0.3 mg/kg, i.v; Q4D×4) demonstrated complete remission (3/5) in nude mice bearing H1975 xenograft, while tumor regrowth was observed in 2 animals from Day 39 onwards until Day 60, at which time the animals in this group were sacrificed. However on Day 81, therapy with anti-5T4 scADC (1 & 3 mg/kg, i.v; Q4D×4) resulted in complete remission (5/5; Day 81) in nude mice bearing H1975 xenografts.

NCI-N87—Subcutaneous Xenograft Antitumor Activity:

In a similar manner to the above-described tumor xenograft studies, xenograft experiments were conducted with the NCI-N87 (gastric carcinoma) cell line. Anti-5T4 scADC prepared in a similar manner as described in Example 10 was administered IV to the tumor-bearing SCID mice (n=10 mice per group, initial tumor volume ~135 mm$^3$) at the following doses: 3 mg/kg, single dose; and 3 mg/kg, Q4D×3. A separate group was administered with unconjugated anti-5T4 scFvFc antibody at 3 mg/kg IV, Q4D×3. One non-treatment related death was assessed in the anti-5T4 scADC 3 mg/kg single dose group, and the data for this animal were excluded from the analysis. On Day 19, the anti-5T4 scADC treatment groups showed tumor growth inhibition of 92 and 87% at 3 mg/kg, single dose; and 3 mg/kg, Q4D×3, respectively. Both anti-5T4 scADC treatment groups had 100% complete regressions, which were durable to the end of the study on Day 75. Treatment with unconjugated anti-5T4 scFvFc antibody resulted in poor antitumor activity with a tumor growth inhibition value of 14% on Day 19; all animals in this treatment group reached a tumor volume endpoint of 800 mm$^3$ by Day 56.

All publications, including, e.g., non-patent literature, patent applications, and patents, cited in this specification are incorporated herein by reference for all purposes. The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A therapeutic drug and targeting conjugate useful in anti-neoplastic therapies comprising an anti-5T4 ligand, the ligand comprising an immunoglobulin or functional fragment which is an anti-5T4 scFvFc, and a poly(1-hydroxymethylethylene hydroxymethyl-formal) (PHF) polymeric scaffold comprising the units shown below which may be randomly connected to each other,

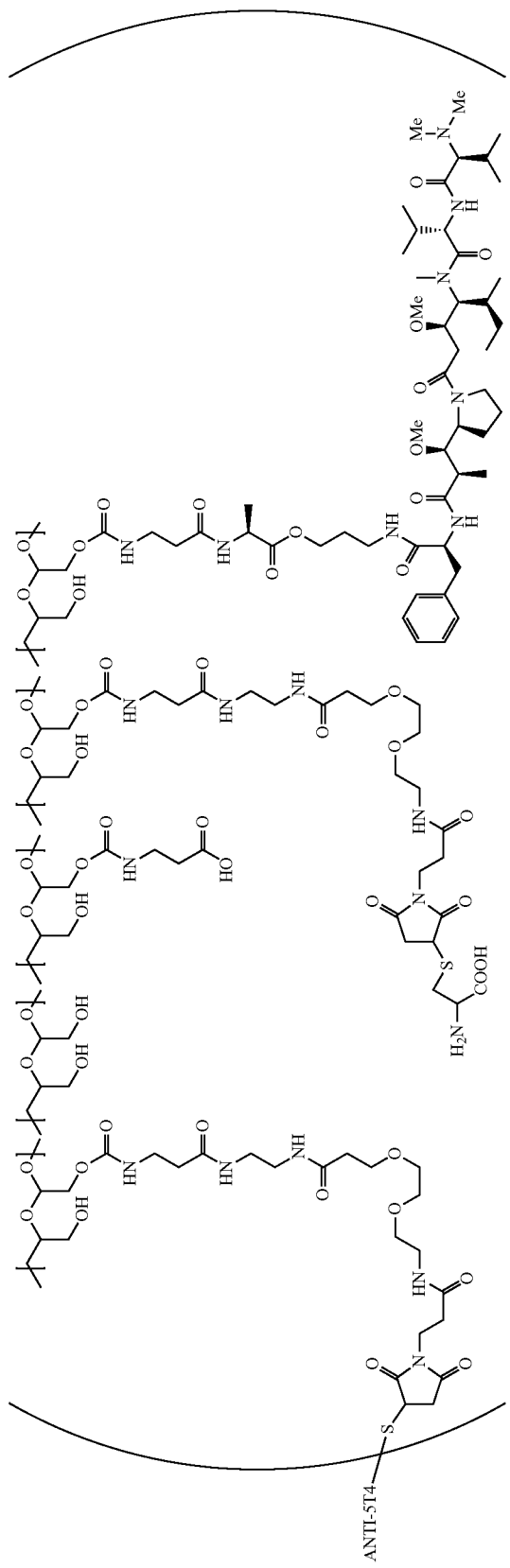

wherein:
ANTI-5T4 is a single chain antibody construct comprising the amino sequence designated as SEQ ID NO: 7;
the sulfur atom is part of the single chain antibody construct;
the PHF has a molecular weight ranging from about 2 kDa to about 40 kDa;
the average polymeric scaffold to anti-5T4 single chain antibody ratio is about 2:1 to about 4:1; and
the auristatin F HPA to anti-5T4 antibody ratio is about 12:1 to about 18:1.

2. A pharmaceutical composition comprising a therapeutic drug and targeting conjugate of claim 1 and a pharmaceutically acceptable carrier.

3. A method of treating a disorder in a subject in need thereof, comprising administering to the subject an effective amount of the pharmaceutical composition of claim 2.

4. The method of claim 3, wherein the disorder is a cancer selected from the group consisting of anal, astrocytoma, leukemia, lymphoma, head and neck, liver, testicular, cervical, sarcoma, hemangioma, esophageal, eye, laryngeal, mouth, mesothelioma, skin, myeloma, oral, rectal, throat, bladder, breast, uterus, ovary, prostate, lung, colon, pancreas, renal, and gastric cancer.

* * * * *

UNITED STATES PATENT AND TRADEMARK OFFICE
CERTIFICATE OF CORRECTION

PATENT NO. : 10,316,080 B2
APPLICATION NO. : 14/512275
DATED : June 11, 2019
INVENTOR(S) : Smith et al.

Page 1 of 4

It is certified that error appears in the above-identified patent and that said Letters Patent is hereby corrected as shown below:

<u>After Column 134 Line 50 to Column 135 Line 57:</u>
Please change:
"SEQ ID NO: A: 5T4-specific murine scFv:

EVQLQQSGPDLVKPGASVKISCKASGYSFTGYYMHWVKQSPGKGLEWIGRINPNNG
VTLYNQKFKDKATLTVDKSSTTAYMELRSLTSEDSAVYYCARSTMITNYVMDYWGQ
GTSVTVSSGGGGSGGGGSGGGGSSIVMTQTPTSLLVSAGDRVTITCKASQSVSNDVA
WYQQKPGQSPKLLISYTSSRYAGVPDRFTGSGSGTDFTLTISSVQAEDAAVYFCQQDY
NSPPTFGGGTKLEIK

SEQ ID NO: B: 5T4-specific humanized scFv:

EVQLVESGGGLVQPGGSLRLSCKASGYSFTGYYMHWVRQAPGKGLEWVSRINPNNG
VTLYNQKFKDRFTISRDNSKNTLYLQMNSLRAEDTAVYYCARSTMITNYVMDYWGQ
GTLVTVSSGGGGSGGGGSGGGGSGGGGSGGGGSDIQMTQSPSSLSASVGDR
VTITCKASQSVSNDVAWYQQKPGKAPKLLIYYTSSRYAGVPSRFSGSGSGTDFTLTISS
LQPEDFATYYCQQDYNSPPTFGGGTKLEIK

SEQ ID NO: C: Human Hinge-CH2-CH3 (Fcgamma1):

EPKSSDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAVEWESNGQPE
NNYKTTPPVLDSDGSFFLYSKLTVDKSRWQQGNVFSCSVMHEALHNHYTQKSLSLSP
GK

SEQ ID NO: Y: Site-specific conjugation-1: ASTC

Signed and Sealed this
Fourteenth Day of April, 2020

Andrei Iancu
*Director of the United States Patent and Trademark Office*

SEQ ID NO: Z: No site-specific conjugation-1: ASTX

SEQ ID NO: D: Chimeric anti-5T4 scFv-Fc:

EVQLQQSGPDLVKPGASVKISCKASGYSFTGYYMHWVKQSPGKGLEWIGRINPNNG
VTLYNQKFKDKATLTVDKSSTTAYMELRSLTSEDSAVYYCARSTMITNYVMDYWGQ
GTSVTVSSGGGGSGGGGSGGGGSSIVMTQTPTSLLVSAGDRVTITCKASQSVSNDVA
WYQQKPGQSPKLLISYTSSRYAGVPDRFTGSGSGTDFTLTISSVQAEDAAVYFCQQDY
NSPPTFGGGTKLEIKASTCEPKSSDKTHTCPPCPAPELLGGPSVFLFPPKPKDTLMISRT
PEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTKNQVSLTCLV
KGFYPSDIAVEWESNGQPENNYKTTPPVLDSDGSFFLYSKLTVDKSRWQQGNVFSCS
VMHEALHNHYTQKSLSLSPGK

SEQ ID NO: E: Humanized anti-5T4 scFv-Fc (ASTC):

EVQLVESGGGLVQPGGSLRLSCKASGYSFTGYYMHWVRQAPGKGLEWVSRINPNNG
VTLYNQKFKDRFTISRDNSKNTLYLQMNSLRAEDTAVYYCARSTMITNYVMDYWGQ
GTLVTVSSGGGGSGGGGSGGGGSGGGGSGGGGSDIQMTQSPSSLSASVGDR
VTITCKASQSVSNDVAWYQQKPGKAPKLLIYYTSSRYAGVPSRFSGSGSGTDFTLTISS
LQPEDFATYYCQQDYNSPPTFGGGTKLEIKASTCEPKSSDKTHTCPPCPAPELLGGPSV
FLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSKLTV
DKSRWQQGNVFSCSVMHEALHNHYTQKSLSLSPGK

SEQ ID NO: F: Humanized anti-5T4 scFv-Fc (ASTX):

EVQLVESGGGLVQPGGSLRLSCKASGYSFTGYYMHWVRQAPGKGLEWVSRINPNNG
VTLYNQKFKDRFTISRDNSKNTLYLQMNSLRAEDTAVYYCARSTMITNYVMDYWGQ
GTLVTVSSGGGGSGGGGSGGGGSGGGGSGGGGSDIQMTQSPSSLSASVGDR
VTITCKASQSVSNDVAWYQQKPGKAPKLLIYYTSSRYAGVPSRFSGSGSGTDFTLTISS
LQPEDFATYYCQQDYNSPPTFGGGTKLEIKASTXEPKSSDKTHTCPPCPAPELLGGPSV
FLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSKLTV
DKSRWQQGNVFSCSVMHEALHNHYTQKSLSLSPGK"

To:
-- SEQ ID NO: 1: 5T4-specific murine scFv:

EVQLQQSGPDLVKPGASVKISCKASGYSFTGYYMHWVKQSPGKGLEWIGRINPNNG
VTLYNQKFKDKATLTVDKSSTTAYMELRSLTSEDSAVYYCARSTMITNYVMDYWGQ
GTSVTVSSGGGGSGGGGSGGGGSSIVMTQTPTSLLVSAGDRVTITCKASQSVSNDVA
WYQQKPGQSPKLLISYTSSRYAGVPDRFTGSGSGTDFTLTISSVQAEDAAVYFCQQDY
NSPPTFGGGTKLEIK

SEQ ID NO: 2: 5T4-specific humanized scFv:

EVQLVESGGGLVQPGGSLRLSCKASGYSFTGYYMHWVRQAPGKGLEWVSRINPNNG
VTLYNQKFKDRFTISRDNSKNTLYLQMNSLRAEDTAVYYCARSTMITNYVMDYWGQ
GTLVTVSSGGGGSGGGGSGGGGSGGGGSGGGGSGGGGSDIQMTQSPSSLSASVGDR
VTITCKASQSVSNDVAWYQQKPGKAPKLLIYYTSSRYAGVPSRFSGSGSGTDFTLTISS
LQPEDFATYYCQQDYNSPPTFGGGTKLEIK

SEQ ID NO: 3: Human Hinge-CH2-CH3 (Fcgamma1):

EPKSSDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAVEWESNGQPE
NNYKTTPPVLDSDGSFFLYSKLTVDKSRWQQGNVFSCSVMHEALHNHYTQKSLSLSP
GK

SEQ ID NO: 4: Site-specific conjugation-1: ASTC

SEQ ID NO: 5: No site-specific conjugation-1: ASTX

SEQ ID NO: 6: Chimeric anti-5T4 scFv-Fc:
EVQLQQSGPDLVKPGASVKISCKASGYSFTGYYMHWVKQSPGKGLEWIGRINPNNG
VTLYNQKFKDKATLTVDKSSTTAYMELRSLTSEDSAVYYCARSTMITNYVMDYWGQ
GTSVTVSSGGGGSGGGGSGGGGSSIVMTQTPTSLLVSAGDRVTITCKASQSVSNDVA
WYQQKPGQSPKLLISYTSSRYAGVPDRFTGSGSGTDFTLTISSVQAEDAAVYFCQQDY
NSPPTFGGGTKLEIKASTCEPKSSDKTHTCPPCPAPELLGGPSVFLFPPKPKDTLMISRT
PEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTKNQVSLTCLV
KGFYPSDIAVEWESNGQPENNYKTTPPVLDSDGSFFLYSKLTVDKSRWQQGNVFSCS
VMHEALHNHYTQKSLSLSPGK

CERTIFICATE OF CORRECTION (continued)
U.S. Pat. No. 10,316,080 B2

SEQ ID NO: 7: Humanized anti-5T4 scFv-Fc (ASTC ('ASTC' disclosed as SEQ ID NO: 4)):
EVQLVESGGGLVQPGGSLRLSCKASGYSFTGYYMHWVRQAPGKGLEWVSRINPNNG
VTLYNQKFKDRFTISRDNSKNTLYLQMNSLRAEDTAVYYCARSTMITNYVMDYWGQ
GTLVTVSSGGGGSGGGGSGGGGSGGGGSGGGGSGGGGSDIQMTQSPSSLSASVGDR
VTITCKASQSVSNDVAWYQQKPGKAPKLLIYYTSSRYAGVPSRFSGSGSGTDFTLTISS
LQPEDFATYYCQQDYNSPPTFGGGTKLEIKASTCEPKSSDKTHTCPPCPAPELLGGPSV
FLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSKLTV
DKSRWQQGNVFSCSVMHEALHNHYTQKSLSLSPGK SEQ ID NO: 8: Humanized anti-5T4 scFv-Fc (ASTX ('ASTX' disclosed as SEQ ID NO: 5)):
EVQLVESGGGLVQPGGSLRLSCKASGYSFTGYYMHWVRQAPGKGLEWVSRINPNNG
VTLYNQKFKDRFTISRDNSKNTLYLQMNSLRAEDTAVYYCARSTMITNYVMDYWGQ
GTLVTVSSGGGGSGGGGSGGGGSGGGGSGGGGSGGGGSDIQMTQSPSSLSASVGDR
VTITCKASQSVSNDVAWYQQKPGKAPKLLIYYTSSRYAGVPSRFSGSGSGTDFTLTISS
LQPEDFATYYCQQDYNSPPTFGGGTKLEIKASTXEPKSSDKTHTCPPCPAPELLGGPSV
FLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSKLTV
DKSRWQQGNVFSCSVMHEALHNHYTQKSLSLSPGK --